(12) United States Patent
Lietzau et al.

(10) Patent No.: US 11,939,511 B2
(45) Date of Patent: *Mar. 26, 2024

(54) LIQUID CRYSTAL MIXTURE AND LIQUID CRYSTAL DISPLAY

(71) Applicant: MERCK PATENT GMBH, Darmstadt (DE)

(72) Inventors: Lars Lietzau, Rossdorf (DE); Simon Siemianowski, Rossdorf (DE); Izumi Saito, Darmstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 417 days.

This patent is subject to a terminal disclaimer.

(21) Appl. No.: 17/049,516

(22) PCT Filed: Apr. 18, 2019

(86) PCT No.: PCT/EP2019/060042
§ 371 (c)(1),
(2) Date: Oct. 21, 2020

(87) PCT Pub. No.: WO2019/206788
PCT Pub. Date: Oct. 31, 2019

(65) Prior Publication Data
US 2021/0292652 A1 Sep. 23, 2021

(30) Foreign Application Priority Data
Apr. 23, 2018 (EP) ..................... 18168775

(51) Int. Cl.
G02F 1/1333 (2006.01)
C07C 13/28 (2006.01)
(Continued)

(52) U.S. Cl.
CPC ............. C09K 19/56 (2013.01); C07C 13/28 (2013.01); C07C 25/18 (2013.01); C07C 25/24 (2013.01);
(Continued)

(58) Field of Classification Search
CPC .......................... C09K 19/56; C09K 19/3003; C09K 19/3066; C09K 19/3098; C09K 19/3402; C09K 19/3491; C09K 19/32; C09K 19/2014; C09K 19/04; C09K 19/3001; C09K 19/3804; C09K 2019/0466; C09K 2019/3004; C09K 2019/3009; C09K 2019/301; C09K 2019/3016; C09K 2019/3025; C09K 2019/3422; C09K 2019/3425; C09K 2019/0448; C09K 2019/122; C09K 2019/123; C09K 2019/3027; C09K 2019/3408; C09K 2019/0444; G02F 1/1333; G02F 1/133738; G02F 1/133788; G02F 1/1341; C07C 13/28; C07C 25/18; C07C 25/24; C07C 43/184; C07C 43/21; C07C 43/225; C07C 69/753; C07C 2601/14; C07C 2602/10; C07D 213/30; C07D 239/26;
(Continued)

(56) References Cited

U.S. PATENT DOCUMENTS 6,613,245 B1 9/2003 Benecke
11,312,907 B2 * 4/2022 Lietzau .............. C09K 19/2014
(Continued)

FOREIGN PATENT DOCUMENTS

CN 105899644 A 8/2016
EP 2843027 A 3/2015
(Continued)

OTHER PUBLICATIONS

International Search Report PCT/EP2019/060042 dated Jul. 19, 2019 (pp. 1-3).
(Continued)

*Primary Examiner* — Geraldina Visconti
(74) *Attorney, Agent, or Firm* — MILLEN, WHITE, ZELANO & BRANIGAN, P.C.; Csaba Henter

(57) ABSTRACT

The invention relates to a compound of formula I,

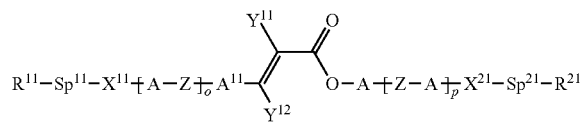

wherein $R^{11}$, $R^{21}$, $A^{11}$, A, Z, $X^{11}$, $X^{21}$, $Y^{11}$, $Y^{12}$, $Sp^{11}$, $Sp^{21}$, o and p have one of the meanings as given in claim 1. The invention further relates to method of production of a compound of formula I, to the use of said compounds in LC media and to LC media comprising one or more compounds of formula I. Further, the invention relates to a method of production of such LC media, to the use of such media in LC devices, and to LC device comprising a LC medium according to the present invention. The present invention further relates to a process for the fabrication such liquid crystal display and to the use of the liquid crystal mixtures according to the invention for the fabrication of such liquid crystal display.

25 Claims, No Drawings

(51) Int. Cl.
| | |
|---|---|
| *C07C 25/18* | (2006.01) |
| *C07C 25/24* | (2006.01) |
| *C07C 43/184* | (2006.01) |
| *C07C 43/21* | (2006.01) |
| *C07C 43/225* | (2006.01) |
| *C07C 69/753* | (2006.01) |
| *C07D 213/30* | (2006.01) |
| *C07D 239/26* | (2006.01) |
| *C07D 307/91* | (2006.01) |
| *C07D 309/06* | (2006.01) |
| *C07D 311/80* | (2006.01) |
| *C07D 319/06* | (2006.01) |
| *C09K 19/30* | (2006.01) |
| *C09K 19/34* | (2006.01) |
| *C09K 19/56* | (2006.01) |
| *G02F 1/1337* | (2006.01) |
| *G02F 1/1341* | (2006.01) |
| *C09K 19/04* | (2006.01) |

(52) U.S. Cl.
CPC ............ *C07C 43/184* (2013.01); *C07C 43/21* (2013.01); *C07C 43/225* (2013.01); *C07C 69/753* (2013.01); *C07D 213/30* (2013.01); *C07D 239/26* (2013.01); *C07D 307/91* (2013.01); *C07D 309/06* (2013.01); *C07D 311/80* (2013.01); *C07D 319/06* (2013.01); *C09K 19/3003* (2013.01); *C09K 19/3066* (2013.01); *C09K 19/3098* (2013.01); *C09K 19/3402* (2013.01); *C09K 19/3491* (2013.01); *G02F 1/133738* (2021.01); *G02F 1/133788* (2013.01); *G02F 1/1341* (2013.01); *C07C 2601/14* (2017.05); *C07C 2602/10* (2017.05); *C09K 2019/0466* (2013.01); *C09K 2019/3004* (2013.01); *C09K 2019/3009* (2013.01); *C09K 2019/301* (2013.01); *C09K 2019/3016* (2013.01); *C09K 2019/3025* (2013.01); *C09K 2019/3422* (2013.01); *C09K 2019/3425* (2013.01)

(58) Field of Classification Search
CPC .. C07D 307/91; C07D 309/06; C07D 311/80; C07D 319/06
See application file for complete search history.

(56) References Cited

U.S. PATENT DOCUMENTS

| | | | |
|---|---|---|---|
| 11,352,560 B2 * | 6/2022 | Lietzau | C09K 19/0403 |
| 11,440,849 B2 | 9/2022 | Shinya et al. | |
| 2015/0299570 A1 | 10/2015 | Kurisawa et al. | |
| 2016/0319192 A1 | 11/2016 | Hirata et al. | |
| 2020/0255740 A1 | 8/2020 | Adlem et al. | |
| 2021/0284912 A1 * | 9/2021 | Lietzau | C09K 19/56 |
| 2021/0292652 A1 * | 9/2021 | Lietzau | C09K 19/3066 |
| 2022/0380672 A1 * | 12/2022 | Siemianowski | C09K 19/2014 |
| 2022/0380673 A1 * | 12/2022 | Siemianowski | C09K 19/12 |

FOREIGN PATENT DOCUMENTS

| | | |
|---|---|---|
| GB | 2306470 A1 | 5/1997 |
| TW | 201726581 A | 8/2017 |
| WO | 0015189 A1 | 2/2000 |
| WO | 17102068 A1 | 6/2017 |

OTHER PUBLICATIONS

B.M.I. van der Zande et al, "Patterned retarders prepared by photoisomerization and photopolymerization of liquid crystalline films" Liqu.Cryst., 2006, vol. 33, No. 6, pp. 723-737.
M.H.Lee et al, "Polyimide-free homogeneous photoalignment induced by polymerisable liquid crystal containing cinnamate moiety" Liqu. Cryst., 2018, vol. 45, No. 9,1342-1352.
English translation of search report in corresponding ROC (Taiwan) Patent Application No. 108113936 dated Dec. 27, 2022 (1 page).

* cited by examiner

LIQUID CRYSTAL MIXTURE AND LIQUID CRYSTAL DISPLAY

The invention relates to a compound of formula I,

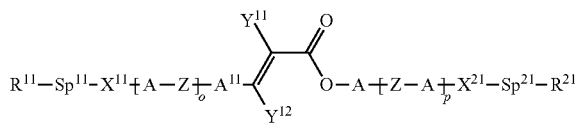

wherein $R^{11}$, $R^{21}$, $A^{11}$, A, Z, $X^{11}$, $X^{21}$, $Y^{11}$, $Y^{12}$, $Sp^{11}$, $Sp^{21}$, o and p have one of the meanings as given in claim 1. The invention further relates to method of production of a compound of formula I, to the use of said compounds in LC media and to LC media comprising one or more compounds of formula I. Further, the invention relates to a method of production of such LC media, to the use of such media in LC devices, and to LC device comprising a LC medium according to the present invention. The present invention further relates to a process for the fabrication such liquid crystal display and to the use of the liquid crystal mixtures according to the invention for the fabrication of such liquid crystal display.

Background and Prior Art

Liquid-crystalline media have been used for decades in electro-optical displays for information display. The liquid crystal displays used at present are usually those of the TN ("twisted nematic") type. However, these have the disadvantage of a strong viewing-angle dependence of the contrast.

In addition, so-called VA ("vertically aligned") displays are known which have a broader viewing angle. The LC cell of a VA display contains a layer of an LC medium between two transparent electrodes, where the LC medium usually has a negative value of the dielectric (DC) anisotropy. In the switched-off state, the molecules of the LC layer are aligned perpendicular to the electrode surfaces (homeotropically) or have a tilted homeotropic alignment. On application of an electrical voltage to the two electrodes, a realignment of the LC molecules parallel to the electrode surfaces takes place. Furthermore, so-called IPS ("in plane switching") displays and later, FFS ("fringe-field switching") displays have been reported (see, inter alia, S. H. Jung et al., Jpn. J. Appl. Phys., Volume 43, No. 3, 2004, 1028), which contain two electrodes on the same substrate, one of which is structured in a comb-shaped manner and the other is unstructured. A strong, so-called "fringe field" is thereby generated, i.e. a strong electric field close to the edge of the electrodes, and, throughout the cell, an electric field which has both a strong vertical component and a strong horizontal component. FFS displays have a low viewing-angle dependence of the contrast. FFS displays usually contain an LC medium with positive dielectric anisotropy, and an alignment layer, usually of polyimide, which provides planar alignment to the molecules of the LC medium.

Furthermore, FFS displays have been disclosed (see S. H. Lee et al., Appl. Phys. Lett. 73(20), 1998, 2882-2883 and S. H. Lee et al., Liquid Crystals 39(9), 2012, 1141-1148), which have similar electrode design and layer thickness as FFS displays, but comprise a layer of an LC medium with negative dielectric anisotropy instead of an LC medium with positive dielectric anisotropy. The LC medium with negative dielectric anisotropy shows a more favorable director orientation that has less tilt and more twist orientation compared to the LC medium with positive dielectric anisotropy, as a result of which these displays have a higher transmission.

A further development are the so-called PS (polymer sustained) or PSA (polymer sustained alignment) displays, for which the term "polymer stabilised" is also occasionally used. The PSA displays are distinguished by the shortening of the response times without significant adverse effects on other parameters, such as, in particular, the favourable viewing-angle dependence of the contrast.

In these displays, a small amount (for example 0.3% by weight, typically <1% by weight) of one or more polymerizable compound(s) is added to the LC medium and, after introduction into the LC cell, is polymerised or crosslinked in situ, usually by UV photopolymerization, between the electrodes with or without an applied electrical voltage. The addition of polymerizable mesogenic or liquid-crystalline compounds, also known as reactive mesogens or "RMs", to the LC mixture has proven particularly suitable. PSA technology has hitherto been employed principally for LC media having negative dielectric anisotropy.

Unless indicated otherwise, the term "PSA" is used below as representative of PS displays and PSA displays.

In the meantime, the PSA principle is being used in diverse classical LC displays. Thus, for example, PSA-VA, PSA-OCB, PSA-IPS, PSA-FFS and PSA-TN displays are known. The polymerisation of the polymerizable compound(s) preferably takes place with an applied electrical voltage in the case of PSA-VA and PSA-OCB displays, and with or without an applied electrical voltage in the case of PSA-IPS displays. As can be demonstrated in test cells, the PS(A) method results in a 'pretilt' in the cell. In the case of PSA-OCB displays, for example, it is possible for the bend structure to be stabilised so that an offset voltage is unnecessary or can be reduced. In the case of PSA-VA displays, the pretilt has a positive effect on the response times. A standard MVA or PVA pixel and electrode layout can be used for PSA-VA displays. In addition, however, it is also possible, for example, to manage with only one structured electrode side and no protrusions, which significantly simplifies production and at the same time results in very good contrast at the same time as very good light transmission.

PSA-VA displays are described, for example, in JP 10-036847 A, EP 1 170 626 A2, U.S. Pat. Nos. 6,861,107, 7,169,449, US 2004/0191428 A1, US 2006/0066793 A1 and US 2006/0103804 A1. PSA-OCB displays are described, for example, in T.-J- Chen et al., Jpn. J. Appl. Phys. 45, 2006, 2702-2704 and S. H. Kim, L.-C- Chien, Jpn. J. Appl. Phys. 43, 2004, 7643-7647. PSA-IPS displays are described, for example, in U.S. Pat. No. 6,177,972 and Appl. Phys. Lett. 1999, 75(21), 3264. PSA-TN displays are described, for example, in Optics Express 2004, 12(7), 1221. PSA-VA-IPS displays are disclosed, for example, in WO 2010/089092 A1.

Like the conventional LC displays described above, PSA displays can be operated as active-matrix or passive-matrix displays. In the case of active-matrix displays, individual pixels are usually addressed by integrated, non-linear active elements, such as, for example, transistors (for example thin-film transistors or "TFTs"), while in the case of passive-matrix displays, individual pixels are usually addressed by the multiplex method, both methods being known from the prior art.

In the prior art, polymerizable compounds of the following formula, for example, are used for PSA-VA:

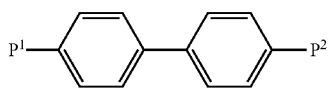

in which P denotes a polymerizable group, usually an acrylate or methacrylate group, as described, for example, in U.S. Pat. No. 7,169,449.

Below the polymer layer which induces the above mentioned pretilt, an orientation layer—usually a polyimide—provides the initial alignment of the liquid crystal regardless of the polymer stabilisation step of the production process.

The effort for the production of a polyimide layer, treatment of the layer and improvement with bumps or polymer layers is relatively great. A simplifying technology which on the one hand reduces production costs and on the other hand helps to optimise the image quality (viewing-angle dependence, contrast, response times) would therefore be desirable. Rubbed polyimide has been used for a long time to align liquid crystals. The rubbing process causes a number of problems: mura, contamination, problems with static discharge, debris, etc.

Photoalignment is a technology for achieving liquid crystal (LC) alignment that avoids rubbing by replacing it with a light-induced orientational ordering of the alignment surface. This can be achieved through the mechanisms of photodecomposition, photodimerization, and photoisomerization (N. A. Clark et al. Langmuir 2010, 26(22), 17482-17488, and literature cited therein) by means of polarised light. However, still a suitably derivatised polyimide layer is required that comprises the photoreactive group. A further improvement would be to avoid the use of polyimide at all. For VA displays this was achieved by adding a self-alignment agent to the LC that induces homeotropic alignment in situ by a self-assembling mechanism as disclosed in WO 2012/104008 and WO 2012/038026.

N. A. Clark et al. Langmuir 2010, 26(22), 17482-17488 have shown that it is possible to self-assemble a compound of the following structure

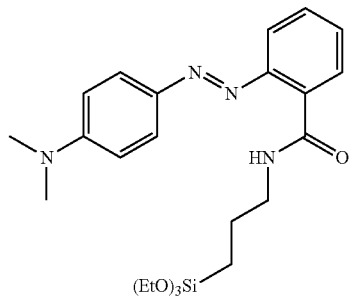

onto a substrate to give a monolayer that is able to be photoaligned to induce homogeneous alignment of a liquid crystal. However, a separate step of self-assembly before manufacture of the LC cell is required and the nature of the azo-group causes reversibility of the alignment when exposed to light.

Another functional group known to enable photoalignment is the phenylethenylcarbonyloxy group (cinnamate). Photocrosslinkable cinnamates are known from the prior art, e.g. of the following structure

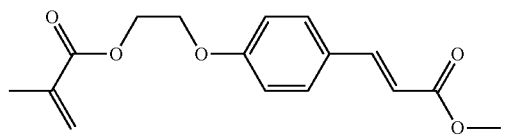 [SMILES: C=C(C)C(=O)OCCOc1ccc(/C=C/C(=O)OC)cc1]

as disclosed in EP0763552. From such compounds, polymers can be obtained, for example the following

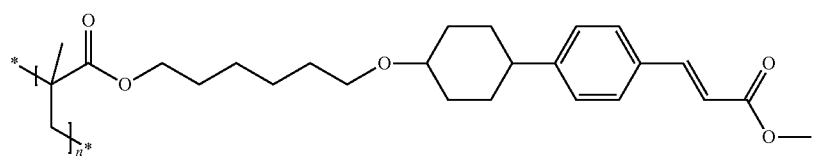

This material was used in a photoalignment process, as disclosed in WO 99/49360, to give an orientation layer for liquid crystals. A disadvantage of orientation layers obtained by this process is that they give lower voltage holding ratios (VHR) than polyimides.

In WO 00/05189 polymerizable direactive mesogenic cinnamates are disclosed for the use in polymerizable LC mixtures for e.g. optical retarders.

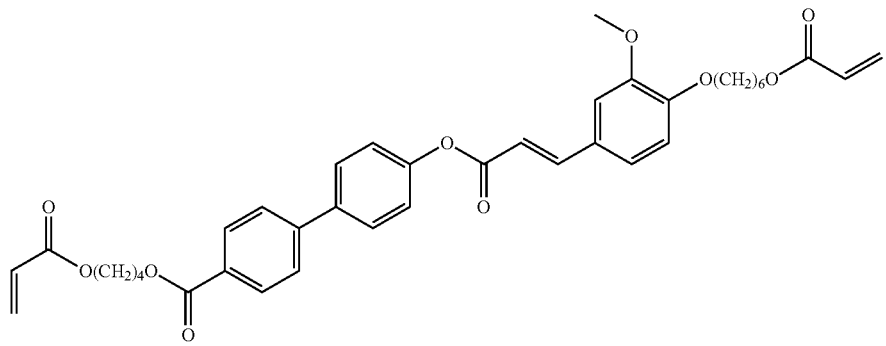

A structurally related compound of the following formula

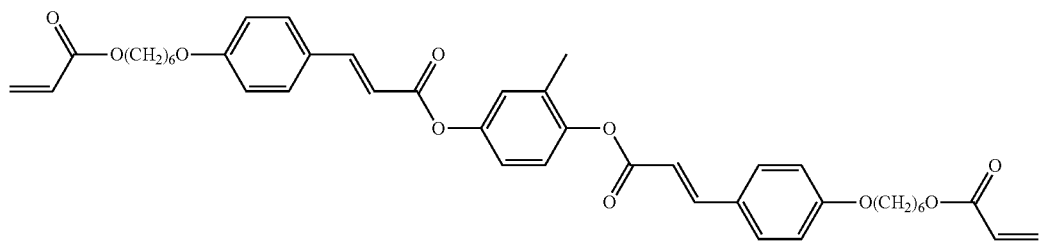

comprising two cinnamic acid moieties is disclosed in GB 2 306 470 A for the use as component in liquid crystalline polymer films. This type of compound has not been used or proposed for the use as photoalignment agent.

A very similar compound is published in B. M. I. van der Zande et al., Liquid Crystals, Vol. 33, No. 6, June 2006, 723-737, in the field of liquid crystalline polymers for patterned retarders, and has the following structure:

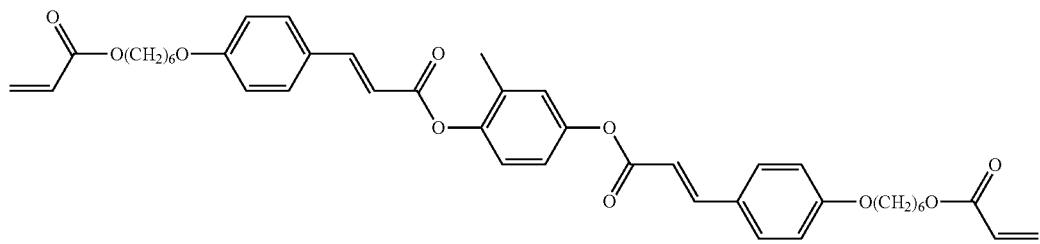

WO 201 ID 02068 A1 discloses the same structure for the purpose of a polyimide-free homogeneous photoalignment method.

Further, M. H. Lee et al. published in Liquid Crystals (https://doi.org/10.1080/02678292.2018.1441459) a polyimide-free homogeneous photoalignment method induced by polymerizable liquid crystal containing cinnamate moiety of the following formula:

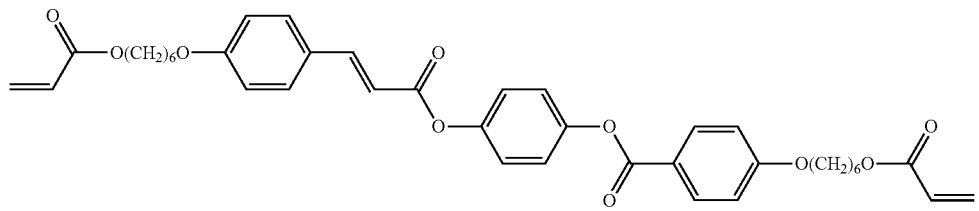

Thus, there is a great demand for new photoreactive mesogens that enable photoalignment of a liquid crystal mixture in situ, i.e. after assembly of the display, by means of linearly polarized light.

In addition to this requirement, the corresponding photoreactive mesogen should provide, preferably at the same time, a liquid crystal display having favourable high dark state and a favourable high voltage holding ratio. Furthermore, the amount of photoreactive mesogens in the nematic LC medium should be a low as possible and the process for the production should be obtainable from a process that is compatible with common mass production processes, e.g. in terms of favourable short processing times.

Other aims of the present invention are immediately evident to the person skilled in the art from the following detailed description.

Surprisingly, the inventors have found out that one or more of the above-mentioned aims can be achieved by providing a compound according to claim 1.

Terms and Definitions

A photoreactive group according to the present invention is a functional group of a molecule that causes a change of the geometry of the molecule either by bond rotation, skeletal rearrangement or atom- or group-transfer, or by dimerization, upon irradiation with light of a suitable wavelength that can be absorbed by the molecule.

The term "mesogenic group" as used herein is known to the person skilled in the art and described in the literature, and means a group which, due to the anisotropy of its attracting and repelling interactions, essentially contributes to causing a liquid-crystal (LC) phase in low-molecular-weight or polymeric substances. Compounds containing mesogenic groups (mesogenic compounds) do not necessarily have to have an LC phase themselves. It is also possible for mesogenic compounds to exhibit LC phase behaviour only after mixing with other compounds and/or after polymerisation. Typical mesogenic groups are, for example, rigid rod- or disc-shaped units. An overview of the terms and definitions used in connection with mesogenic or LC compounds is given in *Pure Appl. Chem.* 2001, 73(5), 888 and C. Tschierske, G. Pelzl, S. Diele, *Angew. Chem.* 2004, 116, 6340-6368.

A photoreactive mesogen according to the present invention is a mesogenic compound comprising one or more photoreactive groups.

Examples of photoreactive groups are —C=C— double bonds and azo groups (—N=N—).

Examples of molecular structures and sub-structures comprising such photoreactive groups are stilbene, (1,2-difluoro-2-phenyl-vinyl)-benzene, cinnamate, 4-phenylbut-3-en-2-one, chalcone, coumarin, chromone, pentalenone and azobenzene.

According to the present application, the term "linearly polarised light" means light, which is at least partially linearly polarized. Preferably, the aligning light is linearly polarized with a degree of polarization of more than 5:1. Wavelengths, intensity and energy of the linearly polarised light are chosen depending on the photosensitivity of the photoalignable material. Typically, the wavelengths are in the UV-A, UV-B and/or UV-C range or in the visible range. Preferably, the linearly polarised light comprises light of wavelengths less than 450 nm, more preferably less than 420 nm at the same time the linearly polarised light preferably comprises light of wavelengths longer than 280 nm, preferably more than nm, more preferably over 350 nm.

The term "organic group" denotes a carbon or hydrocarbon group.

The term "carbon group" denotes a mono- or polyvalent organic group containing at least one carbon atom, where this either contains no further atoms (such as, for example, —C≡C—) or optionally contains one or more further atoms, such as, for example, N, O, S, P, Si, Se, As, Te or Ge (for example carbonyl, etc.). The term "hydrocarbon group" denotes a carbon group which additionally contains one or more H atoms and optionally one or more heteroatoms, such as, for example, N, O, S, P, Si, Se, As, Te or Ge.

"Halogen" denotes F, Cl, Br or I.

A carbon or hydrocarbon group can be a saturated or unsaturated group. Unsaturated groups are, for example, aryl, alkenyl or alkynyl groups. A carbon or hydrocarbon radical having 3 or more atoms can be straight-chain, branched and/or cyclic and may also contain spiro links or condensed rings.

The terms "alkyl", "aryl", "heteroaryl", etc., also encompass polyvalent groups, for example alkylene, arylene, heteroarylene, etc.

The term "aryl" denotes an aromatic carbon group or a group derived therefrom. The term "heteroaryl" denotes "aryl" as defined above, containing one or more heteroatoms.

Preferred carbon and hydrocarbon groups are optionally substituted alkyl, alkenyl, alkynyl, alkoxy, alkylcarbonyl, alkoxycarbonyl, alkylcarbonyloxy and alkoxycarbonyloxy having 1 to 40, preferably 1 to 25, particularly preferably 1 to 18, C atoms, optionally substituted aryl or aryloxy having 6 to 40, preferably 6 to 25, C atoms, or optionally substituted alkylaryl, arylalkyl, alkylaryloxy, arylalkyloxy, arylcarbonyl, aryloxycarbonyl, arylcarbonyloxy and aryloxycarbonyloxy having 6 to 40, preferably 6 to 25, C atoms.

Further preferred carbon and hydrocarbon groups are $C_1$-$C_{40}$ alkyl, $C_2$-$C_{40}$ alkenyl, $C_2$-$C_{40}$ alkynyl, $C_3$-$C_{40}$ allyl, $C_4$-$C_{40}$ alkyldienyl, $C_4$-$C_{40}$ polyenyl, $C_6$-$C_{40}$ aryl, $C_6$-$C_{40}$ alkylaryl, $C_6$-$C_{40}$ arylalkyl, $C_6$-$C_{40}$ alkylaryloxy, $C_6$-$C_{40}$ arylalkyloxy, $C_2$-$C_{40}$ heteroaryl, $C_4$-$C_{40}$ cycloalkyl, $C_4$-$C_{40}$ cycloalkenyl, etc. Particular preference is given to $C_1$-$C_{22}$ alkyl, $C_2$-$C_{22}$ alkenyl, $C_2$-$C_{22}$ alkynyl, $C_3$-$C_{22}$ allyl, $C_4$-$C_{22}$ alkyldienyl, $C_6$-$C_{12}$ aryl, $C_6$-$C_{20}$ arylalkyl and $C_2$-$C_{20}$ heteroaryl.

Further preferred carbon and hydrocarbon groups are straight-chain, branched or cyclic alkyl radicals having 1 to 40, preferably 1 to 25, C atoms, which are unsubstituted or mono- or polysubstituted by F, Cl, Br, I or CN and in which one more non-adjacent $CH_2$ groups may each be replaced, independently of one another, by —C($R^z$)=C($R^z$)—, —C≡C—, —N($R^z$)—, —O—, —S—, —CO—, —CO—O—, —O—CO—, —O—CO—O— in such a way that O and/or S atoms are not linked directly to one another.

$R^z$ preferably denotes H, halogen, a straight-chain, branched or cyclic alkyl chain having 1 to 25 C atoms, in which, in addition, one or more non-adjacent C atoms may be replaced by —O—, —S—, —CO—, —CO—O—, —O—CO— or —O—CO—O— and in which one or more H atoms may be replaced by fluorine, an optionally substituted aryl or aryloxy group having 6 to 40 C atoms, or an optionally substituted heteroaryl or heteroaryloxy group having 2 to 40 C atoms.

Preferred alkyl groups are, for example, methyl, ethyl, n-propyl, isopropyl, n-butyl, isobutyl, s-butyl, t-butyl, 2-methylbutyl, n-pentyl, s-pentyl, cyclopentyl, n-hexyl, cyclohexyl, 2-ethylhexyl, n-heptyl, cycloheptyl, n-octyl, cyclooctyl, n-nonyl, n-decyl, n-undecyl, n-dodecyl, trifluoromethyl, perfluoro-n-butyl, 2,2,2-trifluoroethyl, perfluorooctyl and perfluorohexyl.

Preferred alkenyl groups are, for example, ethenyl, propenyl, butenyl, pentenyl, cyclopentenyl, hexenyl, cyclohexenyl, heptenyl, cycloheptenyl, octenyl and cyclooctenyl.

Preferred alkynyl groups are, for example, ethynyl, propynyl, butynyl, pentynyl, hexynyl and octynyl.

Preferred alkoxy groups are, for example, methoxy, ethoxy, 2-methoxy-ethoxy, n-propoxy, i-propoxy, n-butoxy, i-butoxy, s-butoxy, t-butoxy, 2-methylbutoxy, n-pentoxy, n-hexoxy, n-heptoxy, n-octoxy, n-nonoxy, n-decoxy, n-undecoxy and n-dodecoxy.

Preferred amino groups are, for example, dimethylamino, methylamino, methylphenylamino and phenylamino.

Aryl and heteroaryl groups can be monocyclic or polycyclic, i.e. they can contain one ring (such as, for example, phenyl) or two or more rings, which may also be fused (such as, for example, naphthyl) or covalently bonded (such as, for example, biphenyl), or contain a combination of fused and linked rings. Heteroaryl groups contain one or more heteroatoms, preferably selected from O, N, S and Se. A ring system of this type may also contain individual non-conjugated units, as is the case, for example, in the fluorene basic structure.

Particular preference is given to mono-, bi- or tricyclic aryl groups having 6 to 25 C atoms and mono-, bi- or tricyclic heteroaryl groups having 2 to 25 C atoms, which optionally contain fused rings and are optionally substituted.

Preference is furthermore given to 5-, 6- or 7-membered aryl and heteroaryl groups, in which, in addition, one or more CH groups may be replaced by N, S or O in such a way that O atoms and/or S atoms are not linked directly to one another.

Preferred aryl groups are derived, for example, from the parent structures benzene, biphenyl, terphenyl, [1,1':3',1"]terphenyl, naphthalene, anthracene, binaphthyl, phenanthrene, pyrene, dihydropyrene, chrysene, perylene, tetracene, pentacene, benzopyrene, fluorene, indene, indenofluorene, spirobifluorene, etc.

Preferred heteroaryl groups are, for example, 5-membered rings, such as pyrrole, pyrazole, imidazole, 1,2,3-triazole, 1,2,4-triazole, tetrazole, furan, thiophene, selenophene, oxazole, isoxazole, 1,2-thiazole, 1,3-thiazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 6-membered rings, such as pyridine, pyridazine, pyrimidine, pyrazine, 1,3,5-triazine, 1,2,4-triazine, 1,2,3-triazine, 1,2,4,5-tetrazine, 1,2,3,4-tetrazine, 1,2,3,5-tetrazine, or condensed groups, such as indole, isoindole, indolizine, indazole, benzimidazole, benzotriazole, purine, naphthimidazole, phenanthrimidazole, pyridimidazole, pyrazinimidazole, quinoxalinimidazole, benzoxazole, naphthoxazole, anthroxazole, phenanthroxazole, isoxazole, benzothiazole, benzofuran, isobenzofuran, dibenzofuran, quinoline, isoquinoline, pteridine, benzo-5,6-quinoline, benzo-6,7-quinoline, benzo-7,8-quinoline, benzoisoquinoline, acridine, phenothiazine, phenoxazine, benzopyridazine, benzopyrimidine, quinoxaline, phenazine, naphthyridine, azacarbazole, benzocarboline, phenanthridine, phenanthroline, thieno[2,3b]thiophene, thieno[3,2b]thiophene, dithienothiophene, dihydrothieno [3,4-b]-1,4-dioxin, isobenzothiophene, dibenzothiophene, benzothiadiazothiophene, or combinations of these groups. The heteroaryl groups may also be substituted by alkyl, alkoxy, thioalkyl, fluorine, fluoroalkyl or further aryl or heteroaryl groups.

The (non-aromatic) alicyclic and heterocyclic groups encompass both saturated rings, i.e. those containing exclusively single bonds, and also partially unsaturated rings, i.e. those which may also contain multiple bonds. Heterocyclic rings contain one or more heteroatoms, preferably selected from Si, O, N, S and Se.

The (non-aromatic) alicyclic and heterocyclic groups can be monocyclic, i.e. contain only one ring (such as, for example, cyclohexane), or polycyclic, i.e. contain a plurality of rings (such as, for example, decahydronaphthalene or bicyclooctane). Particular preference is given to saturated groups. Preference is furthermore given to mono-, bi- or tricyclic groups having 3 to 25 C atoms, which optionally contain fused rings and are optionally substituted. Preference is furthermore given to 5-, 6-, 7- or 8-membered carbocyclic groups, in which, in addition, one or more C atoms may be replaced by Si and/or one or more CH groups may be replaced by N and/or one or more non-adjacent $CH_2$ groups may be replaced by —O— and/or —S—.

Preferred alicyclic and heterocyclic groups are, for example, 5-membered groups, such as cyclopentane, tetrahydrofuran, tetrahydrothiofuran, pyrrolidine, 6-membered groups, such as cyclohexane, silinane, cyclohexene, tetrahydropyran, tetrahydrothiopyran, 1,3-dioxane, 1,3-dithiane, piperidine, 7-membered groups, such as cycloheptane, and fused groups, such as tetrahydronaphthalene, decahydronaphthalene, indane, bicyclo[1.1.1]pentane-1,3-diyl, bicyclo[2.2.2]octane-1,4-diyl, spiro[3.3]heptane-2,6-diyl, octahydro-4,7-methanoindane-2,5-diyl.

The aryl, heteroaryl, carbon and hydrocarbon radicals optionally have one or more substituents, which are preferably selected from the group comprising silyl, sulfo, sulfonyl, formyl, amine, imine, nitrile, mercapto, nitro, halogen, $C_{1-12}$ alkyl, $C_{6-12}$ aryl, $C_{1-12}$ alkoxy, hydroxyl, or combinations of these groups.

Preferred substituents are, for example, solubility-promoting groups, such as alkyl or alkoxy, and electron-withdrawing groups, such as fluorine, nitro or nitrile.

Preferred substituents, unless stated otherwise, also referred to as "L" above and below, are F, Cl, Br, I, —CN, —NO$_2$, —NCO, —NCS, —OCN, —SCN, —C(=O)N(R$^z$)$_2$, —C(=O)Y$^1$, —C(=O)R$^z$, —N(R$^z$)$_2$, in which R$^z$ has the meaning indicated above, and Y$^1$ denotes halogen, optionally substituted silyl or aryl having 6 to 40, preferably 6 to 20, C atoms, and straight-chain or branched alkyl, alkoxy, alkylcarbonyl, alkoxycarbonyl, alkylcarbonyloxy or alkoxycarbonyloxy having 1 to 25 C atoms, preferably 2 to 12, in which one or more H atoms may optionally be replaced by F or Cl.

"Substituted silyl or aryl" preferably means substituted by halogen, —CN, R$^{y1}$, —OR$^{y1}$, —CO—R$^{y1}$, —CO—O—R$^{y1}$, —O—CO—R$^{y1}$ or —O—CO—O—R$^{y1}$, in which R$^{y1}$ has the meaning indicated above.

Particularly preferred substituents L are, for example, F, Cl, CN, CH$_3$, C$_2$H$_5$, —CH(CH$_3$)$_2$, OCH$_3$, OC$_2$H$_5$, CF$_5$, OCF$_3$, OCHF$_2$, OC$_2$F$_5$, furthermore phenyl.

Above and below "halogen" denotes F, Cl, Br or I.

Above and below, the terms "alkyl", "aryl", "heteroaryl", etc., also encompass polyvalent groups, for example alkylene, arylene, heteroarylene, etc.

The term "director" is known in prior art and means the preferred orientation direction of the long molecular axes (in case of calamitic compounds) or short molecular axes (in case of discotic compounds) of the liquid-crystalline molecules. In case of uniaxial ordering of such anisotropic molecules, the director is the axis of anisotropy.

The term "alignment" or "orientation" relates to alignment (orientation ordering) of anisotropic units of material such as small molecules or fragments of big molecules in a common direction named "alignment direction". In an aligned layer of liquid-crystalline material, the liquid-crystalline director coincides with the alignment direction so that the alignment direction corresponds to the direction of the anisotropy axis of the material.

The term "planar orientation/alignment", for example in a layer of an liquid-crystalline material, means that the long molecular axes (in case of calamitic compounds) or the short molecular axes (in case of discotic compounds) of a proportion of the liquid-crystalline molecules are oriented substantially parallel (about 180°) to the plane of the layer.

The term "homeotropic orientation/alignment", for example in a layer of a liquid-crystalline material, means that the long molecular axes (in case of calamitic compounds) or the short molecular axes (in case of discotic compounds) of a proportion of the liquid-crystalline molecules are oriented at an angle 9 ("tilt angle") between about 80° to 90° relative to the plane of the layer.

The terms "uniform orientation" or "uniform alignment" of an liquid-crystalline material, for example in a layer of the material, mean that the long molecular axes (in case of calamitic compounds) or the short molecular axes (in case of discotic compounds) of the liquid-crystalline molecules are oriented substantially in the same direction. In other words, the lines of liquid-crystalline director are parallel.

The wavelength of light generally referred to in this application is 550 nm, unless explicitly specified otherwise.

The birefringence Δn herein is defined by the following equation $$\Delta n = n_e - n_o$$

wherein $n_e$ is the extraordinary refractive index and $n_o$ is the ordinary refractive index and the effective average refractive index $n_{av.}$ is given by the following equation $$n_{av.} = [(2n_o^2 + n_e^2)/3]^{1/2}$$

The extraordinary refractive index $n_e$ and the ordinary refractive index $n_o$ can be measured using an Abbe refractometer.

In the present application the term "dielectrically positive" is used for compounds or components with Δε>3.0, "dielectrically neutral" with −1.5≤Δε≤3.0 and "dielectrically negative" with Δε<−1.5. Δε is determined at a frequency of 1 kHz and at 20° C. The dielectric anisotropy of the respective compound is determined from the results of a solution of 10% of the respective individual compound in a nematic host mixture. In case the solubility of the respective compound in the host medium is less than 10% its concentration is reduced by a factor of 2 until the resultant medium is stable enough at least to allow the determination of its properties. Preferably, the concentration is kept at least at 5%, however, to keep the significance of the results as high as possible. The capacitance of the test mixtures are determined both in a cell with homeotropic and with homogeneous alignment. The cell gap of both types of cells is approximately 20 μm. The voltage applied is a rectangular wave with a frequency of 1 kHz and a root mean square value typically of 0.5 V to 1.0 V; however, it is always selected to be below the capacitive threshold of the respective test mixture.

Δε is defined as (ε∥−ε$_⊥$), whereas ε$_{av.}$ is (ε∥+2 ε$_⊥$)/3. The dielectric permittivity of the compounds is determined from the change of the respective values of a host medium upon addition of the compounds of interest. The values are extrapolated to a concentration of the compounds of interest of 100%. A typical host medium is ZLI-4792 or ZLI-2857 both commercially available from Merck, Darmstadt.

For the present invention,

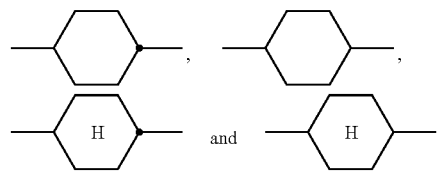

denote trans-1,4-cyclohexylene,

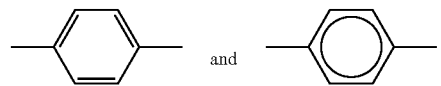

denote 1,4-phenylene.

For the present invention the groups —CO—O—, —COO— —C(=O)O— or —CO$_2$— denote an ester group of formula

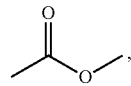

and the groups —O—CO— —OCO—, —OC(=O)—, —O₂C— or —OOC— denote an ester group of formula

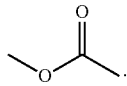

Furthermore, the definitions as given in C. Tschierske, G. Pelzl and S. Diele, Angew. Chem. 2004, 116, 6340-6368 shall apply to non-defined terms related to liquid crystal materials in the instant application.

DETAILED DESCRIPTION

In detail, the present invention relates to compounds or photoreactive mesogens of formula I,

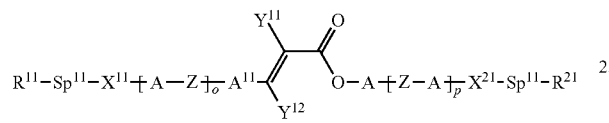

wherein
$A^{11}$ denotes a radical selected from the following groups:
a) a group consisting of 1,4-phenylene and 1,3-phenylene, wherein, in addition, one or two CH groups may be replaced by N and wherein, in addition, one or more H atoms may be replaced by L,
b) a group selected from the group consisting of

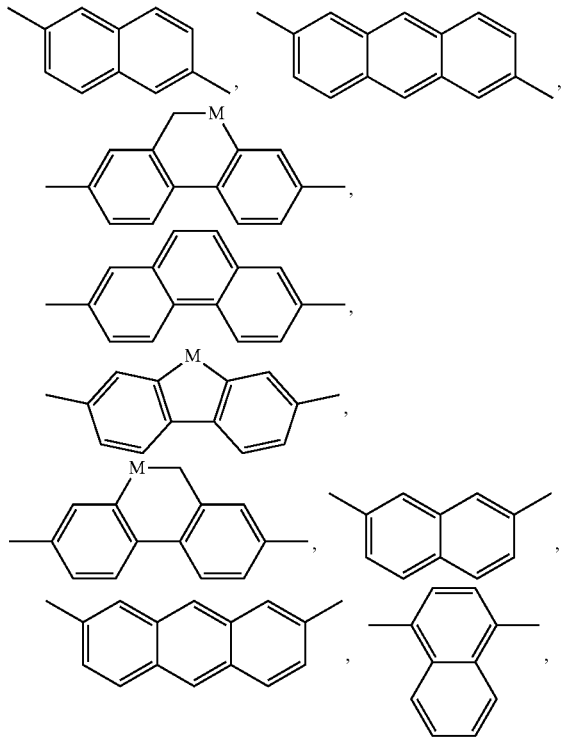

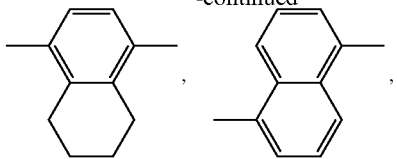

where, in addition, one or more H atoms in these radicals may be replaced by L, and/or one or more double bonds may be replaced by single bonds, and/or one or more CH groups may be replaced by N, A have each, independently of one another, in each occurrence one of the meanings for $A^{11}$ or
a) group consisting of trans-1,4-cyclohexylene, 1,4-cyclohexenylene, wherein, in addition, one or more non-adjacent CH₂ groups may be replaced by —O— and/or —S— and wherein, in addition, one or more H atoms may be replaced by F, or
b) a group consisting of tetrahydropyran-2,5-diyl, 1,3-dioxane-2,5-diyl, tetrahydrofuran-2,5-diyl, cyclobutane-1,3-diyl, piperidine-1,4-diyl, thiophene-2,5-diyl and selenophene-2,5-diyl,
each of which may also be mono- or polysubstituted by L, L on each occurrence, identically or differently, denotes —OH, —F, —Cl, —Br, —I, —CN, —NO₂, SF₅, —NCO, —NCS, —OCN, —SCN, —C(=O)N($R^z$)₂, —C(=O)$R^z$, —N($R^z$)₂, optionally substituted silyl, optionally substituted aryl having 6 to 20 C atoms, or straight-chain or branched or cyclic alkyl, alkoxy, alkylcarbonyl, alkoxycarbonyl, alkylcarbonyloxy or alkoxycarbonyloxy having 1 to 25 C atoms, preferably 1 to 12 C atoms, more preferably 1 to 6 C atoms, in which, in addition, one or more H atoms may be replaced by F or Cl, or $X^{21}$-$Sp^{21}$-$R^{21}$, M denotes —O—, —S—, —CH₂—, —CHR$^z$— or —CR$^y$R$^z$—, and R$^y$ and R$^z$ each, independently of one another, denote H, CN, F or alkyl having 1-12 C atoms, wherein one or more H atoms may be replaced by F,
preferably H, methyl, ethyl, propyl, butyl, more preferably H or methyl,
in particular H, $Y^{11}$ and $Y^{12}$ each, independently of one another, denote H, F, phenyl or optionally fluorinated alkyl having 1-12 C atoms, preferably H, methyl, ethyl, propyl, butyl, more preferably H or methyl,
in particular H, Z denotes, independently of each other, in each occurrence, a single bond, —COO—, —OCO—, —O—CO—O—, —OCH₂—, —CH₂O—, —OCF₂—, —CF₂O—, —(CH₂)$_n$—, —CF₂CF₂—, —CH=CH—, —CF=CF—, —CH=CH—COO—, —OCO—CH=CH—, —CO—S—, —S—CO—, —CS—S—, —S—CS—, —S—CSS— or —C≡C—,
preferably a single bond, —COO—, —OCO—, —OCF₂—, —CF₂O—, or —(CH₂)$_n$—,
more preferably a single bond, —COO—, or —OCO—, n denotes an integer between 2 and 8, preferably 2,
and p denote each and independently 0, 1 or 2, preferably 1, $X^{11}$ and $X^{21}$ denote independently from one another, in each occurrence a single bond, —CO—O—, —O—CO—, —O—COO—, —O—, —CH=CH—, —C≡C—, —CF$_2$—O—, —O—CF$_2$—, —CF$_2$—CF$_2$—, —CH$_2$—O—, —O—CH$_2$—, —CO—S—, —S—CO—, —CS—S—, —S—CS—, —S—CSS— or —S—, preferably, a single bond —CO—O—, —O—CO—, —O—COO—, or —O—, more preferably a single bond or —O—, $Sp^{11}$ and $Sp^{21}$ denote each and independently, in each occurrence a single bond or a spacer group comprising 1 to 20 C atoms, wherein one or more non-adjacent and non-terminal CH$_2$ groups may also be replaced by —O—, —S—, —NH—, —N(CH$_3$)—, —CO—, —O—CO—, —S—CO—, —O—COO—, —CO—S—, —CO—O—, —CF$_2$—, —CF$_2$O—, —OCF$_2$—, —C(OH)—, —CH(alkyl)-, —CH(alkenyl)-, —CH(alkoxyl)-, —CH(oxaalkyl)-, —CH=CH— or —C≡C—, however in such a way that no two O-atoms are adjacent to one another and no two groups selected from —O—CO—, —S—CO—, —O—COO—, —CO—S—, —CO—O— and —CH=CH— are adjacent to each other, preferably alkylene having 1 to 20, preferably 1 to 12, C atoms, which is optionally mono- or polysubstituted by F, Cl, Br, I or CN, more preferably straight-chain ethylene, propylene, butylene, pentylene, hexylene, heptylene, octylene, nonylene, decylene, undecylene, dodecylene, $R^{11}$ denotes a group

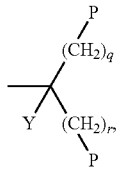

preferably a group

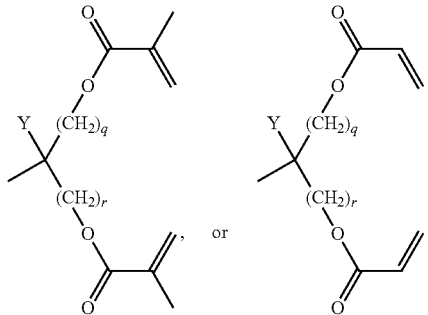

Y denotes H, F, phenyl or optionally fluorinated alkyl having 1-12 C atoms, preferably H, methyl, ethyl, propyl, butyl, more preferably H or methyl, in particular H, $R^{21}$ denotes $R^{11}$, P, or halogen, CN, optionally fluorinated alkyl or alkenyl with up to 15 C atoms in which one or more non-adjacent CH$_2$-groups may be replaced by —O—, —S—, —CO—, —C(O)O—, —O—C(O)—, O—C(O)—O—, preferably P or $R^{11}$, more preferably P, P each and independently from another in each occurrence a polymerizable group, q and r denotes each and independently an integer from 0 to 8, preferably q+r≥1 and ≤16, more preferably q and r each and independently denotes an integer from 1 to 8.

In the instant application, polymerizable groups (P) are groups that are suitable for a polymerisation reaction, such as, for example, free-radical or ionic chain polymerisation, polyaddition or polycondensation, or for a polymer-analogous reaction, for example addition or condensation onto a main polymer chain. Particular preference is given to groups for chain polymerisation, in particular those containing a C=C double bond or —C≡C— triple bond, and groups which are suitable for polymerisation with ring opening, such as, for example, oxetane or epoxide groups.

Preferred groups P are selected from the group consisting of CH$_2$=CW$^1$—CO—O—, CH$_2$=CW$^1$—CO—,

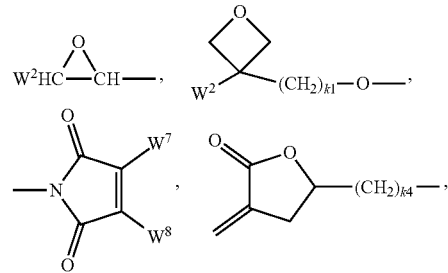

CH$_2$=CW$^2$—(O)$_{k3}$—, CW$^1$=CH—CO—(O)$_{k3}$—, CW$^1$=CH—CO—NH—, CH$_2$=CW$^1$—CO—NH—, CH$_3$—CH=CH—O—, (CH$_2$=CH)$_2$CH—OCO—, (CH$_2$=CH—CH$_2$)$_2$CH—OCO—, (CH$_2$=CH)$_2$CH—O—, (CH$_2$=CH—CH$_2$)$_2$N—, (CH$_2$=CH—CH$_2$)$_2$N—CO—, HO—CW$^2$W$^3$—, HS—CW$^2$W$^3$—, HW$^2$N—, HO—CW$^2$W$^3$—NH—, CH$_2$=CW$^1$—CO—NH—, CH$_2$=CH—(COO)$_{k1}$-Phe-(O)$_{k2}$—, CH$_2$=CH—(CO)$_{k1}$-Phe-(O)$_{k2}$—, Phe-CH=CH—, HOOC—, OCN— and W$^4$W$^5$W$^6$Si—, wherein W$^1$ denotes H, F, Cl, CN, CF$_3$, phenyl or alkyl having 1 to 5 C atoms, in particular H, F, Cl or CH$_3$, W$^2$ and W$^3$ each, independently of one another, denote H or alkyl having 1 to 5 C atoms, in particular H, methyl, ethyl or n-propyl, W$^4$, W$^5$ and W$^6$ each, independently of one another, denote Cl, oxaalkyl or oxacarbonylalkyl having 1 to 5 C atoms, W$^7$ and W$^8$ each, independently of one another, denote H, Cl or alkyl having 1 to 5 C atoms, Phe denotes 1,4-phenylene, which is optionally substituted by one or more radicals L as defined above which are other than P-Sp-, $k_1$, $k_2$ and $k_3$ each, independently of one another, denote 0 or 1, $k_3$ preferably denotes 1, and $k_4$ denotes an integer from 1 to 10.

Particularly preferred groups P are selected from the group consisting of CH$_2$=CW$^1$—CO—O—, in particular CH$_2$=CH—CO—O—, CH$_2$=C(CH$_3$)—CO—O— and CH$_2$=CF—CO—O—, furthermore CH$_2$=CH—O—, (CH$_2$=CH)$_2$CH—O—CO—, (CH$_2$=CH)$_2$CH—O—,

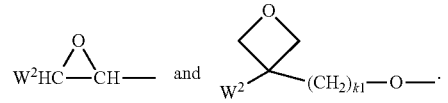

Very particularly preferred groups P are selected from the group consisting of acrylate, methacrylate, fluoroacrylate, furthermore vinyloxy, chloroacrylate, oxetane and epoxide groups, and of these preferably an acrylate or methacrylate group.

The compounds of formula I are preferably selected from compounds of the sub-formulae I-1 to I-9,

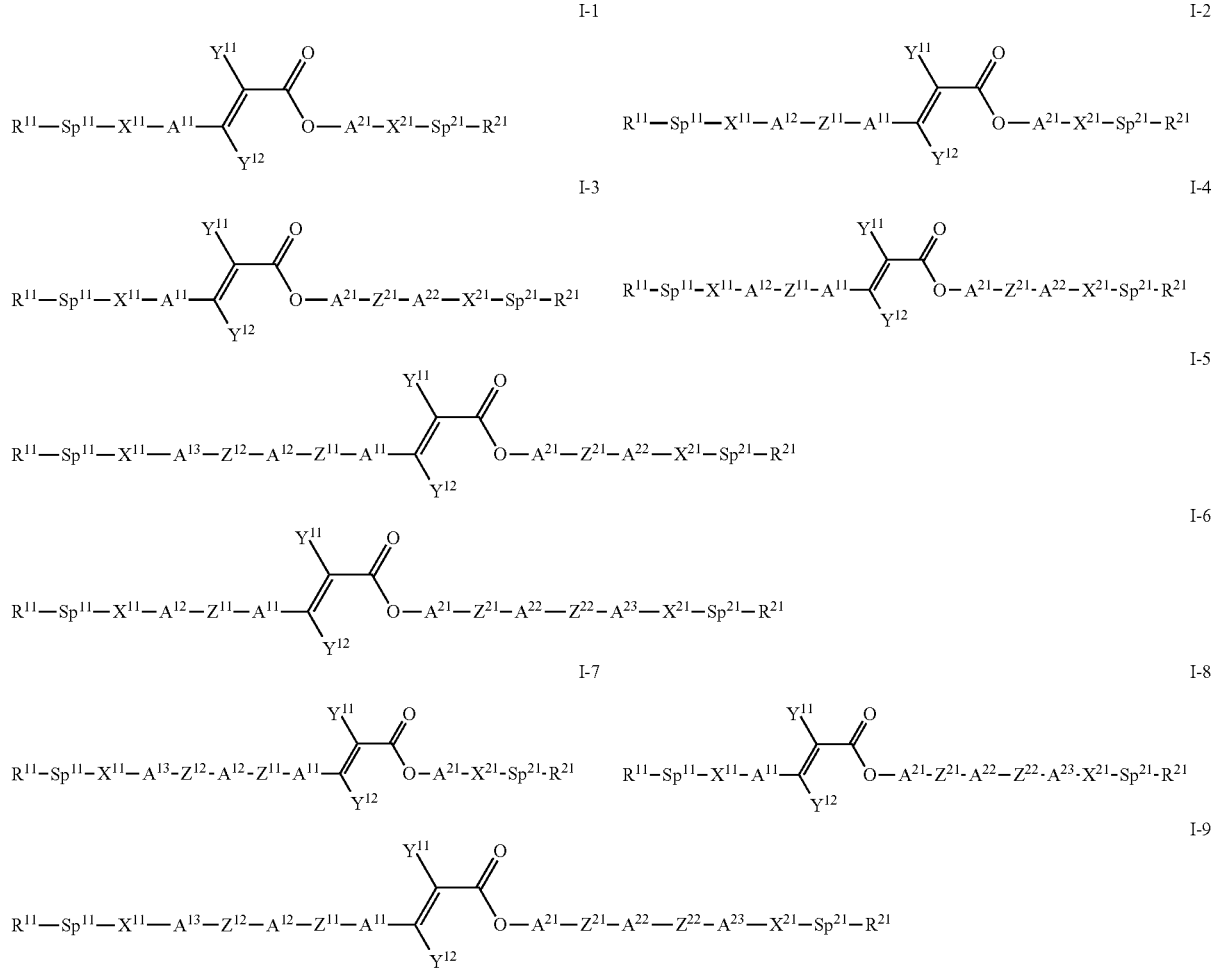

wherein $R^{11}$, $R^{21}$, $A^{11}$, $X^{11}$, $X^{12}$, $Y^{11}$, $Y^{12}$, $Sp^{11}$, and $Sp^{12}$ have one of the meanings as given above in formula I, $A^{12}$ to $A^{23}$ have one of the meanings for A in formula I, and $Z^{11}$ to $Z^{22}$ have one of the meanings for Z as given above under formula I.

Further preferred compounds of formula I are selected from the compounds of formulae I-2 to I-5.

Preferred compounds of formula I-2 are selected from the following sub formula:

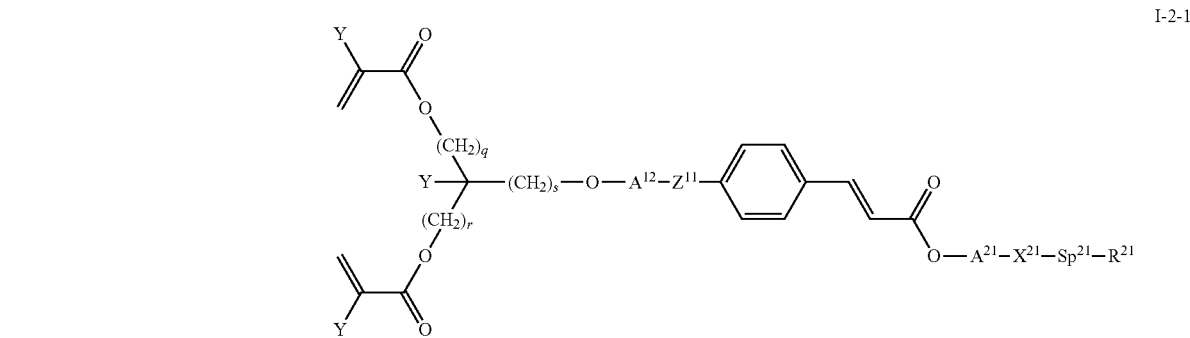

wherein Y, $R^{21}$, $X^{21}$, and $Sp^{21}$ have one of the meanings as given above in formula I, and $Z^{11}$ has one of the meanings for Z as given above under formula I, r and q denote 1, 2 or 3 and s denotes an integer from 1 to 6, $A^{12}$, $A^{21}$ have one of the meanings for A given above under formula I, preferably $A^{12}$, $A^{21}$ denote each and independently a group consisting of 1,4-phenylene, wherein, in addition, one or two CH groups may be replaced by N and wherein, in addition, one or more H atoms may be replaced by L as given above under formula I, or a group consisting of trans-1,4-cyclohexylene, 1,4-cyclohexenylene, wherein, in addition, one or more non-adjacent $CH_2$ groups may be replaced by —O— and/or —S— and wherein, in addition, one or more H atoms may be replaced by F.

Preferred compounds of formula I-3 are selected from the following subformulae,

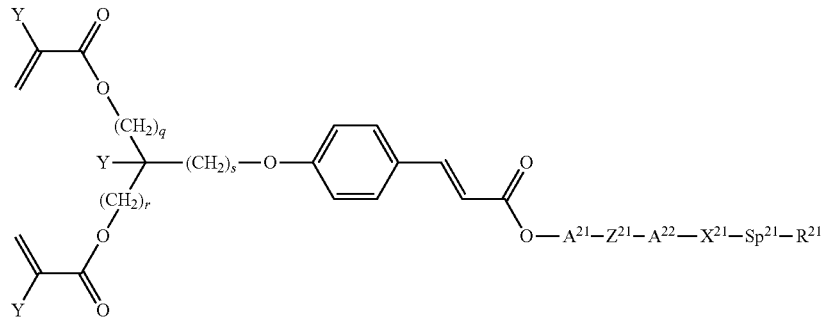

I-3-1

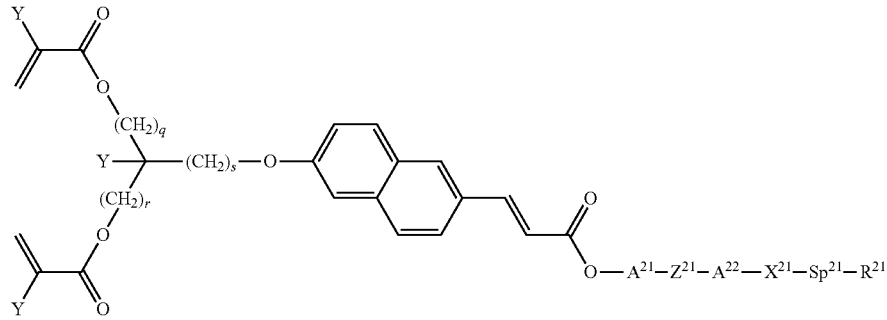

I-3-2

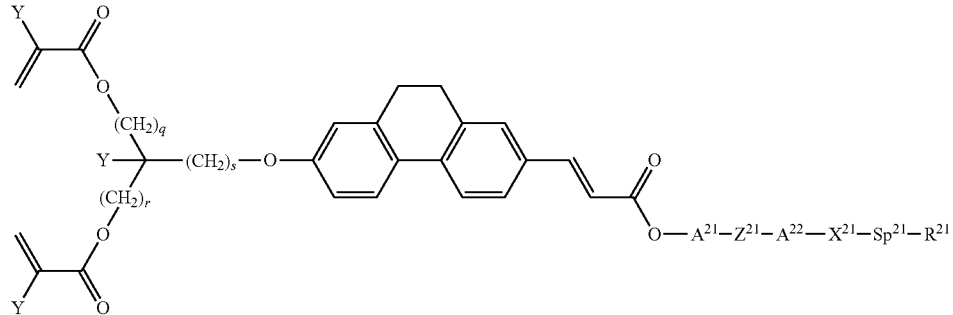

I-3-3 wherein Y, $R^{21}$, $X^{21}$, and $Sp^{21}$ have one of the meanings as given above in PGP-43 ci formula I, $Z^{21}$ has one of the meanings for Z as given above under formula I, r and q denote 1, 2 or 3, s denotes an integer from 1 to 6 and $A^{21}$ and $A^{22}$ have one of the meanings for As given above under formula I. Preferably $A^{21}$ and $A^{22}$ denote each and independently a group consisting of 1,4-phenylene, wherein, in addition, one or two CH groups may be replaced by N and wherein, in addition, one or more H atoms may be replaced by L as given above under formula I, or a group consisting of trans-1,4-cyclohexylene, 1,4-cyclohexenylene, wherein, in addition, one or more non-adjacent $CH_2$ groups may be replaced by —O— and/or —S— and wherein, in addition, one or more H atoms may be replaced by F.

Preferred compounds of formula I-4 are selected from the following subformulae,

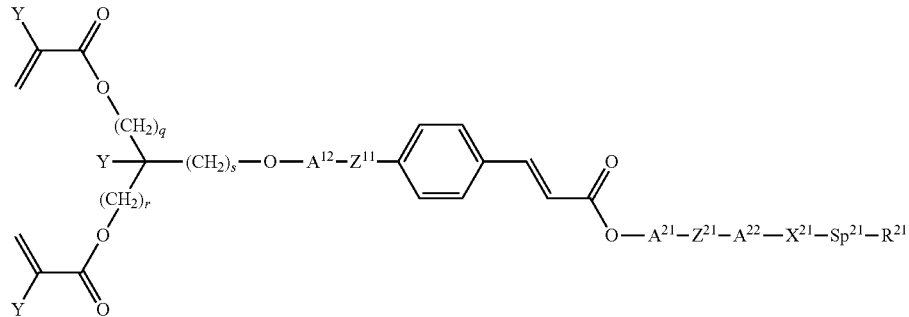

I-4-1 wherein Y, $R^{21}$, $X^{21}$, and $Sp^{21}$ have one of the meanings as given above in formula I, $A^{12}$, $A^{21}$ and $A^{22}$ have one of the meanings for A as given above under formula I, $Z^{11}$, and $Z^{21}$ have one of the meanings for Z as given above under formula I, r and q denote 1, 2 or 3, s denotes an integer from 1 to 6, and $A^{12}$, $A^{21}$ and $A^{22}$ have one of the meanings for A s given above under formula I. Preferably $A^{12}$, $A^{21}$ and $A^{22}$ denote each and independently a group consisting of 1,4-phenylene, wherein one or two CH groups may be replaced by N and wherein, in addition, one or more H atoms may be replaced by L as given above under formula I, or a group consisting of trans-1,4-cyclohexylene, 1,4-cyclohexenylene, wherein, in addition, one or more non-adjacent $CH_2$ groups may be replaced by —O— and/or —S— and wherein, in addition, one or more H atoms may be replaced by F.

Preferred compounds of formula I-5 are selected from the following sub formula,

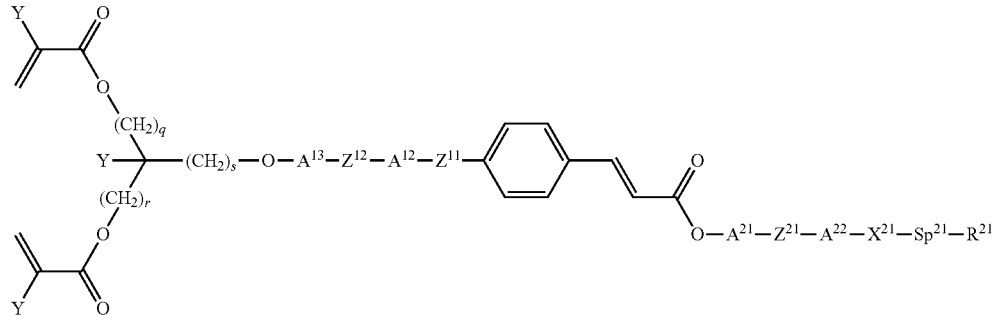

I-5-1 wherein Y, $R^{21}$, $X^{21}$, and $Sp^{21}$ have one of the meanings as given above in formula I, $Z^{11}$, $Z^{12}$ and $Z^{21}$ have one of the meanings for Z as given above under formula I, r and q denote 1, 2 or 3, s denotes an integer from 1 to 6, and $A^{12}$, $A^{13}$, $A^{21}$ and $A^{22}$ have one of the meanings for A as given above under formula I. Preferably, $A^{12}$, $A^{13}$, $A^{21}$ and $A^{22}$ denote each and independently a group consisting of 1,4-phenylene, wherein one or two CH groups may be replaced by N and wherein, in addition, one or more H atoms may be replaced by L as given above under formula I, or a group consisting of trans-1,4-cyclohexylene, 1,4-cyclohexenylene, wherein, in addition, one or more non-adjacent $CH_2$ groups may be replaced by —O— and/or —S— and wherein, in addition, one or more H atoms may be replaced by F.

Preferred compounds of formula I-2-1 are compounds of the following sub-formula,

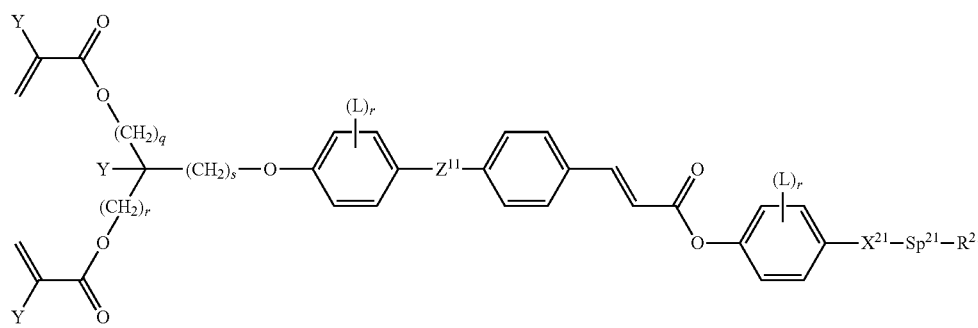

I-2-1a wherein Y, $R^{21}$, $X^{21}$, and $Sp^{21}$ have one of the meanings as given above in formula I, $Z^{11}$ has one of the meanings for Z as given above under formula I, r and q denote 1, 2 or 3, s denotes an integer from 1 to 6, and the group

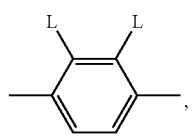

is each and independently

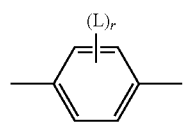

or denotes

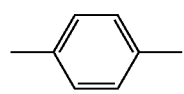

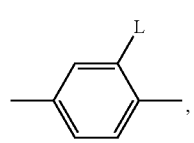

or furthermore

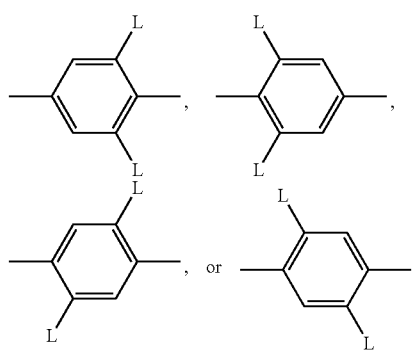

wherein L have one of the meanings as given above in formula I, and preferably denotes F, Cl, $OCH_3$, $COCH_3$ or alkyl having 1 to 6 C Atoms, such as methyl, ethyl, propyl, butyl, pentyl, hexyl, cyclopropyl, cylobutyl, cyclopentyl, cyclohexyl, or $X^{21}$-$Sp^{21}$-$R^{21}$.

Preferred compounds of formulae I-3-1 to I-3-3 are compounds of the following sub-formulae:

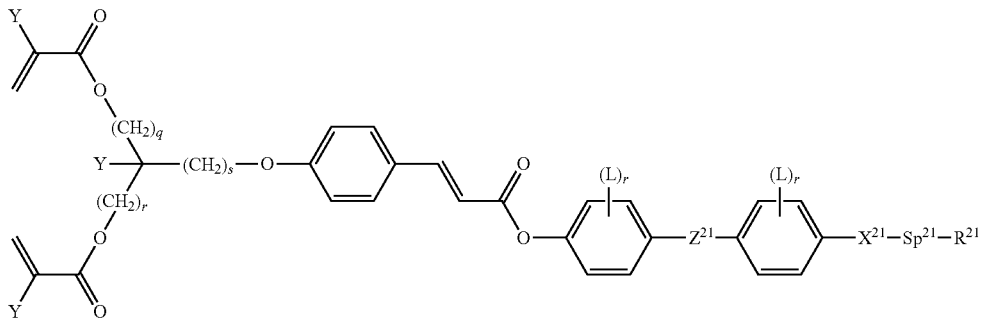
I-3-1a
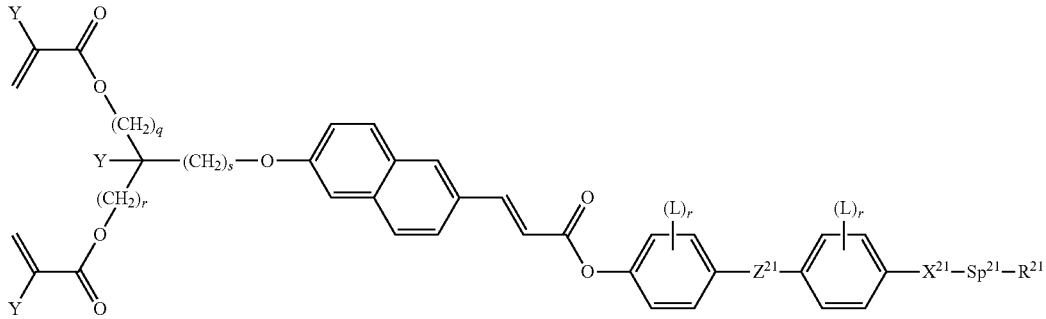
I-3-2a
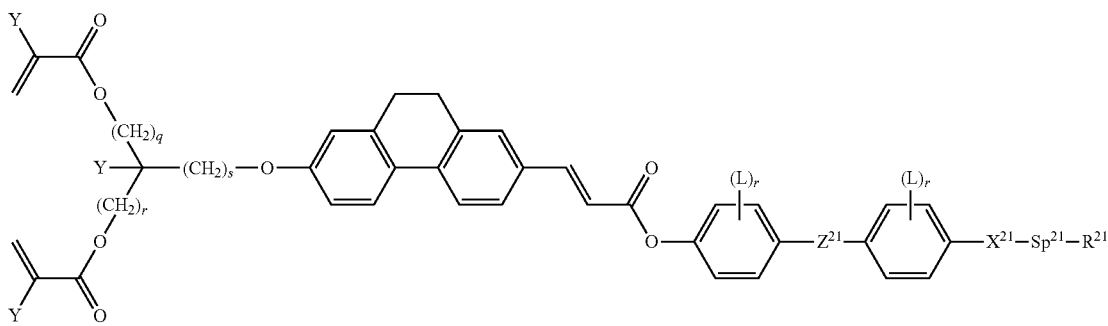
I-3-3a
wherein Y, $R^{21}$, $X^{21}$, and $Sp^{21}$ have one of the meanings as given above in formula I, $Z^{21}$ has one of the meanings for Z as given above under formula I, r and q denote 1, 2 or 3 and s denotes an integer from 1 to 6, and
the group
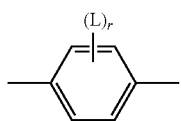
is each and independently
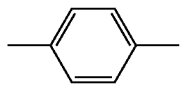
or denotes
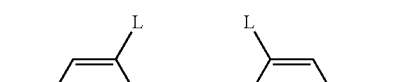
furthermore
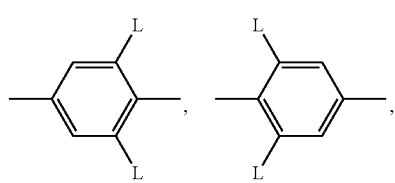

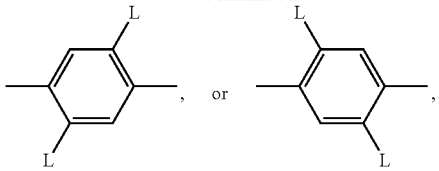

wherein L have one of the meanings as given above in formula I, and preferably is F, Cl, OCH$_3$, COCH$_3$ or alkyl having 1 to 6 C Atoms, such as methyl, ethyl, propyl, butyl, pentyl, hexyl, cyclopropyl, cylobutyl, cyclopentyl, cyclohexyl, or X$^{21}$-Sp$^{21}$-R$^{21}$.

Preferred compounds of formulae I-4-1 are compounds of the following sub-formula:

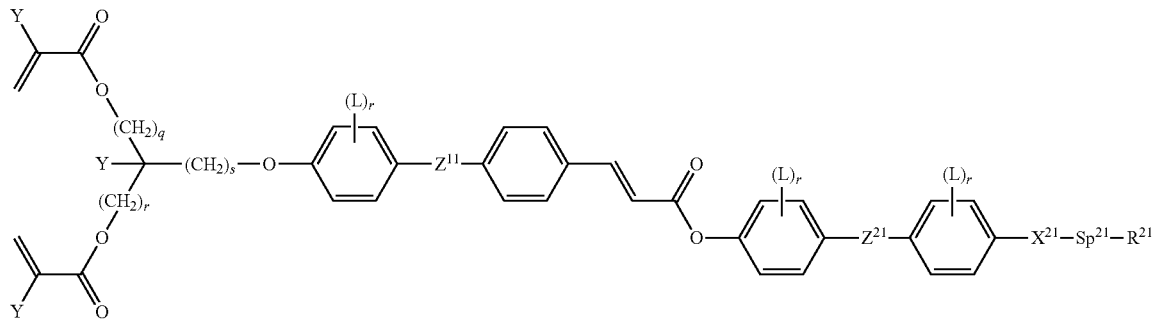

I-4-1a wherein Y, R$^{21}$, X$^{21}$, and Sp$^{21}$ have one of the meanings as given above in formula I, Z$^{11}$ and Z$^{21}$ has one of the meanings for Z as given above under formula I, r and q denote 1, 2 or 3 and s denotes an integer from 1 to 6, and the group

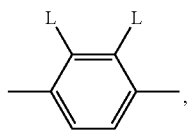

is each and independently

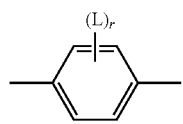

or
denotes

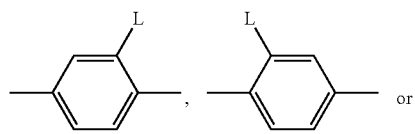

-continued

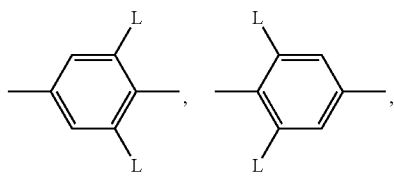

furthermore

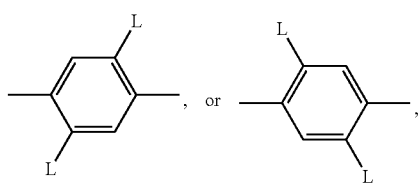

wherein L have one of the meanings as given above in formula I, and preferably F, Cl, OCH$_3$, COCH$_3$ or alkyl having 1 to 6 C Atoms, such as methyl, ethyl, propyl, butyl, pentyl, hexyl, cyclopropyl, cylobutyl, cyclopentyl, cyclohexyl, or X$^{21}$-Sp$^{21}$-R$^{21}$.

Preferred compounds of formulae I-5-1 are compounds of the following sub-formula.

I-5-1a

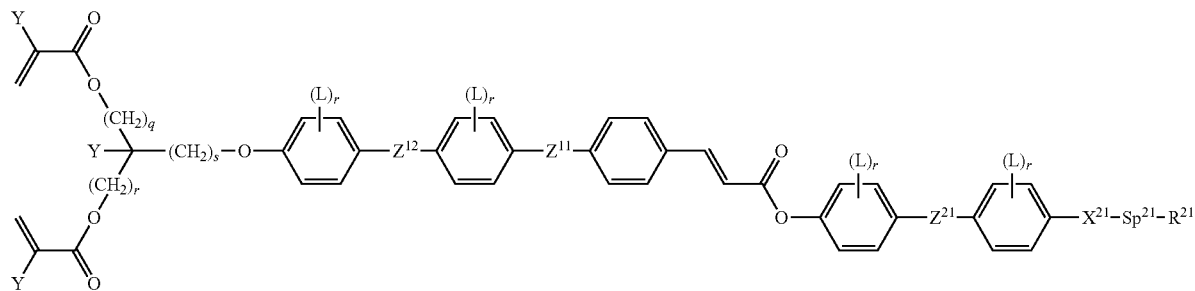

wherein Y, $R^{21}$, $X^{21}$, and $Sp^{21}$ have one of the meanings as given above in formula I, $Z^{11}$, $Z^{12}$ and $Z^{21}$ has each and independently one of the meanings for Z as given above under formula I, r and q denote 1, 2 or 3 and s denotes an integer from 1 to 6, and
the group

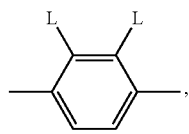

is each and independently

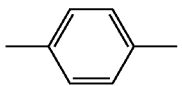

or
denotes

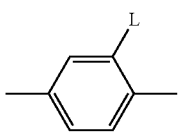

-continued

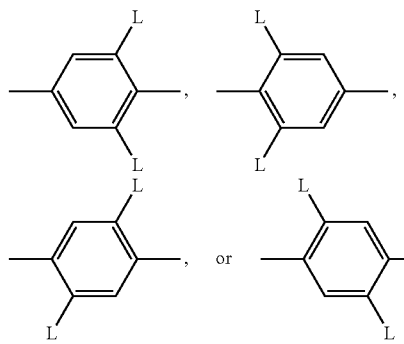

furthermore wherein L have one of the meanings as given above in formula I, and preferably is F, Cl, $OCH_3$, $COCH_3$ or alkyl having 1 to 6 C Atoms, such as, methyl, ethyl, propyl, butyl, pentyl, hexyl, cyclopropyl, cylobutyl, cyclopentyl, cyclohexyl, or $X^{21}$-$Sp^{21}$-$R^{21}$.

Further preferred compounds of formula I-2-1 are compounds of the following sub-formula:

I-2-1a-1

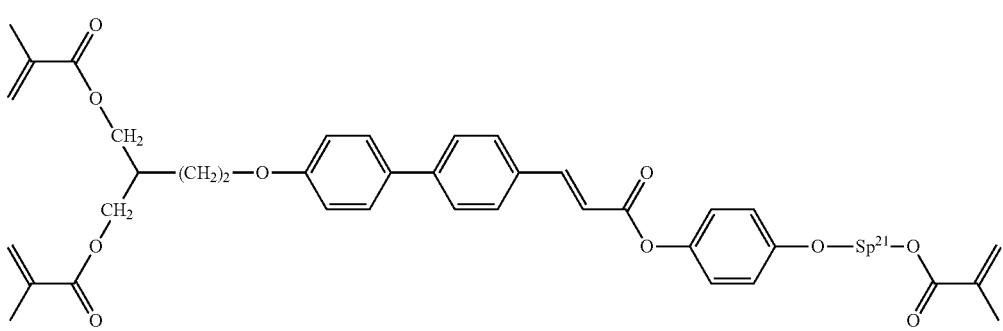

I-2-1a-2
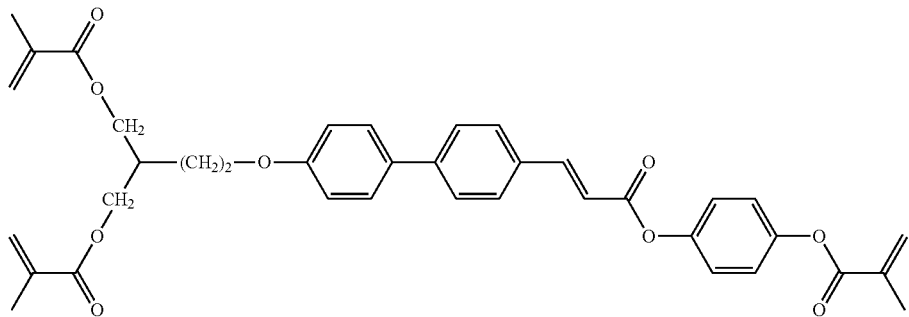
I-2-1a-3
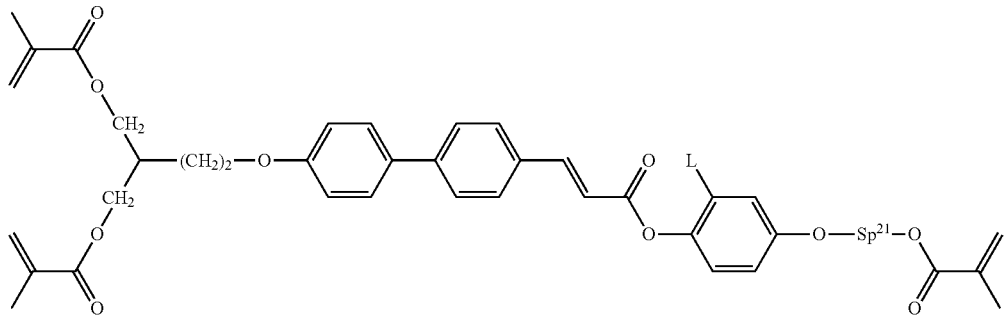
I-2-1a-4
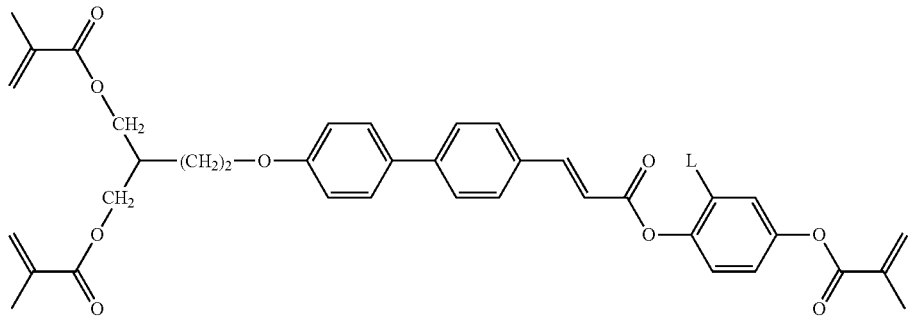
I-2-1a-5
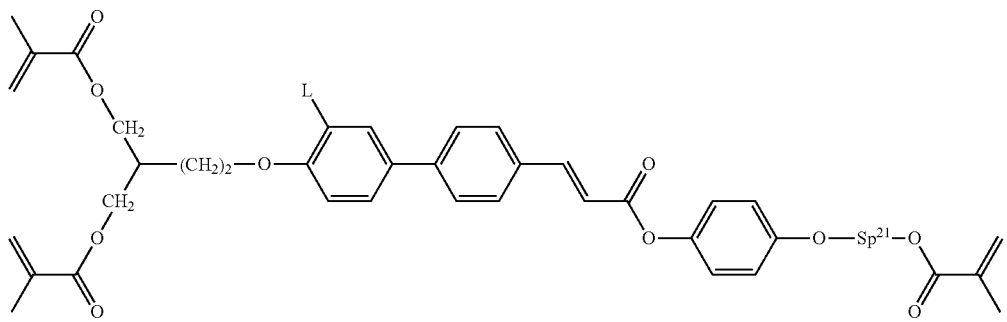
I-2-1a-6
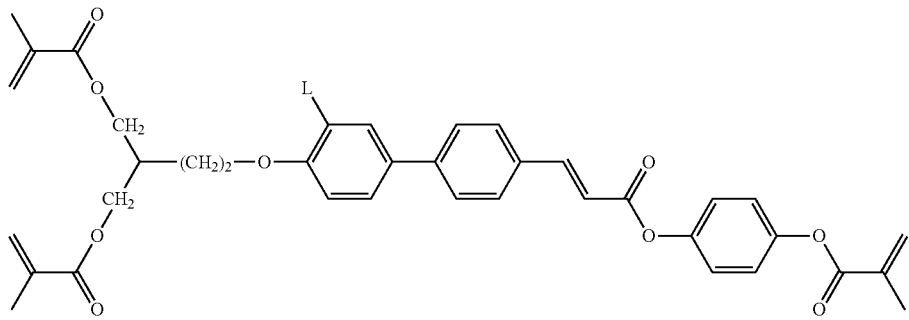

I-2-1a-7
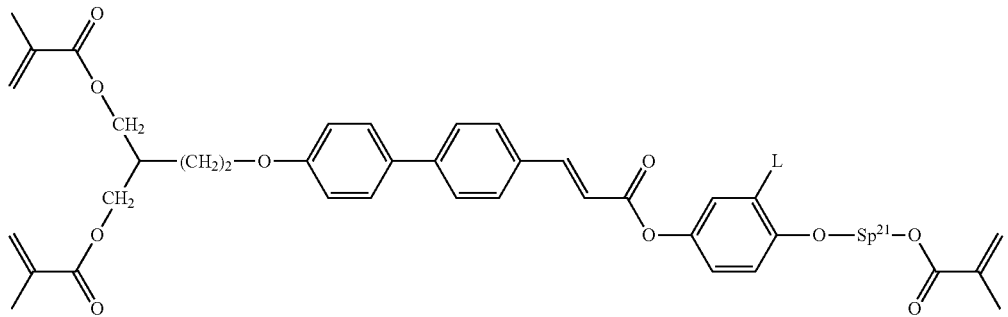
I-2-1a-8
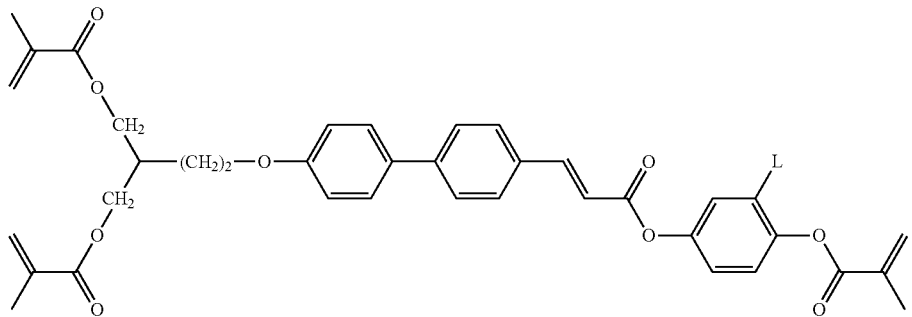
I-2-1a-9
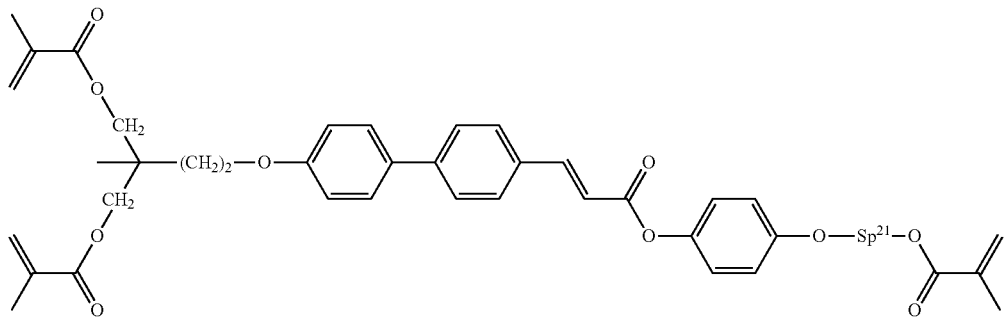
I-2-1a-10
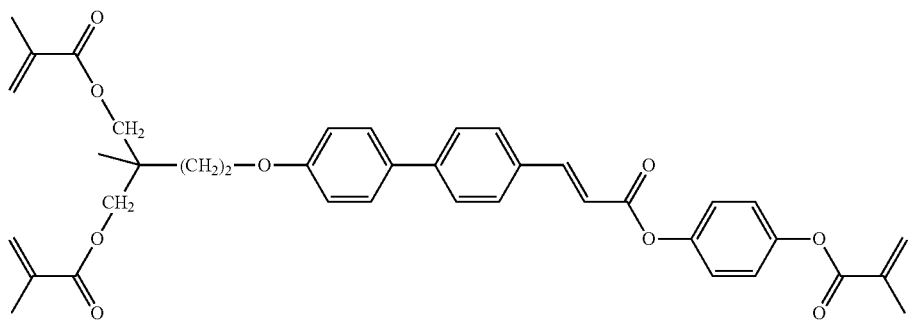
I-2-1a-11
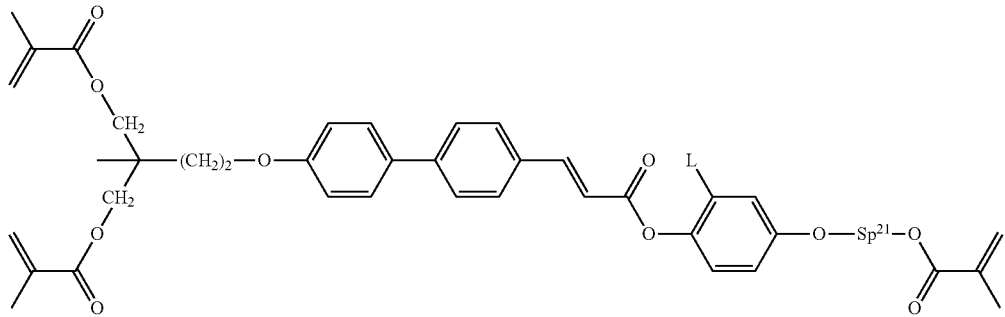

I-2-1a-12
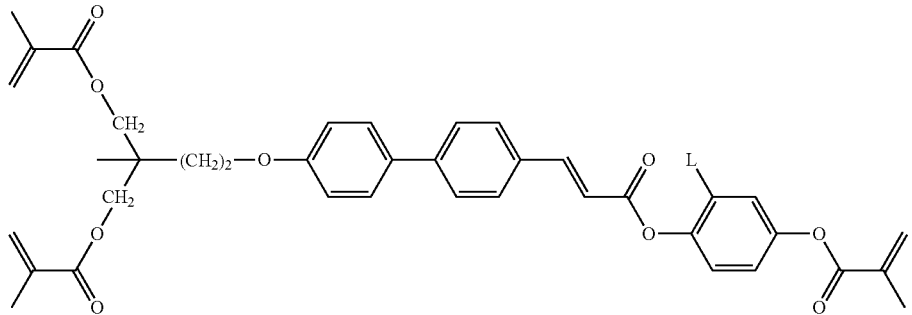
I-2-1a-13
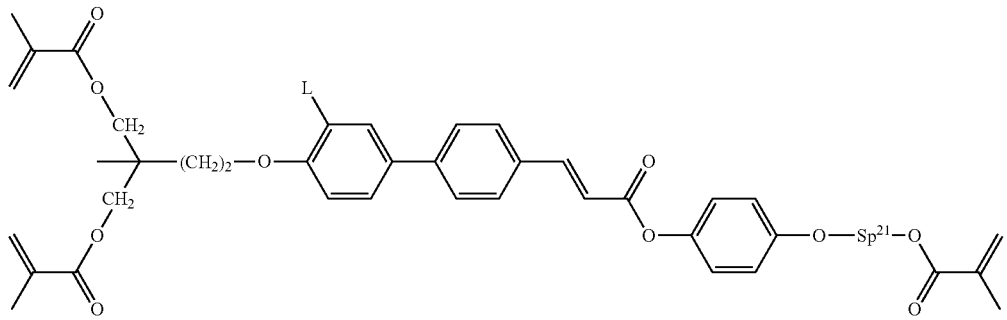
I-2-1a-14
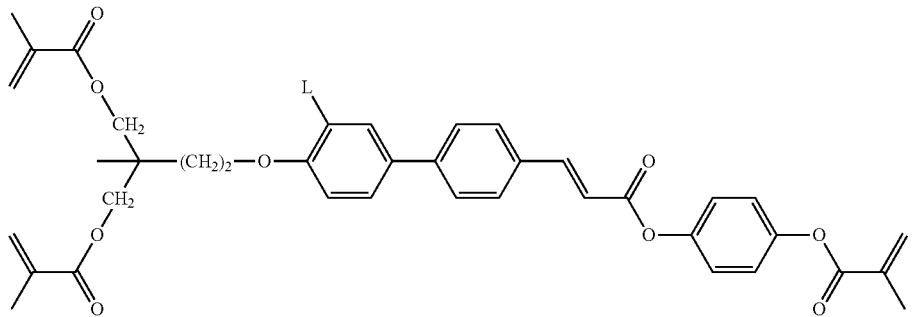
I-2-1a-15
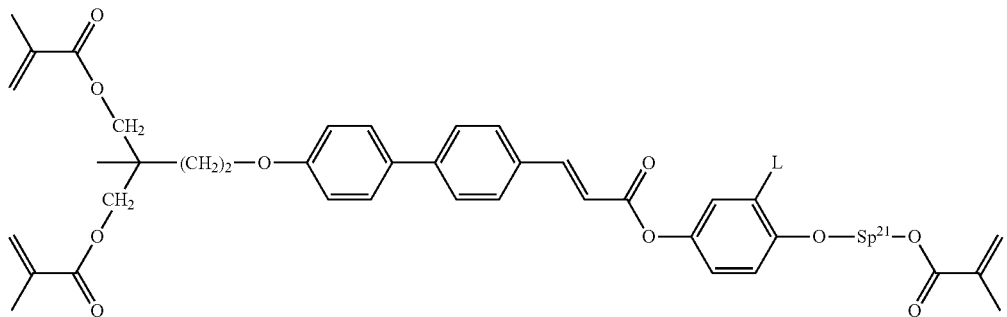
I-2-1a-16
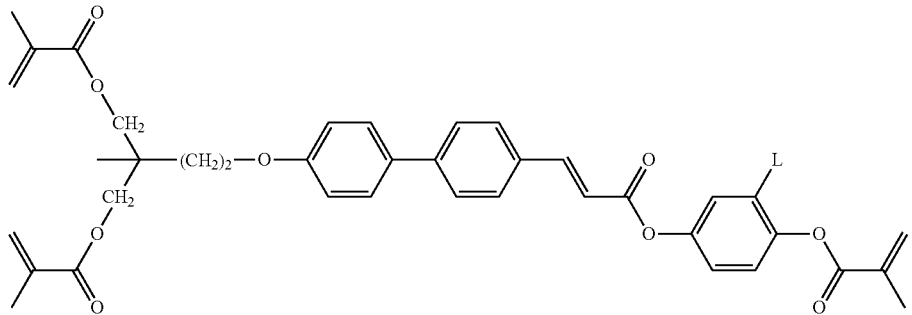

wherein $Sp^{21}$ has one of the meanings as given above in formula I and L is preferably F, Cl, $OCH_3$, $COCH_3$ or alkyl having 1 to 6 C Atoms, such as, methyl, ethyl, propyl, butyl, pentyl, hexyl, cyclopropyl, cylobutyl, cyclopentyl, or cyclohexyl, or $X^{21}$-$Sp^{21}$-$R^{21}$.
Further preferred compounds of formulae I-3-1 to I-3-3 are compounds of the following sub-formulae:
I-3-1a-1
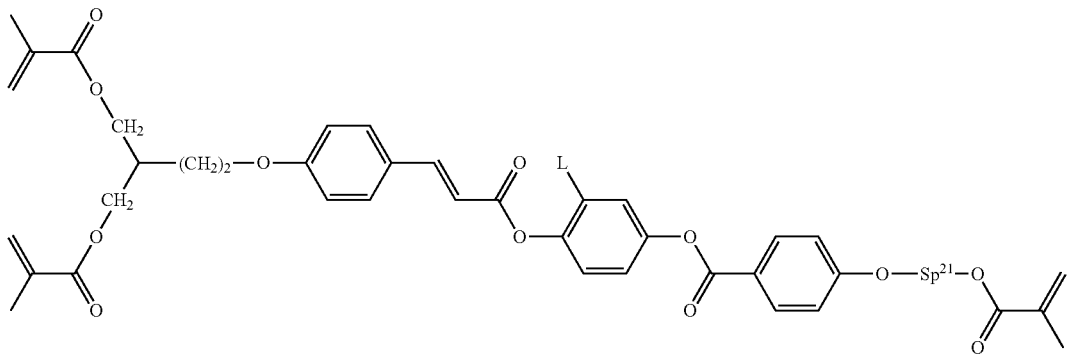
I-3-1a-2
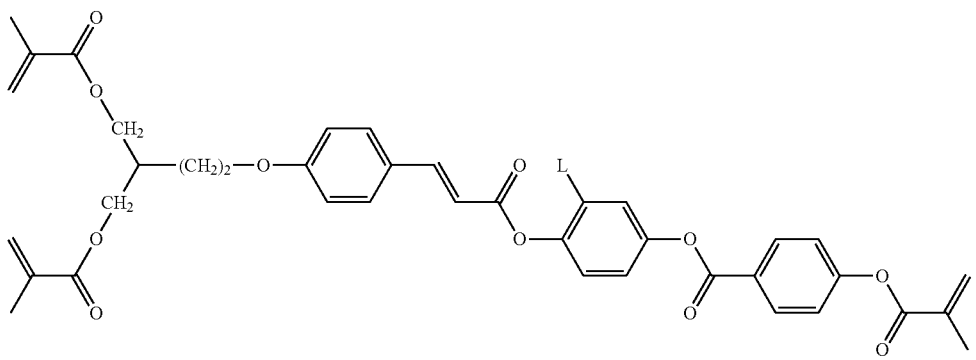
I-3-1a-3
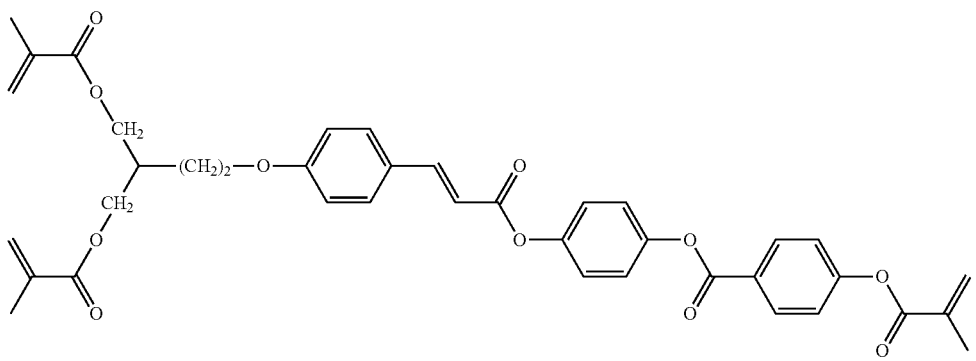
I-3-1a-4
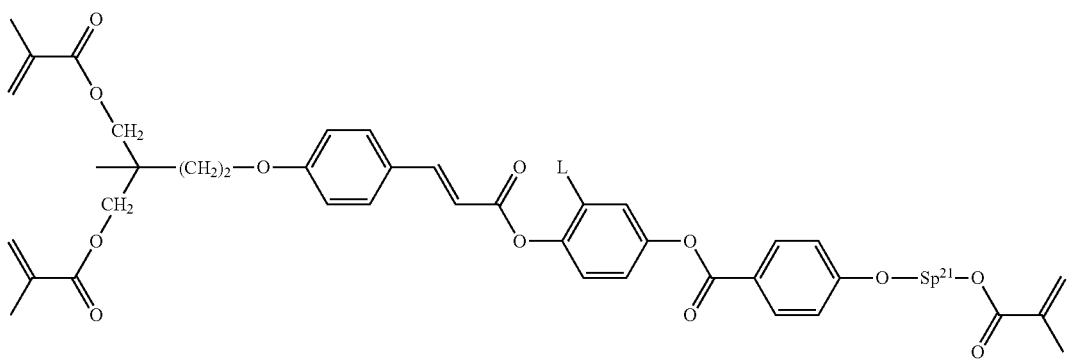

-continued
I-3-1a-5
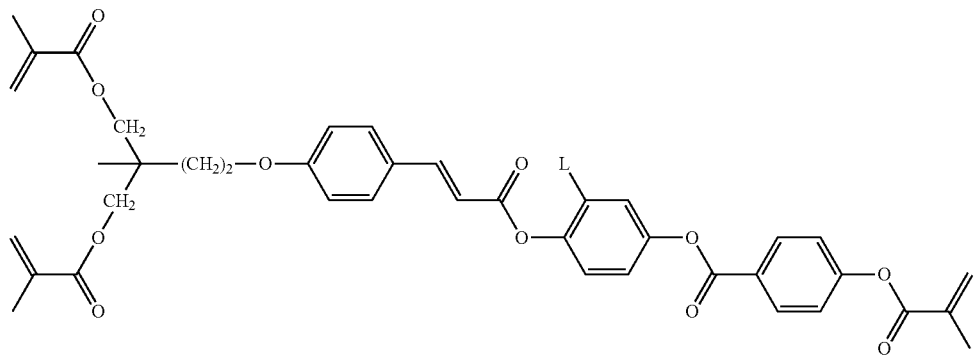
I-3-1a-6
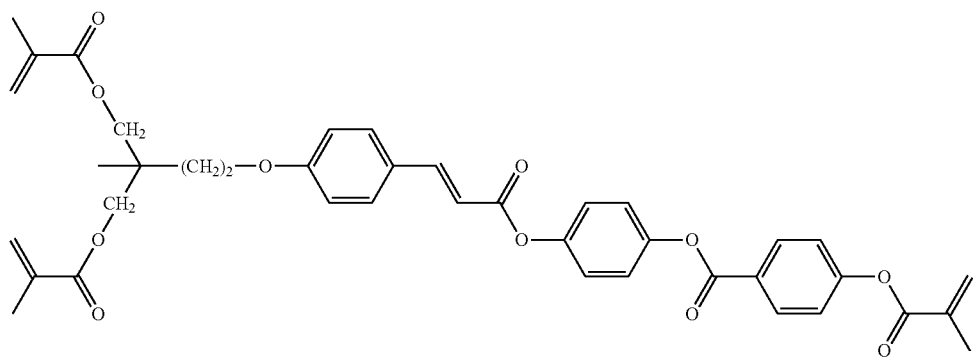
I-3-2a-1
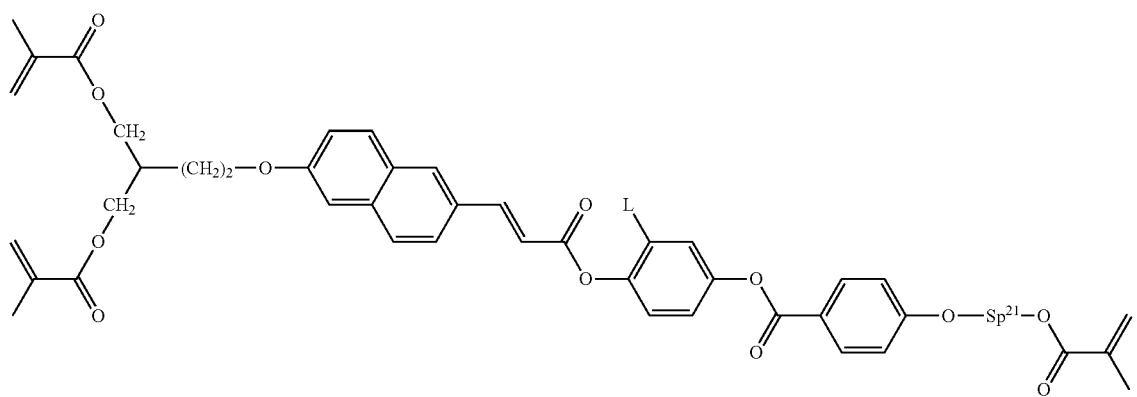
I-3-2a-2
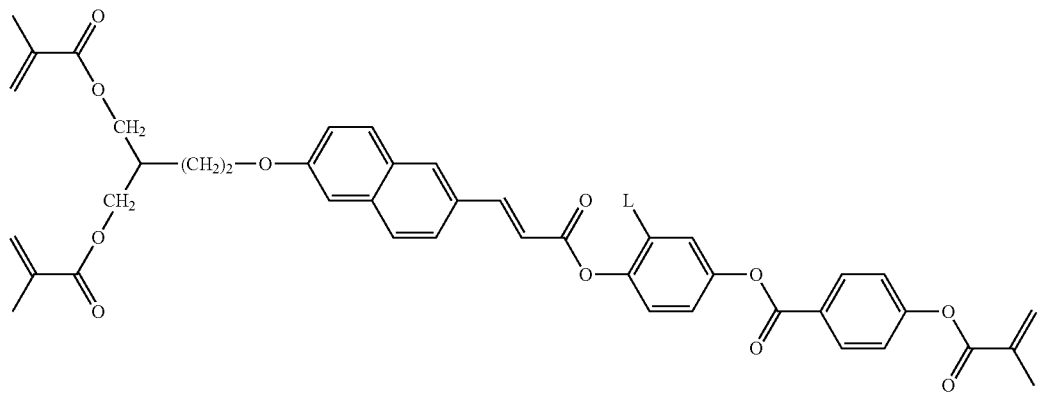

-continued
I-3-2a-3
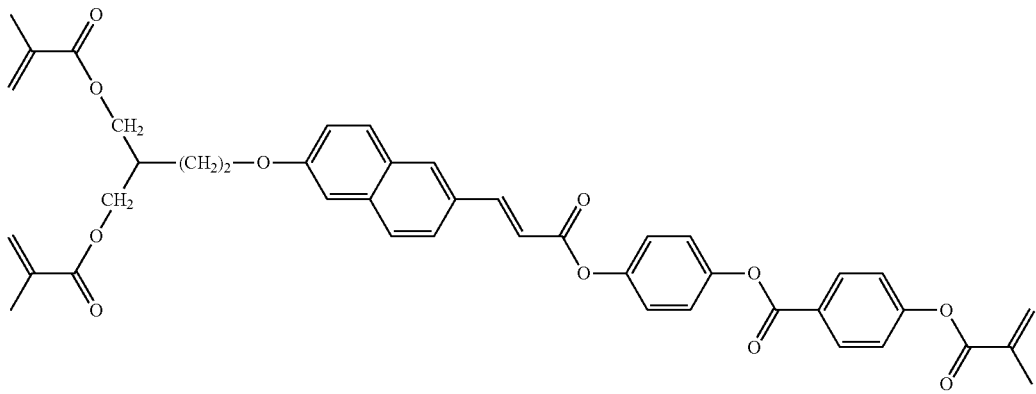
I-3-2a-4
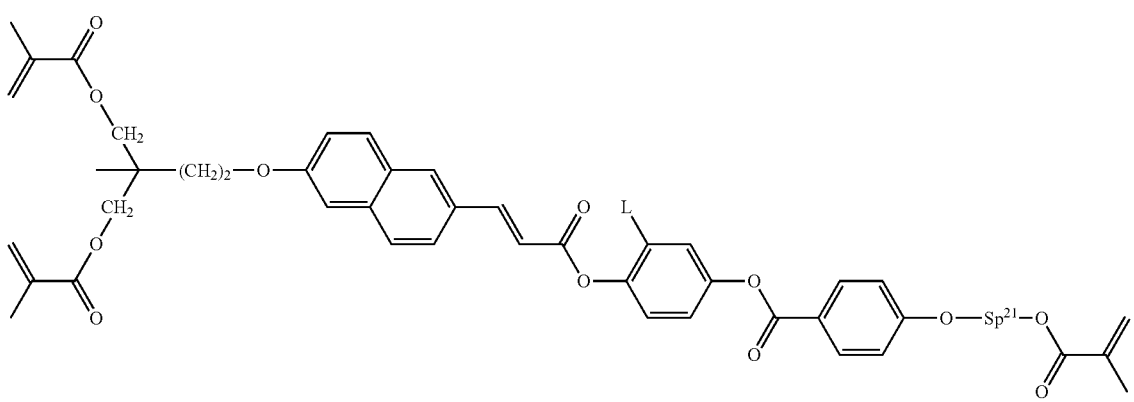
I-3-2a-5
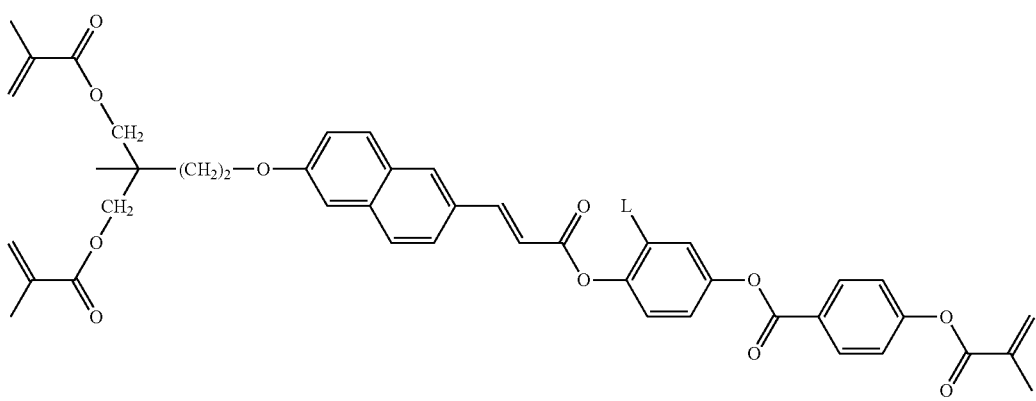
I-3-2a-6
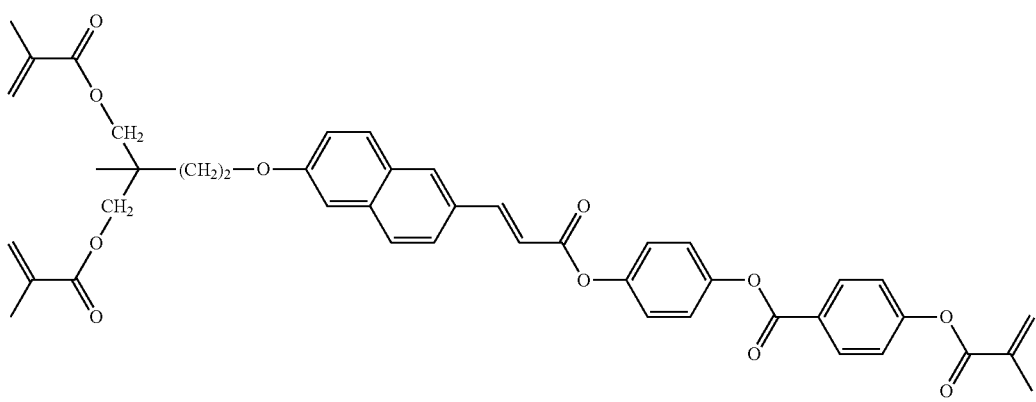

-continued
I-3-3a-1
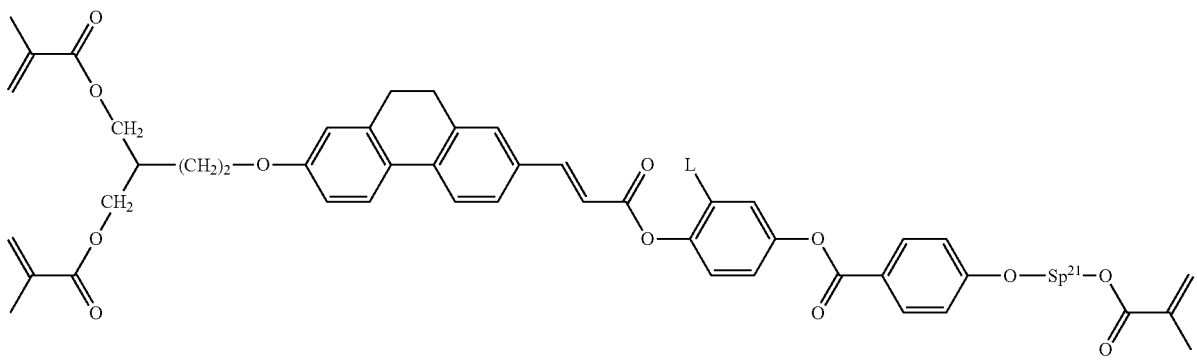
I-3-3a-2
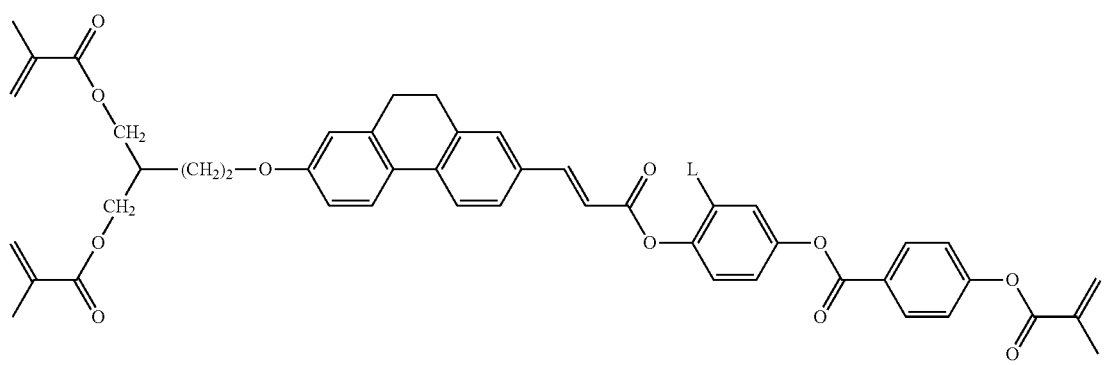
I-3-3a-3
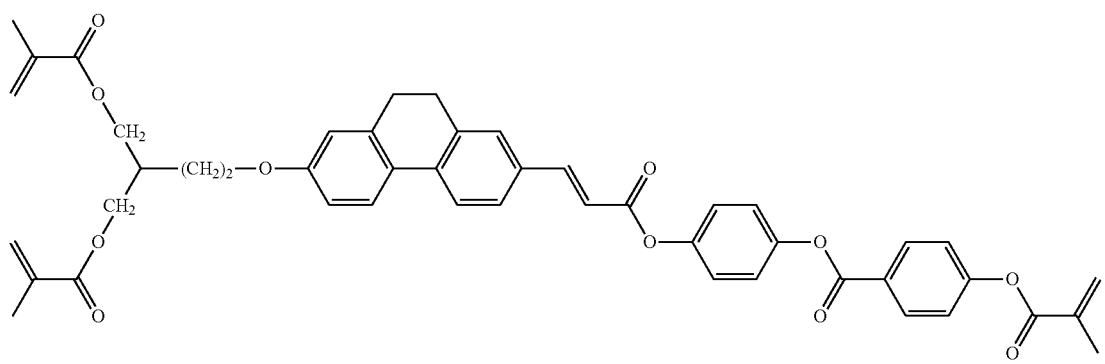
I-3-3a-4
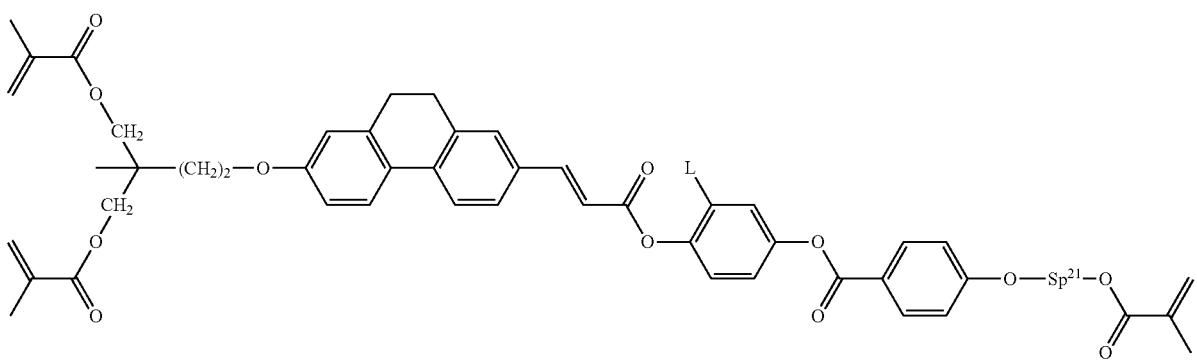

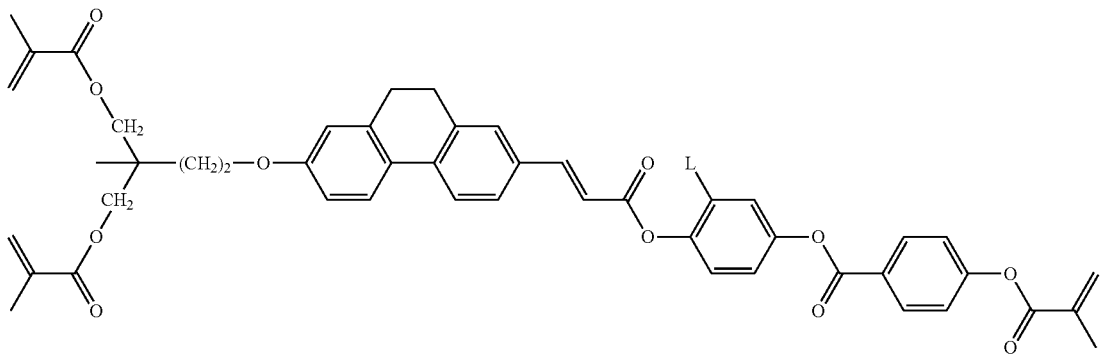
I-3-3a-5
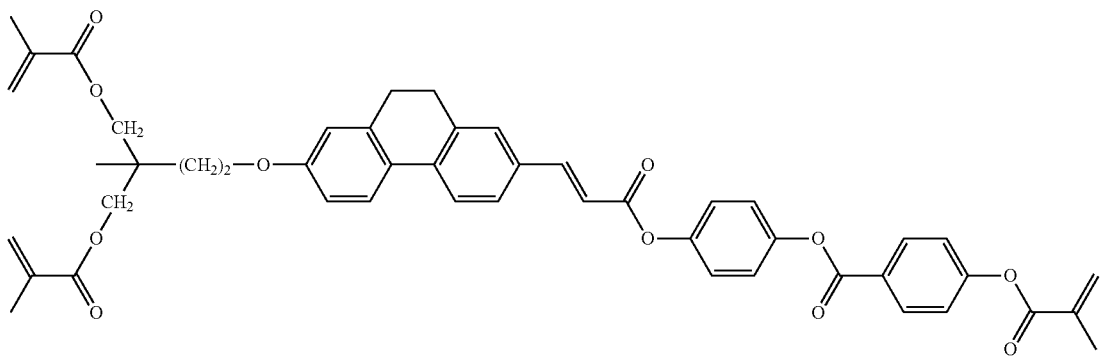
I-3-3a-6
wherein $Sp^{21}$ has one of the meanings as given above in formula I and L denotes F, Cl, $OCH_3$, $COCH_3$ or alkyl having 1 to 6 C Atoms, methyl, ethyl, propyl, butyl, pentyl, hexyl, cyclopropyl, cylobutyl, cyclopentyl, or cyclohexyl, or $X^{21}$-$Sp^{21}$-$R^{21}$.
Further preferred compounds of formulae I-4-1 are compounds of the following sub-formulae:
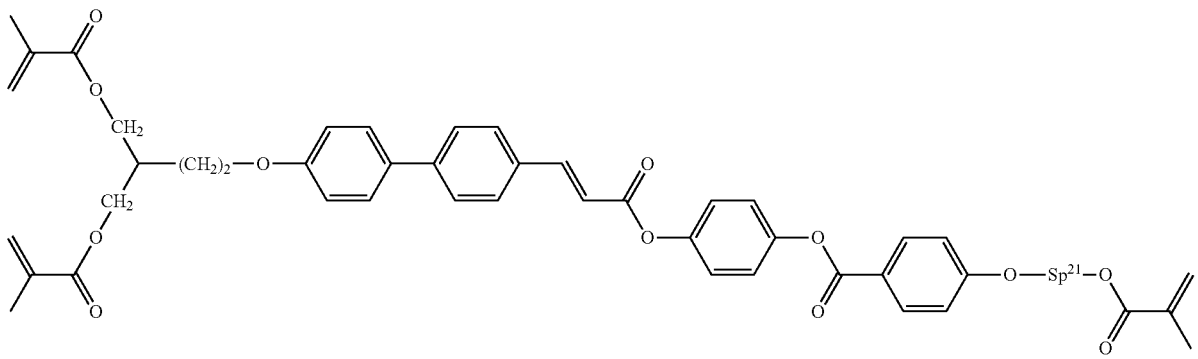
I-4-1a-1

-continued
I-4-1a-2
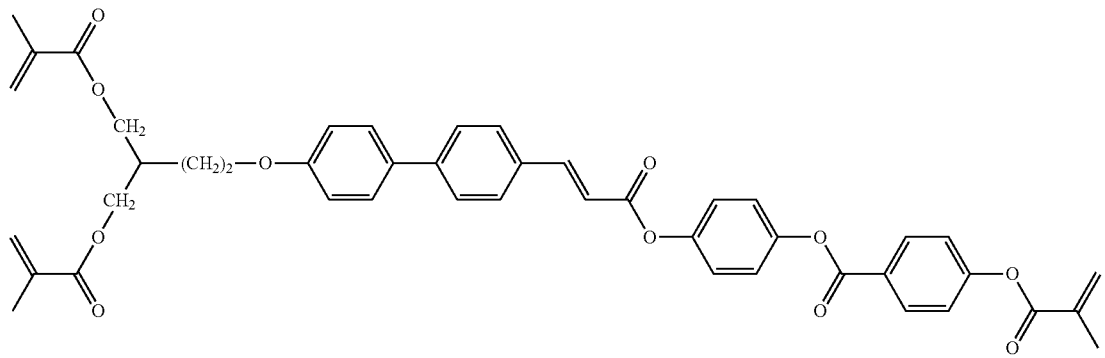
I-4-1a-3
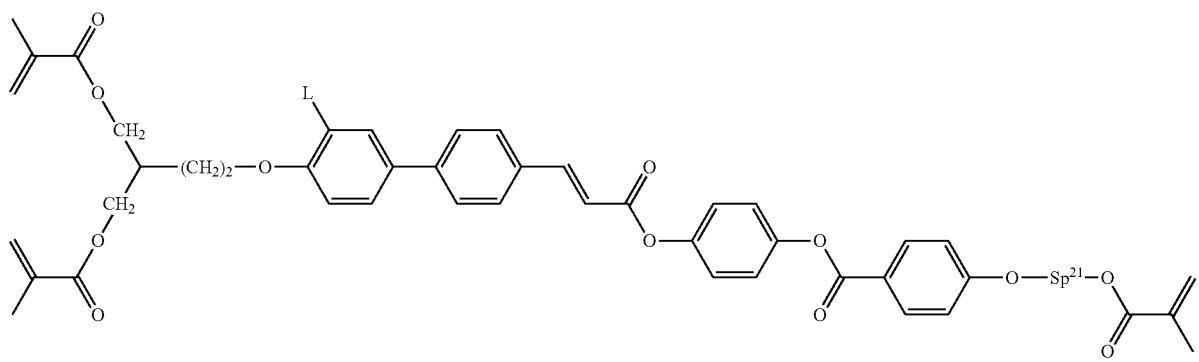
I-4-1a-4
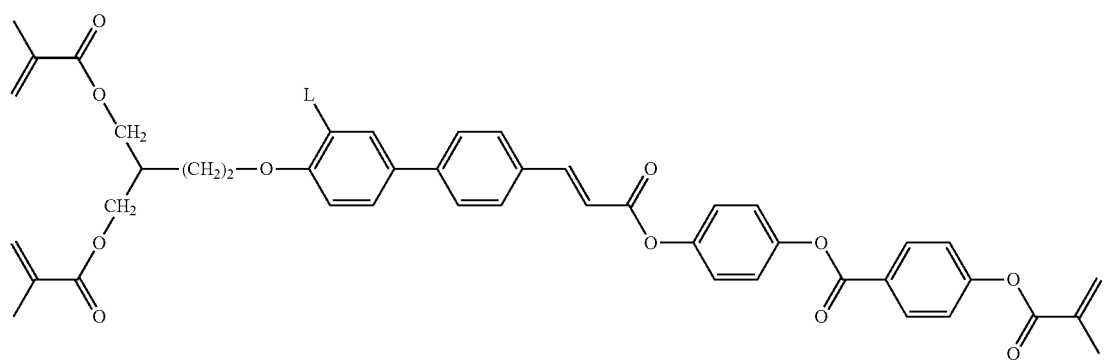
I-4-1a-5
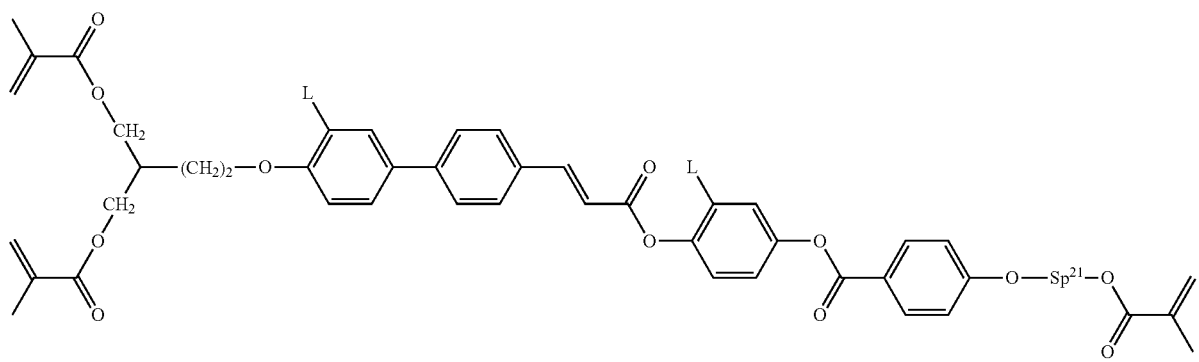

-continued
I-4-1a-6
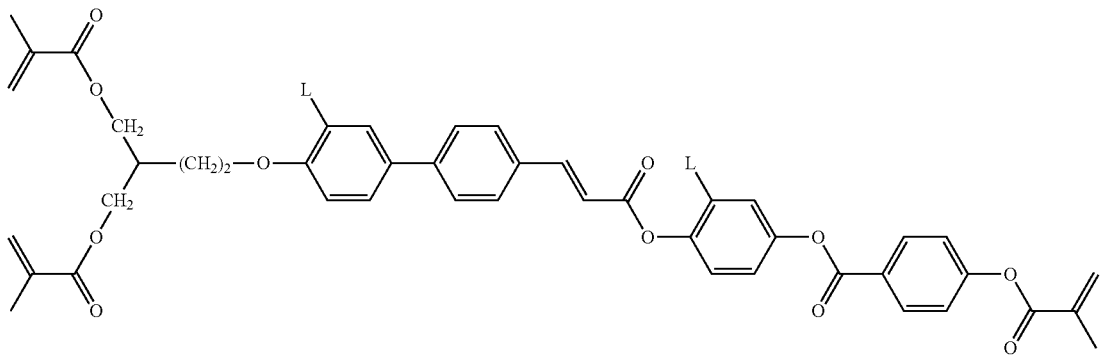
I-4-1a-7
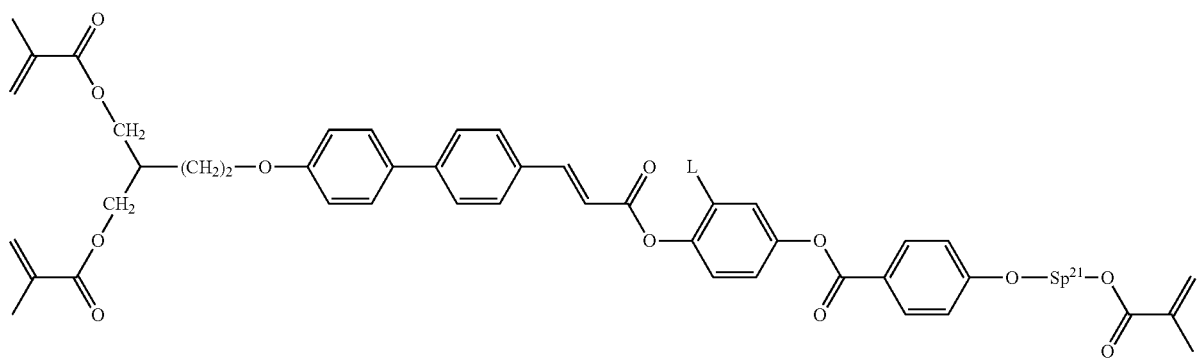
I-4-1a-8
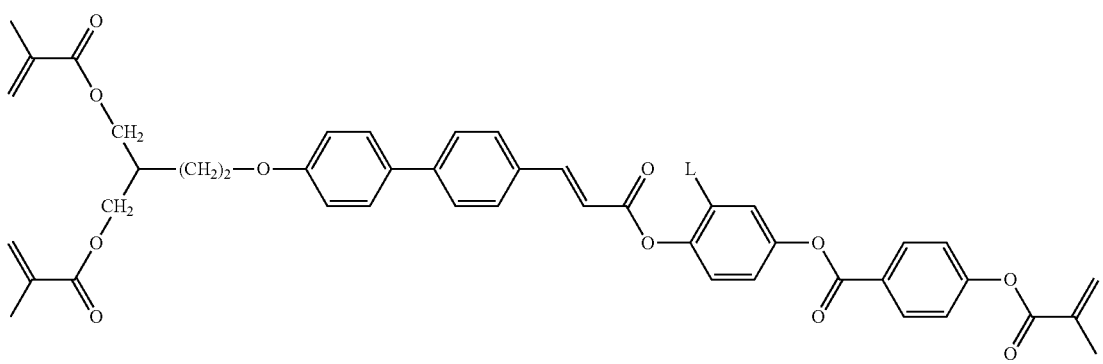
I-4-1a-9
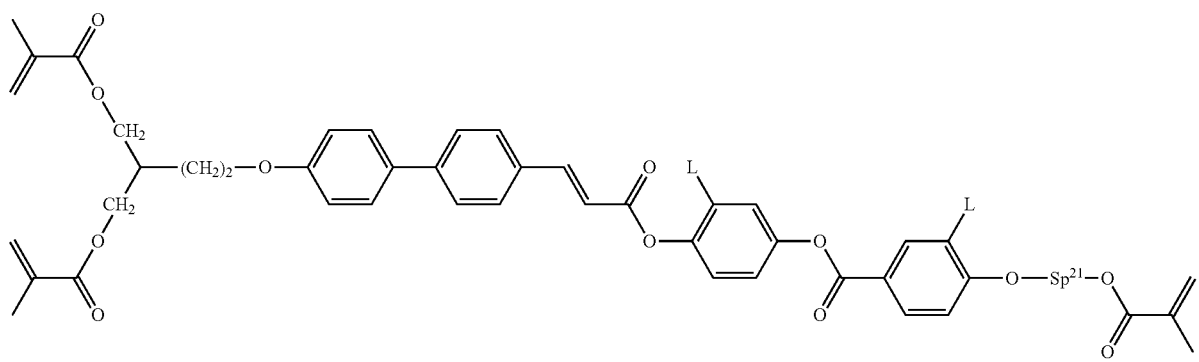

I-4-1a-10
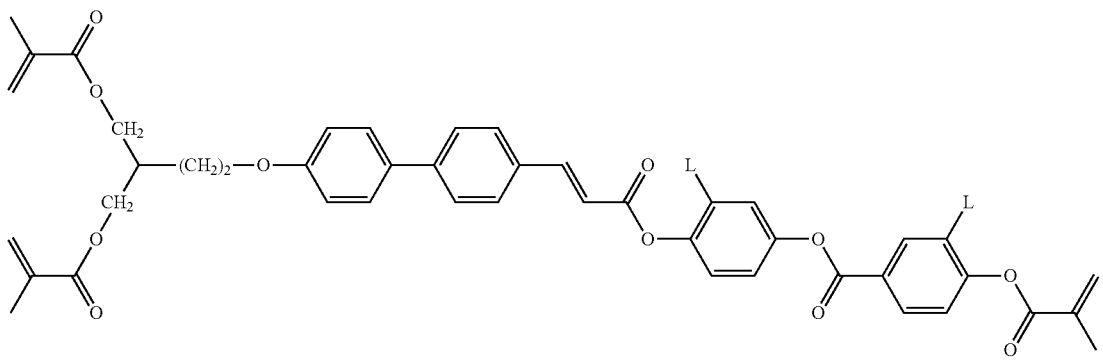
I-4-1a-11
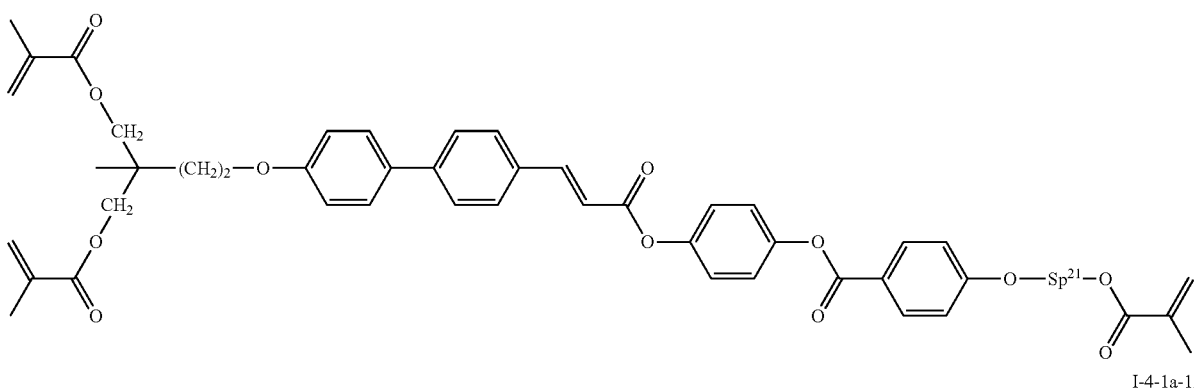
I-4-1a-12
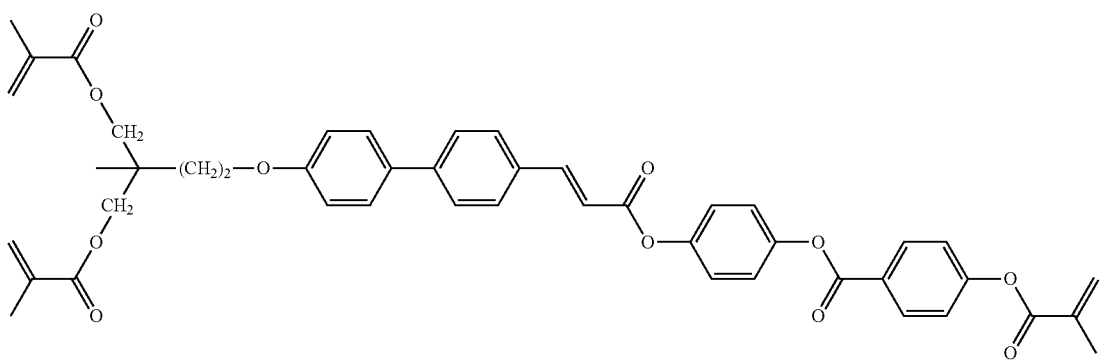
I-4-1a-13
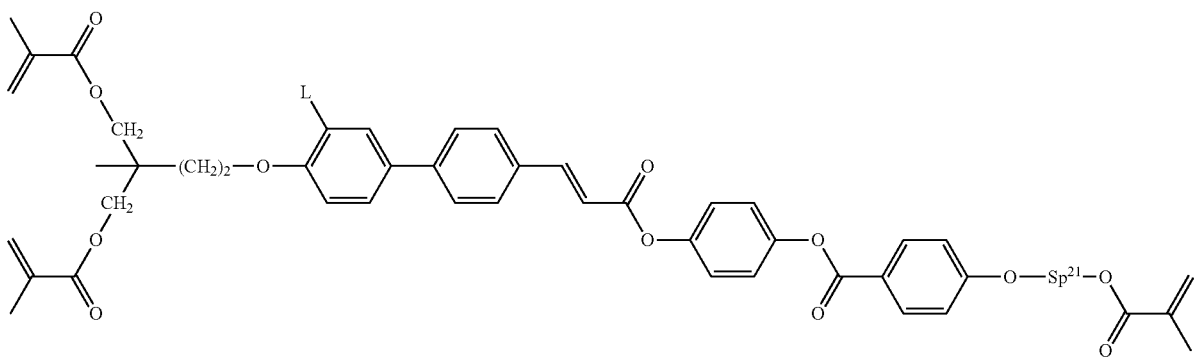

I-4-1a-14
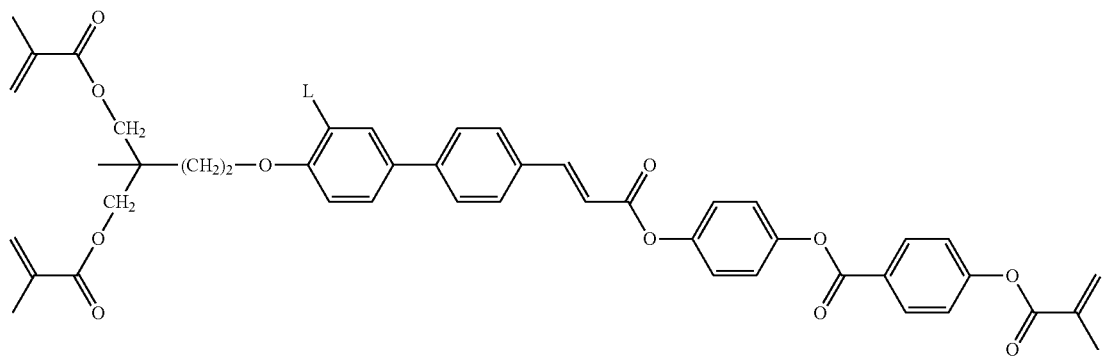
I-4-1a-15
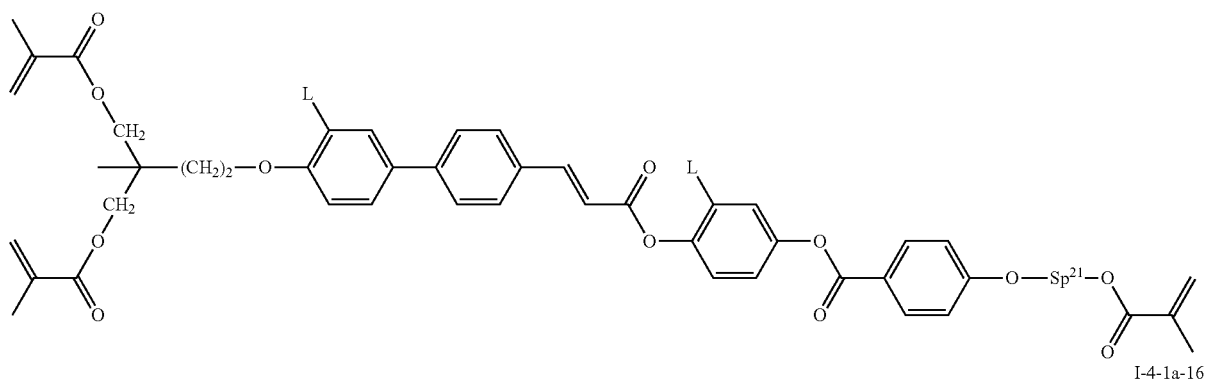
I-4-1a-16
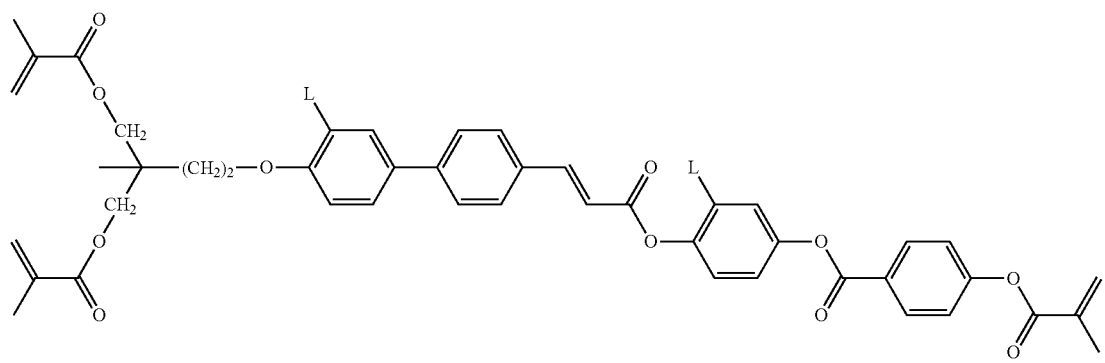
I-4-1a-17
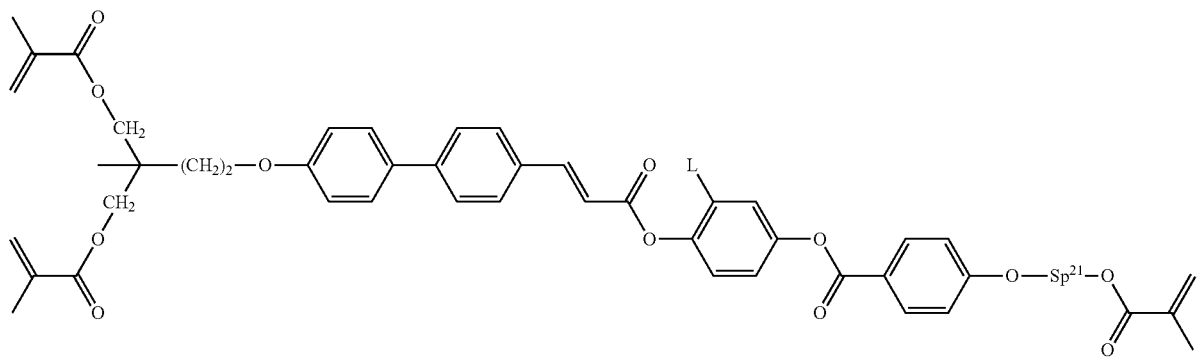

I-4-1a-18
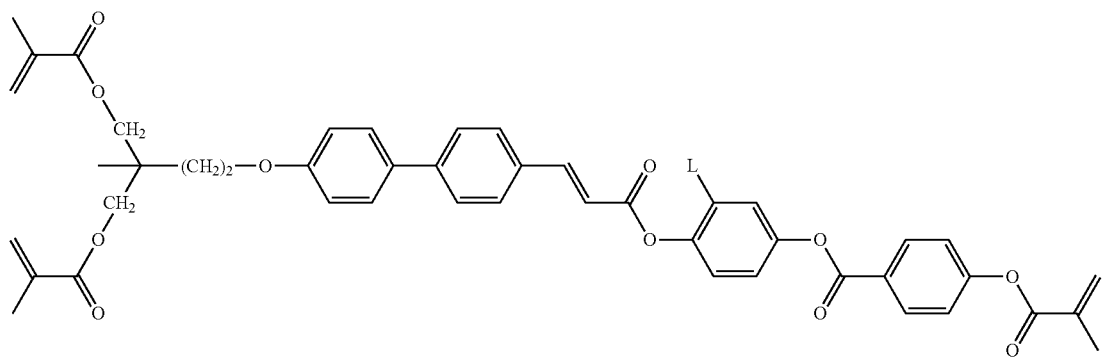
I-4-1a-19
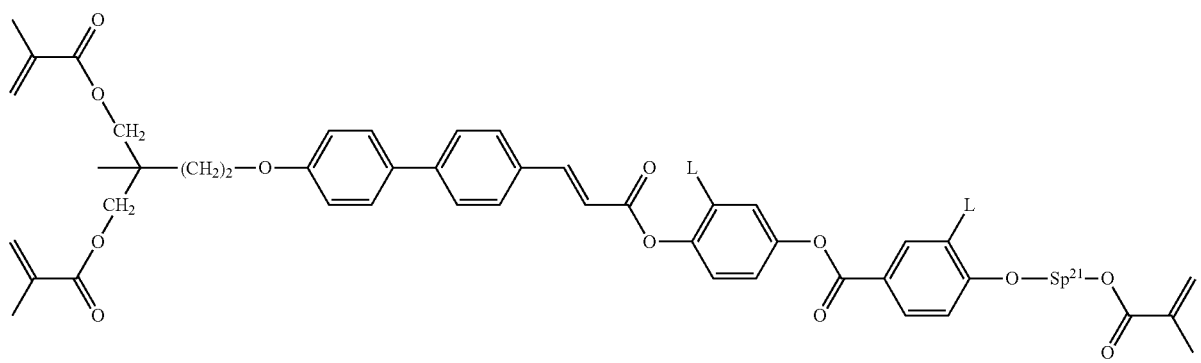
I-4-1a-20
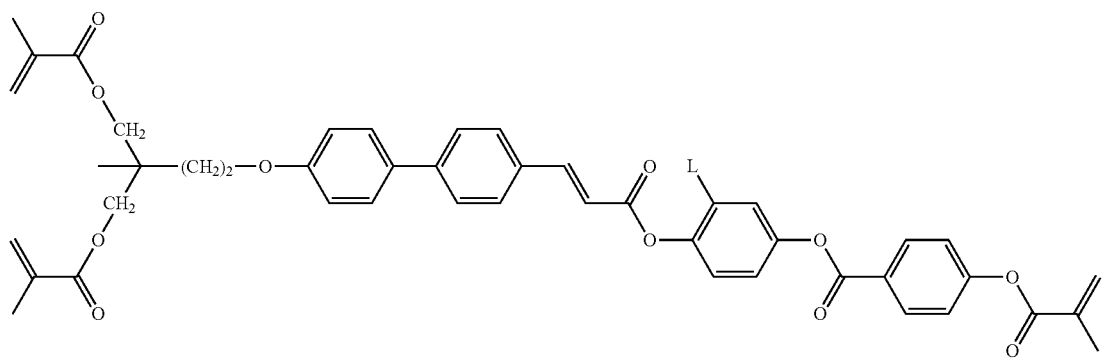

wherein Sp²¹ has one of the meanings as given above in formula I and L each and independently denotes F, Cl, OCH₃, COCH₃ or alkyl having 1 to 6 C Atoms, such as, methyl, ethyl, propyl, butyl, pentyl, hexyl, cyclopropyl, cylobutyl, cyclopentyl, or cyclohexyl or $X^{21}$-$Sp^{21}$-$R^{21}$.
Further preferred compounds of formulae I-5-1 are compounds of the following sub-formulae:
I-5-1a-1
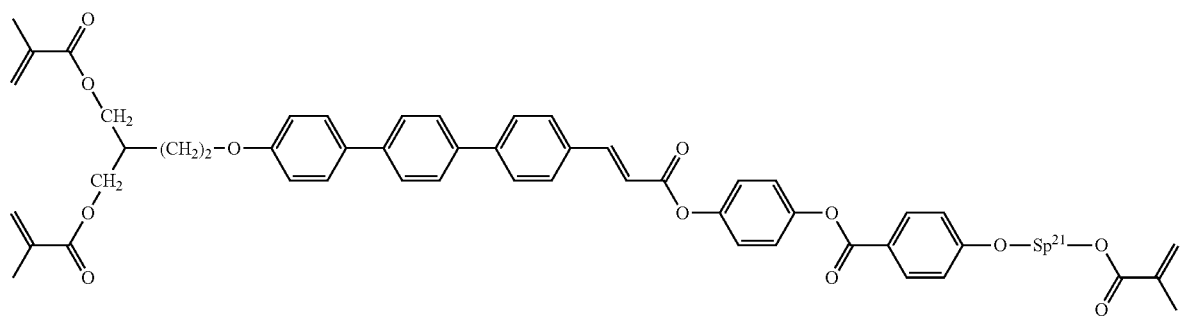
I-5-1a-2
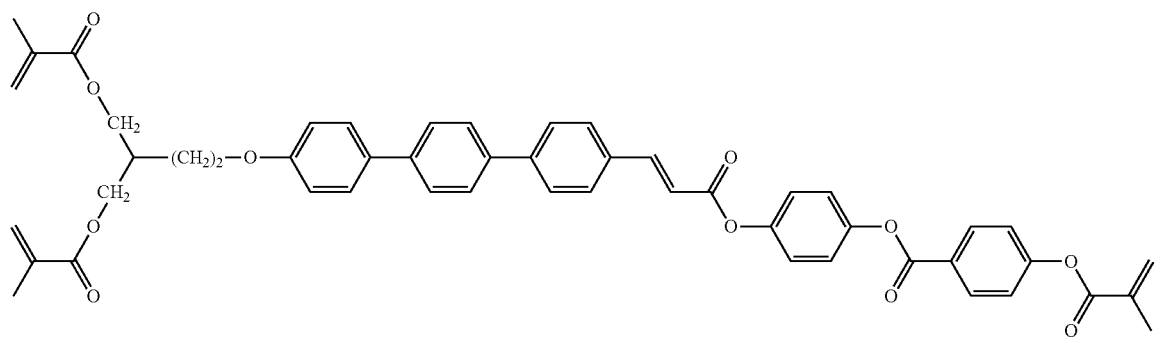
I-5-1a-3
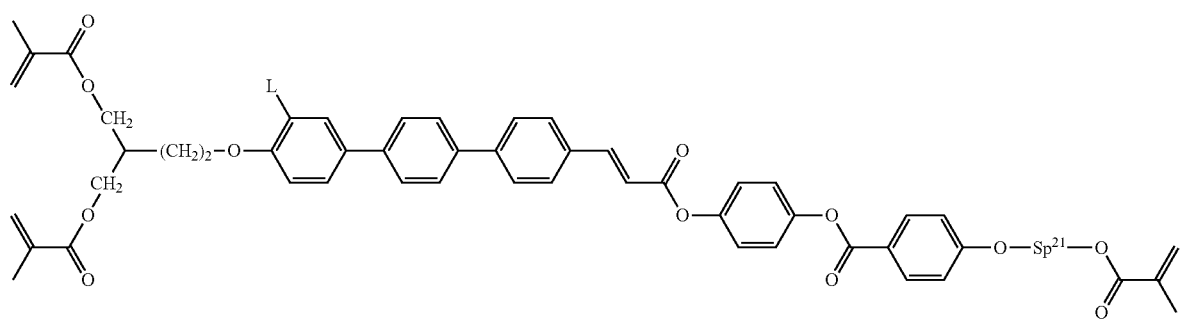
I-5-1a-4
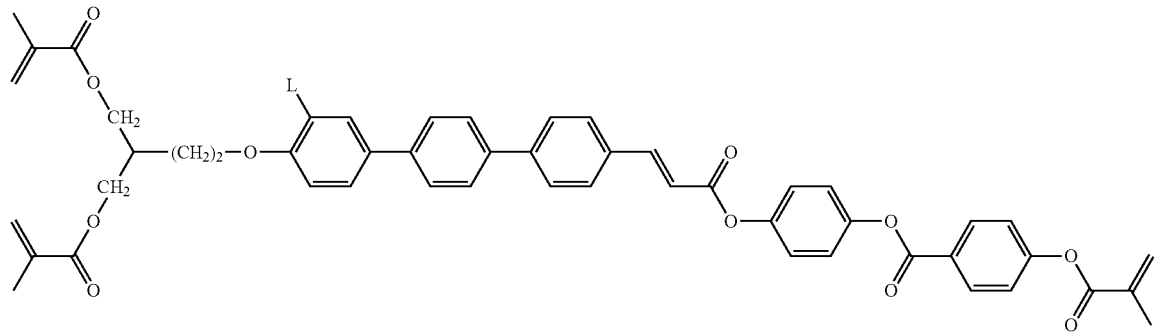

-continued
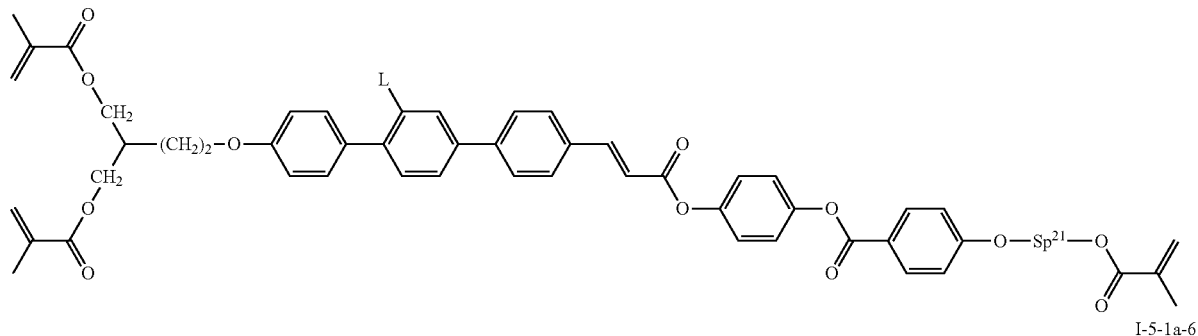
I-5-1a-5
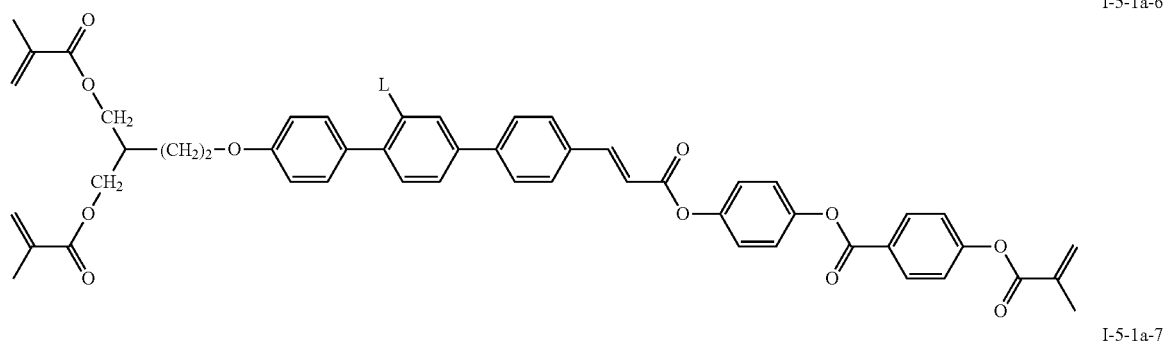
I-5-1a-6
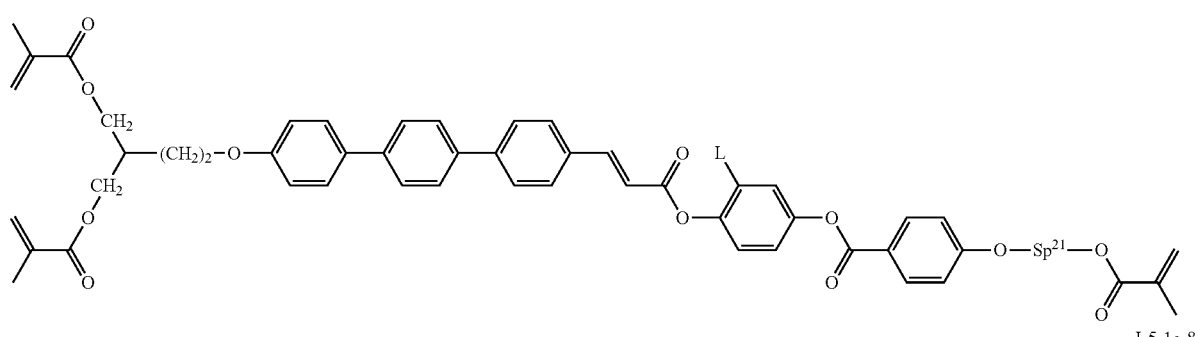
I-5-1a-7
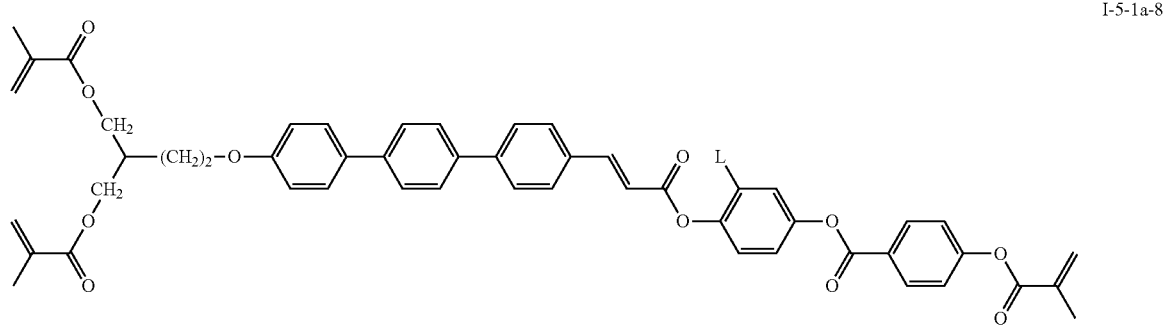
I-5-1a-8
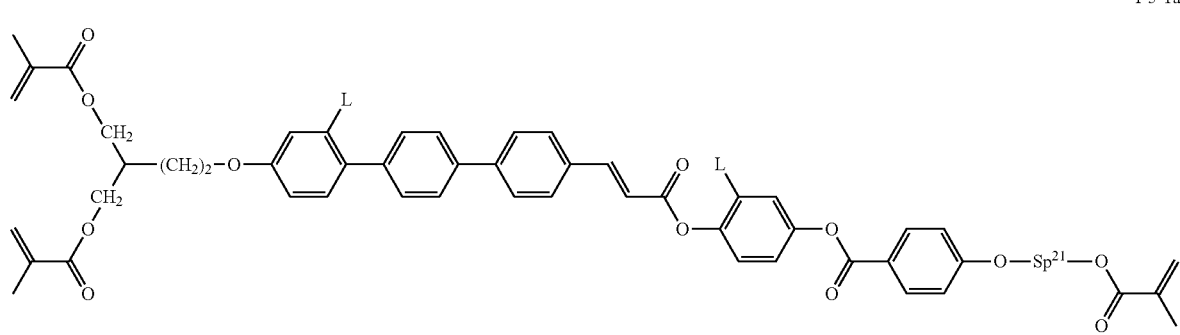
I-5-1a-9

I-5-1a-10
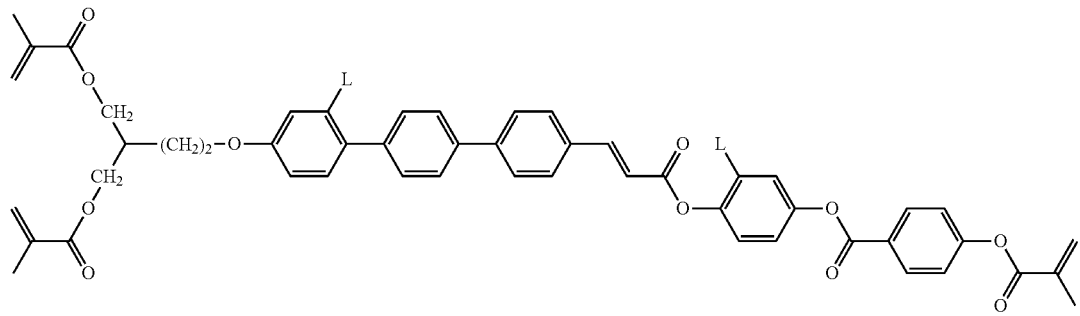
I-5-1a-11
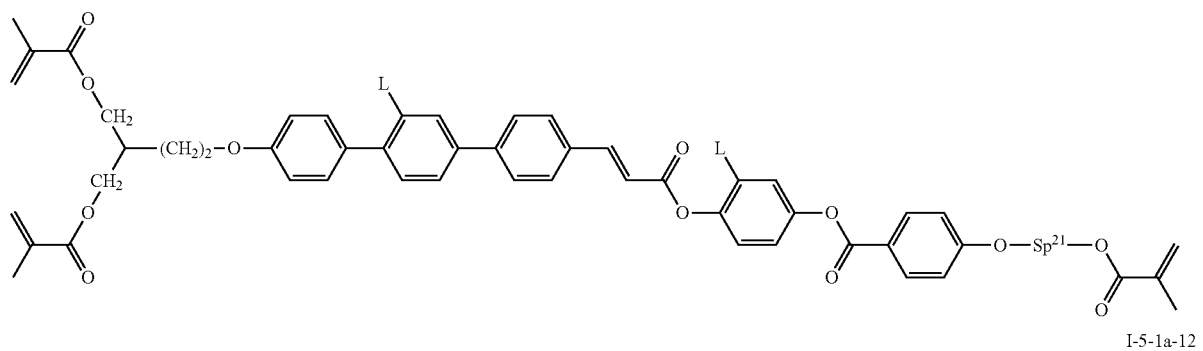
I-5-1a-12
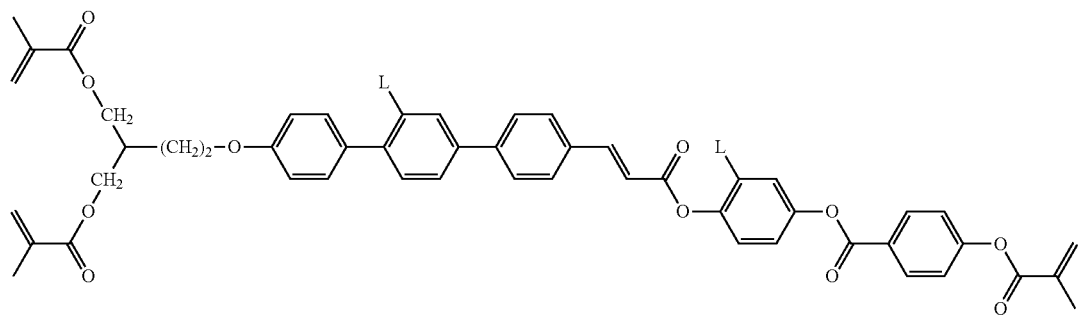
I-5-1a-13
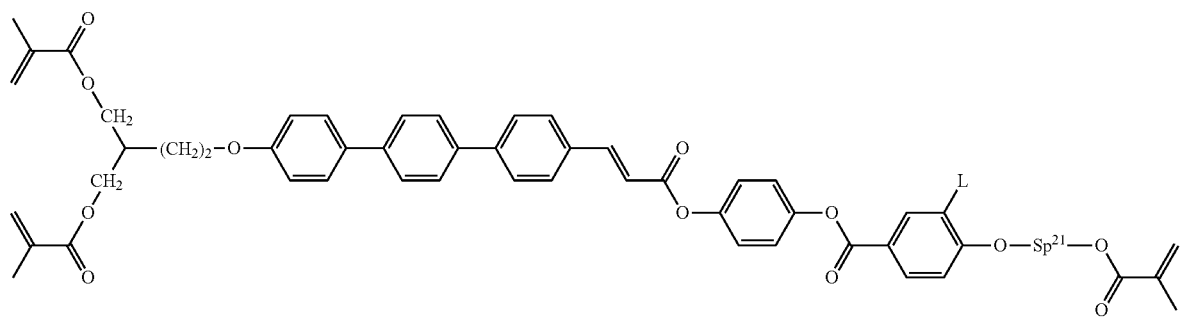

-continued
I-5-1a-14
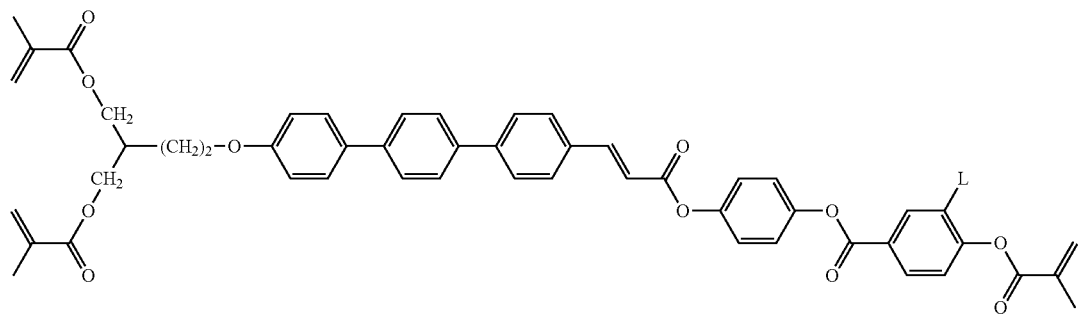
I-5-1a-15
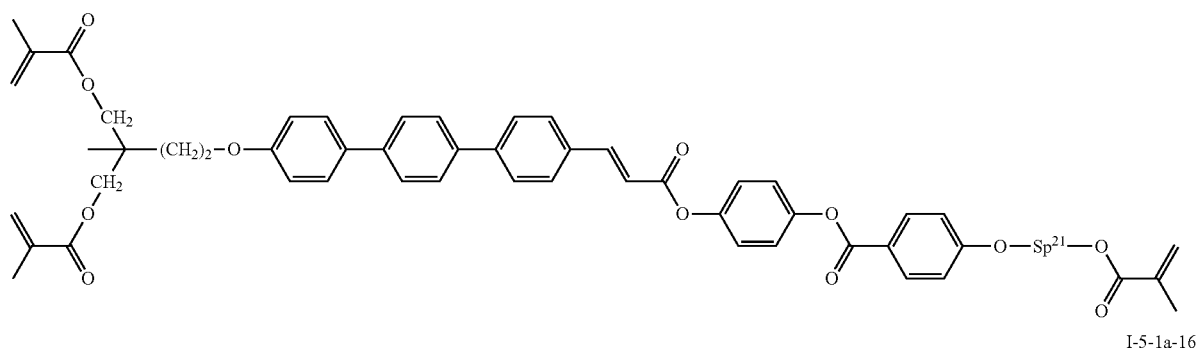
I-5-1a-16
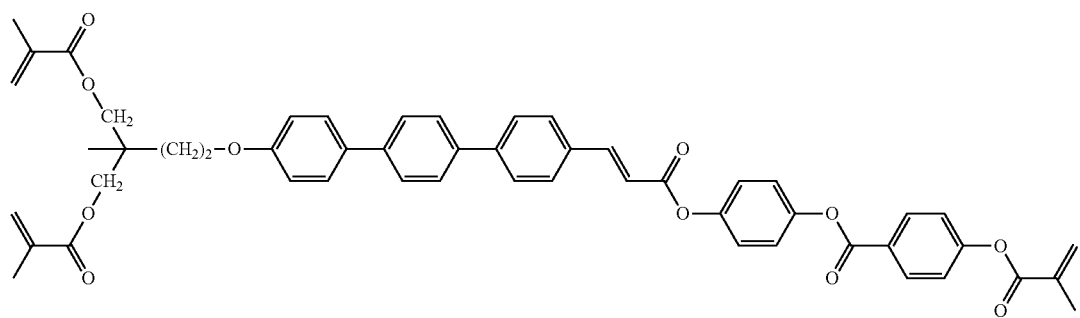
I-5-1a-17
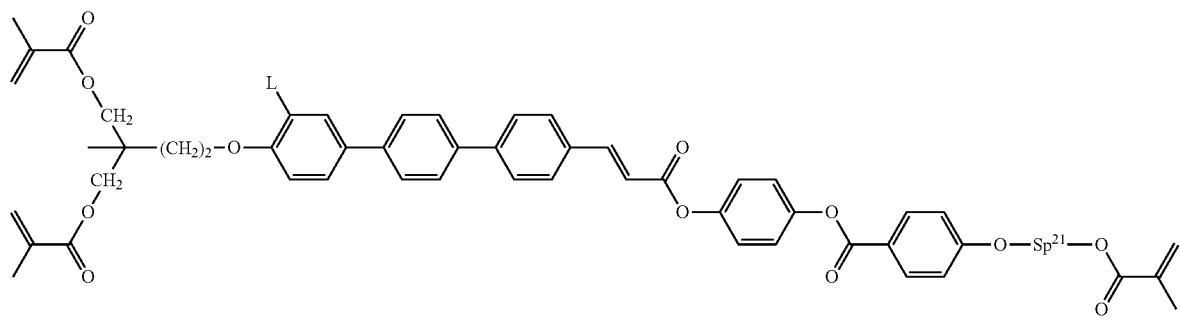

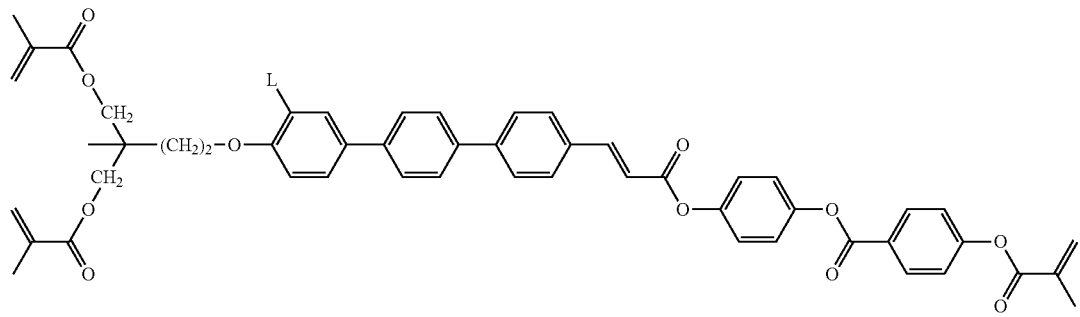
I-5-1a-18
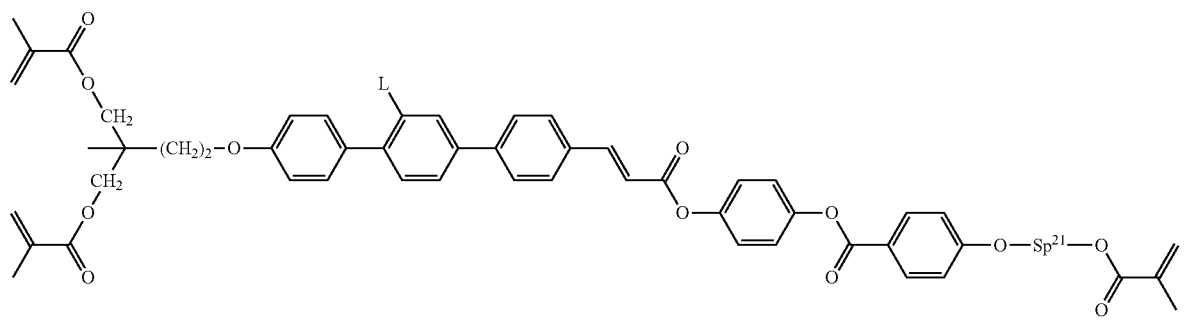
I-5-1a-19
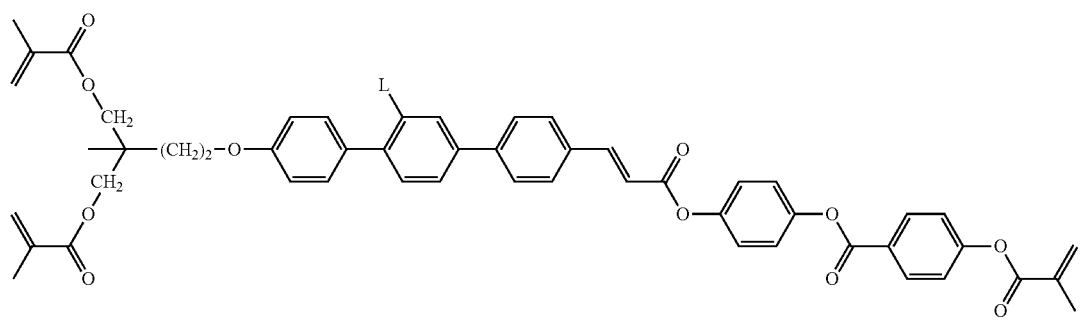
I-5-1a-20
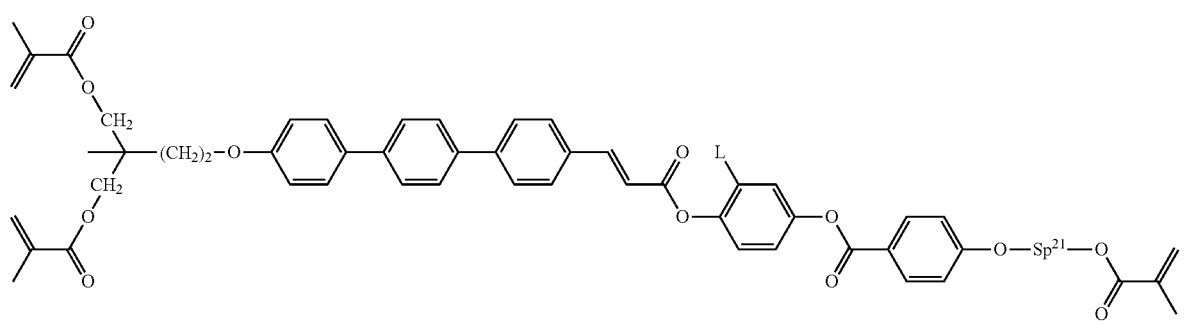
I-5-1a-21

I-5-1a-22
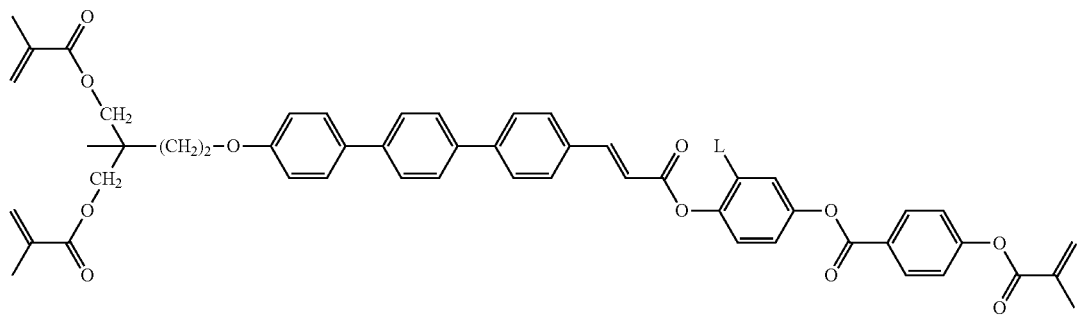
I-5-1a-23
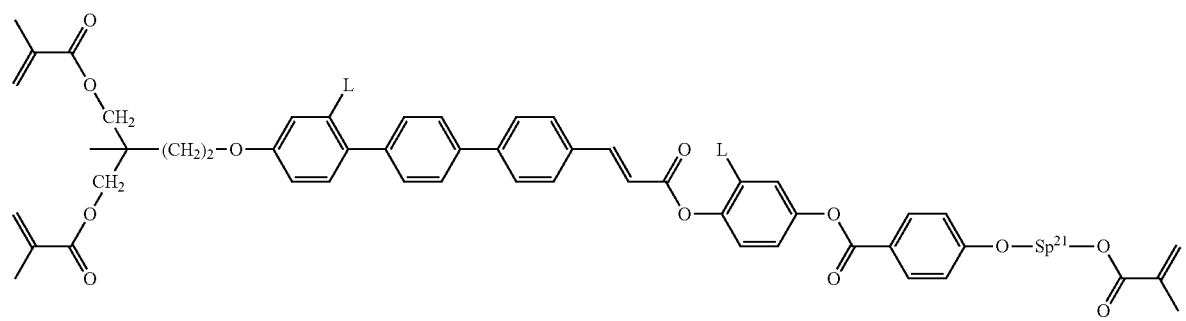
I-5-1a-24
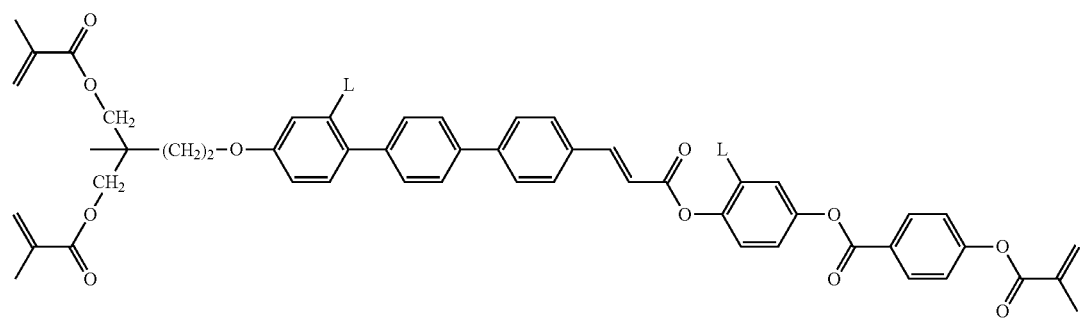
I-5-1a-25
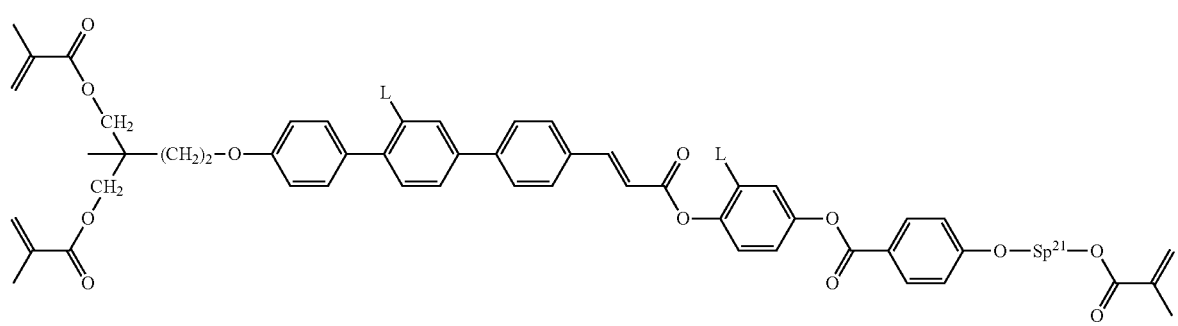

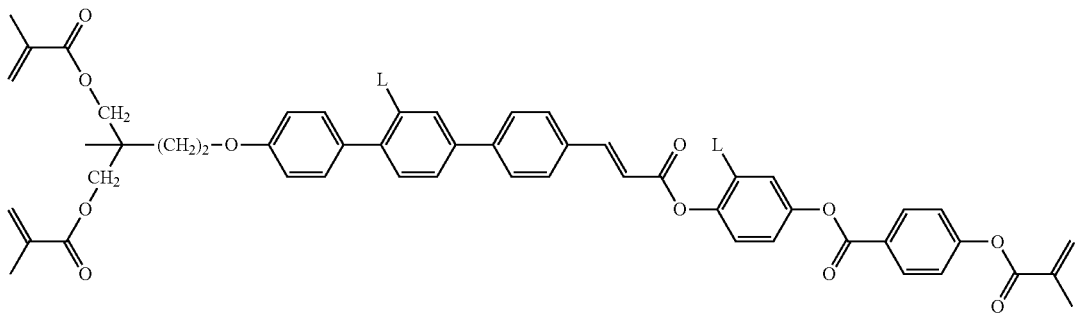

I-5-1a-26

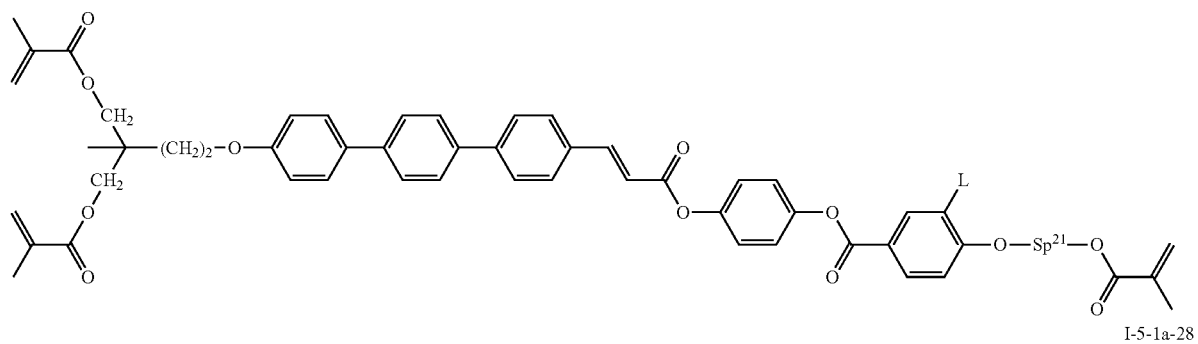

I-5-1a-27

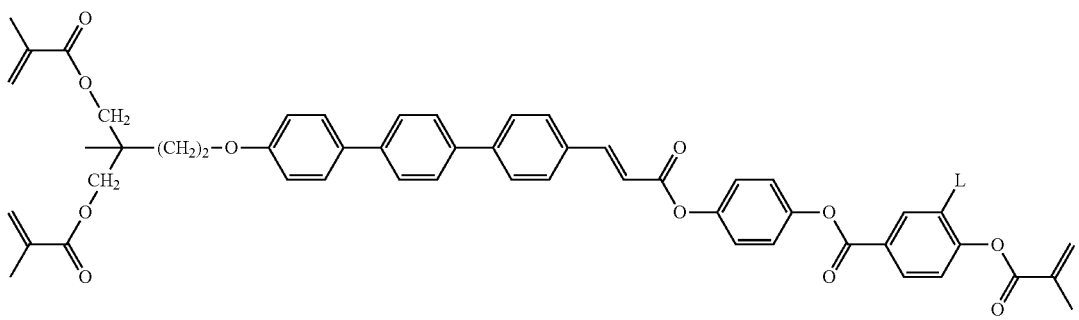

I-5-1a-28 wherein $Sp^{21}$ has one of the meanings as given above in formula I and L each and independently denotes F, Cl, $OCH_3$, $COCH_3$ or alkyl having 1 to 6 C Atoms, such as, methyl, ethyl, propyl, butyl, pentyl, hexyl, cyclopropyl, cylobutyl, cyclopentyl, or cyclohexyl or $X^{21}$-$Sp^{21}$-$R^{21}$.

Especially preferred compounds of formula I-4-1a-8 and I-4-1a-16 are compounds of the following sub-formula:

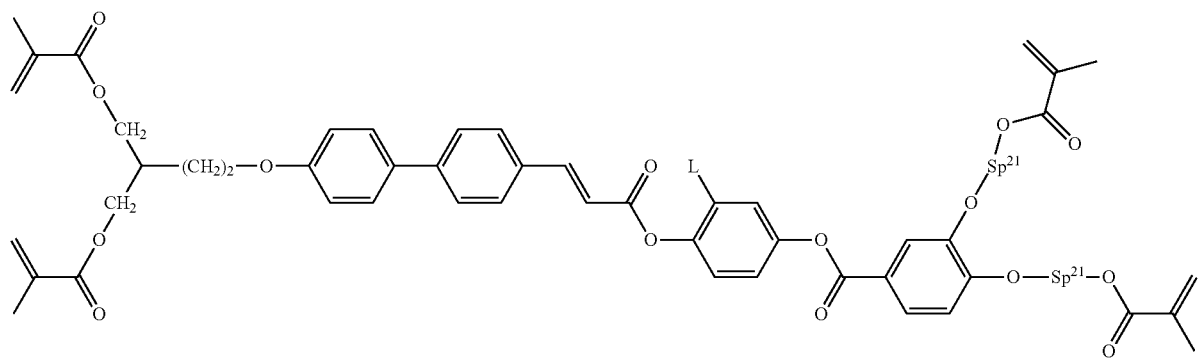

I-4-1a-8-1

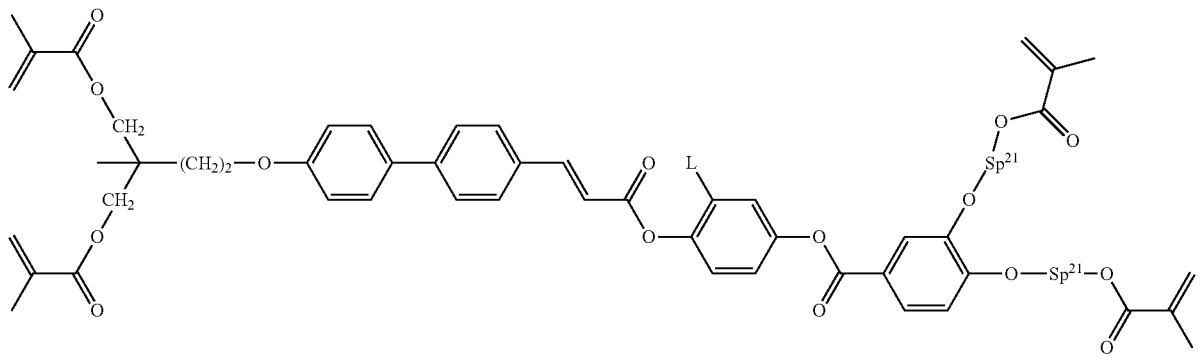

wherein $Sp^{21}$ has each and independently one of the meanings as given above in formula I, preferably both $Sp^{21}$ are identical, and L denotes F, Cl, $OCH_3$, $COCH_3$, or alkyl having 1 to 6 C Atoms, such as, methyl, ethyl, propyl, butyl, pentyl, hexyl, cyclopropyl, cylobutyl, cyclopentyl, or cyclohexyl.

The compounds of formula I and subformulae thereof are preferably synthesised according to or in analogy to the procedures described in WO 2017/102068 and JP 2006-6232809:

Preferred intermediate compounds (7) from which the compounds of formula I are preferably synthesised, are obtainable or obtained according to or in analogy to the procedure described in the following scheme:

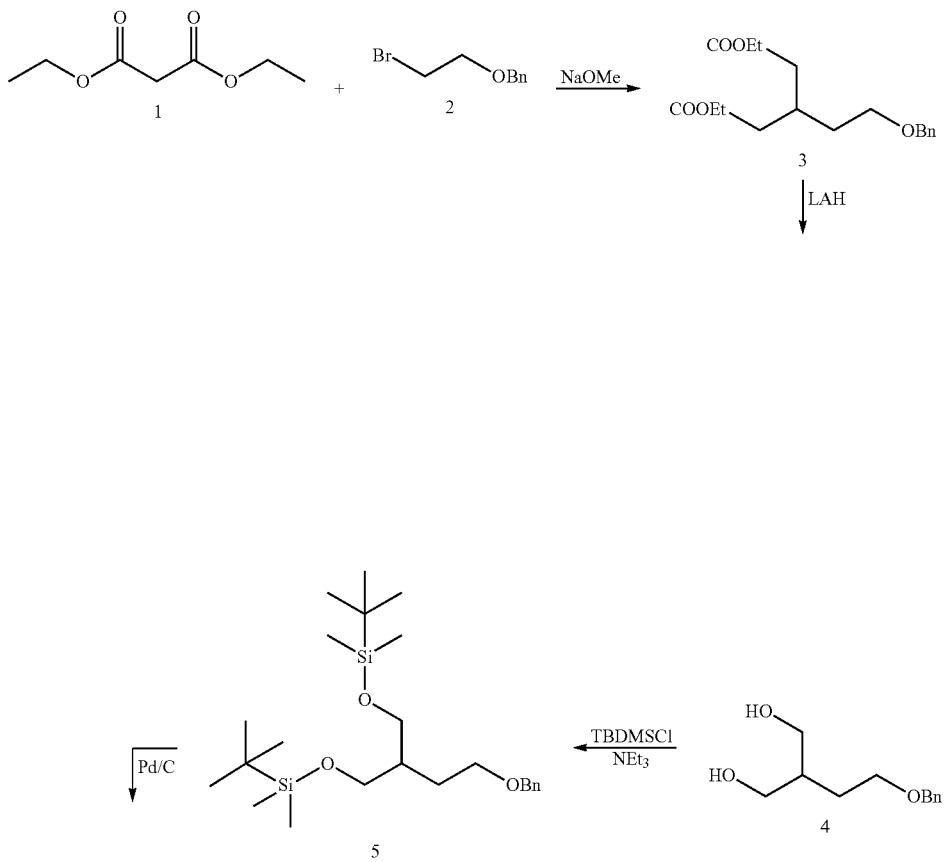

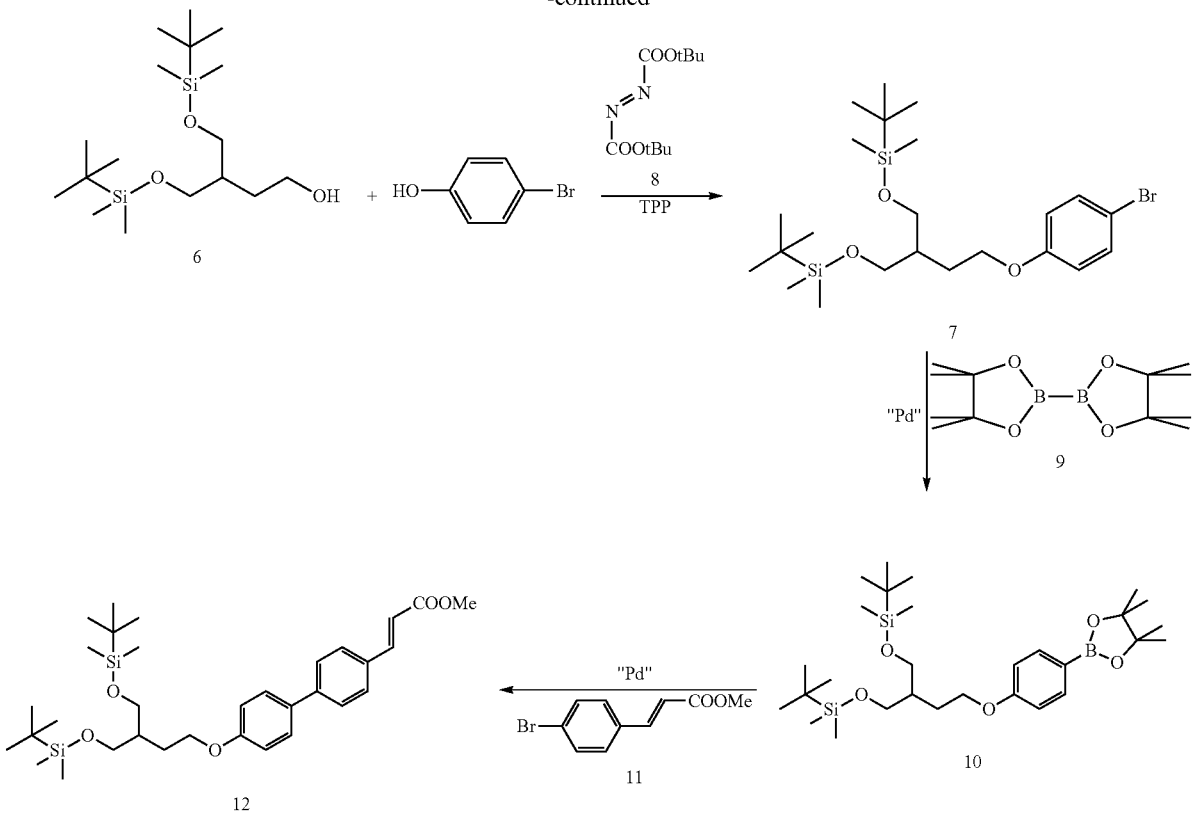

The compounds of formula I and subformulae thereof can be preferably utilized in a mixture comprising one or more mesogenic or liquid-crystalline compounds.

Therefore, the present invention relates to the use compounds of formula I and subformulae thereof in a liquid crystal mixture.

Further the present invention relates to liquid crystal mixtures comprising a photoalignment component A) comprising one or more photoreactive mesogens of formula I, and a liquid-crystalline component B), hereinafter also referred to as "LC host mixture", comprising one or more mesogenic or liquid-crystalline compounds.

The media according to the invention preferably comprise from 0.01 to 10%, particularly preferably from 0.05 to 5% and most preferably from 0.1 to 3% of component A) comprising compounds of formula I according to the invention.

The media preferably comprise one, two or three, more preferably one or two and most preferably one compound of the formula I according to the invention.

In a preferred embodiment component A) consists of compounds of formula I.

In a preferred embodiment, the LC-host mixture (component B) according to the present invention comprises one or more, preferably two or more, low-molecular-weight (i.e. monomeric or unpolymerized) compounds. The latter are stable or unreactive with respect to a polymerisation reaction or photoalignment under the conditions used for the polymerisation of the polymerizable compounds or photoalignment of the photoreactive mesogen of formula I.

In principle, a suitable host mixture is any dielectrically negative or positive LC mixture which is suitable for use in conventional VA, IPS or FFS displays.

Suitable LC mixtures are known to the person skilled in the art and are described in the literature. LC media for VA displays having negative dielectric anisotropy are described in for example EP 1 378 557 A1.

Suitable LC mixtures having positive dielectric anisotropy which are suitable for LCDs and especially for IPS displays are known, for example, from JP 07-181 439 (A), EP 0 667 555, EP 0 673 986, DE 195 09 410, DE 195 28 106, DE 195 28 107, WO 96/23 851, WO 96/28 521 and WO2012/079676.

Preferred embodiments of the liquid-crystalline medium having negative or positive dielectric anisotropy according to the invention are indicated below and explained in more detail by means of the working examples.

The LC host mixture is preferably a nematic LC mixture, and preferably does not have a chiral LC phase.

In a preferred embodiment of the present invention the LC medium contains an LC host mixture with negative dielectric anisotropy. Preferred embodiments of such an LC medium, and the corresponding LC host mixture, are those of sections a)-z) below:

a) LC medium which comprises one or more compounds of the formulae CY and/or PY:

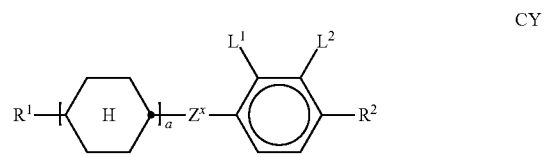

CY

PY

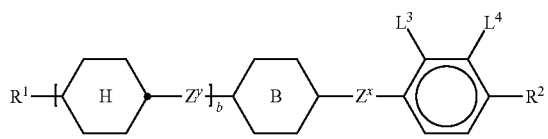

wherein
a denotes 1 or 2,
b denotes 0 or 1,

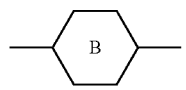

denotes

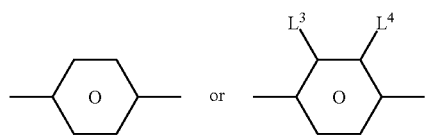

R[1] and R[2] each, independently of one another, denote alkyl having 1 to 12 C atoms, where, in addition, one or two non-adjacent CH$_2$ groups may be replaced by —O—, —CH=CH—, —CO—, —OCO— or —COO— in such a way that O atoms are not linked directly to one another, preferably alkyl or alkoxy having 1 to 6 C atoms, Z$^x$ and Z$^y$ each, independently of one another, denote —CH$_2$CH$_2$—, —CH=CH—, —CF$_2$O—, —OCF$_2$—, —CH$_2$O—, —OCH$_2$—, —CO—O—, —O—CO—, —C$_2$F$_4$—, —CF=CF—, —CH=CH—CH$_2$O— or a single bond, preferably a single bond, L$^{1-4}$ each, independently of one another, denote F, Cl, OCF$_3$, CF$_3$, CH$_3$, CH$_2$F, CHF$_2$.

Preferably, both L$^1$ and L$^2$ denote F or one of L$^1$ and L$^2$ denotes F and the other denotes Cl, or both L$^3$ and L$^4$ denote F or one of L$^3$ and L$^4$ denotes F and the other denotes Cl.

The compounds of the formula CY are preferably selected from the group consisting of the following sub-formulae:

CY1
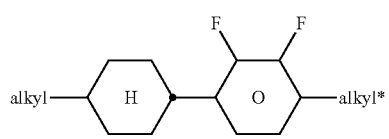

CY2
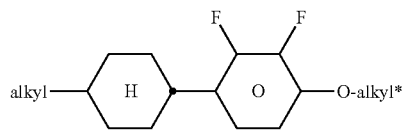

CY3
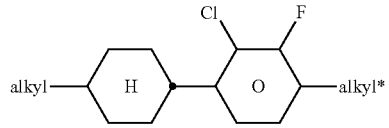

CY4
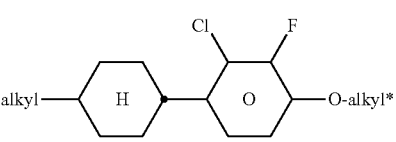

CY5
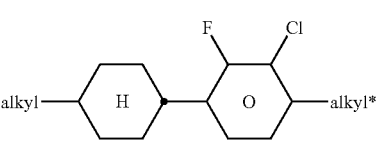

CY6
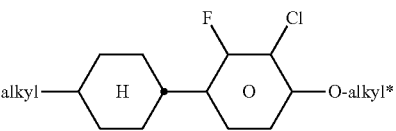

CY7
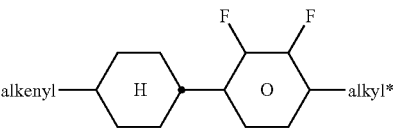

CY8
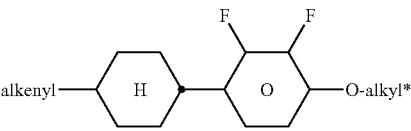

CY9
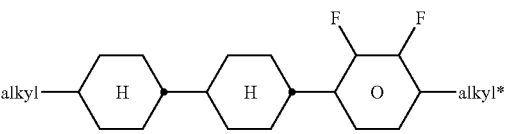

CY10
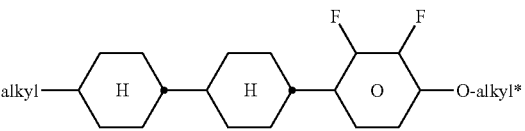

CY11
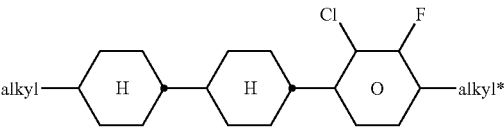

CY12
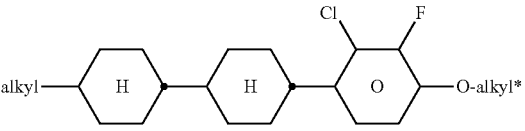

CY13
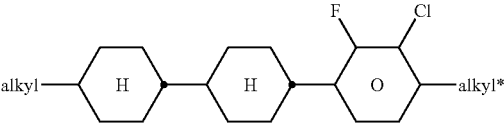

CY14
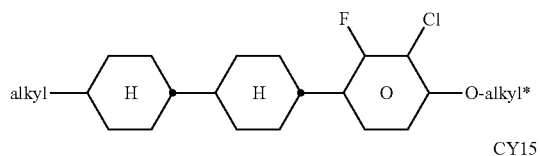
CY15
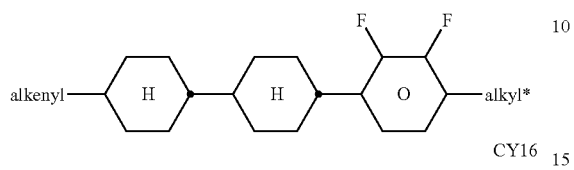
CY16
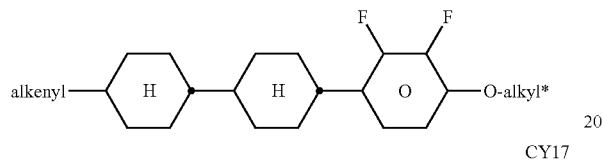
CY17
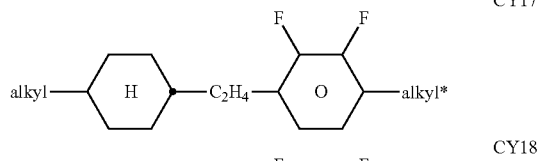
CY18
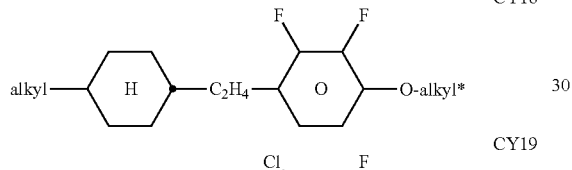
CY19
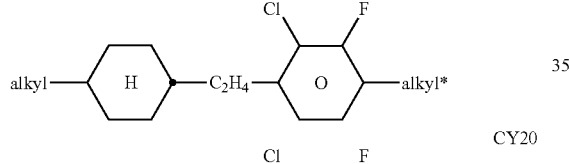
CY20
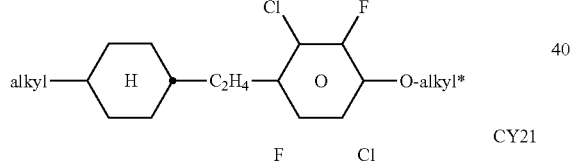
CY21
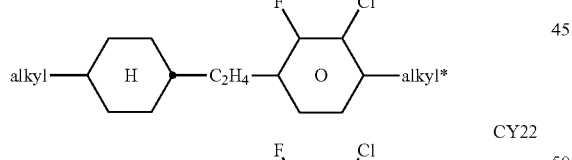
CY22
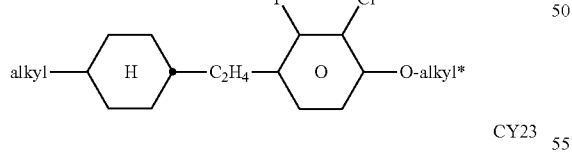
CY23
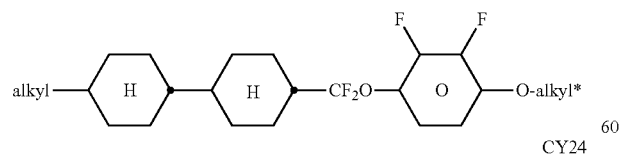
CY24
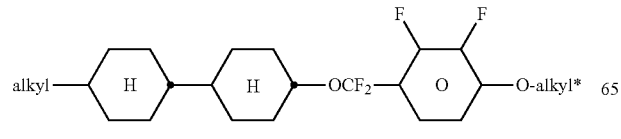

CY25
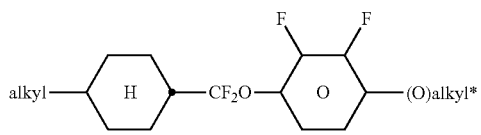
CY26
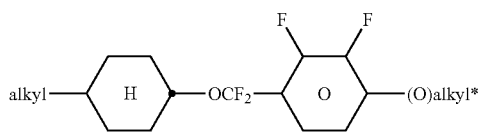
CY27
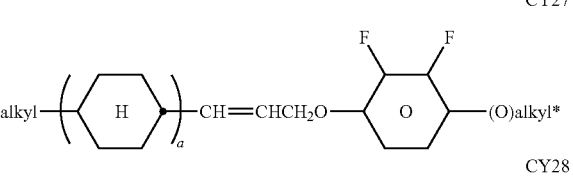
CY28
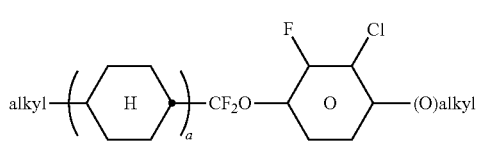
CY29
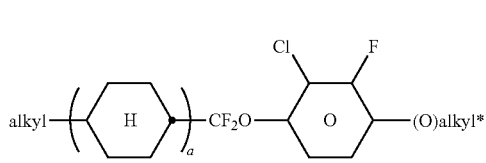
CY30
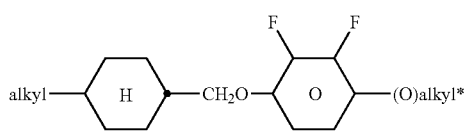
CY31
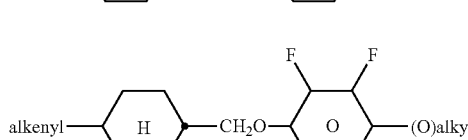
CY32
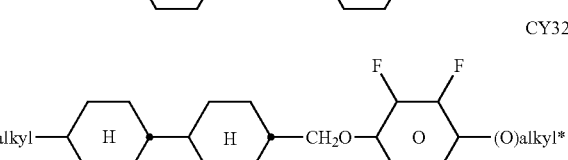
CY33
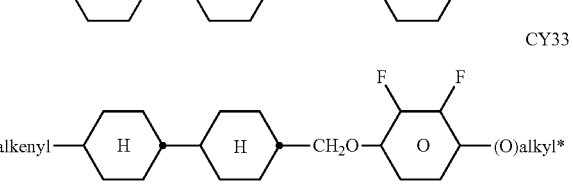

wherein a denotes 1 or 2, alkyl and alkyl* each, independently of one another, denote a straight-chain alkyl radical having 1-6 C atoms, and alkenyl denotes a straight-chain alkenyl radical having 2-6 C atoms, and (O) denotes an oxygen atom or a single bond. Alkenyl preferably denotes $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

The compounds of the formula PY are preferably selected from the group consisting of the following sub-formulae:
PY1
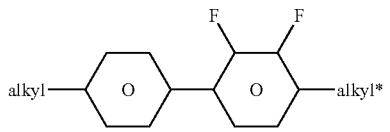
PY2
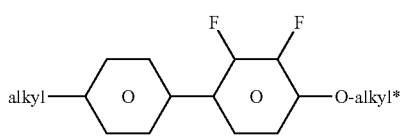
PY3
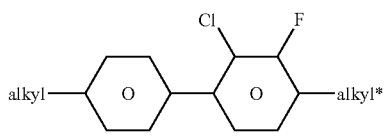
PY4
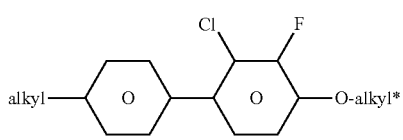
PY5
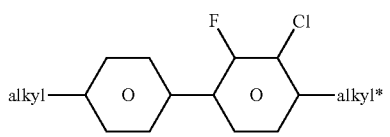
PY6
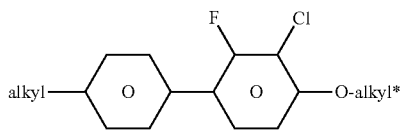
PY7
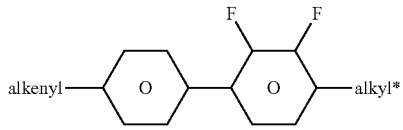
PY8
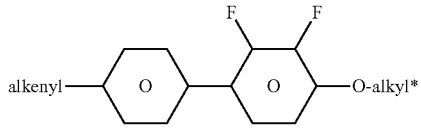
PY9
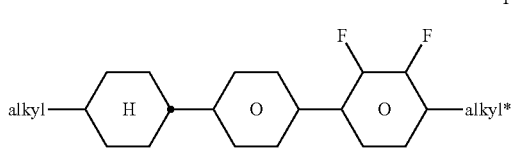
PY10
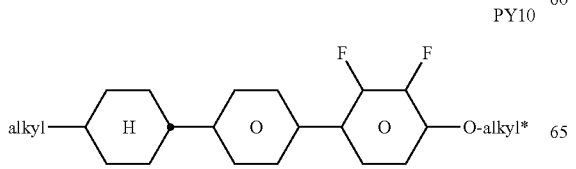
PY11
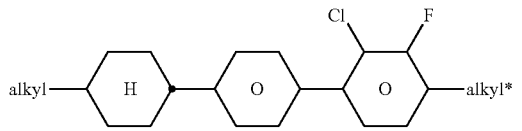
PY12
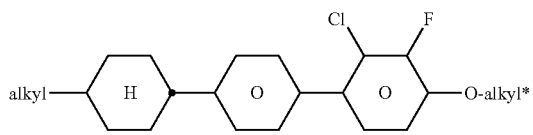
PY13
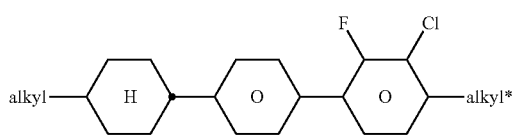
PY14
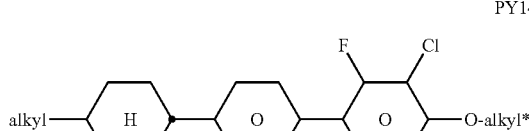
PY15
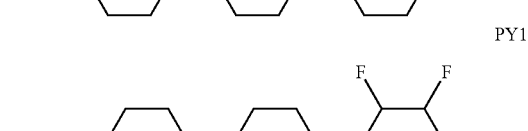
PY16
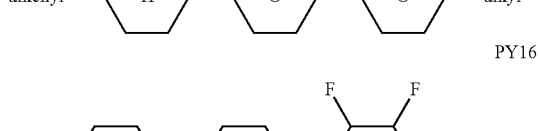
PY17
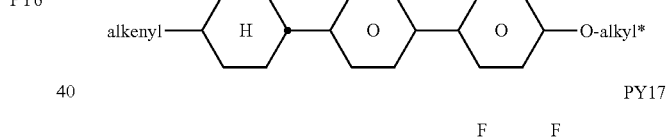
PY18
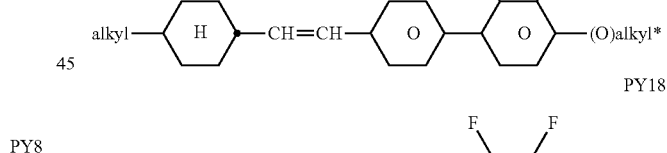
PY19
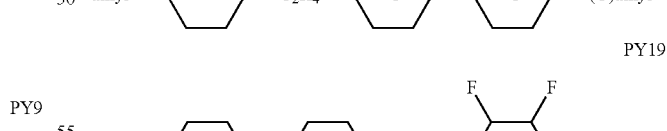
PY20
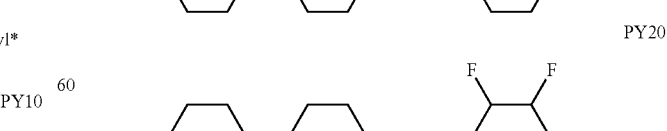
wherein alkyl and alkyl* each, independently of one another, denote a straight-chain alkyl radical having 1-6 C atoms, and alkenyl denotes a straight-chain alkenyl radical having 2-6 C atoms, and (O) denotes an oxygen atom or a single bond. Alkenyl preferably denotes $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

b) LC medium which additionally comprises one or more compounds of the following formula:

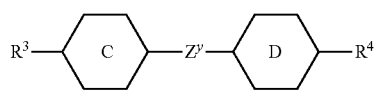
ZK in which the individual radicals have the following meanings:

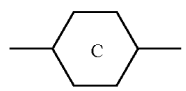

denotes

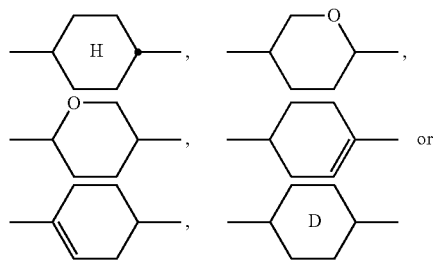

denotes

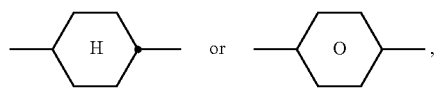

$R^3$ and $R^4$ each, independently of one another, denote alkyl having 1 to 12 C atoms, in which, in addition, one or two non-adjacent $CH_2$ groups may be replaced by $-O-$, $-CH=CH-$, $-CO-$, $-O-CO-$ or $-CO-O-$ in such a way that O atoms are not linked directly to one another, $Z^y$ denotes $-CH_2CH_2-$, $-CH=CH-$, $-CF_2O-$, $-OCF_2-$, $-CH_2O-$, $-OCH_2-$, $-CO-O-$, $-O-CO-$, $-C_2F_4-$, $-CF=CF-$, $-CH=CH-CH_2O-$ or a single bond, preferably a single bond.

The compounds of the formula ZK are preferably selected from the group consisting of the following sub-formulae:

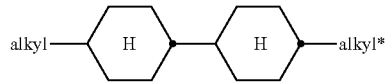
ZK1

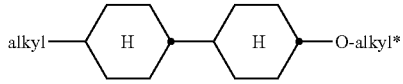
ZK2

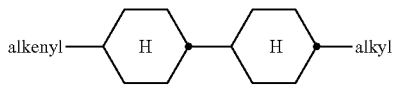
ZK3

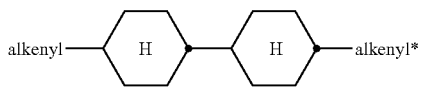
ZK4

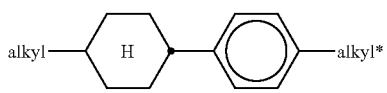
ZK5

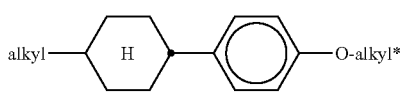
ZK6

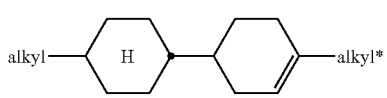
ZK7

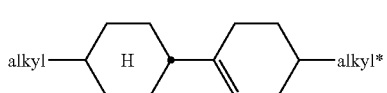
ZK8

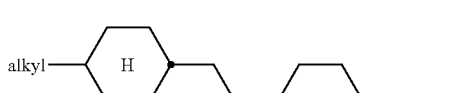
ZK9

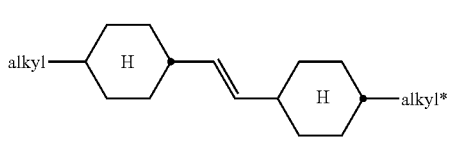
ZK10 in which alkyl and alkyl* each, independently of one another, denote a straight-chain alkyl radical having 1-6 C atoms, and alkenyl denotes a straight-chain alkenyl radical having 2-6 C atoms. Alkenyl preferably denotes $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

Especially preferred are compounds of formula ZK1 and ZK3.

Particularly preferred compounds of formula ZK are selected from the following sub-formulae:

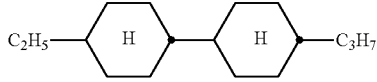
ZK1a

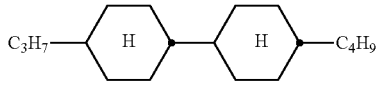
ZK1b

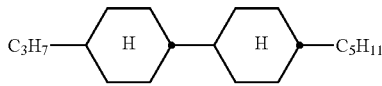
ZK1c

-continued

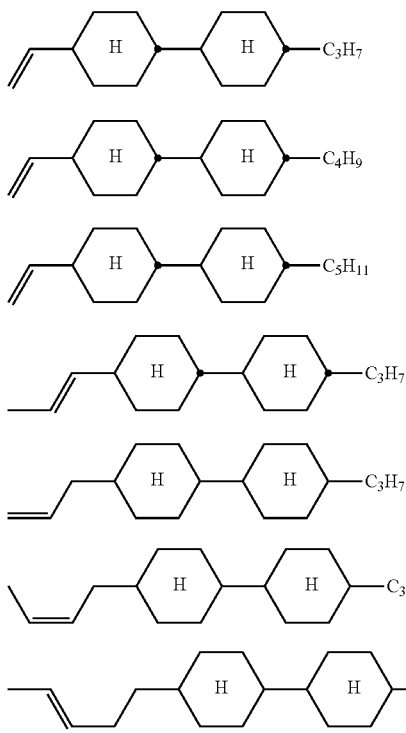

wherein the propyl, butyl and pentyl groups are straight-chain groups.

Most preferred are compounds of formula ZK1a and ZK3a.

c) LC medium which additionally comprises one or more compounds of the following formula:

DK in which the individual radicals on each occurrence, identically or differently, have the following meanings:

R⁵ and R⁶ each, independently of one another, denote alkyl having 1 to 12 C atoms, where, in addition, one or two non-adjacent CH₂ groups may be replaced by —O—, —CH=CH—, —CO—, —OCO— or —COO— in such a way that O atoms are not linked directly to one another, preferably alkyl or alkoxy having 1 to 6 C atoms,

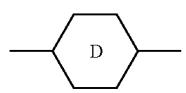

denotes

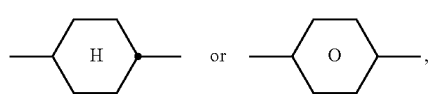

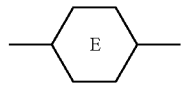
ZK3a denotes

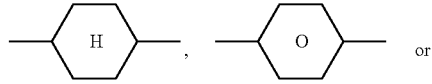

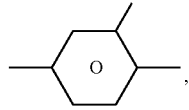

and e denotes 1 or 2.

The compounds of the formula DK are preferably selected from the group consisting of the following sub-formulae:

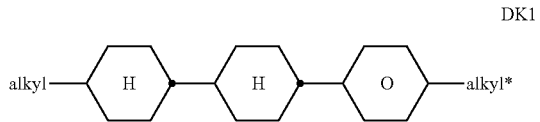
DK1

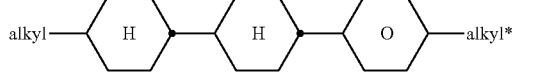
DK2

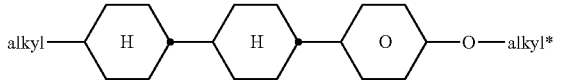
DK3

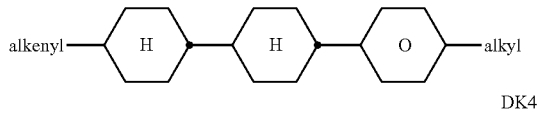
DK4

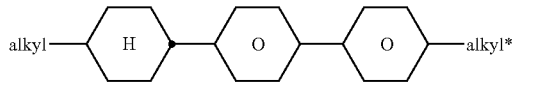
DK5

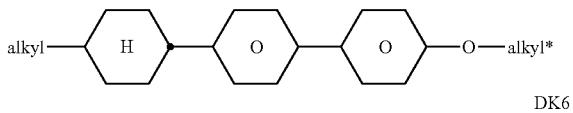
DK6

DK7

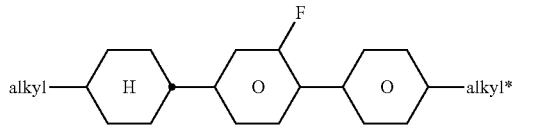
DK8

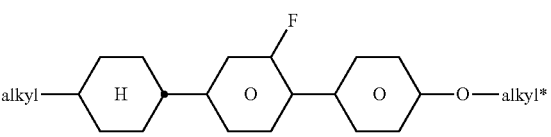

-continued

DK9
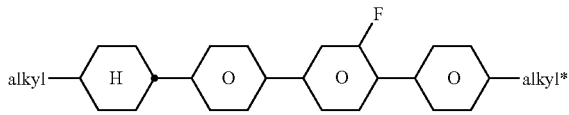

DK10
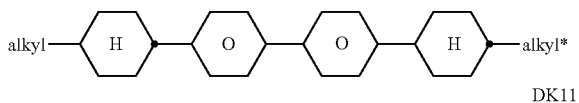

DK11
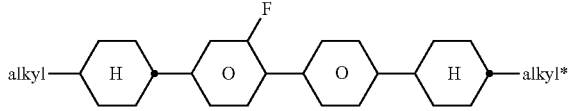

DK12
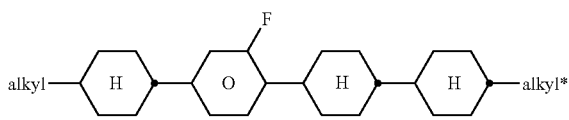

in which alkyl and alkyl* each, independently of one another, denote a straight-chain alkyl radical having 1-6 C atoms, and alkenyl denotes a straight-chain alkenyl radical having 2-6 C atoms. Alkenyl preferably denotes CH$_2$=CH—, CH$_2$=CHCH$_2$CH$_2$—, CH$_3$—CH=CH—, CH$_3$—CH$_2$—CH=CH—, CH$_3$—(CH$_2$)$_2$—CH=CH—, CH$_3$—(CH$_2$)$_3$—CH=CH— or CH$_3$—CH=CH—(CH$_2$)$_2$—.

d) LC medium which additionally comprises one or more compounds of the following formula:

LY
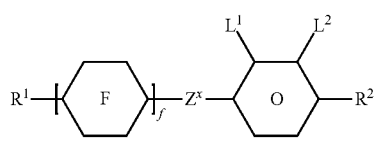

in which the individual radicals have the following meanings:

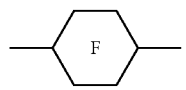

denotes

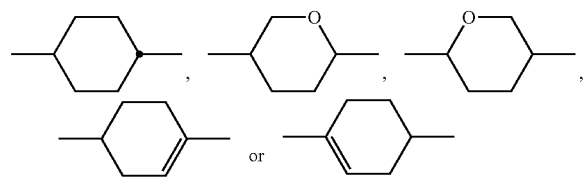

with at least one ring F being different from cyclohexylene,
f denotes 1 or 2,
R$^1$ and R$^2$ each, independently of one another, denote alkyl having 1 to 12 C atoms, where, in addition, one or two non-adjacent CH$_2$ groups may be replaced by —O—, —CH=CH—, —CO—, —OCO— or —COO— in such a way that O atoms are not linked directly to one another,
Z$^x$ denotes —CH$_2$CH$_2$—, —CH=CH—, —CF$_2$O—, —OCF$_2$—, —CH$_2$O—, —OCH$_2$—, —CO—O—, —O—CO—, —C$_2$F$_4$—, —CF=CF—, —CH=CH—CH$_2$O— or a single bond, preferably a single bond,
L$^1$ and L$^2$ each, independently of one another, denote F, Cl, OCF$_3$, CF$_3$, CH$_3$, CH$_2$F, CHF$_2$.

Preferably, both radicals L$^1$ and L$^2$ denote F or one of the radicals L$^1$ and L$^2$ denotes F and the other denotes Cl.

The compounds of the formula LY are preferably selected from the group consisting of the following sub-formulae:

LY1
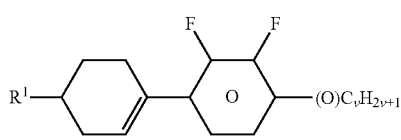

LY2
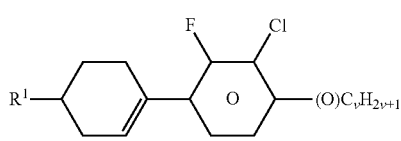

LY3
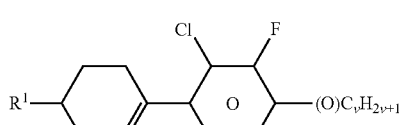

LY4
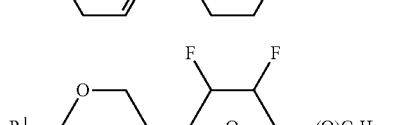

LY5
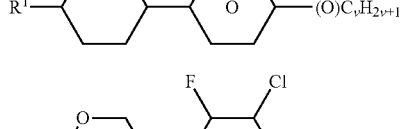

LY6
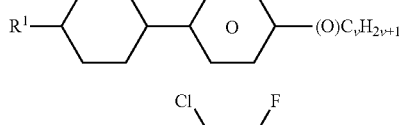

LY7
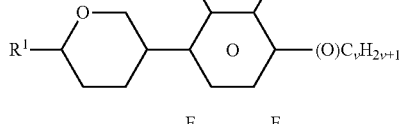

LY8
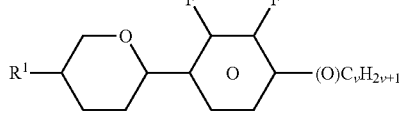

LY9
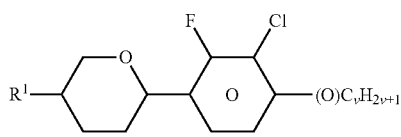

LY10
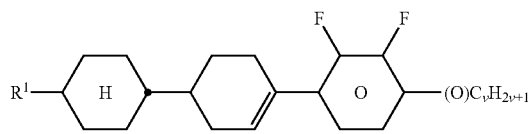

LY11
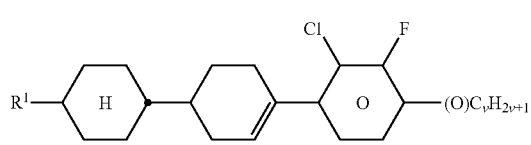

LY12
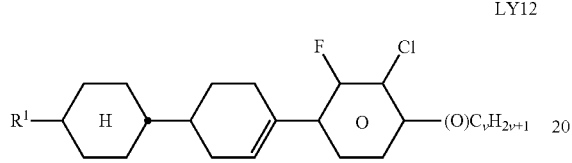

LY13
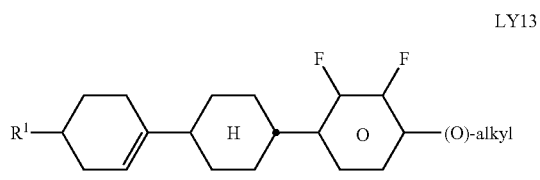

LY14

LY15
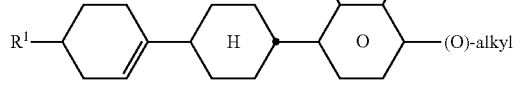

LY16
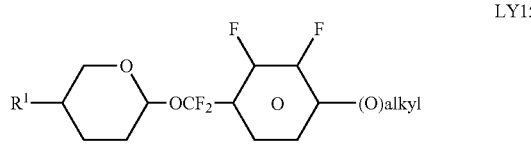

LY17
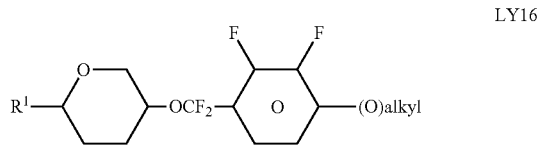

LY18
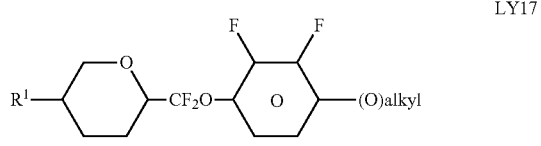

LY19
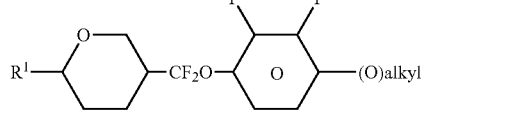

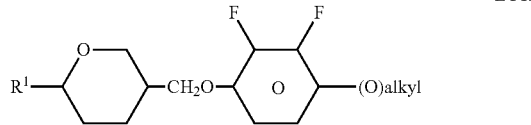

LY20
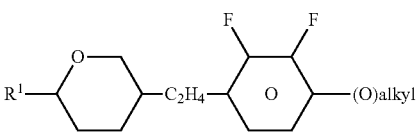

LY21
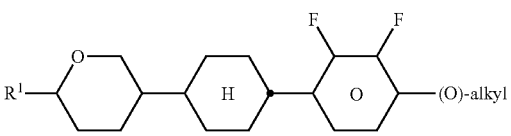

LY22
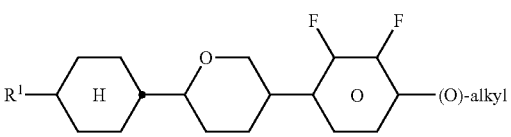

LY23
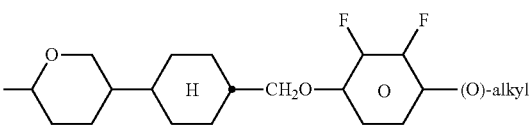

LY24
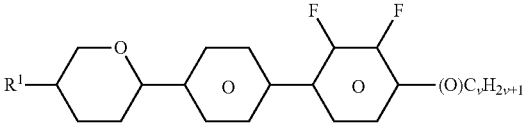

in which $R^1$ has the meaning indicated above, alkyl denotes a straight-chain alkyl radical having 1-6 C atoms, (O) denotes an oxygen atom or a single bond, and v denotes an integer from 1 to 6. $R^1$ preferably denotes straight-chain alkyl having 1 to 6 C atoms or straight-chain alkenyl having 2 to 6 C atoms, in particular $CH_3$, $C_2H_5$, $n\text{-}C_3H_7$, $n\text{-}C_4H_9$, $n\text{-}C_5H_{11}$, $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

e) LC medium which additionally comprises one or more compounds selected from the group consisting of the following formulae:

G1
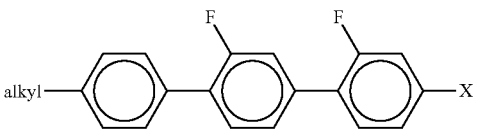

G2
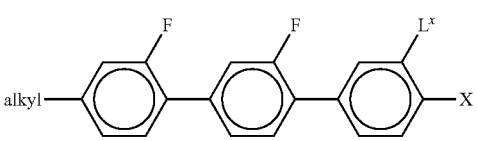

G3
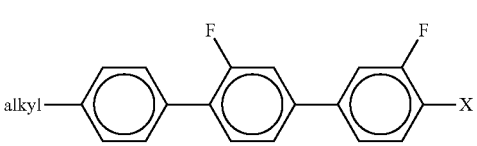

G4

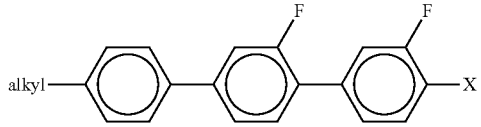

in which alkyl denotes $C_{1-6}$-alkyl, $L^x$ denotes H or F, and X denotes F, Cl, $OCF_3$, $OCHF_2$ or $OCH=CF_2$. Particular preference is given to compounds of the formula G1 in which X denotes F.

f) LC medium which additionally comprises one or more compounds selected from the group consisting of the following formulae:

Y1

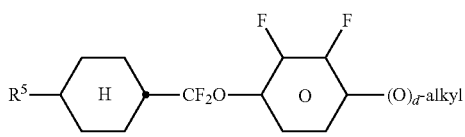

Y2

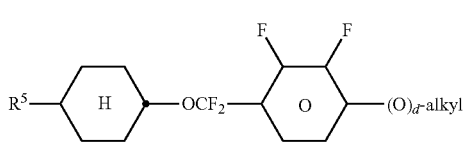

Y3

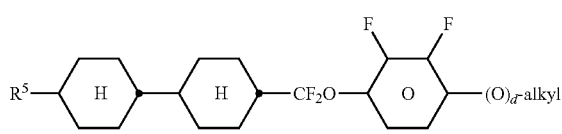

Y4

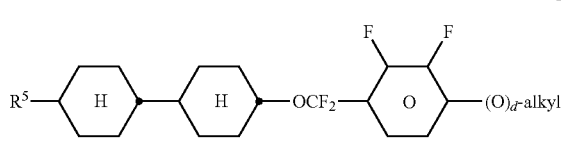

Y5

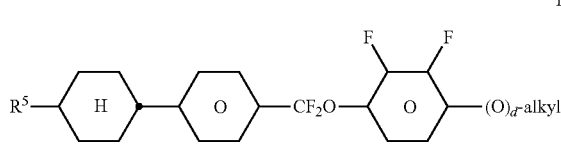

Y6

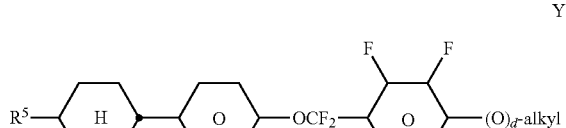

Y7

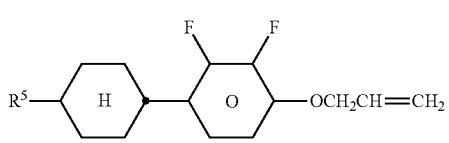

Y8

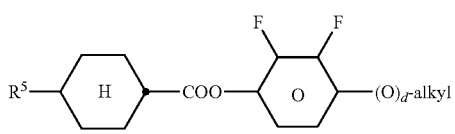

Y9

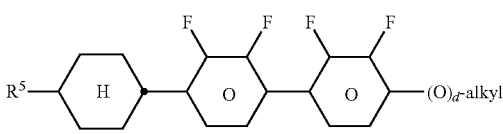

Y10

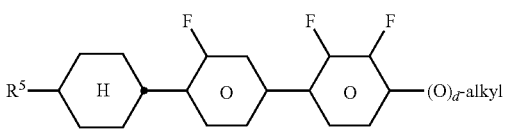

Y11

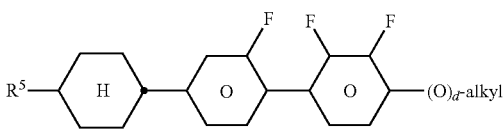

Y12

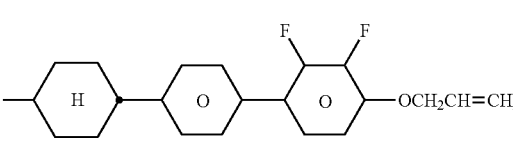

Y13

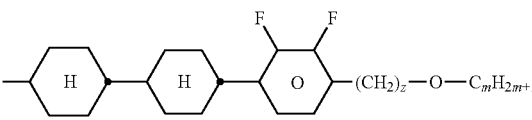

Y14

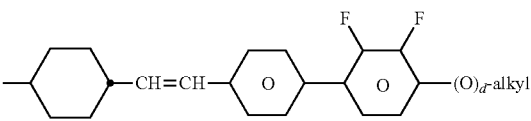

Y15

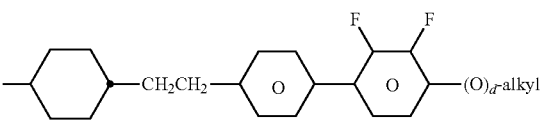

Y16

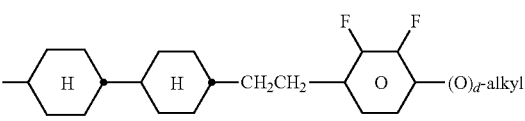

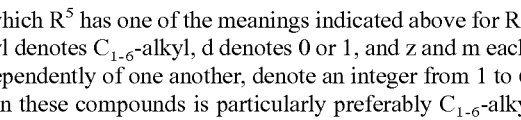

in which $R^5$ has one of the meanings indicated above for $R^1$, alkyl denotes $C_{1-6}$-alkyl, d denotes 0 or 1, and z and m each, independently of one another, denote an integer from 1 to 6. $R^5$ in these compounds is particularly preferably $C_{1-6}$-alkyl or -alkoxy or $C_{2-6}$-alkenyl, d is preferably 1. The LC medium according to the invention preferably comprises one or more compounds of the above-mentioned formulae in amounts of ≥5% by weight.

g) LC medium which additionally comprises one or more biphenyl compounds selected from the group consisting of the following formulae:

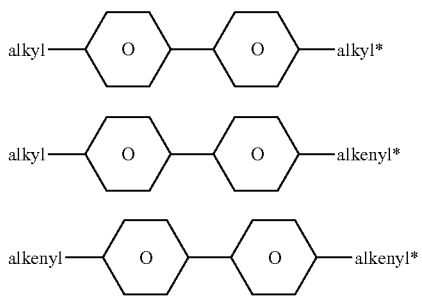

in which alkyl and alkyl* each, independently of one another, denote a straight-chain alkyl radical having 1-6 C atoms, and alkenyl and alkenyl* each, independently of one another, denote a straight-chain alkenyl radical having 2-6 C atoms. Alkenyl and alkenyl* preferably denote CH$_2$=CH—, CH$_2$=CHCH$_2$CH$_2$—, CH$_3$—CH=CH—, CH$_3$—CH$_2$—CH=CH—, CH$_3$—(CH$_2$)$_2$—CH=CH—, CH$_3$—(CH$_2$)$_3$—CH=CH— or CH$_3$—CH=CH—(CH$_2$)$_2$—.

The proportion of the biphenyls of the formulae B1 to B3 in the LC mixture is preferably at least 3% by weight, in particular ≥5% by weight.

The compounds of the formula B2 are particularly preferred.

The compounds of the formulae B1 to B3 are preferably selected from the group consisting of the following sub-formulae:

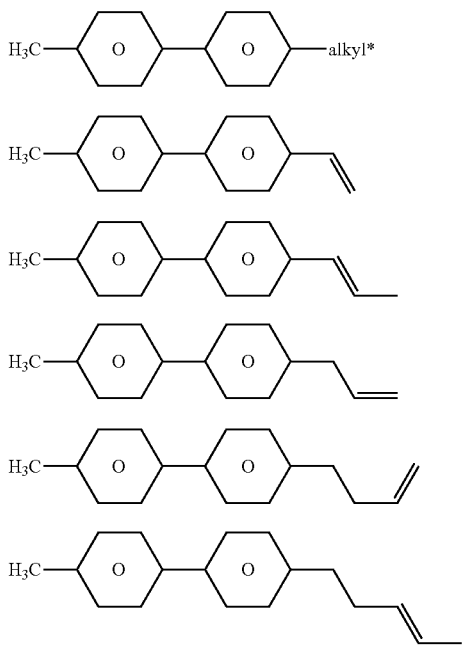

in which alkyl* denotes an alkyl radical having 1-6 C atoms. The medium according to the invention particularly preferably comprises one or more compounds of the formulae B1a and/or B2e.

h) LC medium which additionally comprises one or more terphenyl compounds of the following formula:

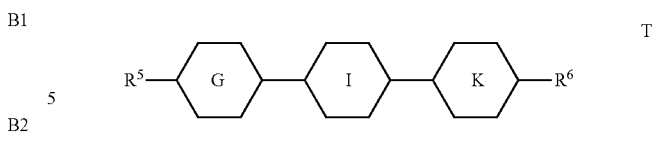

in which R$^5$ and R$^6$ each, independently of one another, have one of the meanings indicated above, and

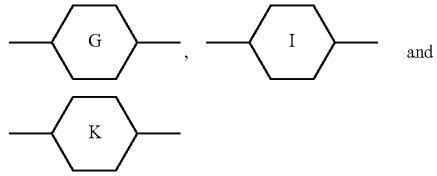

each, independently of one another, denote

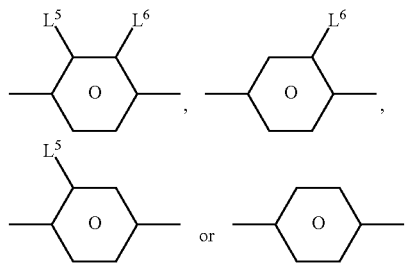

in which L$^5$ denotes F or Cl, preferably F, and L$^6$ denotes F, Cl, OCF$_3$, CF$_3$, CH$_3$, CH$_2$F or CHF$_2$, preferably F.

The compounds of the formula T are preferably selected from the group consisting of the following sub-formulae:

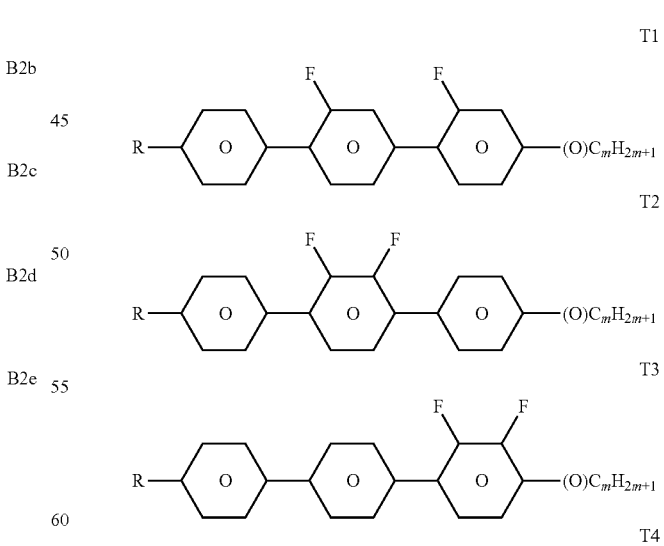

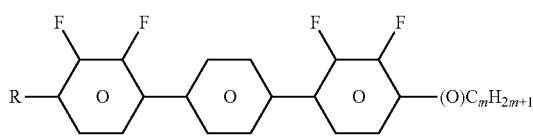

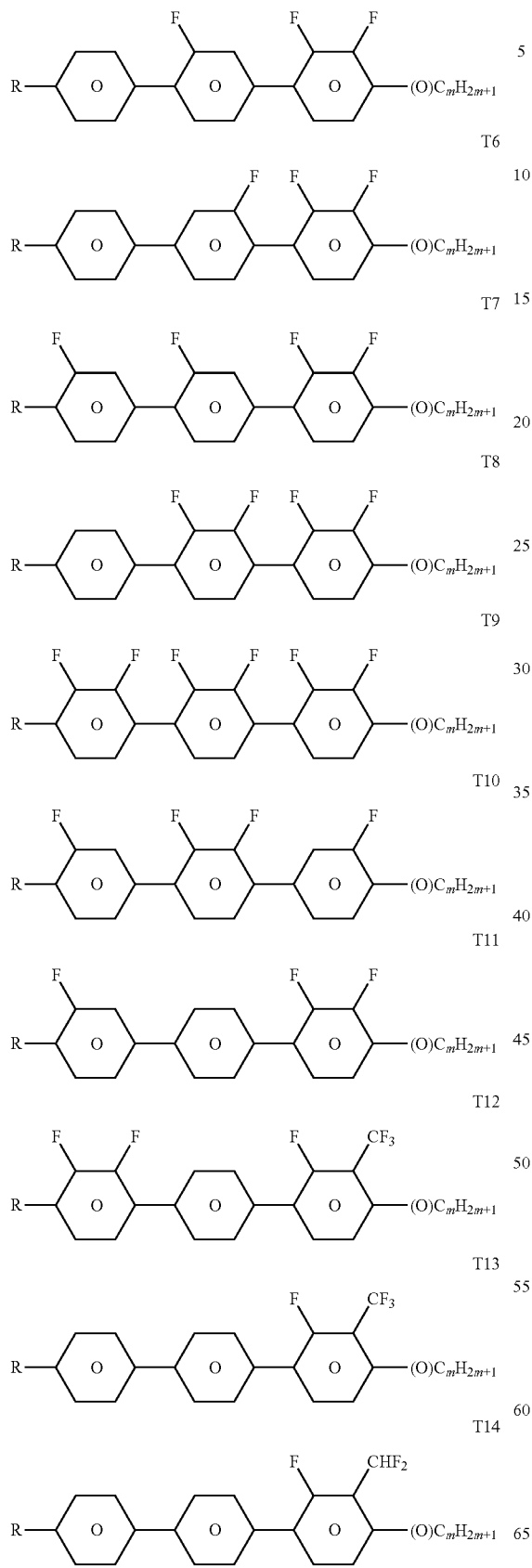
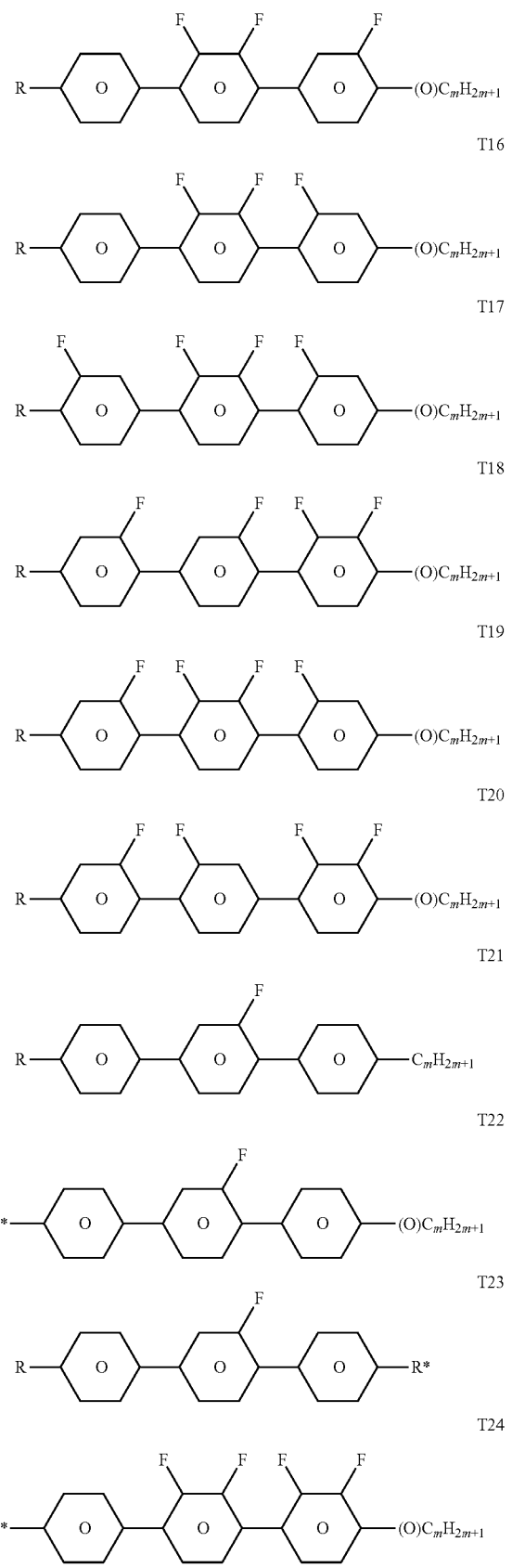

T25

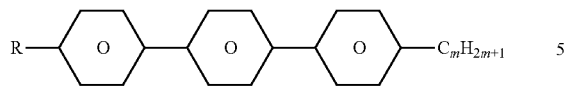

T26

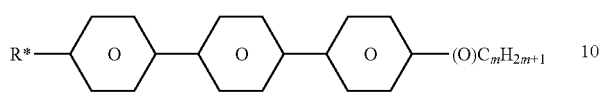

T27

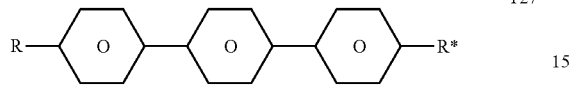

in which R denotes a straight-chain alkyl or alkoxy radical having 1-7 C atoms, R* denotes a straight-chain alkenyl radical having 2-7 C atoms, (O) denotes an oxygen atom or a single bond, and m denotes an integer from 1 to 6. R* preferably denotes $CH_2\!=\!CH\!-\!$, $CH_2\!=\!CHCH_2CH_2\!-\!$, $CH_3\!-\!CH\!=\!CH\!-\!$, $CH_3\!-\!CH_2\!-\!CH\!=\!CH\!-\!$, $CH_3\!-\!(CH_2)_2\!-\!CH\!=\!CH\!-\!$, $CH_3\!-\!(CH_2)_3\!-\!CH\!=\!CH\!-\!$ or $CH_3\!-\!CH\!=\!CH\!-\!(CH_2)_2\!-\!$.

R preferably denotes methyl, ethyl, propyl, butyl, pentyl, hexyl, methoxy, ethoxy, propoxy, butoxy or pentoxy.

The LC medium according to the invention preferably comprises the terphenyls of the formula T and the preferred sub-formulae thereof in an amount of 0.5-30% by weight, in particular 1-20% by weight.

Particular preference is given to compounds of the formulae T1, T2, T3 and T21. In these compounds, R preferably denotes alkyl, furthermore alkoxy, each having 1-5 C atoms.

The terphenyls are preferably employed in mixtures according to the invention if the Δn value of the mixture is to be ≥0.1. Preferred mixtures comprise 2-20% by weight of one or more terphenyl compounds of the formula T, preferably selected from the group of compounds T1 to T22.

i) LC medium which additionally comprises one or more compounds selected from the group consisting of the following formulae:

O1

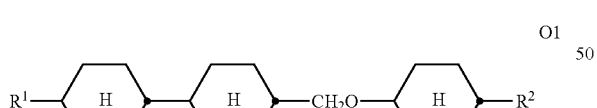

O2

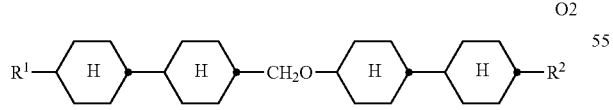

O3

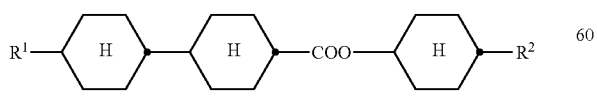

O4

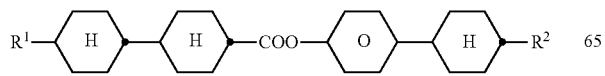

O5

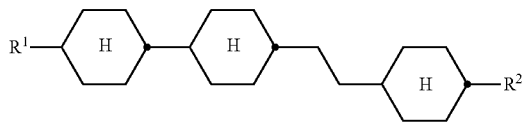

O6

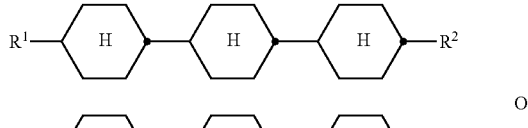

O7

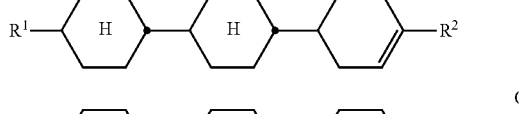

O8

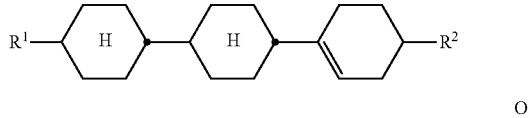

O9

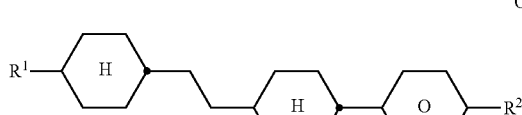

O10

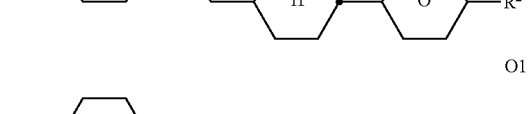

O11

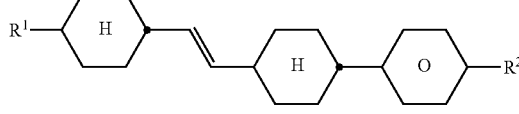

in which $R^1$ and $R^2$ have the meanings indicated above and preferably each, independently of one another, denote straight-chain alkyl having 1 to 6 C atoms or straight-chain alkenyl having 2 to 6 C atoms.

Preferred media comprise one or more compounds selected from the formulae O1, O3 and O4.

k) LC medium which additionally comprises one or more compounds of the following formula:

FI

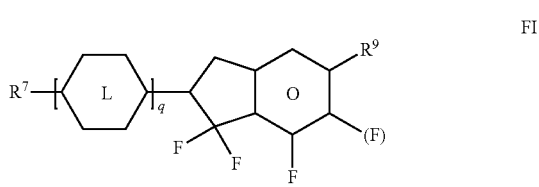

in which

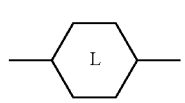

denotes

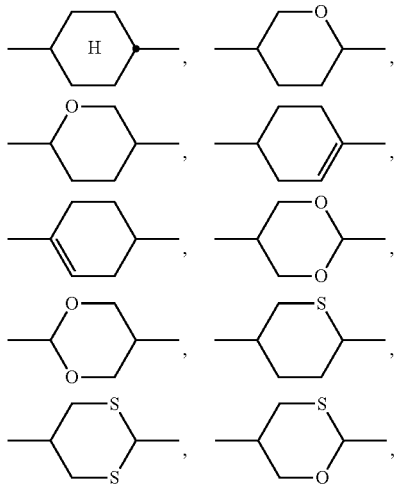

$R^9$ denotes H, $CH_3$, $C_2H_5$ or n-$C_3H_7$, (F) denotes an optional fluorine substituent, and q denotes 1, 2 or 3, and $R^7$ has one of the meanings indicated for $R^1$, preferably in amounts of >3% by weight, in particular ≥5% by weight and very particularly preferably 5-30% by weight.

Particularly preferred compounds of the formula FI are selected from the group consisting of the following sub-formulae:

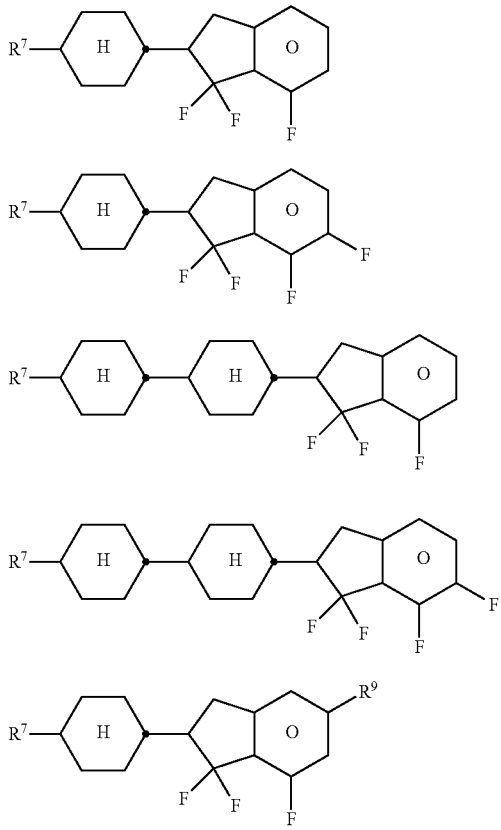

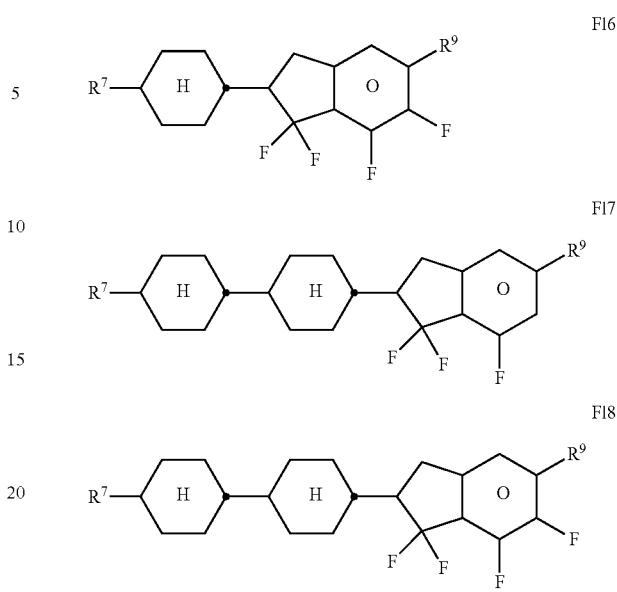

in which $R^7$ preferably denotes straight-chain alkyl, and $R^9$ denotes $CH_3$, $C_2H_5$ or n-$C_3H_7$. Particular preference is given to the compounds of the formulae FI1, FI2 and FI3.

l) LC medium which additionally comprises one or more compounds selected from the group consisting of the following formulae:

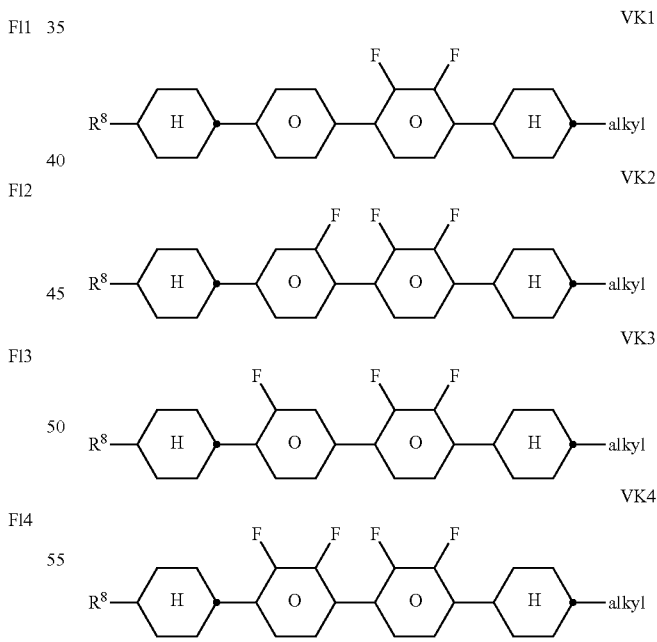

in which $R^8$ has the meaning indicated for $R^1$, and alkyl denotes a straight-chain alkyl radical having 1-6 C atoms.

m) LC medium which additionally comprises one or more compounds which contain a tetrahydronaphthyl or naphthyl unit, such as, for example, the compounds selected from the group consisting of the following formulae:

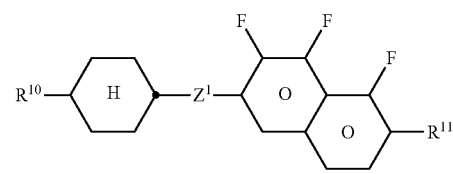
N1

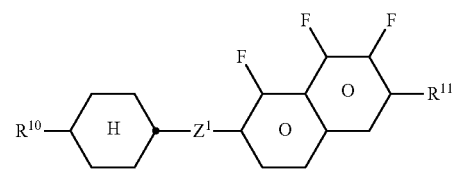
N2

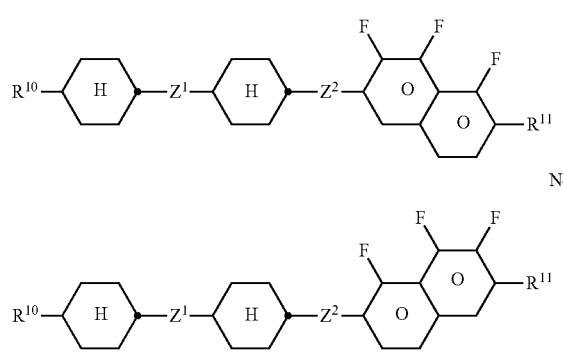
N3

N4

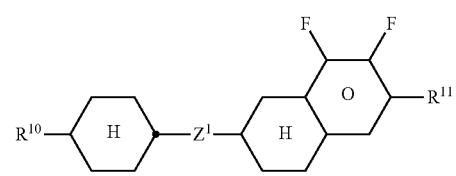
N5

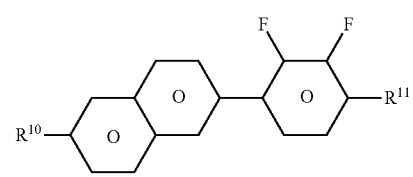
N6

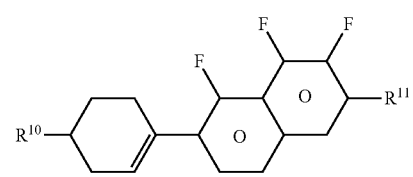
N7

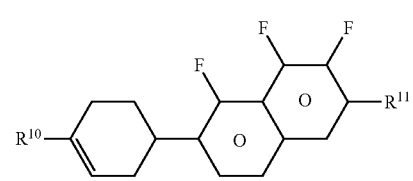
N8

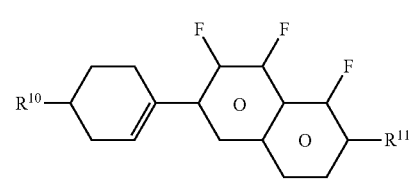
N9

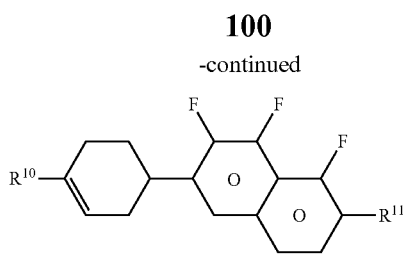
N10 in which
  $R^{10}$ and $R^{11}$ each, independently of one another, denote alkyl having 1 to 12 C atoms, where, in addition, one or two non-adjacent $CH_2$ groups may be replaced by —O—, —CH=CH—, —CO—, —OCO— or —COO— in such a way that O atoms are not linked directly to one another, preferably alkyl or alkoxy having 1 to 6 C atoms,
and $R^{10}$ and $R^{11}$ preferably denote straight-chain alkyl or alkoxy having 1 to 6 C atoms or straight-chain alkenyl having 2 to 6 C atoms, and
  $Z^1$ and $Z^2$ each, independently of one another, denote —$C_2H_4$—, —CH=CH—, —$(CH_2)_4$—, —$(CH_2)_3O$—, —$O(CH_2)_3$—, —CH=CH—$CH_2CH_2$—, —$CH_2CH_2$CH=CH—, —$CH_2O$—, —$OCH_2$—, —CO—O—, —O—CO—, —$C_2F_4$—, —CF=CF—, —CF=CH—, —CH=CF—, —$CH_2$— or a single bond.

n) LC medium which additionally comprises one or more difluoro-dibenzochromans and/or chromans of the following formulae:

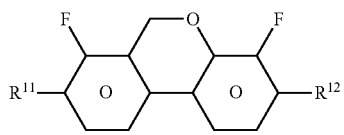
BC

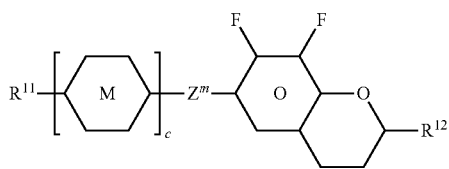
CR

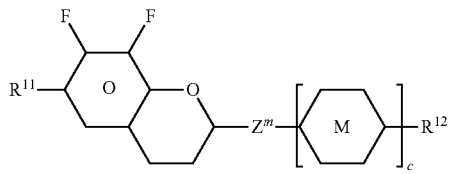
RC in which
  $R^{11}$ and $R^{12}$ each, independently of one another, have one of the meanings indicated above for $R^{11}$ under formula N1
  ring M is trans-1,4-cyclohexylene or 1,4-phenylene,
  $Z^m$ —$C_2H_4$—, —$CH_2O$—, —$OCH_2$—, —CO—O— or —O—CO—,
  c is 0, 1 or 2,
preferably in amounts of 3 to 20% by weight, in particular in amounts of 3 to 15% by weight.
  Particularly preferred compounds of the formulae BC, CR and RC are selected from the group consisting of the following sub-formulae:

BC1 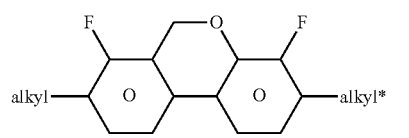
BC2 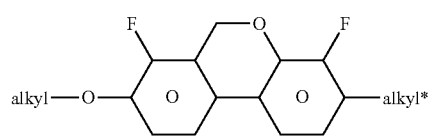
BC3 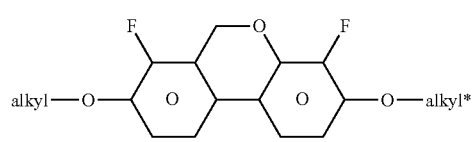
BC4 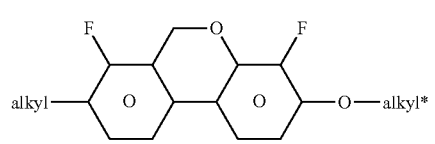
BC5 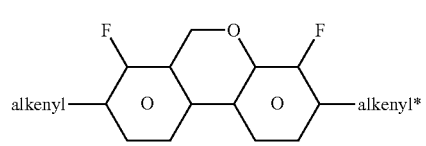
BC6 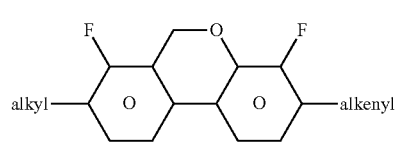
BC7 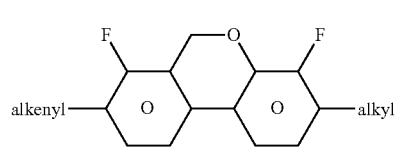
CR1 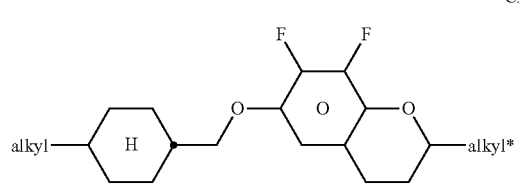
CR2 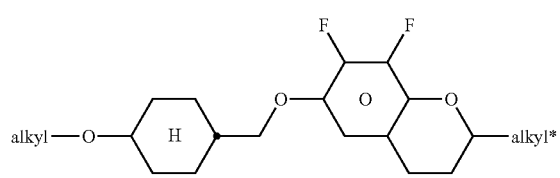
CR3 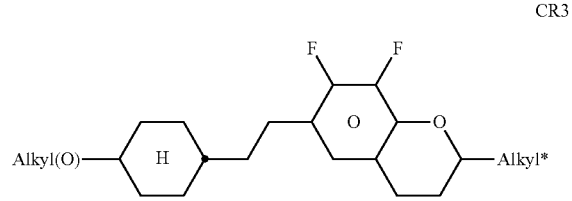
-continued
CR4 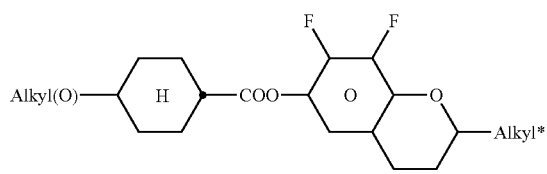
CR5 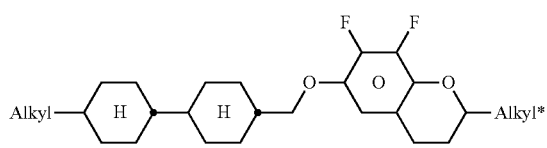
CR6 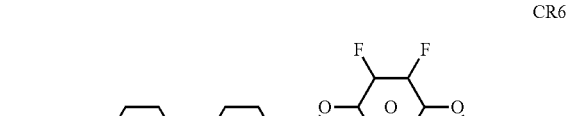
CR7 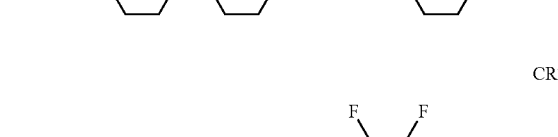
CR8 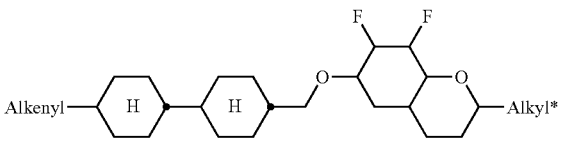
CR9 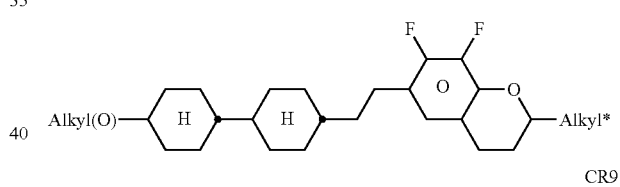
RC1 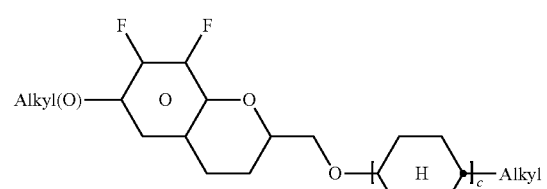
RC2 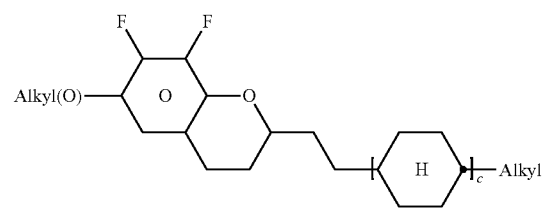

-continued

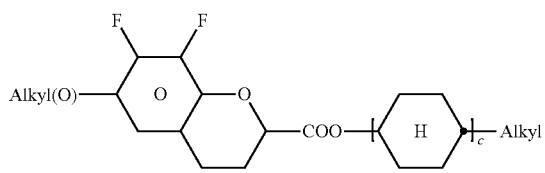
RC3 in which alkyl and alkyl* each, independently of one another, denote a straight-chain alkyl radical having 1-6 C atoms, (O) denotes an oxygen atom or a single bond, c is 1 or 2, and alkenyl and alkenyl* each, independently of one another, denote a straight-chain alkenyl radical having 2-6 C atoms. Alkenyl and alkenyl* preferably denote CH$_2$=CH—, CH$_2$=CHCH$_2$CH$_2$—, CH$_3$—CH=CH—, CH$_3$—CH$_2$—CH=CH—, CH$_3$—(CH$_2$)$_2$—CH=CH—, CH$_3$—(CH$_2$)$_3$—CH=CH— or CH$_3$—CH=CH—(CH$_2$)$_2$—.

Very particular preference is given to mixtures comprising one, two or three compounds of the formula BC-2.

o) LC medium which additionally comprises one or more fluorinated phenanthrenes and/or dibenzofurans of the following formulae:

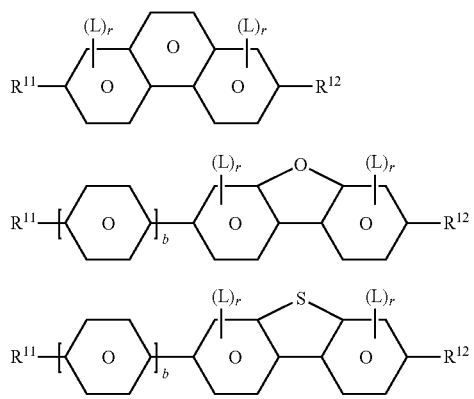
PH

BF

BS in which R$^{11}$ and R$^{12}$ each, independently of one another, have one of the meanings indicated above for R$^{11}$ under formula N1, b denotes or 1, L denotes F, and r denotes 1, 2 or 3.

Particularly preferred compounds of the formulae PH and BF are selected from the group consisting of the following sub-formulae:

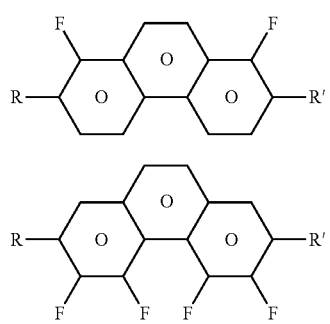
PH1

PH2

-continued

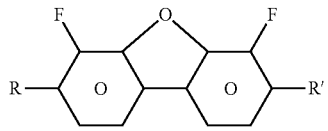
BF1

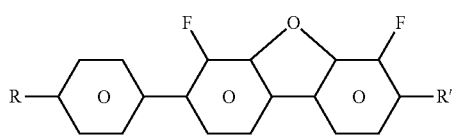
BF2

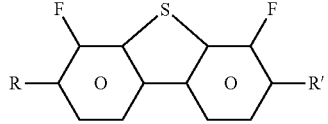
BS1

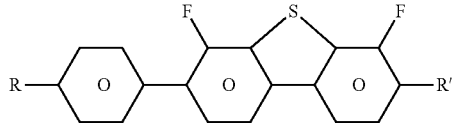
BS2 in which R and R' each, independently of one another, denote a straight-chain alkyl or alkoxy radical having 1-7 C atoms.

p) LC medium which additionally comprises one or more monocyclic compounds of the following formula

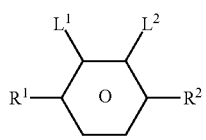
Y wherein
R$^1$ and R$^2$ each, independently of one another, denote alkyl having 1 to 12 C atoms, where, in addition, one or two non-adjacent CH$_2$ groups may be replaced by —O—, —CH=CH—, —CO—, —OCO— or —COO— in such a way that O atoms are not linked directly to one another, preferably alkyl or alkoxy having 1 to 6 C atoms,
L$^1$ and L$^2$ each, independently of one another, denote F, Cl, OCF$_3$, CF$_3$, CH$_3$, CH$_2$F, CHF$_2$.

Preferably, both L$^1$ and L$^2$ denote F or one of L$^1$ and L$^2$ denotes F and the other denotes Cl, The compounds of the formula Y are preferably selected from the group consisting of the following sub-formulae:

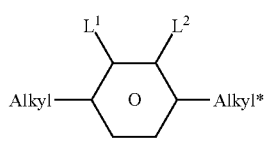
Y1

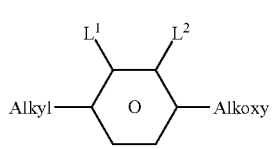
Y2

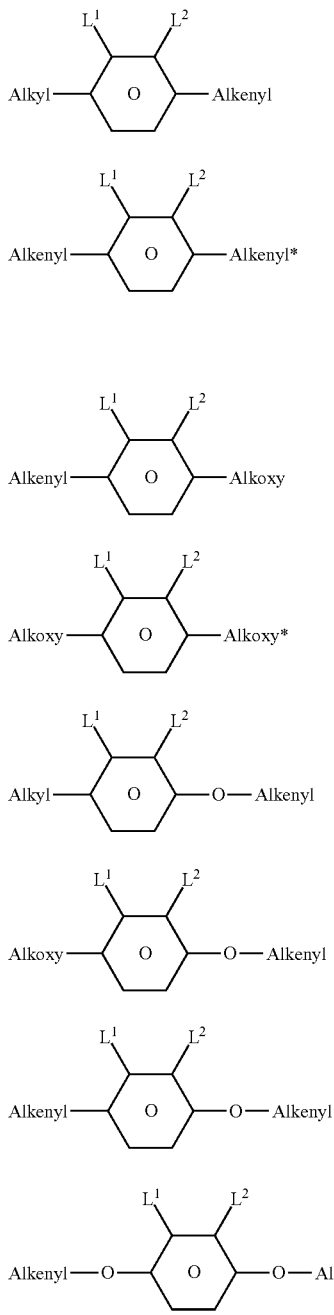

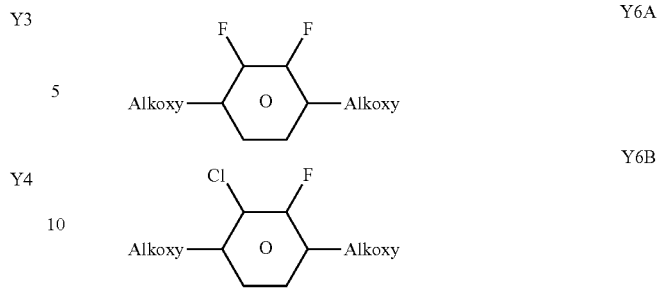

wherein Alkoxy preferably denotes straight-chain alkoxy with 3, 4, or 5 C atoms.

in which, Alkyl and Alkyl* each, independently of one another, denote a straight-chain alkyl radical having 1-6 C atoms, Alkoxy denotes a straight-chain alkoxy radical having 1-6 C atoms, Alkenyl and Alkenyl* each, independently of one another, denote a straight-chain alkenyl radical having 2-6 C atoms, and O denotes an oxygen atom or a single bond. Alkenyl and Alkenyl* preferably denote $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

Particularly preferred compounds of the formula Y are selected from the group consisting of the following sub-formulae:

q) LC medium which, apart from the stabilisers according to the invention, in particular of the formula I or sub-formulae thereof and the comonomers, comprises no compounds which contain a terminal vinyloxy group ($-O-CH=CH_2$).

r) LC medium which comprises 1 to 5, preferably 1, 2 or 3, stabilisers, preferably selected from stabilisers according to the invention, in particular of the formula I or sub-formulae thereof.

s) LC medium in which the proportion of stabilisers, in particular of the formula I or sub-formulae thereof, in the mixture as a whole is 1 to ppm, preferably 100 to 1000 ppm.

t) LC medium which comprises 1 to 8, preferably 1 to 5, compounds of the formulae CY1, CY2, PY1 and/or PY2. The proportion of these compounds in the mixture as a whole is preferably 5 to 60%, particularly preferably 10 to 35%. The content of these individual compounds is preferably in each case 2 to 20%.

u) LC medium which comprises 1 to 8, preferably 1 to 5, compounds of the formulae CY9, CY10, PY9 and/or PY10. The proportion of these compounds in the mixture as a whole is preferably 5 to 60%, particularly preferably 10 to 35%. The content of these individual compounds is preferably in each case 2 to 20%.

v) LC medium which comprises 1 to 10, preferably 1 to 8, compounds of the formula ZK, in particular compounds of the formulae ZK1, ZK2 and/or ZK6. The proportion of these compounds in the mixture as a whole is preferably 3 to 25%, particularly preferably 5 to 45%. The content of these individual compounds is preferably in each case 2 to 20%.

w) LC medium in which the proportion of compounds of the formulae CY, PY and ZK in the mixture as a whole is greater than 70%, preferably greater than 80%.

x) LC medium in which the LC host mixture contains one or more compounds containing an alkenyl group, preferably selected from the group consisting of formula CY, PY and LY, wherein one or both of $R^1$ and $R^2$ denote straight-chain alkenyl having 2-6 C atoms, formula ZK and DK, wherein one or both of $R^3$ and $R^4$ or one or both of $R^5$ and $R^6$ denote straight-chain alkenyl having 2-6 C atoms, and formula B2 and B3, very preferably selected from formulae CY15, CY16, CY24, CY32, PY15, PY16, ZK3, ZK4, DK3, DK6, B2 and B3, most preferably selected from formulae ZK3, ZK4, B2 and B3. The concentration of these compounds in the LC host mixture is preferably from 2 to 70%, very preferably from 3 to 55%.

y) LC medium which contains one or more, preferably 1 to 5, compounds selected of formula PY1-PY8, very preferably of formula PY2. The proportion of these compounds in the mixture as a whole is preferably 1 to 30%, particularly preferably 2 to 20%. The content of these individual compounds is preferably in each case 1 to 20%.

z) LC medium which contains one or more, preferably 1, 2 or 3, compounds of formula T2. The content of these compounds in the mixture as a whole is preferably 1 to 20%.

In another preferred embodiment of the present invention the LC medium contains an LC host mixture with positive dielectric anisotropy. Preferred embodiments of such an LC medium, and the corresponding LC host mixture, are those of sections aa)-mmm) below:

aa) LC-medium, characterised in that it comprises one or more compounds selected from the group of compounds of the formulae II and III

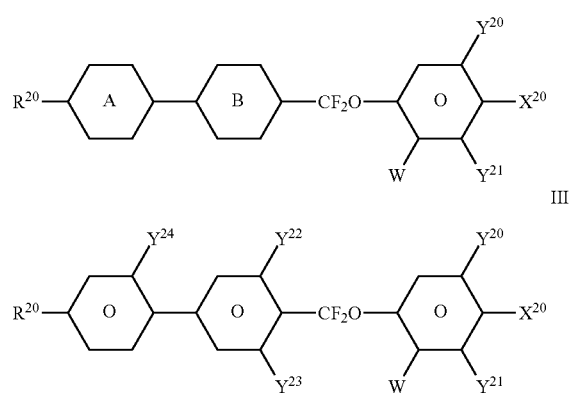

wherein
$R^{20}$ each, identically or differently, denote a halogenated or unsubstituted alkyl or alkoxy radical having 1 to 15 C atoms, where, in addition, one or more $CH_2$ groups in these radicals may each be replaced, independently of one another,
by —C≡C—, —$CF_2$O—, —CH=CH—,

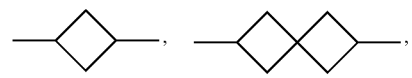

—O—, —CO—O— or —O—CO— in such a way that O atoms are not linked directly to one another,
$X^{20}$ each, identically or differently, denote F, Cl, CN, $SF_5$, SCN, NCS, a halogenated alkyl radical, a halogenated alkenyl radical, a halogenated alkoxy radical or a halogenated alkenyloxy radical, each having up to 6 C atoms, and
$Y^{20-24}$ each, identically or differently, denote H or F;
W denotes H or methyl,

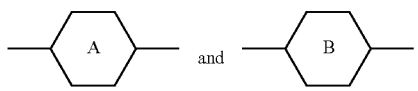

each, independently of one another, denote

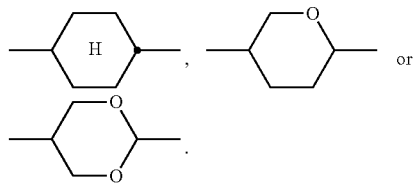

The compounds of the formula II are preferably selected from the following formulae:

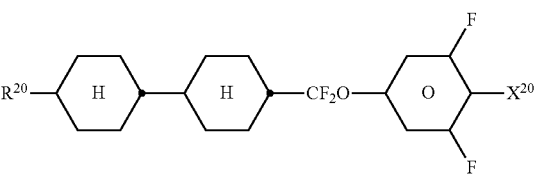

IIa

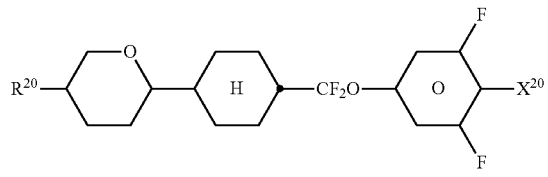

IIb

IIc

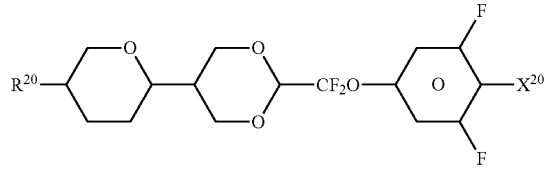

IId

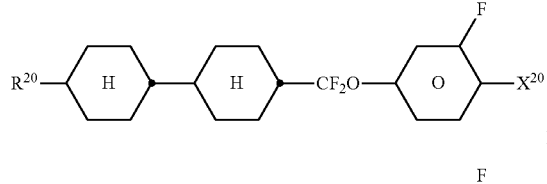

IIe

IIf

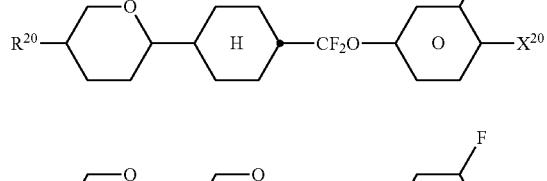

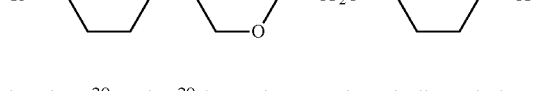

wherein $R^{20}$ and $X^{20}$ have the meanings indicated above.
$R^{20}$ preferably denotes alkyl having 1 to 6 C atoms. $X^{20}$ preferably denotes F. Particular preference is given to compounds of the formulae IIa and IIb, in particular compounds of the formulae IIa and IIb wherein X denotes F.

The compounds of the formula III are preferably selected from the following formulae:

IIIa
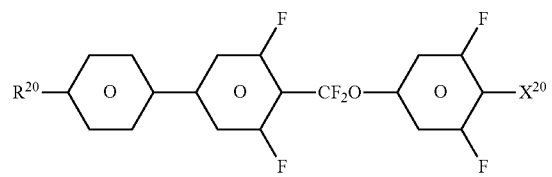

IIIb
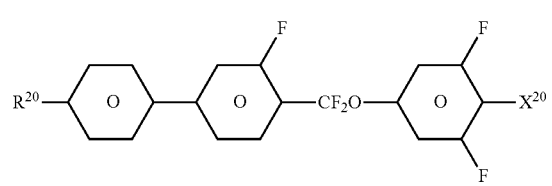

IIIc
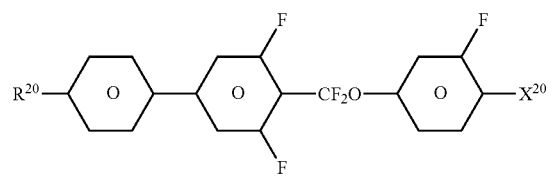

IIId
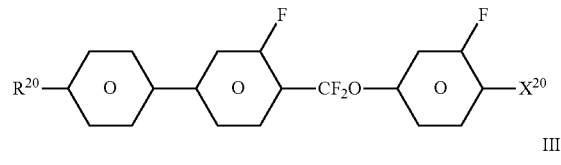

IIIe
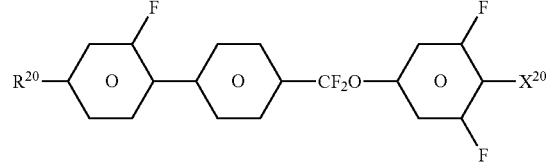

wherein $R^{20}$ and $X^{20}$ have the meanings indicated above.

$R^{20}$ preferably denotes alkyl having 1 to 6 C atoms. $X^{20}$ preferably denotes F. Particular preference is given to compounds of the formulae IIIa and IIIe, in particular compounds of the formula IIIa;

bb) LC-medium additionally comprising one or more compounds selected from the following formulae:

IV
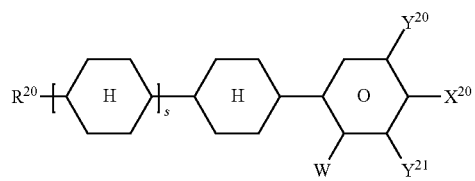

V
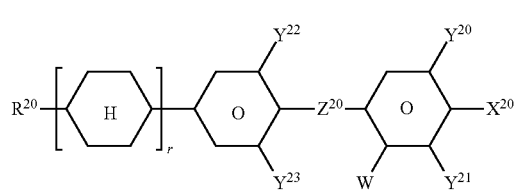

VI
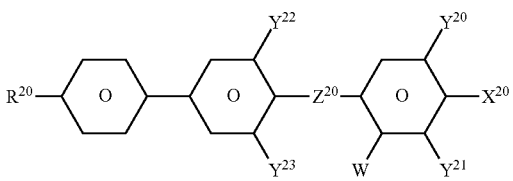

VII
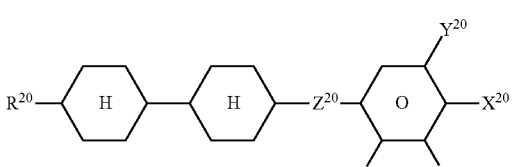

VIII
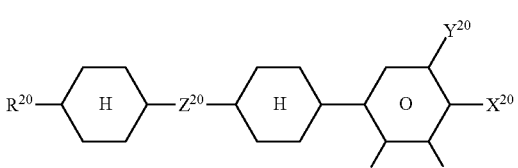

wherein
$R^{20}$, $X^{20}$, W and $Y^{20-23}$ have the meanings indicated above under formula II, and
$Z^{20}$ denotes —$C_2H_4$—, —$(CH_2)_4$—, —CH=CH—, —CF=CF, —$C_2F_4$—, —$CH_2CF_2$—, —$CF_2CH_2$—, —$CH_2O$—, —$OCH_2$—, —COO— or —$OCF_2$—, in formulae V and VI also a single bond, in formulae V and VIII also —$CF_2O$—,
r denotes 0 or 1, and
s denotes 0 or 1;

The compounds of the formula IV are preferably selected from the following formulae:

IVa
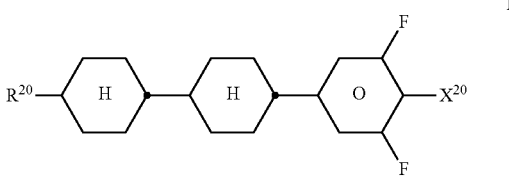

IVb
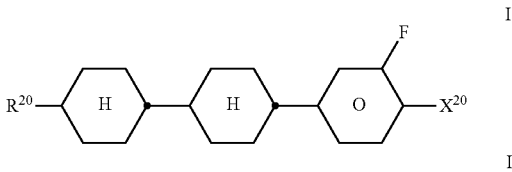

IVc
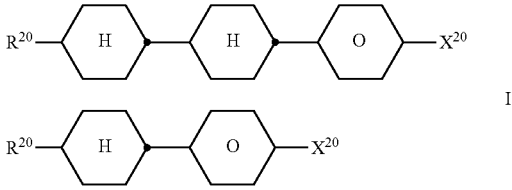

IVd
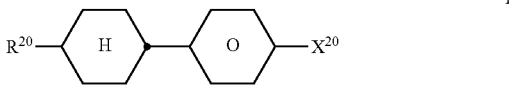

wherein $R^{20}$ and $X^{20}$ have the meanings indicated above.
$R^{20}$ preferably denotes alkyl having 1 to 6 C atoms. $X^{20}$ preferably denotes F or $OCF_3$, furthermore OCF=$CF_2$ or Cl;

The compounds of the formula V are preferably selected from the following formulae:

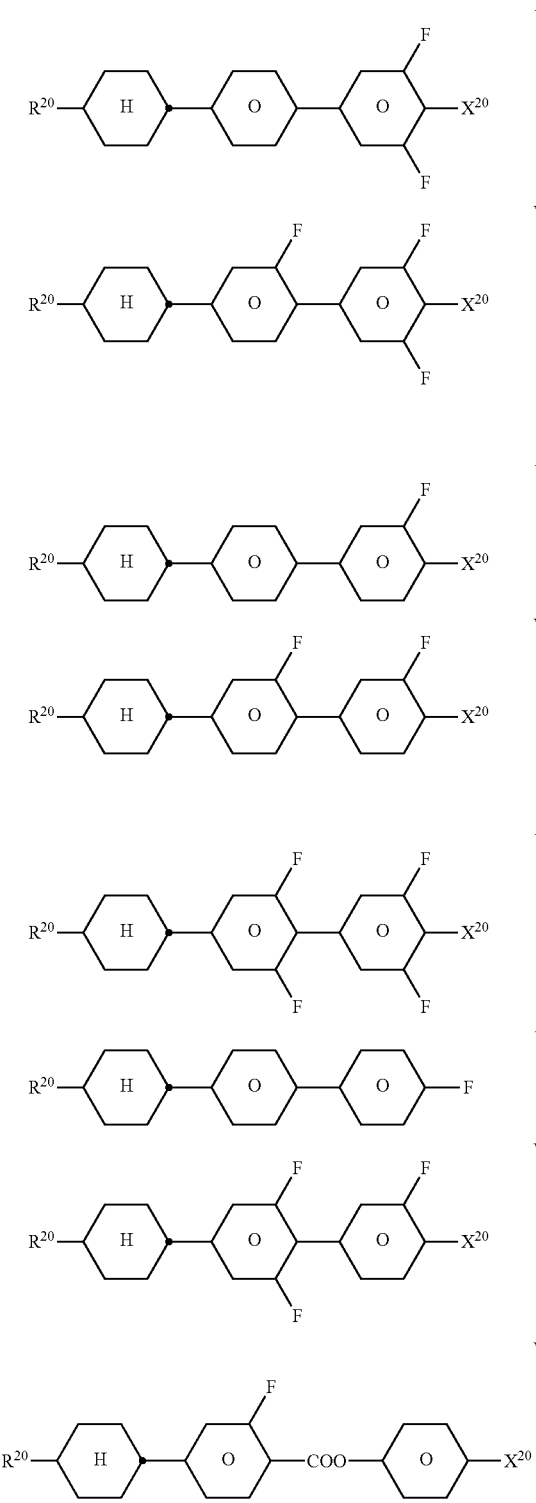

wherein $R^{20}$ and $X^{20}$ have the meanings indicated above.

$R^{20}$ preferably denotes alkyl having 1 to 6 C atoms. $X^{20}$ preferably denotes F and $OCF_3$, furthermore $OCHF_2$, $CF_3$, $OCF{=}CF_2$ and $OCH{=}CF_2$;

The compounds of the formula VI are preferably selected from the following formulae:

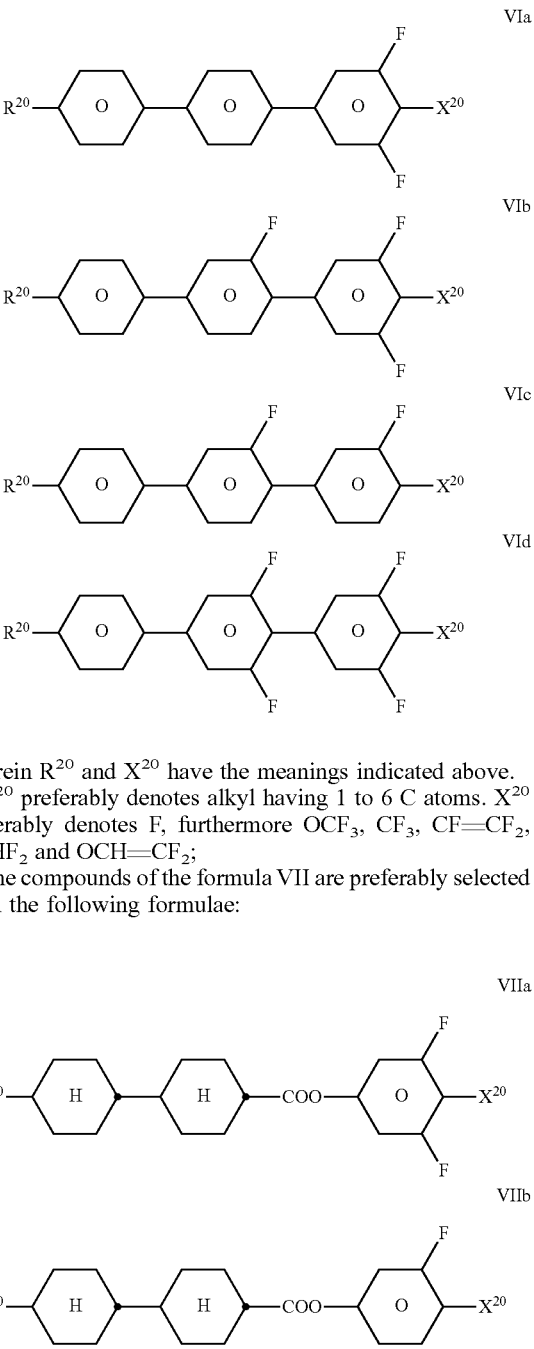

wherein $R^{20}$ and $X^{20}$ have the meanings indicated above.

$R^{20}$ preferably denotes alkyl having 1 to 6 C atoms. $X^{20}$ preferably denotes F, furthermore $OCF_3$, $CF_3$, $CF{=}CF_2$, $OCHF_2$ and $OCH{=}CF_2$;

The compounds of the formula VII are preferably selected from the following formulae:

wherein $R^{20}$ and $X^{20}$ have the meanings indicated above.

$R^{20}$ preferably denotes alkyl having 1 to 6 C atoms. $X^{20}$ preferably denotes F, furthermore $OCF_3$, $OCHF_2$ and $OCH{=}CF_2$.

cc) The medium additionally comprises one or more compounds selected from the formulae ZK1 to ZK10 given above. Especially preferred are compounds of formula ZK1 and ZK3. Particularly preferred compounds of formula ZK are selected from the sub-formulae ZK1a, ZK1 b, ZK1c, ZK3a, ZK3b, ZK3c and ZK3d.

dd) The medium additionally comprises one or more compounds selected from the formulae DK1 to DK12 given above. Especially preferred compounds are DK3.

ee) The medium additionally comprises one or more compounds selected from the following formulae:

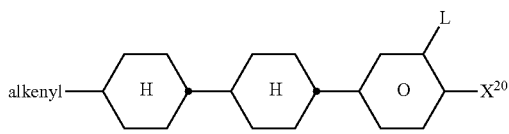

IX wherein $X^{20}$ has the meanings indicated above, and

L denotes H or F,

"alkenyl" denotes $C_{2-6}$-alkenyl.

ff) The compounds of the formulae DK-3a and IX are preferably selected from the following formulae:

DK3a

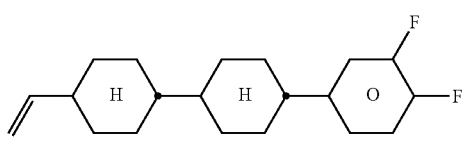

IXa wherein "alkyl" denotes $C_{1-6}$-alkyl, preferably n-$C_3H_7$, n-$C_4H_9$ or n-$C_5H_{11}$, in particular n-$C_3H_7$.

gg) The medium additionally comprises one or more compounds selected from the formulae B1, B2 and B3 given above, preferably from the formula B2. The compounds of the formulae B1 to B3 are particularly preferably selected from the formulae B1a, B2a, B2b and B2c.

hh) The medium additionally comprises one or more compounds selected from the following formula:

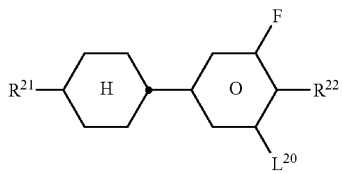

X wherein $L^{20}$ denotes H or F, and $R^{21}$ and $R^{22}$ each, identically or differently, denote n-alkyl, alkoxy, oxaalkyl, fluoroalkyl or alkenyl, each having up to 6 C atoms, and preferably each, identically or differently, denote alkyl having 1 to 6 C atoms.

ii) The medium comprises one or more compounds of the following formulae:

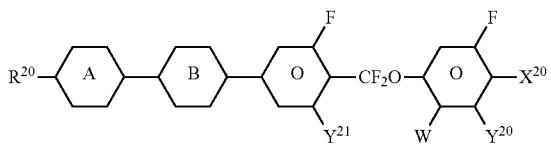

XI

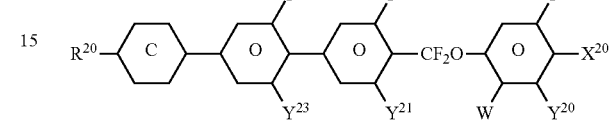

XII

Wherein W, $R^{20}$, $X^{20}$ and $Y^{20-23}$ have the meanings indicated in formula III, and

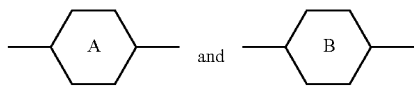

each, independently of one another, denote

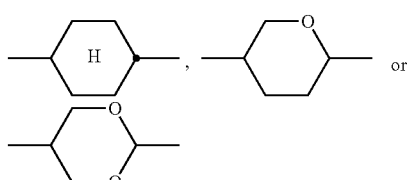

and

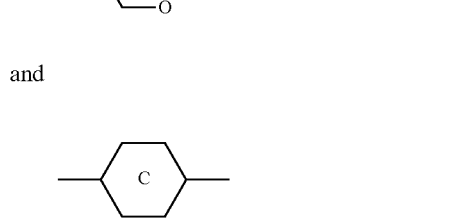

denotes

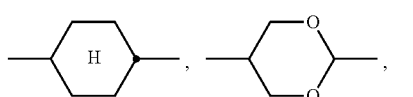

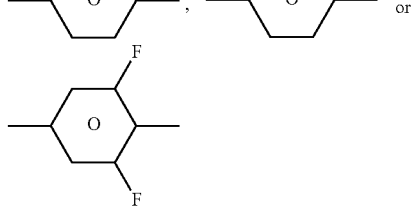

The compounds of the formulae XI and XII are preferably selected from the following formulae:

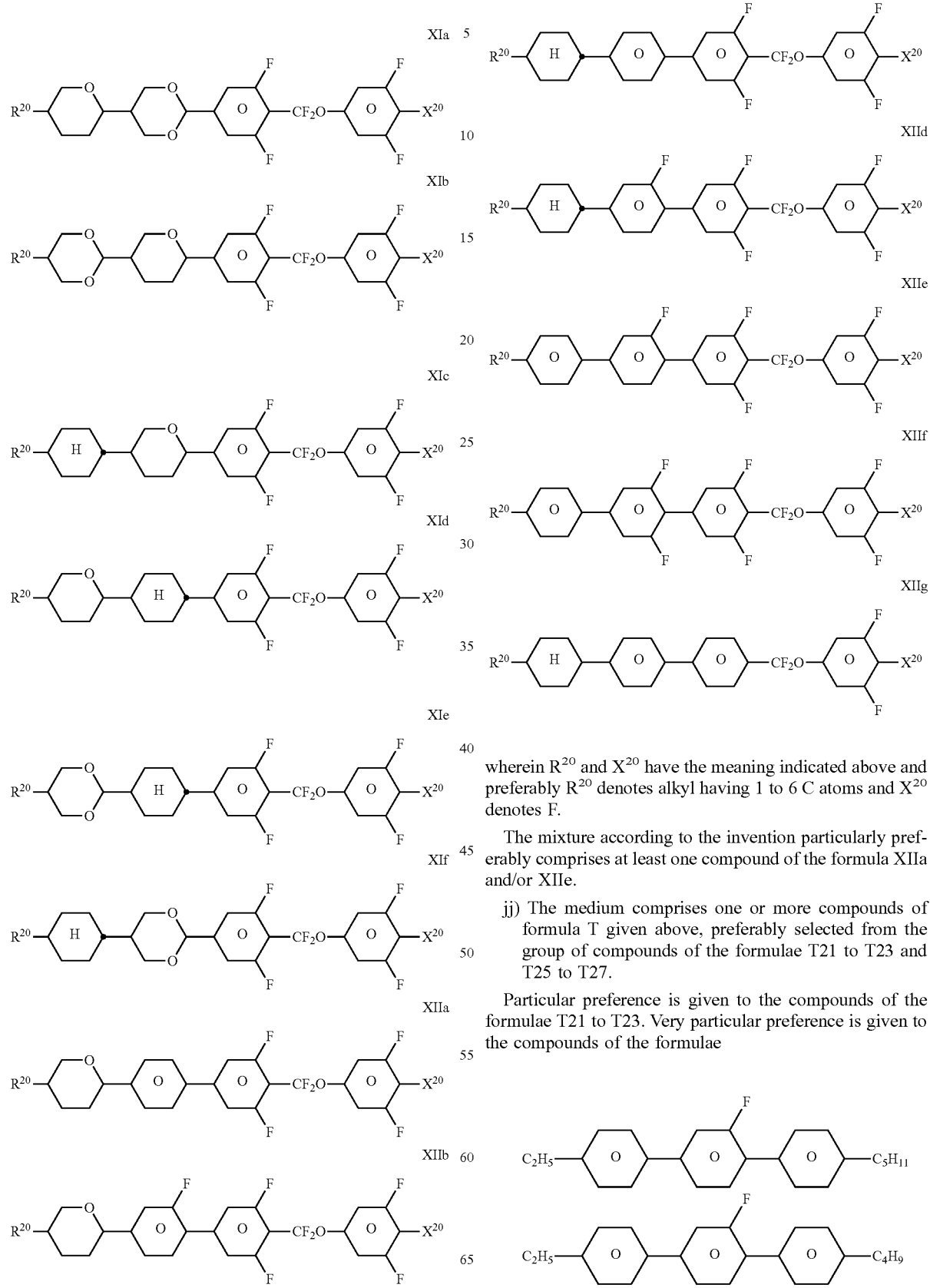

wherein $R^{20}$ and $X^{20}$ have the meaning indicated above and preferably $R^{20}$ denotes alkyl having 1 to 6 C atoms and $X^{20}$ denotes F.

The mixture according to the invention particularly preferably comprises at least one compound of the formula XIIa and/or XIIe.

jj) The medium comprises one or more compounds of formula T given above, preferably selected from the group of compounds of the formulae T21 to T23 and T25 to T27.

Particular preference is given to the compounds of the formulae T21 to T23. Very particular preference is given to the compounds of the formulae

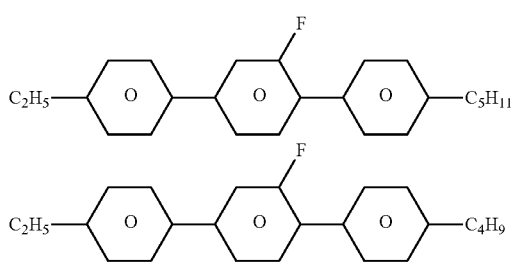

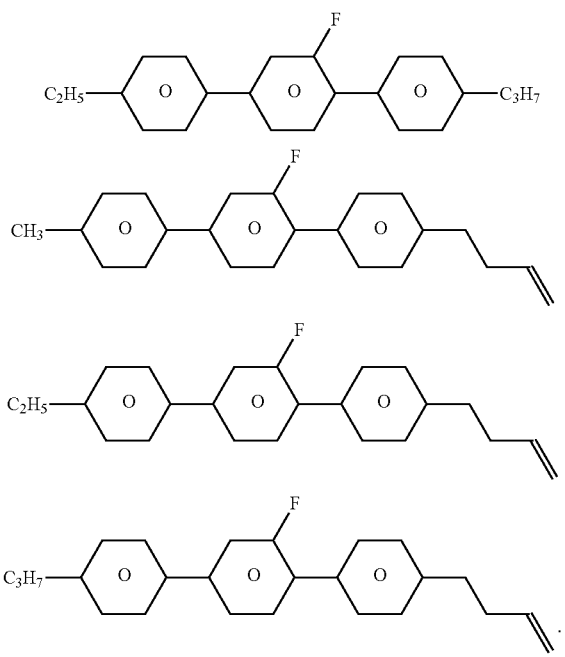

kk) The medium comprises one or more compounds selected from the group of formulae DK9, DK10 and DK11 given above.

ll) The medium additionally comprises one or more compounds selected from the following formulae:

XIII

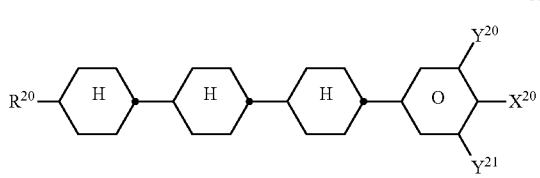

XIV

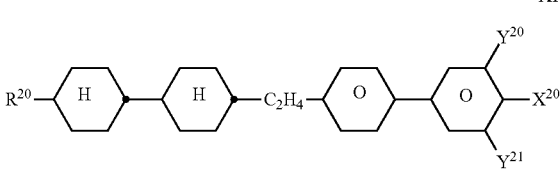

XV

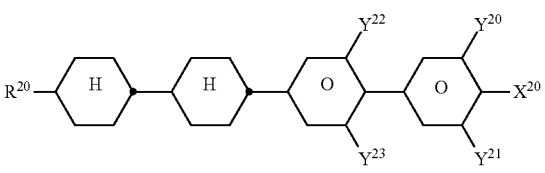

XVI

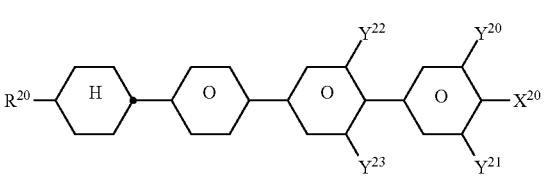

XVII

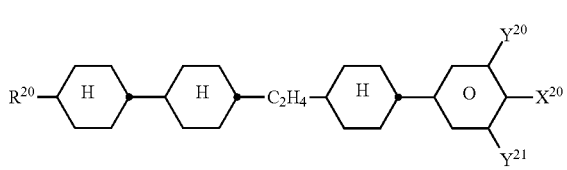

XVIII

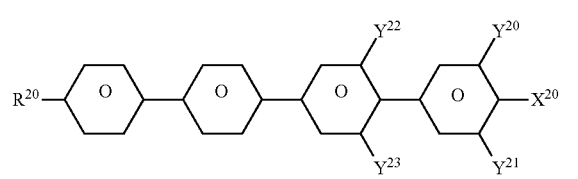

wherein $R^{20}$ and $X^{20}$ each, independently of one another, have one of the meanings indicated above, and $Y^{20-23}$ each, independently of one another, denote H or F. $X^{20}$ is preferably F, Cl, $CF_3$, $OCF_3$ or $OCHF_2$. $R^{20}$ preferably denotes alkyl, alkoxy, oxaalkyl, fluoroalkyl or alkenyl, each having up to 6 C atoms.

The mixture according to the invention particularly preferably comprises one or more compounds of the formula XVIII-a, XVIII-a

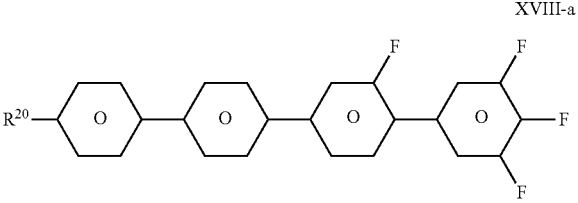

wherein $R^{20}$ has the meanings indicated above. $R^{20}$ preferably denotes straight-chain alkyl, in particular ethyl, n-propyl, n-butyl and n-pentyl and very particularly preferably n-propyl. The compound(s) of the formula XVIII, in particular of the formula XVIII-a, is (are) preferably employed in the mixtures according to the invention in amounts of 0.5-20% by weight, particularly preferably 1-15% by weight.

mm) The medium additionally comprises one or more compounds of the formula XIX,

XIX

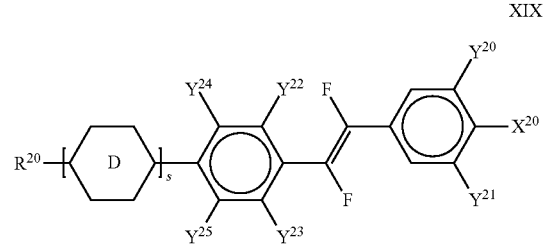

wherein $R^{20}$, $X^{20}$ and $Y^{20-25}$ have the meanings indicated in formula I, s denotes 0 or 1, and

denotes

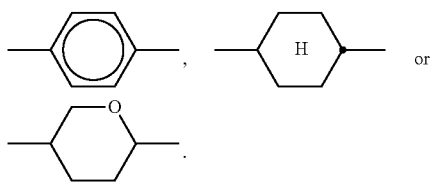

In the formula XIX, $X^{20}$ may also denote an alkyl radical having 1-6 C atoms or an alkoxy radical having 1-6 C atoms. The alkyl or alkoxy radical is preferably straight-chain.

$R^{20}$ preferably denotes alkyl having 1 to 6 C atoms. $X^{20}$ preferably denotes F;

The compounds of the formula XIX are preferably selected from the following formulae:

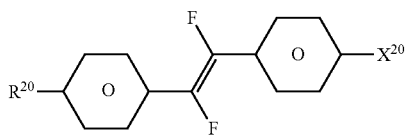
XIXa

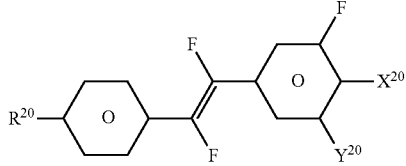
XIXb

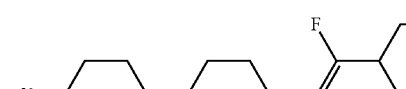
XIXc

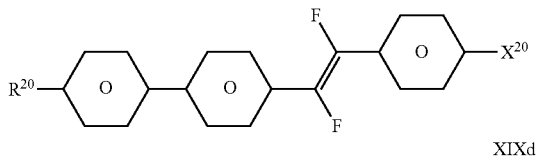
XIXd

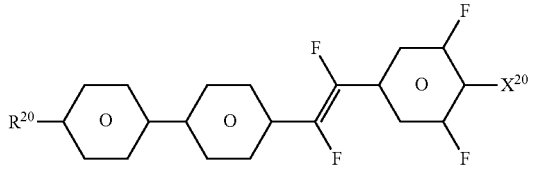
XIXe

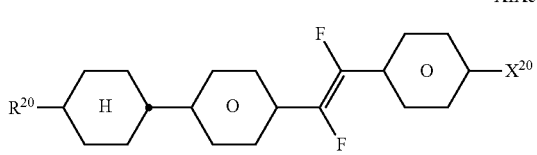

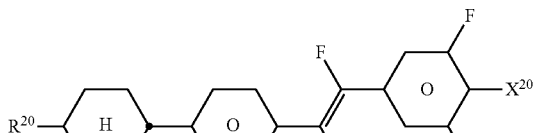
XIXf

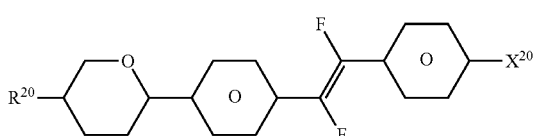
XIXg

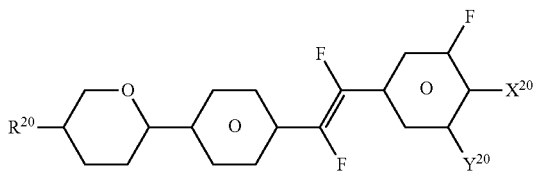
XIXh wherein $R^{20}$, $X^{20}$ and $Y^{20}$ have the meanings indicated above. $R^{20}$ preferably denotes alkyl having 1 to 6 C atoms. $X^{20}$ preferably denotes F, and $Y^{20}$ is preferably F;

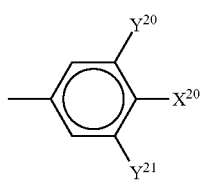

is preferably

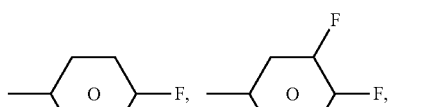

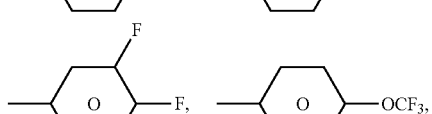

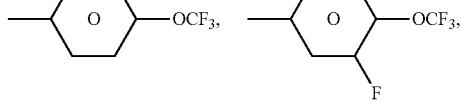

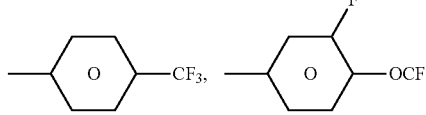

-continued

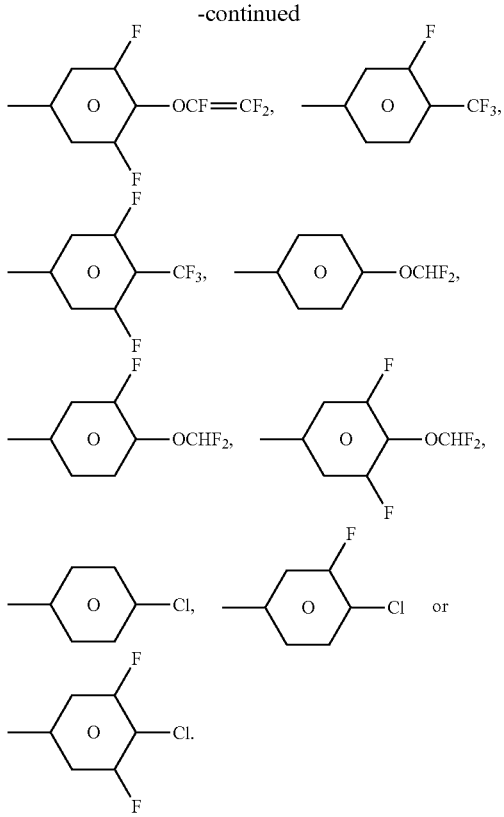

$R^{20}$ is straight-chain alkyl or alkenyl having 2 to 6 C atoms;

nn) The medium comprises one or more compounds of the formulae G1 to G4 given above, preferably selected from G1 and G2 wherein alkyl denotes $C_{1-6}$-alkyl, $L^x$ denotes H and X denotes F or Cl. In G2, X particularly preferably denotes Cl.

oo) The medium comprises one or more compounds of the following formulae:

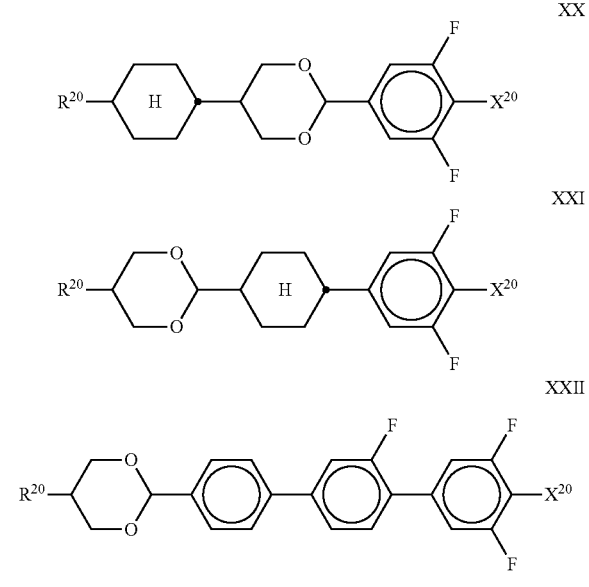

wherein $R^{20}$ and $X^{20}$ have the meanings indicated above. $R^{20}$ preferably denotes alkyl having 1 to 6 C atoms. $X^{20}$ preferably denotes F. The medium according to the invention particularly preferably comprises one or more compounds of the formula XXII wherein $X^{20}$ preferably denotes F. The compound(s) of the formulae XX-XXII is (are) preferably employed in the mixtures according to the invention in amounts of 1-20% by weight, particularly preferably 1-15% by weight. Particularly preferred mixtures comprise at least one compound of the formula XXII.

pp) The medium comprises one or more compounds of the following pyrimidine or pyridine compounds of the formulae

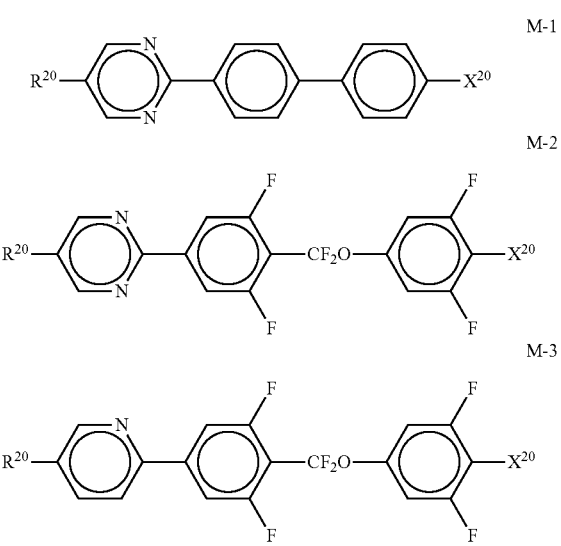

wherein $R^{20}$ and $X^{20}$ have the meanings indicated above. $R^{20}$ preferably denotes alkyl having 1 to 6 C atoms. $X^{20}$ preferably denotes F. The medium according to the invention particularly preferably comprises one or more compounds of the formula M-1, wherein $X^{20}$ preferably denotes F. The compound(s) of the formulae M-1-M-3 is (are) preferably employed in the mixtures according to the invention in amounts of 1-20% by weight, particularly preferably 1-15% by weight.

Further preferred embodiments are indicated below:

qq) The medium comprises two or more compounds of the formula XII, in particular of the formula XIIe;

rr) The medium comprises 2-30% by weight, preferably 3-20% by weight, particularly preferably 3-15% by weight, of compounds of the formula XII;

ss) Besides the compounds of the formulae XII, the medium comprises further compounds selected from the group of the compounds of the formulae II, III, IX-XIII, XVII and XVIII;

tt) The proportion of compounds of the formulae II, III, IX-XI, XIII, XVII and XVIII in the mixture as a whole is 40 to 95% by weight;

uu) The medium comprises 10-50% by weight, particularly preferably 12-40% by weight, of compounds of the formulae II and/or III;

vv) The medium comprises 20-70% by weight, particularly preferably 25-65% by weight, of compounds of the formulae IX-XIII;

ww) The medium comprises 4-30% by weight, particularly preferably 5-20% by weight, of compounds of the formula XVII;

xx) The medium comprises 1-20% by weight, particularly preferably 2-15% by weight, of compounds of the formula XVIII;
yy) The medium comprises at least two compounds of the formulae

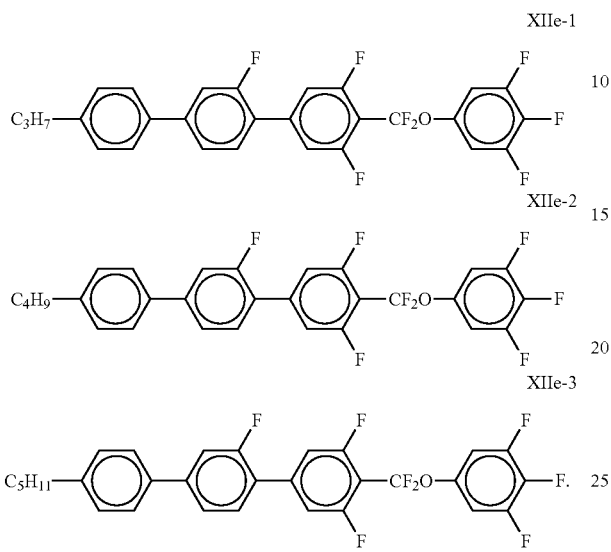

zz) The medium comprises at least two compounds of the formulae

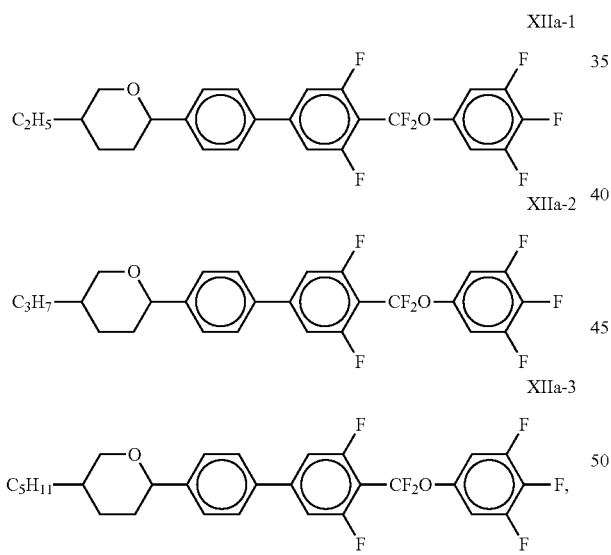

aaa) The medium comprises at least two compounds of the formula XIIa and at least two compounds of the formula XIIe.
bbb) The medium comprises at least one compound of the formula XIIa and at least one compound of the formula XIIe and at least one compound of the formula IIIa.
ccc) The medium comprises at least two compounds of the formula XIIa and at least two compounds of the formula XIIe and at least one compound of the formula IIIa.
ddd) The medium comprises in total ≥25% by weight, preferably ≥30% by weight, of one or more compounds of the formula XII.

eee) The medium comprises ≥20% by weight, preferably ≥24% by weight, preferably 25-60% by weight, of compounds of the formula ZK3, in particular the compound of the formula ZK3a,

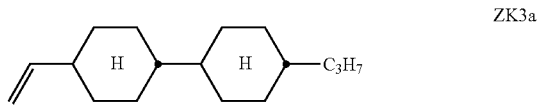

fff) The medium comprises at least one compound selected from the group of compounds ZK3a, ZK3b and ZK3c, preferably ZK3a, in combination with compound ZK3d

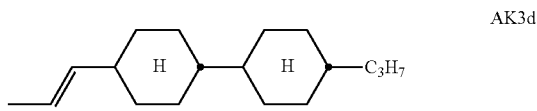

ggg) The medium comprises at least one compound of the formula DPGU-n-F.
hhh) The medium comprises at least one compound of the formula CDUQU-n-F.
iii) The medium comprises at least one compound of the formula CPU-n-OXF.
jjj) The medium comprises at least one compound of the formula CPGU-3-OT.
kkk) The medium comprises at least one compound of the formula PPGU-n-F.
lll) The medium comprises at least one compound of the formula PGP-n-m, preferably two or three compounds.
mmm) The medium comprises at least one compound of the formula PGP-2-2V having the structure

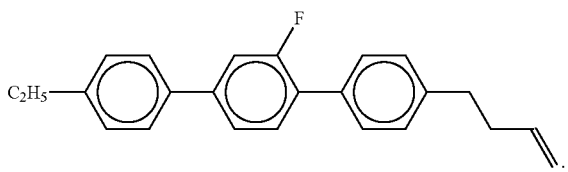

In a preferred embodiment, the liquid crystal mixture according to the present invention further comprises a polymerizable component C) comprising one or more polymerizable compounds.

The polymerizable compounds can be selected from isotropic or mesogenic polymerizable compounds known to the skilled person in the art.

Preferably, the polymerizable component C) comprises one or more polymerizable compounds of formula P,

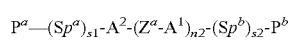

wherein the individual radicals have the following meanings:
$P^a$, $P^b$ each, independently of one another, denote a polymerizable group,
$Sp^a$, $Sp^b$ on each occurrence, identically or differently, denote a spacer group,
s1, s2 each, independently of one another, denote 0 or 1,
$A^1$, $A^2$ each, independently of one another, denote a radical selected from the following groups:

a) the group consisting of trans-1,4-cyclohexylene, 1,4-cyclohexenylene and 4,4'-bicyclohexylene, wherein, in addition, one or more non-adjacent CH$_2$ groups may be replaced by —O— and/or —S— and wherein, in addition, one or more H atoms may be replaced by F, b) the group consisting of 1,4-phenylene and 1,3-phenylene, wherein, in addition, one or two CH groups may be replaced by N and wherein, in addition, one or more H atoms may be replaced by L, c) the group consisting of tetrahydropyran-2,5-diyl, 1,3-dioxane-2,5-diyl, tetrahydrofuran-2,5-diyl, cyclobutane-1,3-diyl, piperidine-1,4-diyl, thiophene-2,5-diyl and selenophene-2,5-diyl, each of which may also be mono- or polysubstituted by L, d) the group consisting of saturated, partially unsaturated or fully unsaturated, and optionally substituted, polycyclic radicals having 5 to 20 cyclic C atoms, one or more of which may, in addition, be replaced by heteroatoms, preferably selected from the group consisting of

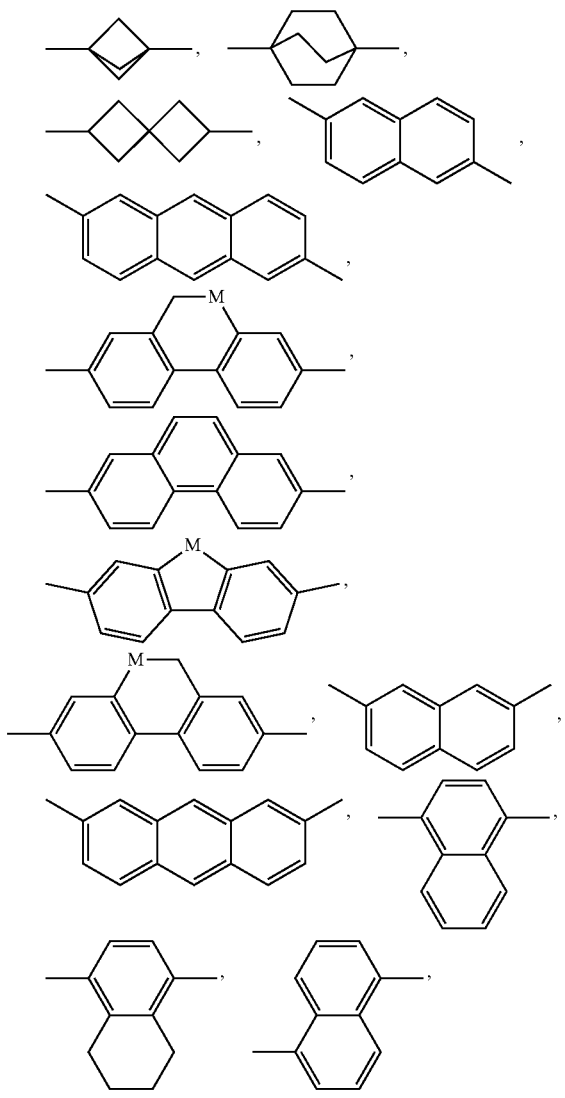

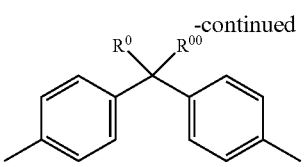

where, in addition, one or more H atoms in these radicals may be replaced by L, and/or one or more double bonds may be replaced by single bonds, and/or one or more CH groups may be replaced by N, n2 denotes 0, 1, 2 or 3, $Z^a$ in each case, independently of one another, denotes —CO—O—, —O—CO—, —CH$_2$O—, —OCH$_2$—, —CF$_2$O—, —OCF$_2$—, or —(CH$_2$)$_n$—, where n is 2, 3 or 4, —O—, —CO—, —C(R$^y$R$^z$)—, —CH$_2$CF$_2$—, —CF$_2$CF$_2$— or a single bond, L on each occurrence, identically or differently, denotes F, Cl, CN, SCN, SF$_5$ or straight-chain or branched, in each case optionally fluorinated, alkyl, alkoxy, alkylcarbonyl, alkoxycarbonyl, alkylcarbonyloxy or alkoxycarbonyloxy having 1 to 12 C atoms, $R^y$, $R^z$ each, independently of one another, denote H, F or straight-chain or branched alkyl having 1 to 12 C atoms, wherein, in addition, one or more H atoms may be replaced by F, M denotes —O—, —S—, —CH$_2$—, —CHY$^1$— or —CY$^1$Y$^2$—, and $Y^1$ and $Y^2$ each, independently of one another, have one of the meanings indicated above for $R^y$ or denote Cl or CN.

Preferred spacer groups Sp$^{a, b}$ are selected from the formula Sp"-X", so that the radicals P-Sp- and P$^{a/b}$-Sp$^{a/b}$- conforms to the formulae P-Sp"-X"— and P$^{a/b}$-Sp"-X"—, respectively, wherein Sp" denotes alkylene having 1 to 20, preferably 1 to 12, C atoms, which is optionally mono- or polysubstituted by F, Cl, Br, I or CN and wherein, in addition, one or more non-adjacent CH$_2$ groups may each be replaced, independently of one another, by —O—, —S—, —NH—, —N(R$^0$)—, —Si(R$^{00}$R$^{000}$)—, —CO—, —CO—O—, —O—CO—, —O—CO—O—, —S—CO—, —CO—S—, —N(R$^{00}$)—CO—O—, —O—CO—N(R$^{00}$)—, —N(R$^{00}$)—CO—N(R$^{00}$)—, —CH=CH— or —C≡C— in such a way that O and/or S atoms are not linked directly to one another, X" denotes —O—, —S—, —CO—, —CO—O—, —O—CO—, —O—CO—O—, —CO—N(R$^{00}$)—, —N(R$^{00}$)—CO—, —N(R$^{00}$)—CO—N(R$^{00}$)—, —OCH$_2$—, —CH$_2$O—, —SCH$_2$—, —CH$_2$S—, —CF$_2$O—, —OCF$_2$—, —CF$_2$S—, —SCF$_2$—, —CF$_2$CH$_2$—, —CH$_2$CF$_2$—, —CF$_2$CF$_2$—, —CH=N—, —N=CH—, —N=N—, —CH=CR$^0$—, —CY$^3$=CY$^4$—, —C≡C—, —CH=CH—CO—O—, —O—CO—CH=CH— or a single bond, $R^0$, $R^{00}$ and $R^{000}$ each, independently of one another, denote H or alkyl having 1 to 12 C atoms, and $Y^3$ and $Y^4$ each, identically or differently, denote H, F, Cl or CN.

X" is preferably —O—, —S—, —CO—, —C(O)O—, —OC(O)—, —O—C(O)O—, —CO—NR$^0$—, —NR$^0$—CO—, —NR$^0$—CO—NR$^0$— or a single bond.

Typical spacer groups Sp" are, for example, —(CH$_2$)$_{p1}$—, —(CH$_2$CH$_2$O)$_{q1}$—CH$_2$CH$_2$—, —CH$_2$CH$_2$—S—

CH₂CH₂—, —CH₂CH₂—NH—CH₂CH₂— or —(SiR⁰⁰R⁰⁰⁰—O)ₚ₁—, wherein p1 is an integer from 1 to 12, q1 is an integer from 1 to 3, and R⁰⁰ and R⁰⁰⁰ have the meanings indicated above.

Particularly preferred groups -Sp"-X"— are —(CH₂)ₚ₁—, —(CH₂)ₚ₁—O—, —(CH₂)ₚ₁-θ—CO—, —(CH₂)ₚ₁—O—CO—O—, wherein p1 and q1 have the meanings indicated above.

Particularly preferred groups Sp" are, for example, in each case straight-chain ethylene, propylene, butylene, pentylene, hexylene, heptylene, octylene, nonylene, decylene, undecylene, dodecylene, octadecylene, ethyl-eneoxyethyl-ene, methyleneoxybutylene, ethylenethioethylene, ethylene-N-methyliminoethylene, 1-methylalkylene, ethenylene, propenylene and butenylene.

Particularly preferred monomers of formula P are the following:

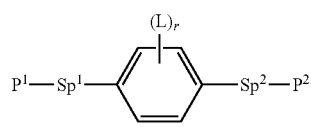
P1

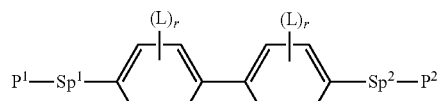
P2

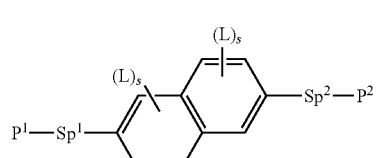
P3

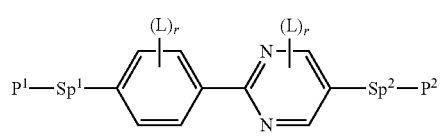
P4

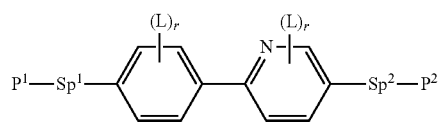
P5

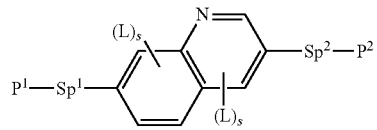
P6

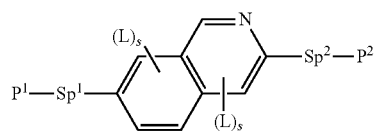
P7

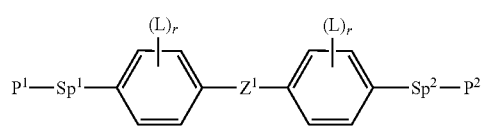
P8

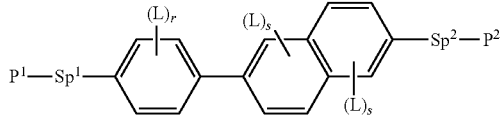
P9

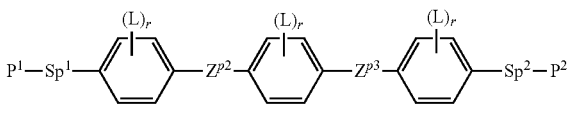
P10

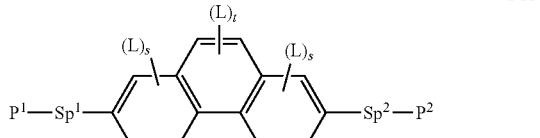
P11

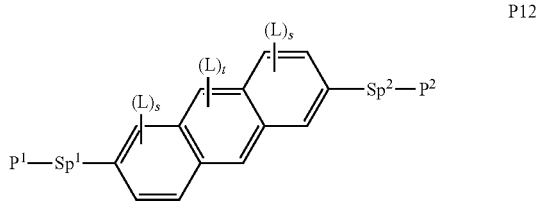
P12

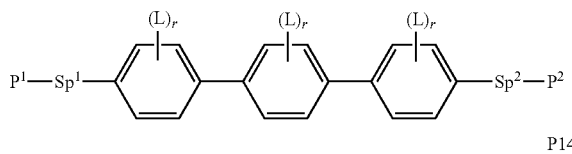
P13

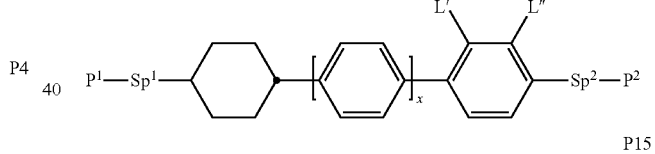
P14

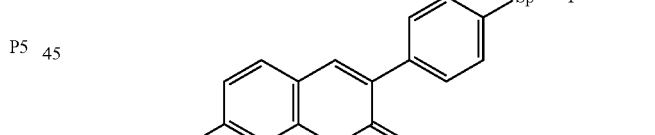
P15

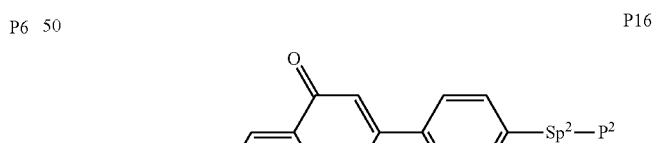
P16

P17

-continued

P18
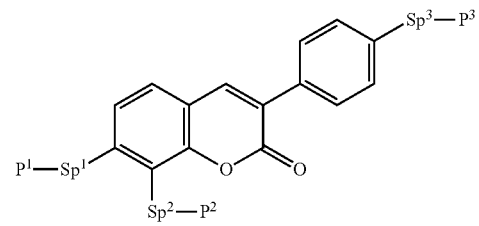

P19

P20

P21
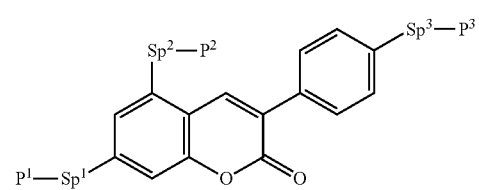

P22

P23
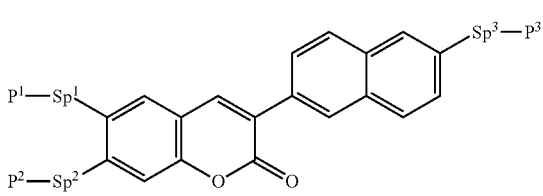

P24
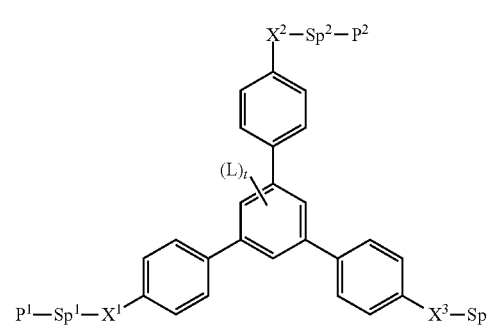

-continued

P25

P26
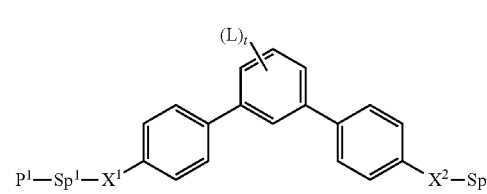

P27

P28
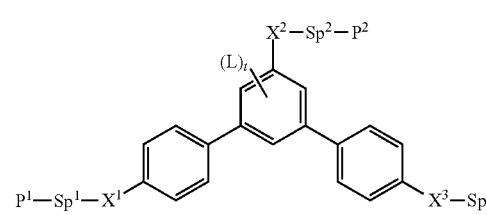

P29

P30

P31
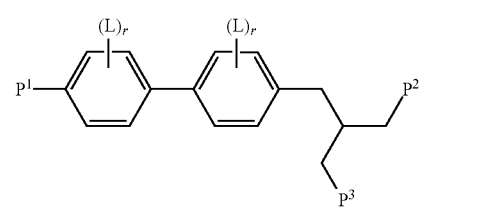

wherein the individual radicals have the following meanings:

$P^1$ to $P^3$ each, independently of one another, denote a polymerizable group as defined for formula P, preferably an acrylate, methacrylate, fluoroacrylate, oxetane, vinyloxy or epoxide group, $Sp^1$ to $Sp^3$ each, independently of one another, denote a single bond or a spacer group, preferably having one of the meanings indicated above and below for $Sp^a$, and particularly preferably —$(CH_2)_{p1}$—, —$(CH_2)_{p1}$—O—, —$(CH_2)_{p1}$—CO—O— or —$(CH_2)_{p1}$—O—CO—O—, wherein p1 is an integer from 1 to 12, and where the linking to the adjacent ring in the last-mentioned groups takes place via the O atom, where, in addition, one or more of the radicals $P^1$-$Sp^1$-, $P^2$-$Sp^2$- and $P^3$-$Sp^3$- may denote a radical $R^{aa}$, with the proviso that at least one of the radicals $P^1$-$Sp^1$-, $P^2$-$Sp^2$- and $P^3$-$Sp^3$- present does not denote $R^{aa}$, $R^{aa}$ denotes H, F, Cl, CN or straight-chain or branched alkyl having 1 to 25 C atoms, wherein, in addition, one or more non-adjacent $CH_2$ groups may each be replaced, independently of one another, by $C(R^0)=C(R^{00})-$, $-C\equiv C-$, $-N(R^0)-$, $-O-$, $-S-$, $-CO-$, $-CO-O-$, $-O-CO-$, $-O-CO-O-$ in such a way that O and/or S atoms are not linked directly to one another, and wherein, in addition, one or more H atoms may be replaced by F, Cl, CN or $P^1$-$Sp^1$-, particularly preferably straight-chain or branched, optionally mono- or polyfluorinated alkyl, alkoxy, alkenyl, alkynyl, alkylcarbonyl, alkoxycarbonyl or alkylcarbonyloxy having 1 to 12 C atoms (where the alkenyl and alkynyl radicals have at least two C atoms and the branched radicals have at least three C atoms), $R^0$, $R^{00}$ each, independently of one another, denote H or alkyl having 1 to 12 C atoms, $R^y$ and $R^z$ each, independently of one another, denote H, F, $CH_3$ or $CF_3$, $Z^{p1}$ denotes $-O-$, $-CO-$, $-C(R^yR^z)-$ or $-CF_2CF_2-$, $Z^{p2}$ and $Z^{p3}$ each, independently of one another, denote $-CO-O-$, $-O-CO-$, $-CH_2O-$, $-OCH_2-$, $-CF_2O-$, $-OCF_2-$ or $-(CH_2)_{n3}-$, where n3 is 2, 3 or 4, L on each occurrence, identically or differently, denotes F, Cl, CN, SCN, $SF_5$ or straight-chain or branched, optionally mono- or polyfluorinated alkyl, alkoxy, alkenyl, alkynyl, alkylcarbonyl, alkoxycarbonyl, alkylcarbonyloxy or alkoxycarbonyloxy having 1 to 12 C atoms, preferably F, L' and L" each, independently of one another, denote H, F or Cl, r denotes 0, 1, 2, 3 or 4, s denotes 0, 1, 2 or 3, t denotes 0, 1 or 2, and x denotes 0 or 1.

In a particularly preferred embodiment of the present invention the LC mixture, or component C), comprises one or more compounds of formula P10-1.

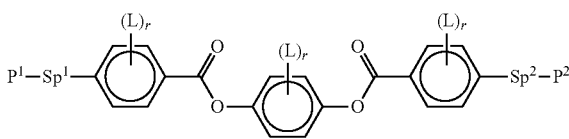

P10-1 wherein the parameters are defined as described above and $P^1$ and $P^2$ preferably denote acrylate or methacrylate.

Particularly preferred compounds of formula P10-1 are selected from the group of the following subformulae

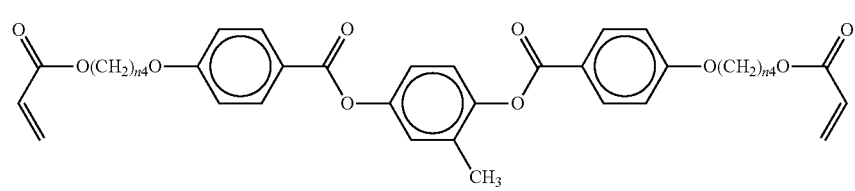

P10-1-1

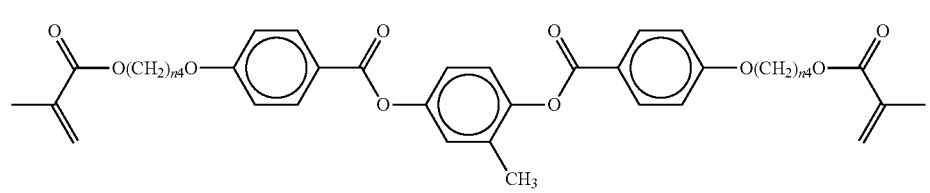

P10-1-2 wherein each n4 denote independently of each other an integer between 2 and 10, preferably 3, 4, 5 or 6.

The polymerizable compounds of formulae I and P are also suitable for polymerisation without an initiator, which is associated with considerable advantages, such as, for example, lower material costs and, in particular, reduced contamination of the LC medium by possible residual amounts of the initiator or degradation products thereof. The polymerisation can thus also be carried out without addition of an initiator. The LC medium thus, in a preferred embodiment, comprises no polymerisation initiator.

The polymerizable component C) or the LC medium as a whole may also comprise one or more stabilisers in order to prevent undesired spontaneous polymerisation of the RMs, for example during storage or transport. Suitable types and amounts of stabilisers are known to the person skilled in the art and are described in the literature. Particularly suitable are, for example, the commercially available stabilisers from the Irganox® series (BASF SE), such as, for example, Irganox® 1076. If stabilisers are employed, their proportion, based on the total amount of the RMs or the polymerizable component, is preferably 10-10,000 ppm, particularly preferably 50-1000 ppm.

The media according to the invention preferably comprise from 0.01 to 10%, particularly preferably from 0.05 to 7.5% and most preferably from 0.1 to 5% of the compounds of component C) comprising compounds of formula P according to the invention. The media preferably comprise one, two or three, more preferably one or two and most preferably one compound of the formula P according to the invention.

By means of suitable additives, the liquid-crystalline phases of the present invention can be modified in such a way that they can be used in all types of liquid-crystal display element that have been disclosed hitherto. Additives of this type are known to the person skilled in the art and are described in detail in the literature (H. Kelker/R. Hatz, Handbook of Liquid Crystals, Verlag Chemie, Weinheim, 1980). For example, pleochroic dyes can be added for the production of coloured guest-host systems or substances can be added in order to modify the dielectric anisotropy, the viscosity and/or the alignment of the nematic phases.

The media according to the invention are prepared in a manner conventional per se. In general, the components are dissolved in one another, preferably at elevated temperature.

Accordingly the present invention relates further to method for the production of an LC medium according to the present invention, comprising the step of mixing one or more compounds of formula I with a liquid-crystalline component B) comprising one or more mesogenic or liquid-crystalline compounds as described above.

The present invention further relates to a process for the fabrication of liquid crystal displays comprising at least the steps of:
  providing a first substrate which includes a pixel electrode and a common electrode for generating an electric field substantially parallel to a surface of the first substrate in the pixel region;
  providing a second substrate, the second substrate being disposed opposite to the first substrate;
  interposing a liquid crystal mixture between the first substrate and the second substrate, the liquid crystal mixture comprising one or more compounds of formula I, component B) and optionally component C);
  irradiating the liquid crystal mixture with linearly polarised light causing photoalignment of the liquid crystal;
  curing the polymerizable compounds of the liquid crystal mixture by irradiation with ultraviolet light or visible light having a wavelength of 450 nm or below.

The present invention further relates to the use of the liquid crystal mixtures according to the invention for the fabrication of a liquid crystal display.

The present invention further relates to liquid crystal displays fabricated by the process described above.

In the following, the production process according to the present invention is described in greater detail.

The first substrate includes a pixel electrode and a common electrode for generating an electric field substantially parallel to a surface of the first substrate in the pixel region. Various kinds of displays having at least two electrodes on one substrate are known to the skilled person wherein the most significant difference is that either both the pixel electrode and the common electrode are structured, as it is typical for IPS displays, or only the pixel electrode is structured and the common electrode is unstructured, which is the case for FFS displays.

It has to be understood that the present invention refers to any kind of electrode configurations suitable for generating an electric field substantially parallel to a surface of the first substrate in the pixel region; mentioned above, i.e. IPS as well as FFS displays.

The process according to the present invention is independent of the kind of substrate or material of the surface which is in contact with the liquid crystal mixture according to the invention, during and after this process. Examples of materials used for the substrates or surfaces are organic polymers including polyimide, indium tin oxide (ITO), indium zinc oxide (IZO), silicon nitride ($SiN_x$) and silicon dioxide ($SiO_2$). The process is especially suitable for the use in displays containing substrates that do not have a polyimide layer on one or more of the surfaces that are in contact with the liquid crystal.

In case one or more substrates contain a polyimide layer, the polyimide can be rubbed or not rubbed, preferably not rubbed.

Hence, the invention relates to a display produced by the process according to the invention in which the substrates contain a rubbed or unrubbed polyimide layer, preferably an unrubbed polyimide layer.

The invention further relates to a display produced by the process according to the invention in which none or only one of the top and bottom substrates contains a polyimide layer.

In one embodiment of the present invention the liquid crystal composition is injected between the first and second substrates or is filled into the cell by capillary force after combining the first and second substrates. In an alternative embodiment, the liquid crystal composition may be interposed between the first and second substrates by combining the second substrate to the first substrate after loading the liquid crystal composition on the first substrate. Preferably, the liquid crystal is dispensed dropwise onto a first substrate in a process known as "one drop filling" (ODF) process, as disclosed in for example JPS63-179323 and JPH10-239694, or using the Ink Jet Printing (IJP) method.

In a preferred embodiment, the process according to the invention contains a process step where the liquid crystal inside the display panel is allowed to rest for a period of time in order to evenly redistribute the liquid crystal medium inside the panel (herein referred to as "annealing").

However it is likewise preferred that the annealing step is combined with a previous step, such as edge sealant pre-curing. In which case a 'separate' annealing step may not be necessary at all.

For the production of the displays according to the present invention, the photoreactive mesogen of formula I is preferably allowed to redistribute in the panel. After filling and assembly, the display panel is annealed for a time between 1 min and 3 h, preferably between 2 min and 1 h and most preferably between 5 min and 30 min. The annealing is preferably performed at room temperature.

In an alternative embodiment, the annealing is performed at elevated temperature, preferably at above 20° C. and below 140° C., more preferably above 40° C. and below 100° C. and most preferably above 50° C. and below 80° C.

In a preferred embodiment, one or more of the process steps of filling the display, annealing, photoalignment and curing of the polymerizable compound is performed at a temperature above the clearing point of the liquid crystal host mixture.

During the photoalignment of the liquid crystal inside the liquid crystal panel, anisotropy is induced by exposing the display or the liquid crystal layer to linearly polarised light.

In a preferred embodiment of the present invention the photoreactive component A) comprising one or more compounds of formula I, is photoaligned in a first step using linearly polarised light and in a second step further cured using linearly polarized or unpolarised UV light. In the second step the optional component C) is also further cured.

In another preferred embodiment, the linearly polarised light applied according to the inventive process is ultraviolet light which enables simultaneous photoalignment and photocuring of the photoreactive component A) comprising one or more compounds of formula I, and, if present, photocuring of the polymerizable component C).

Photoalignment of the photoreactive compounds of formula I and curing of the polymerizable groups of compounds of formula I and the curing of the optional polymerizable compounds of formula P can be performed simultaneously or stepwise. In case the process is split into different steps, the individual steps can be performed at the same temperature or at different temperatures.

After the photoalignment and curing step(s) a so-called "post-curing" step can optionally be performed by irradiation with UV-light and/or visible light (both either linearly or unpolarised) at reduced temperature in order to remove unreacted polymerizable compounds. The post-curing is preferably performed at above 0° C. and below the clearing point of the utilized LC mixture, preferably 20° C. and below 60° C., and most preferably above 20° C. and below 40° C.

The polymerizable compounds are optionally polymerised or crosslinked (if a polymerizable compound contains two or more polymerizable groups) with the application of an electrical field. The polymerisation can be carried out in one or more steps.

Suitable and preferred polymerisation methods for component C) are, for example, thermal or photopolymerization, preferably photopolymerization, in particular UV photopolymerization. One or more initiators can optionally also be added here. Suitable conditions for the polymerisation and suitable types and amounts of initiators are known to the person skilled in the art and are described in the literature. Suitable for free-radical polymerisation are, for example, the commercially available photoinitiators Irgacure651®, Irgacure184®, Irgacure907®, Irgacure369® or Darocurel 173® (BASF SE). If an initiator is employed, its proportion is preferably 0.001 to 5% by weight, particularly preferably 0.001 to 1% by weight.

The present invention also relates to electro-optical liquid-crystal display elements containing a liquid-crystalline medium according to the invention, which is preferably homogeneously aligned. In a preferred embodiment the liquid crystal display is of the IPS or FFS mode.

Further combinations of the embodiments and variants of the invention in accordance with the description arise from the claims.

The invention is explained in greater detail below with reference to working examples, but without intending to be restricted thereby. The person skilled in the art will be able to glean from the examples working details that are not given in detail in the general description, generalise them in accordance with general expert knowledge and apply them to a specific problem.

Besides the usual and well-known abbreviations, the following abbreviations are used:

C: crystalline phase; N: nematic phase; Sm: smectic phase; I: isotropic phase. The numbers between these symbols show the transition temperatures of the substance concerned.

Temperature data are in ° C., unless indicated otherwise.

Physical, physicochemical or electro-optical parameters are determined by generally known methods, as described, inter alia, in the brochure "Merck Liquid Crystals—Licristal®—Physical Properties of Liquid Crystals—Description of the Measurement Methods", 1998, Merck KGaA, Darmstadt.

Above and below, $\Delta n$ denotes the optical anisotropy (589 nm, 20° C.) and $\Delta\varepsilon$ denotes the dielectric anisotropy (1 kHz, 20° C.). The dielectric anisotropy $\Delta\varepsilon$ is determined at 20° C. and 1 kHz. The optical anisotropy $\Delta n$ is determined at 20° C. and a wavelength of 589.3 nm.

The $\Delta\varepsilon$ and $\Delta n$ values and the rotational viscosity ($\gamma^1$) of the compounds according to the invention are obtained by linear extrapolation from liquid-crystalline mixtures consisting of 5 to 10% of the respective compound according to the invention and 90-95% of the commercially available liquid-crystal mixture ZLI-2857 (for $\Delta\varepsilon$) or ZLI-4792 (for $\Delta n$, $\gamma_1$) (mixtures, Merck KGaA, Darmstadt).

The compounds used in the present invention are prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se, which are not mentioned here in greater detail.

In the present invention and especially in the following examples, the structures of the mesogenic compounds are indicated by means of abbreviations, also called acronyms. In these acronyms, the chemical formulae are abbreviated as follows using Tables A to C below. All groups $C_nH_{2n+1}$, $C_mH_{2m+1}$ and $C_lH_{2l+1}$ or $C_nH_{2n-1}$, $C_mH_{2m-1}$ and $C_lH_{2l-1}$ denote straight-chain alkyl or alkenyl, preferably 1E-alkenyl, each having n, m and l C atoms respectively. Table A lists the codes used for the ring elements of the core structures of the compounds, while Table B shows the linking groups. Table C gives the meanings of the codes for the left-hand or right-hand end groups. The acronyms are composed of the codes for the ring elements with optional linking groups, followed by a first hyphen and the codes for the left-hand end group, and a second hyphen and the codes for the right-hand end group. Table D shows illustrative structures of compounds together with their respective abbreviations.

TABLE A

| | Ring elements |
|---|---|
| C | cyclohexane |
| P | 1,4-phenylene |
| D | 1,3-dioxane |
| A | tetrahydropyran |
| G | 2-fluoro-1,4-phenylene |
| U | 2,3-difluoro-1,4-phenylene |

TABLE A-continued
| | Ring elements | | | Ring elements |
|---|---|---|---|---|
| Y | 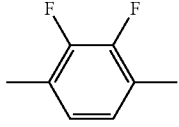 | K | 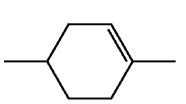 |
| DI | 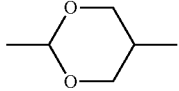 | L | 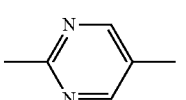 |
| AI | 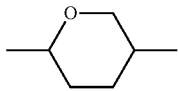 | MI | 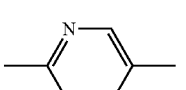 |
| GI | 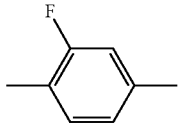 | NI | 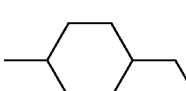 |
| UI | 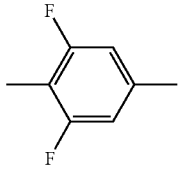 | dH | 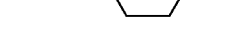 |
| M | 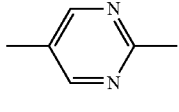 | N3fl | 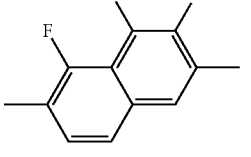 |
| N | 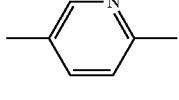 | tHl | 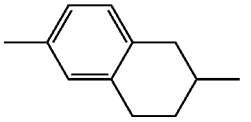 |
| Np | 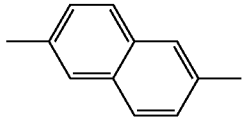 | tH2fl | 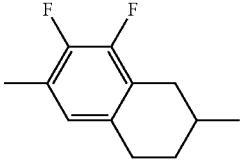 |
| N3f | 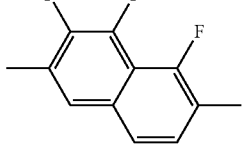 | KI | 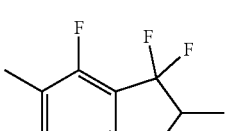 |
| tH | 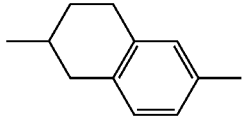 | LI | 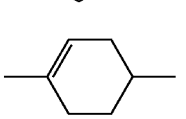 |
| tH2f | 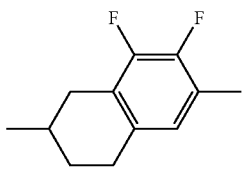 | F | 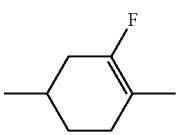 |

TABLE A-continued

Ring elements

| | | |
|---|---|---|
| Nf | 3-fluoro-2,5-dimethylpyridine structure | |
| Fl | 1-fluoro-3,4-dimethylcyclohexene structure | |
| Nfl | 3-fluoro-2,5-dimethylpyridine (alt) structure | |

TABLE B

Linking groups

| | | | |
|---|---|---|---|
| E | —$CH_2CH_2$— | Z | —CO—O— |
| V | —CH=CH— | ZI | —O—CO— |
| X | —CF=CH— | O | —$CH_2$—O— |
| XI | —CH=CF— | OI | —O—$CH_2$— |
| B | —CF=CF— | Q | —$CF_2$—O— |
| T | —C≡C— | QI | —O—$CF_2$— |
| W | —$CF_2CF_2$— | T | —C≡C— |

TABLE C

End groups

| Left-hand side | | Right-hand side | |
|---|---|---|---|
| Use alone | | | |
| -n- | $C_nH_{2n+1}$— | -n | —$C_nH_{2n+1}$ |
| -nO- | $C_nH_{2n+1}$—O— | -nO | —O—$C_nH_{2n+1}$ |
| -V- | $CH_2$=CH— | -V | —CH=$CH_2$ |
| -nV- | $C_nH_{2n+1}$—CH=CH— | -nV | —$C_nH_{2n}$—CH=$CH_2$ |
| -Vn- | $CH_2$=CH—$C_nH_{2n+1}$— | -Vn | —CH=CH—$C_nH_{2n+1}$ |
| -nVm- | $C_nH_{2n+1}$—CH=CH—$C_mH_{2m}$— | -nVm | —$C_nH_{2n}$—CH=CH—$C_mH_{2m+1}$ |
| -N- | N≡C— | -N | —C≡N |
| -S- | S=C=N— | -S | —N=C=S |
| -F- | F— | -F | —F |
| -CL- | Cl— | -CL | —Cl |
| -M- | $CFH_2$— | -M | —$CFH_2$ |
| -D- | $CF_2H$— | -D | —$CF_2H$ |
| -T- | $CF_3$— | -T | —$CF_3$ |
| -MO- | $CFH_2O$— | -OM | —$OCFH_2$ |
| -DO- | $CF_2HO$— | -OD | —$OCF_2H$ |
| -TO- | $CF_3O$— | -OT | —$OCF_3$ |
| -FXO- | $CF_2$=CH—O— | -OXF | —O—CH=$CF_2$ |
| -A- | H—C≡C— | -A | —C≡C—H |
| -nA- | $C_nH_{2n+1}$—C≡C— | -An | —C≡C—$C_nH_{2n+1}$ |
| -NA- | N≡C—C≡C— | -AN | —C≡C—C≡N |
| Use together with one another and with others | | | |
| -...A...- | —C≡— | -...A... | —C≡— |
| -...V...- | —CH=CH— | -...V... | —CH=CH— |
| -...Z...- | —CO—O— | -...Z... | —CO—O— |
| -...ZI...- | —O—CO— | -...ZI... | —O—CO— |
| -...K...- | —CO— | -...K... | —CO— |
| -...W...- | —CF=CF— | -...W... | —CF=CF— | wherein n and m each denote integers, and the three dots are place-holders for other abbreviations from this table.

The following table shows illustrative structures together with their respective abbreviations. These are shown in order to illustrate the meaning of the rules for the abbreviations. They furthermore represent compounds which are preferably used.

TABLE D

Illustrative structures $C_nH_{2n+1}$—⬡—⬡—$C_mH_{2m+1}$

CC-n-m $C_nH_{2n+1}$—⬡—⬡—O—$C_mH_{2m+1}$

CC-n-Om $C_nH_{2n+1}$—⬡—⬡—CH=CH$_2$

CC-n-V $C_nH_{2n+1}$—⬡—⬡—CH=CH—$C_mH_{2m+1}$

CC-n-Vm $C_nH_{2n+1}$—⬡—⬡—$(CH_2)_m$—CH=CH$_2$

CC-n-mV $C_nH_{2n+1}$—⬡—⬡—$(CH_2)_m$—CH=CH—$C_lH_{2l+1}$

CC-n-mVl $H_2C$=CH—⬡—⬡—CH=CH$_2$

CC-V-V $CH_2$=CH—⬡—⬡—$(CH_2)_m$—CH=CH$_2$

CC-V-mV $CH_2$=CH—⬡—⬡—CH=CH—$C_mH_{2m+1}$

CC-V-Vm $CH_2$=CH—$(CH_2)_n$—⬡—⬡—$(CH_2)_m$—CH=CH$_2$

CC-Vn-mV

TABLE D-continued

| Illustrative structures |
|---|

$C_nH_{2n+1}$—CH=CH—[Cy]—[Cy]—$(CH_2)_m$—CH=$CH_2$

CC-nV-mV $C_nH_{2n+1}$—CH=CH—[Cy]—[Cy]—CH=CH—$C_mH_{2m+1}$

CC-nV-Vm $C_nH_{2n+1}$—[Cy]—[Ph]—$C_mH_{2m+1}$

CP-n-m $C_nH_{2n+1}$O—[Cy]—[Ph]—$C_mH_{2m+1}$

CP--nO-m $C_nH_{2n+1}$—[Cy]—[Ph]—O$C_mH_{2m+1}$

CP-n-Om $CH_2$=CH—[Cy]—[Ph]—$C_mH_{2m+1}$

CP-V-m $CH_2$=CH—$(CH_2)_n$—[Cy]—[Ph]—$C_mH_{2m+1}$

CP-Vn-m $C_nH_{2n+1}$—CH=CH—[Cy]—[Ph]—$C_mH_{2m+1}$

CP-nV-m $H_2C$=CH—[Cy]—[Ph]—CH=$CH_2$

CP-V-V $CH_2$=CH—[Cy]—[Ph]—$(CH_2)_m$—CH=$CH_2$

CP-V-mV $CH_2$=CH—[Cy]—[Ph]—CH=CH—$C_mH_{2m+1}$

CP-V-Vm

TABLE D-continued

Illustrative structures $CH_2=CH-(CH_2)_n$—[Cy]—[Ph]—$(CH_2)_m-CH=CH_2$

CP-Vn-mV $C_nH_{2n+1}$—$CH=CH$—[Cy]—[Ph]—$(CH_2)_m-CH=CH_2$

CP-nV-mV $C_nH_{2n+1}$—$CH=CH$—[Cy]—[Ph]—$CH=CH-C_mH_{2m+1}$

CP-nV-Vm $C_nH_{2n+1}$—[Ph]—[Ph]—$C_mH_{2m+1}$

PP-n-m $C_nH_{2n+1}O$—[Ph]—[Ph]—$C_mH_{2m+1}$

PP-nO-m $C_nH_{2n+1}$—[Ph]—[Ph]—$OC_mH_{2m+1}$

PP-n-Om $C_nH_{2n+1}$—[Ph]—[Ph]—$CH=CH_2$

PP-n-V $C_nH_{2n+1}$—[Ph]—[Ph]—$CH=CH-C_mH_{2m+1}$

PP-n-Vm $C_nH_{2n+1}$—[Ph]—[Ph]—$(C_mH_{2m})-CH=CH_2$

PP-n-mV $C_nH_{2n+1}$—[Ph]—[Ph]—$(CH_2)_m-CH=CH-C_lH_{2l+1}$

PP-n-mVl $C_nH_{2n+1}$—[Cy]—[Cy]—[Ph]—$C_mH_{2m+1}$

CCP-n-m

TABLE D-continued

Illustrative structures $C_nH_{2n+1}O$—⟨cyclohexyl⟩—⟨cyclohexyl⟩—⟨phenyl⟩—$C_mH_{2m+1}$ CCP-nO-m $C_nH_{2n+1}$—⟨cyclohexyl⟩—⟨cyclohexyl⟩—⟨phenyl⟩—$OC_mH_{2m+1}$ CCP-n-Om $C_nH_{2n+1}$—⟨cyclohexyl⟩—⟨cyclohexyl⟩—⟨phenyl⟩—$CH\!=\!CH_2$ CCP-n-V $C_nH_{2n+1}$—⟨cyclohexyl⟩—⟨cyclohexyl⟩—⟨phenyl⟩—$CH\!=\!CH$—$C_mH_{2m+1}$ CCP-n-Vm $C_nH_{2n+1}$—⟨cyclohexyl⟩—⟨cyclohexyl⟩—⟨phenyl⟩—$(C_mH_{2m})$—$CH\!=\!CH_2$ CCP-n-mV $C_nH_{2n+1}$—⟨cyclohexyl⟩—⟨cyclohexyl⟩—⟨phenyl⟩—$(C_mH_{2m})$—$CH\!=\!CH$—$C_lH_{2l+1}$ CCP-n-mVl $H_2C\!=\!CH$—⟨cyclohexyl⟩—⟨cyclohexyl⟩—⟨phenyl⟩—$C_mH_{2m+1}$ CCP-V-m $C_nH_{2n+1}$—$CH\!=\!CH$—⟨cyclohexyl⟩—⟨cyclohexyl⟩—⟨phenyl⟩—$C_mH_{2m+1}$ CCP-nV-m $CH_2\!=\!CH$—$(CH_2)_n$—⟨cyclohexyl⟩—⟨cyclohexyl⟩—⟨phenyl⟩—$C_mH_{2m+1}$ CCP-Vn-m $C_nH_{2n+1}$—$CH\!=\!CH$—$(CH_2)_m$—⟨cyclohexyl⟩—⟨cyclohexyl⟩—⟨phenyl⟩—$C_lH_{2l+1}$ CCP-nVm-l $C_nH_{2n+1}$—⟨cyclohexyl⟩—⟨phenyl⟩—⟨phenyl⟩—$C_mH_{2m+1}$ CPP-n-m TABLE D-continued
Illustrative structures
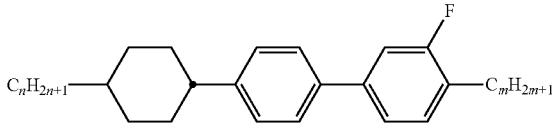
CPG-n-m
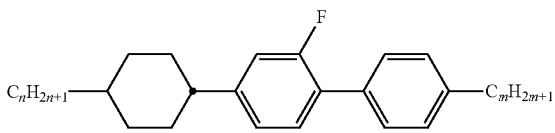
CGP-n-m
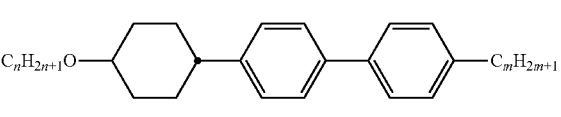
CPP-nO-m
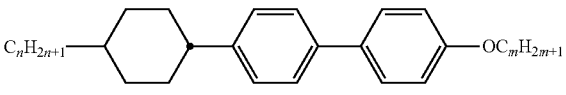
CPP-n-Om
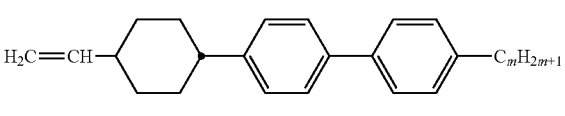
CPP-V-m
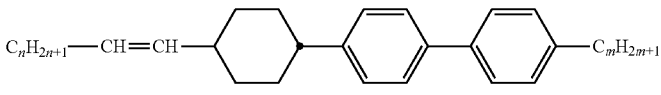
CPP-nV-m
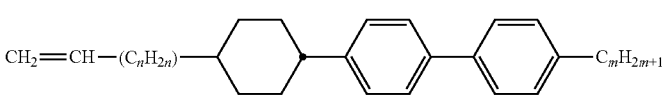
CPP-Vn-m
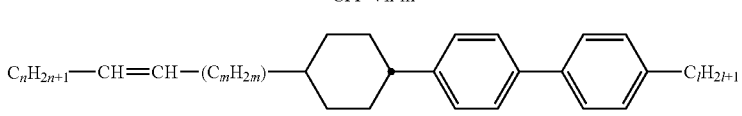
CPP-nVm-l
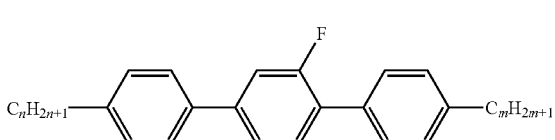
PGP-n-m
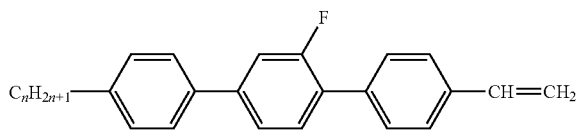
PGP-n-V TABLE D-continued Illustrative structures PGP-n-Vm PGP-n-mV PGP-n-mVI CCEC-n-m CCEC-n-Om CCEP-n-m CCEP-n-Om CPPC-n-m CGPC-n-m CCPC-n-m TABLE D-continued
Illustrative structures
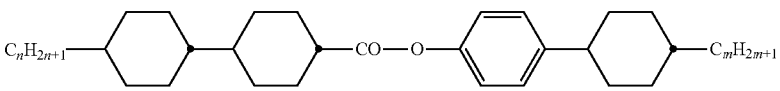
CCZPC-n-m
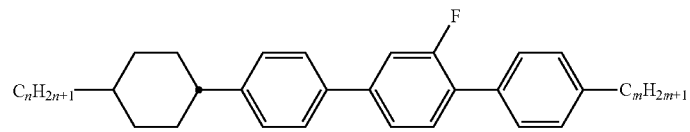
CPGP-n-m
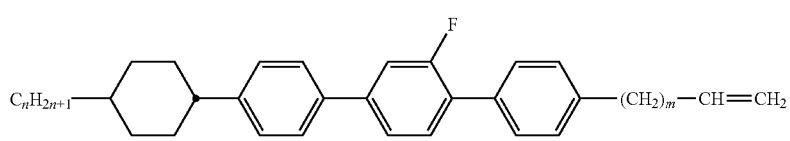
CPGP-n-mV
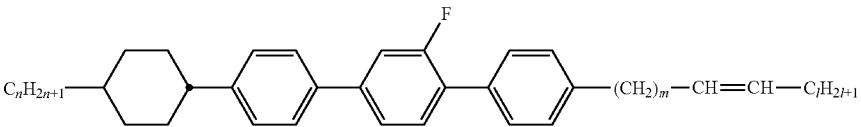
CPGP-n-mVI
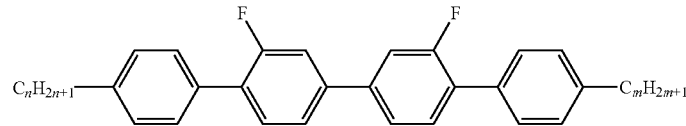
PGIGP-n-m
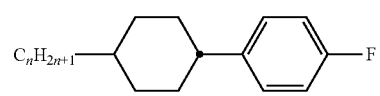
CP-n-F
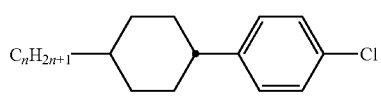
CP-n-CL
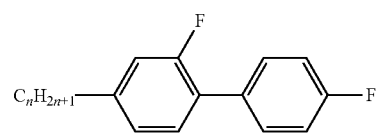
GP-n-F
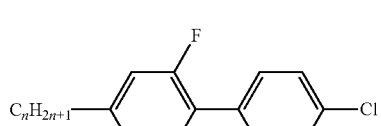
GP-n-CL TABLE D-continued
Illustrative structures
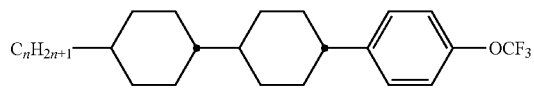
CCP-n-OT
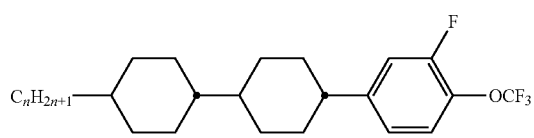
CCG-n-OT
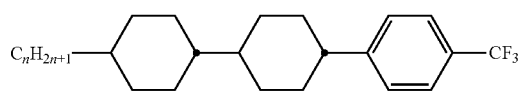
CCP-n-T
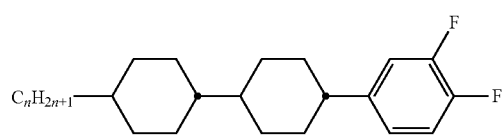
CCG-n-F
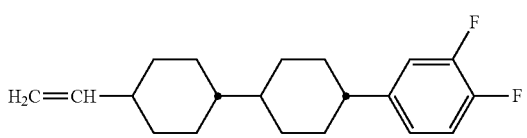
CCG-V-F
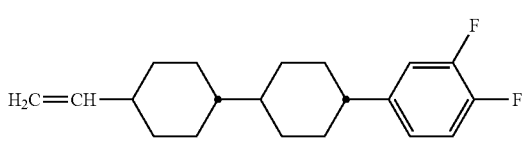
CCG-V-F
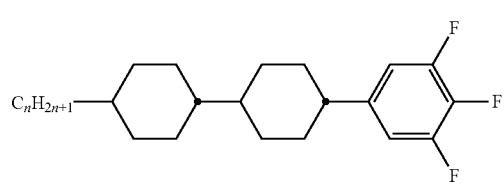
CCU-n-F
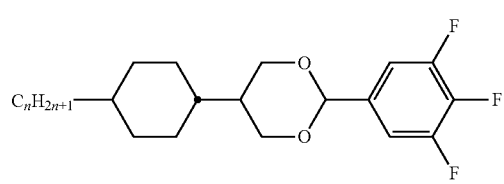
CDU-n-F TABLE D-continued
Illustrative structures
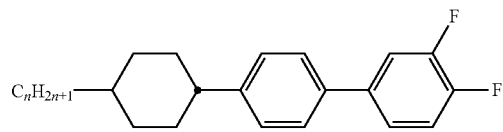
CPG-n-F
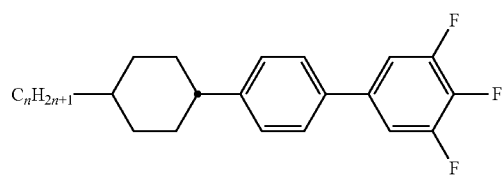
CPU-n-F
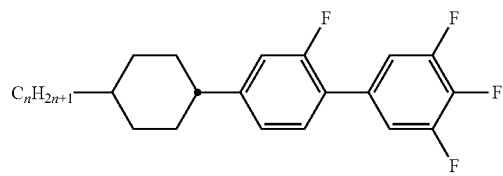
CGU-n-F
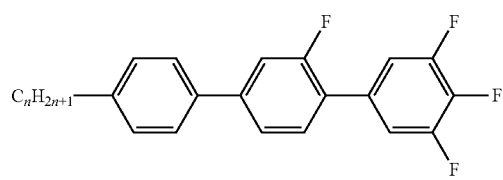
PGU-n-F
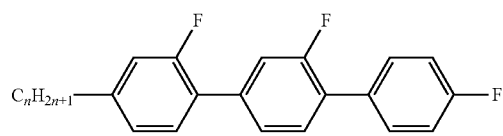
GGP-n-F
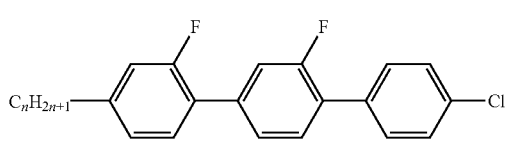
GGP-n-CL
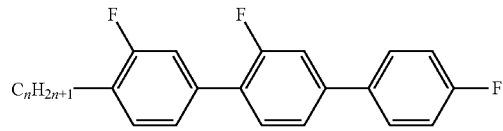
PGIGI-n-F
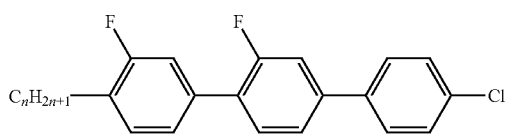
PGIGI-n-CL TABLE D-continued
Illustrative structures
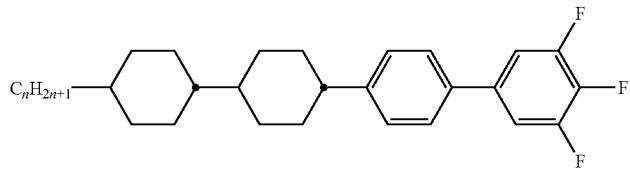
CCPU-n-F
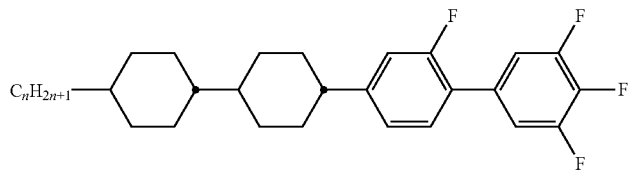
CCGU-n-F
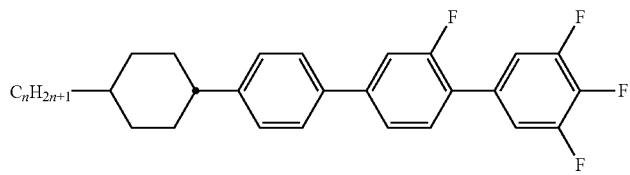
CPGU-n-F
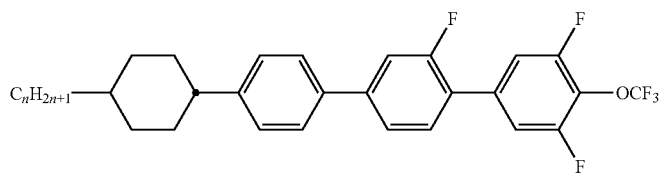
CPGU-n-OT
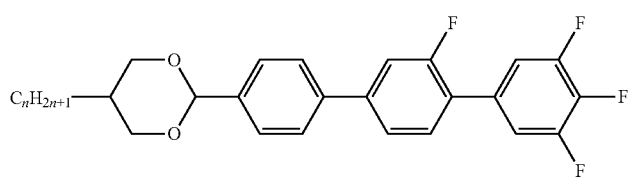
DPGU-n-F
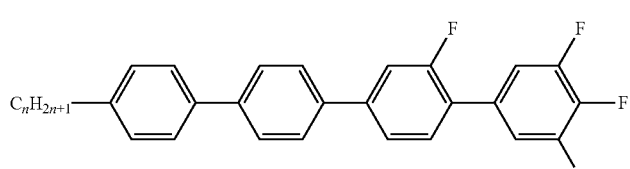
PPGU-n-F
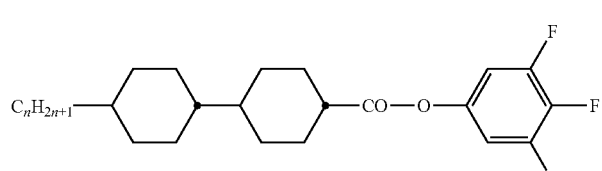
CCZU-n-F TABLE D-continued
Illustrative structures
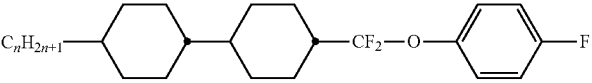
CCQP-n-F
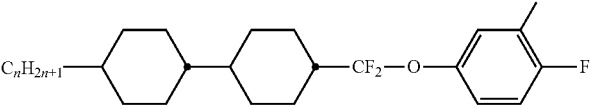
CCQG-n-F
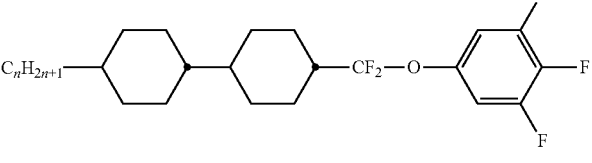
CCQU-n-F
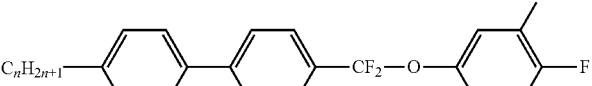
PPQG-n-F
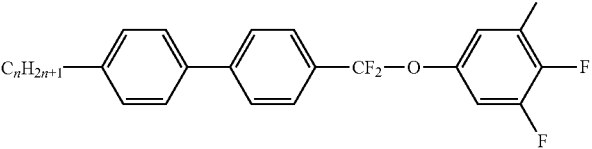
PPQU-n-F
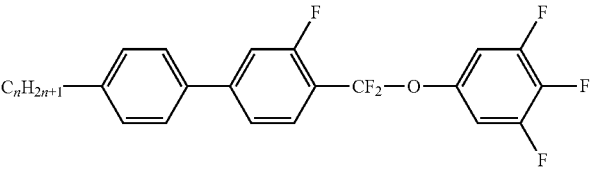
PGQU-n-F
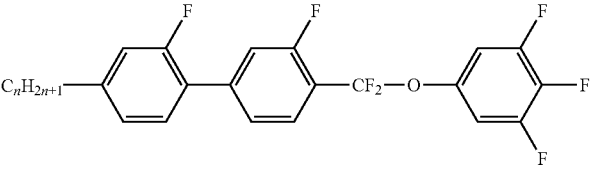
GGQU-n-F
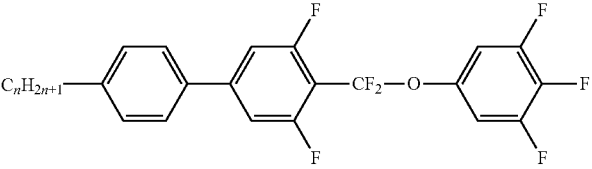
PUQU-n-F TABLE D-continued
Illustrative structures
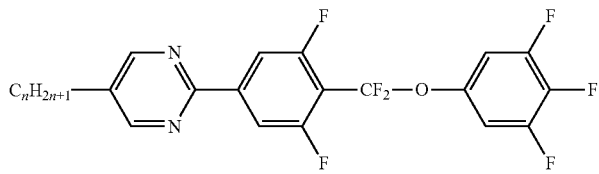
MUQU-n-F
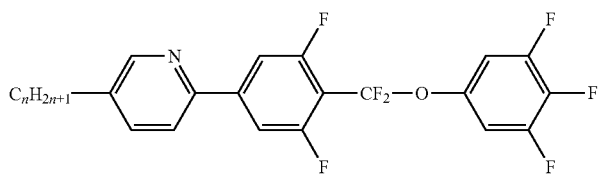
NUQU-n-F
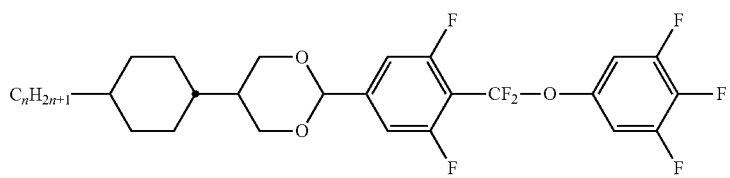
CDUQU-n-F
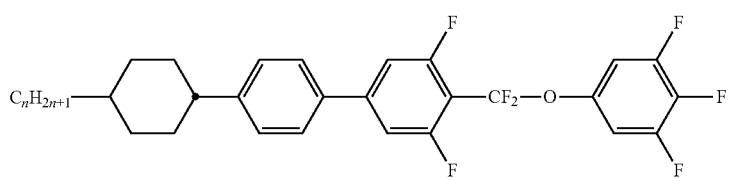
CPUQU-n-F
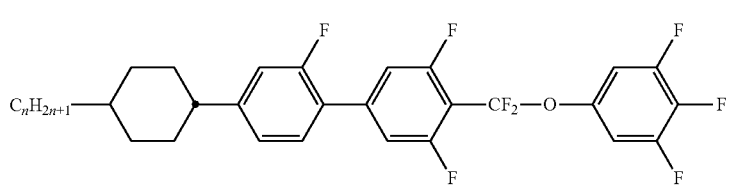
CGUQU-n-F
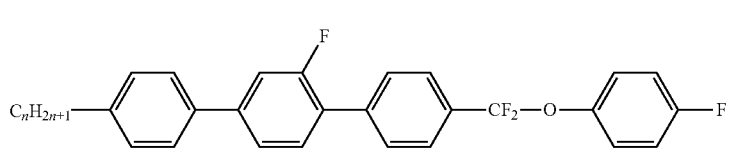
PGPQP-n-F
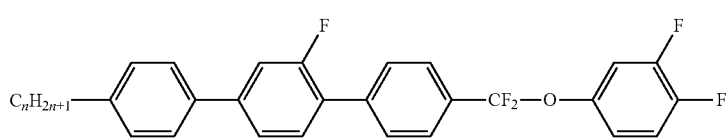
PGPQG-n-F TABLE D-continued
Illustrative structures
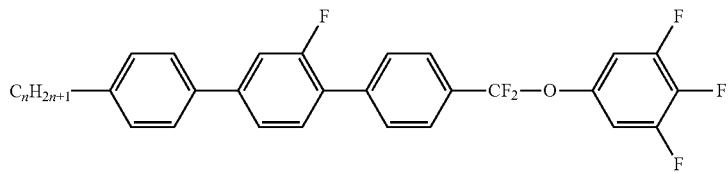
PGPQU-n-F
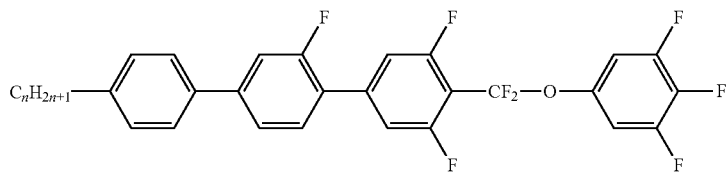
PGUQU-n-F
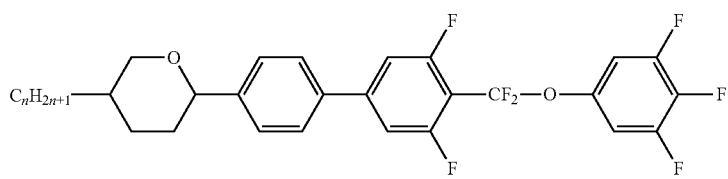
APUQU-n-F
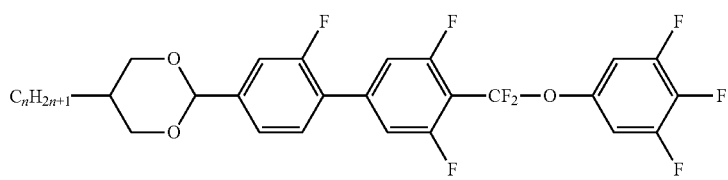
DGUQU-n-F
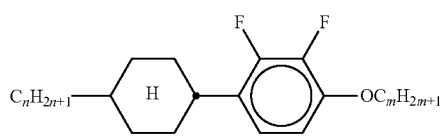
CY-n-Om
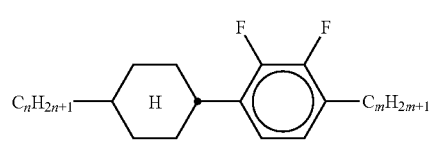
CY-n-m
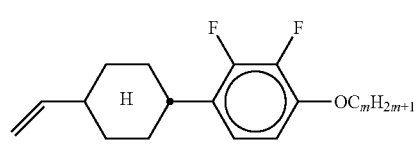
CY-V-Om TABLE D-continued
Illustrative structures
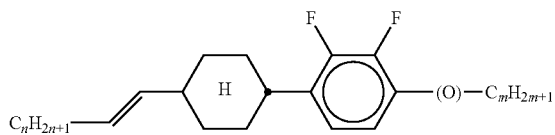
CY-nV-(O)m
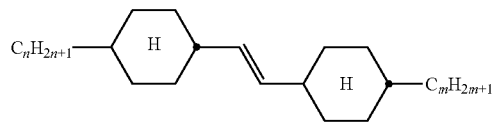
CVC-n-m
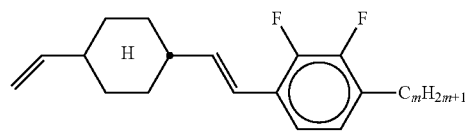
CVY-V-m
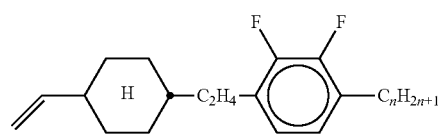
CEY-V-m
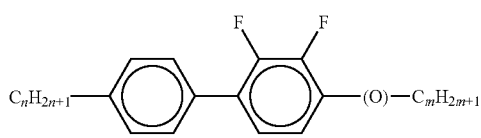
PY-n-(O)m
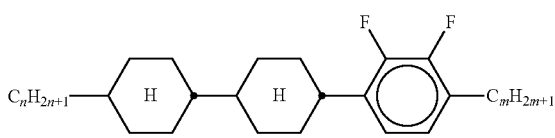
CCY-n-m
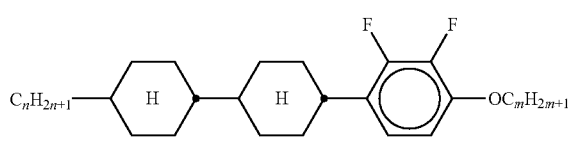
CCY-n-Om
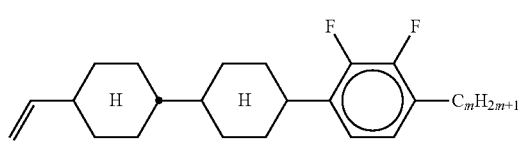
CCY-V-m TABLE D-continued
Illustrative structures
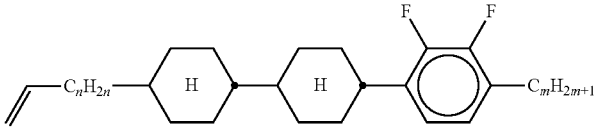
CCY-Vn-m
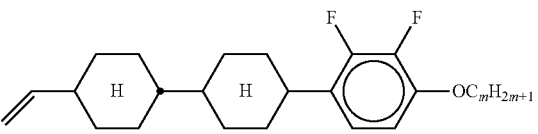
CCY-V-Om
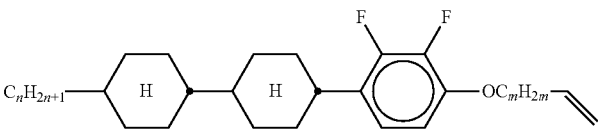
CCY-n-OmV
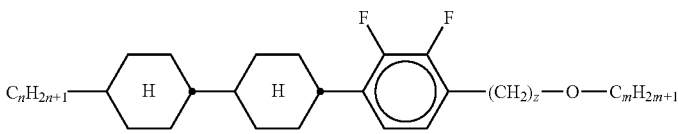
CCY-n-zOm
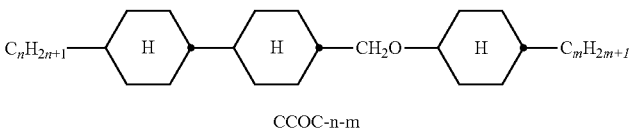
CCOC-n-m
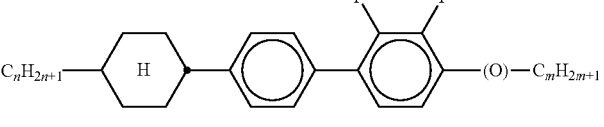
CPY-n-(O)m
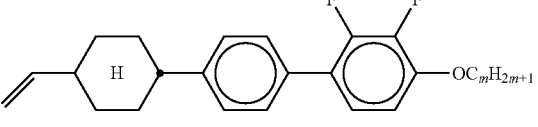
CPY-V-Om
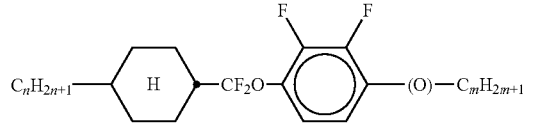
CQY-n-(O)m
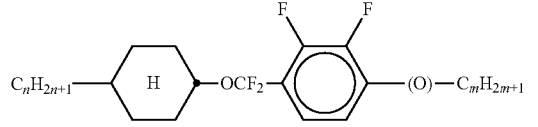
CQIY-n-(O)m TABLE D-continued
Illustrative structures
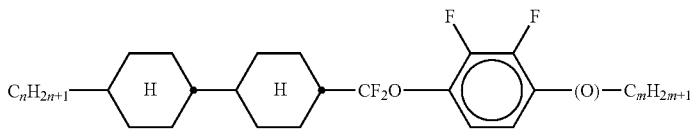
CCQY-n-(O)m
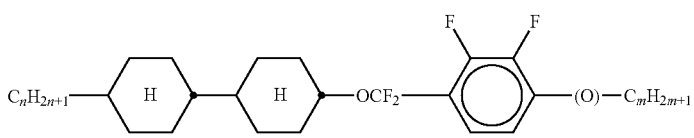
CCQIY-n-(O)m
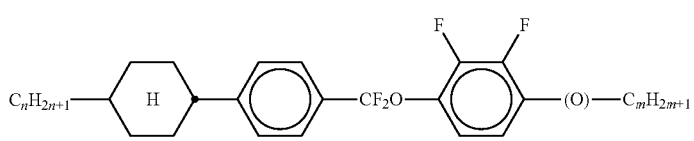
CPQY-n-(O)m
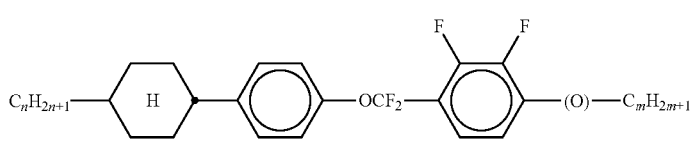
CPQIY-n-Om
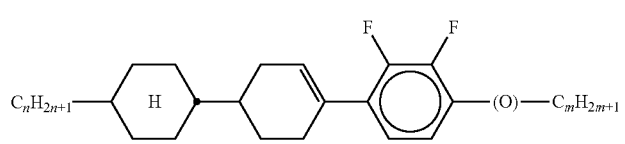
CLY-n-(O)m
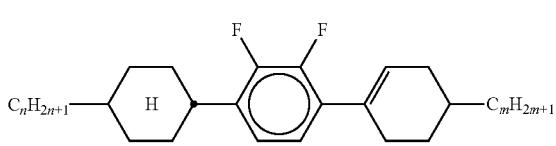
CYLI-n-m
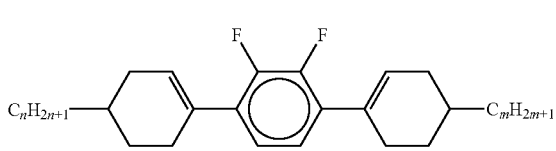
LYLI-n-m
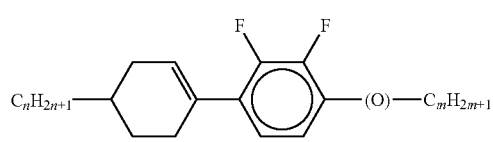
LY-n-(O)m TABLE D-continued
Illustrative structures
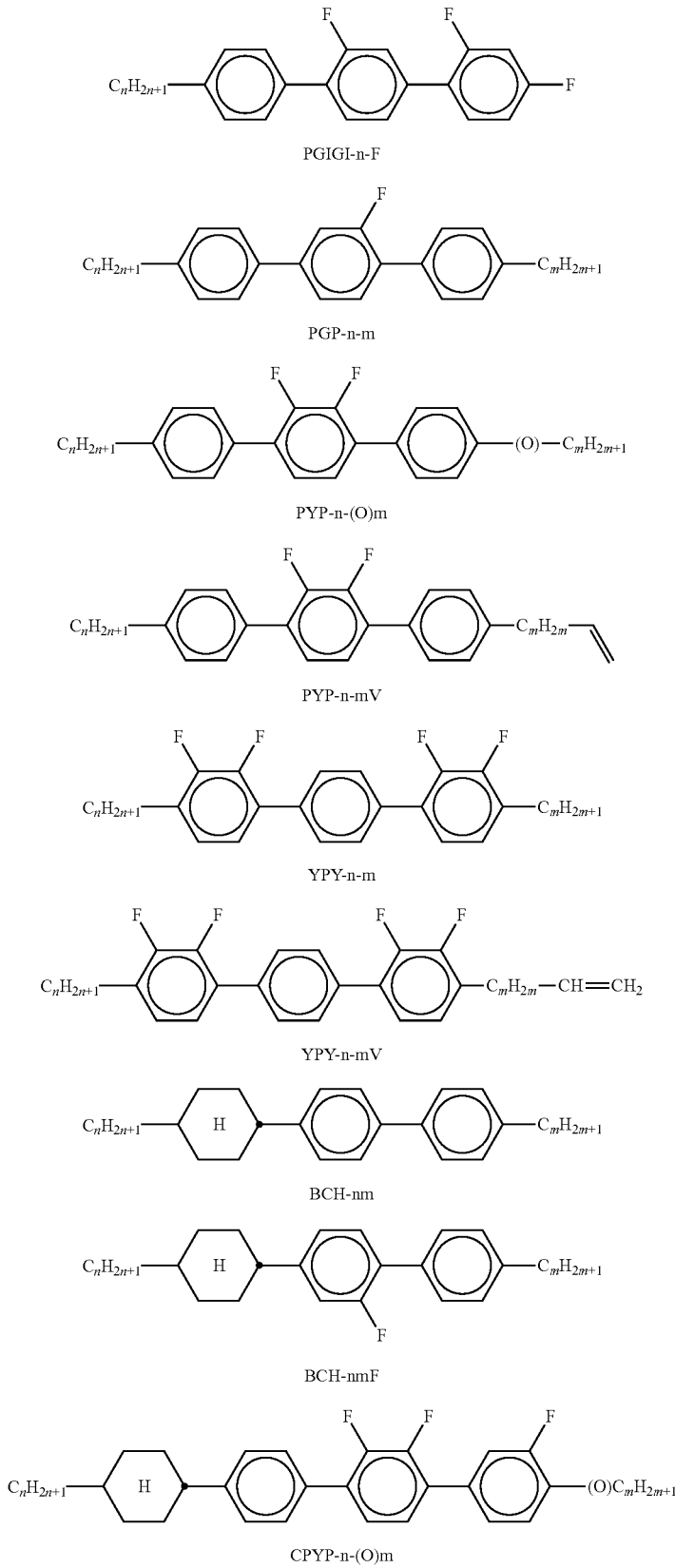
PGIGI-n-F
PGP-n-m
PYP-n-(O)m
PYP-n-mV
YPY-n-m
YPY-n-mV
BCH-nm
BCH-nmF
CPYP-n-(O)m TABLE D-continued
Illustrative structures
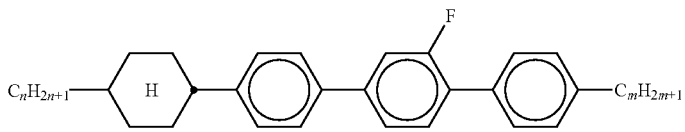
CPGP-n-m
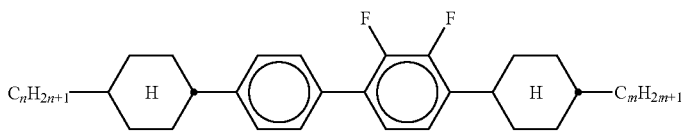
CPYC-n-m
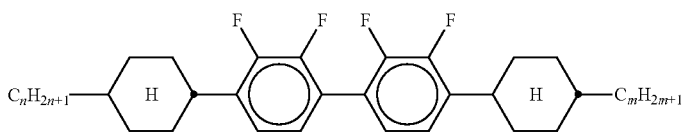
CYYC-n-m
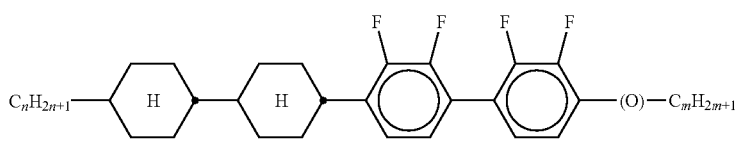
CCYY-n-m
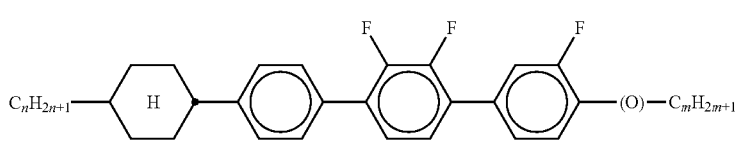
CPYG-n-(O)m
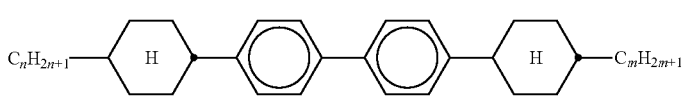
CBC-nm
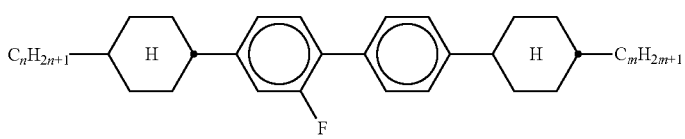
CBC-nmF
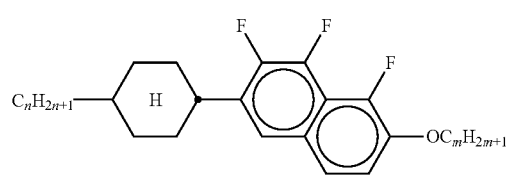
CNap-n-Om TABLE D-continued
Illustrative structures
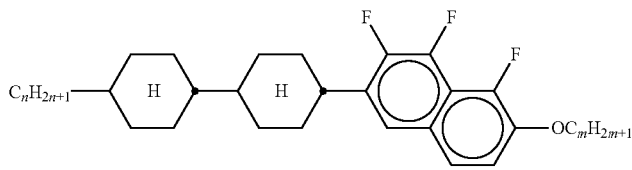
CCNap-n-Om
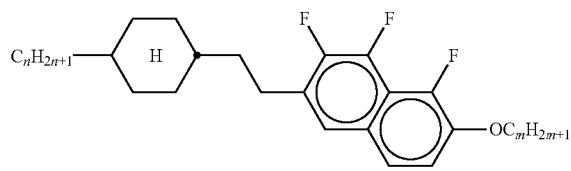
CENap-n-Om
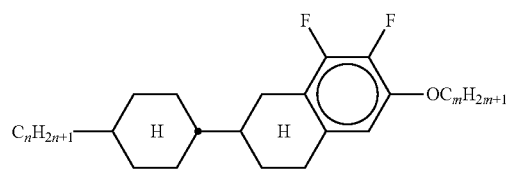
CTNap-n-Om
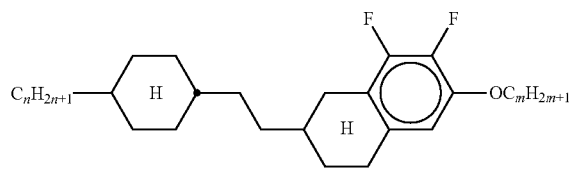
CETNap-n-Om
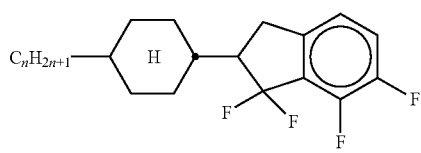
CK-n-F
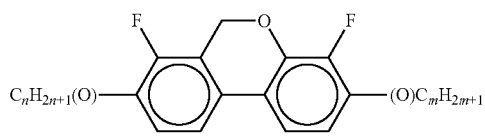
DFDBC-n(O)-(O)m
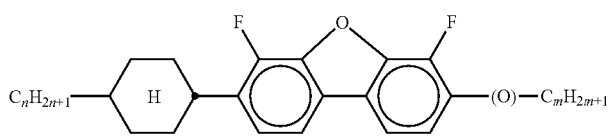
C-DFDBF-n-(O)m wherein n, m and l preferably, independently of one another, denote 1 to 7.
The following table, Table E, shows illustrative compounds which can be used as additional stabilisers in the mesogenic media according to the present invention.
TABLE E
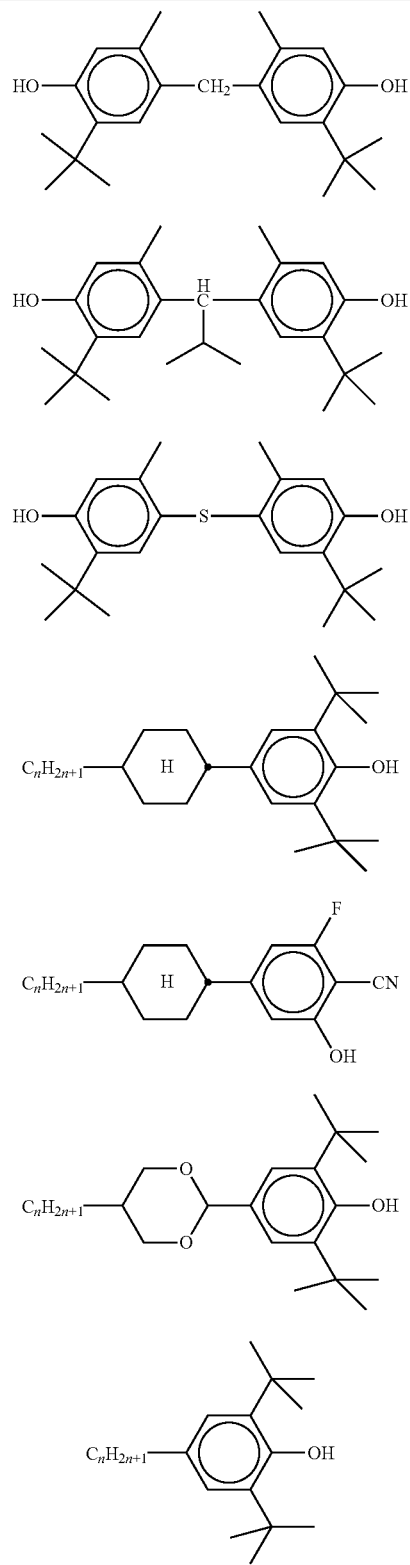

TABLE E-continued
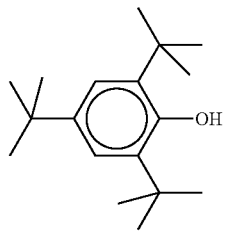
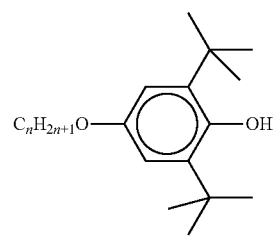
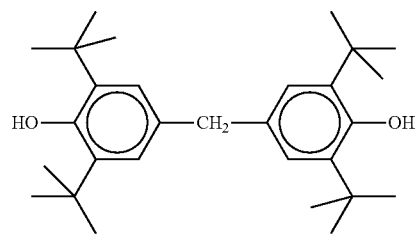
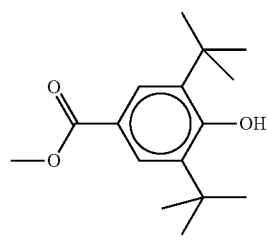
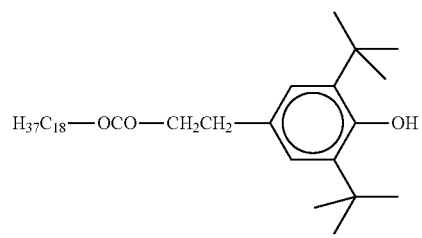
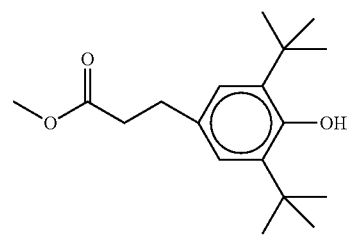

TABLE E-continued
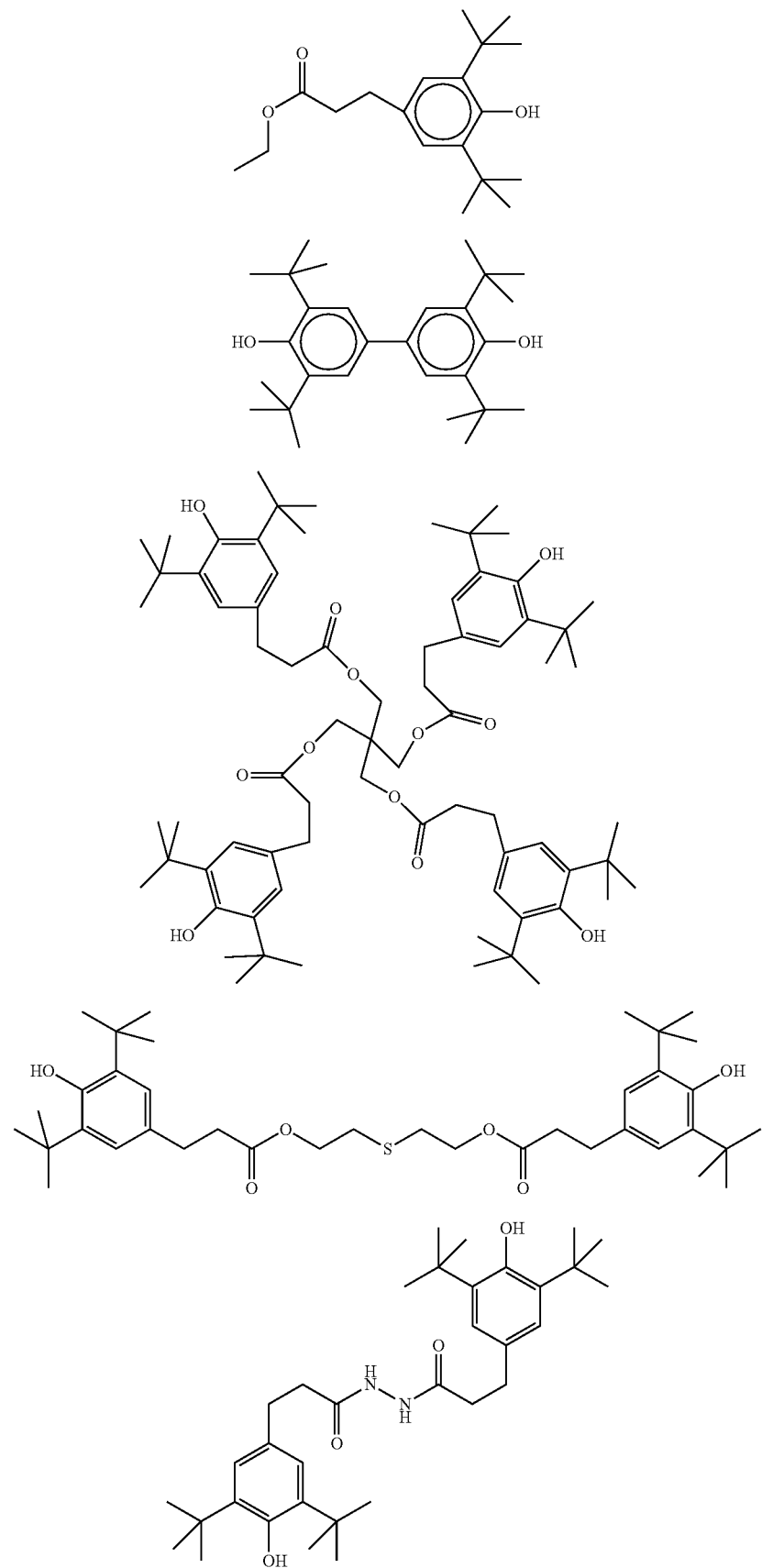

TABLE E-continued
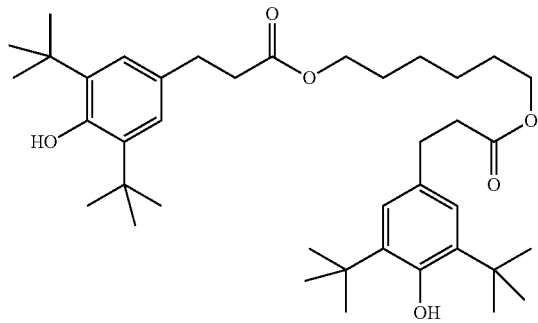 [SMILES: CC(C)(C)c1cc(CCC(=O)OCCCCCCOC(=O)CCc2cc(C(C)(C)C)c(O)c(C(C)(C)C)c2)cc(C(C)(C)C)c1O]
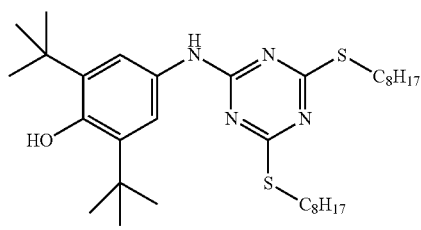
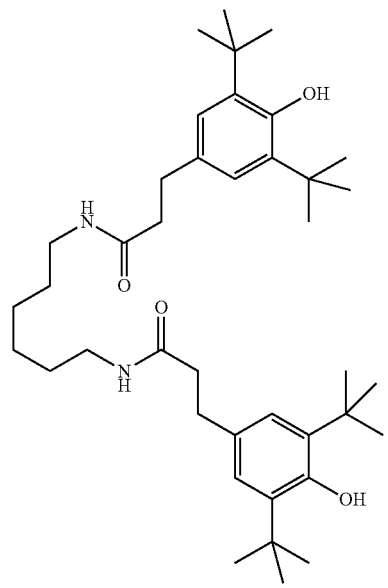 [SMILES: CC(C)(C)c1cc(CCC(=O)NCCCCCCNC(=O)CCc2cc(C(C)(C)C)c(O)c(C(C)(C)C)c2)cc(C(C)(C)C)c1O]
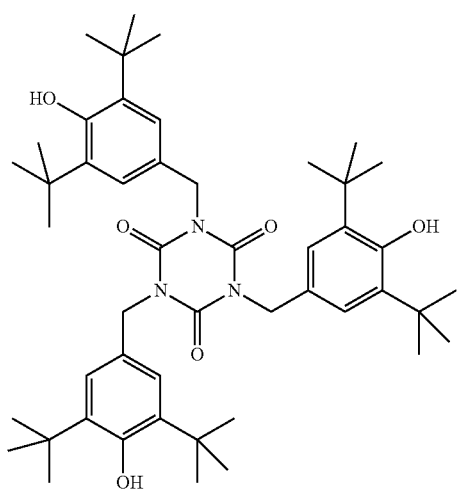 [SMILES: CC(C)(C)c1cc(Cn2c(=O)n(Cc3cc(C(C)(C)C)c(O)c(C(C)(C)C)c3)c(=O)n(Cc3cc(C(C)(C)C)c(O)c(C(C)(C)C)c3)c2=O)cc(C(C)(C)C)c1O]

TABLE E-continued
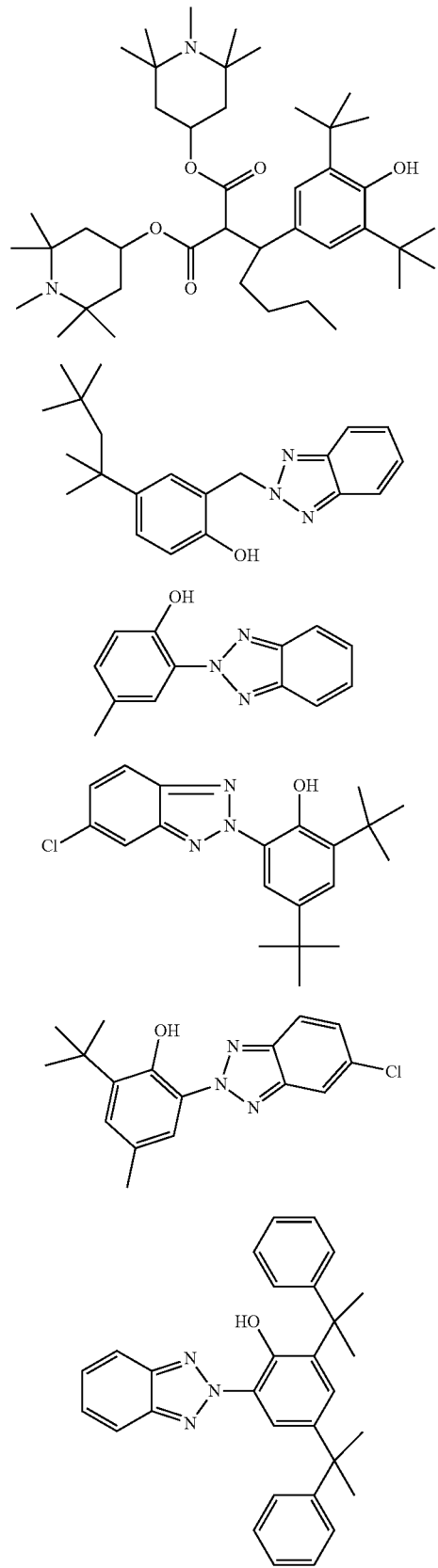

TABLE E-continued
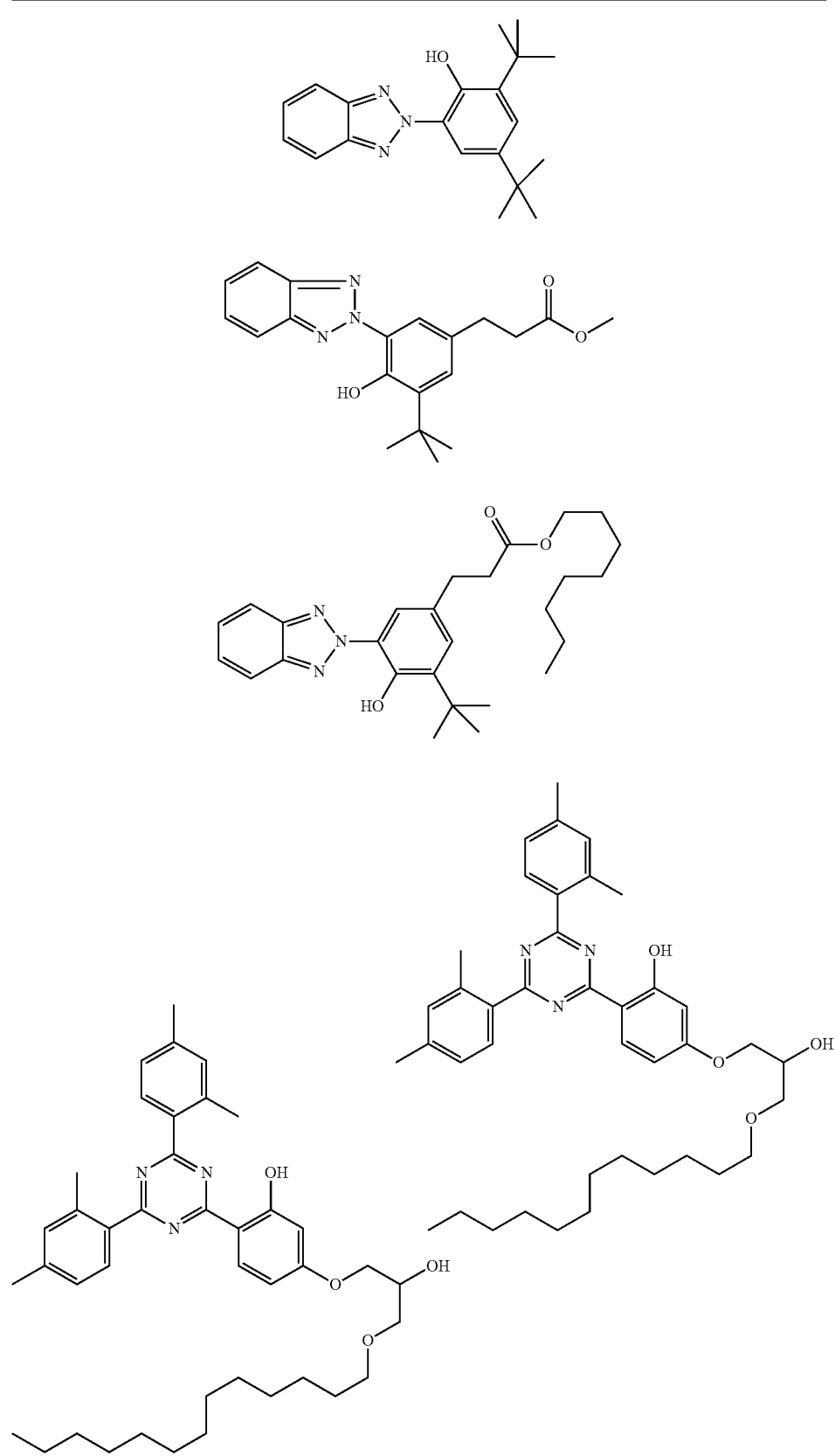

TABLE E-continued
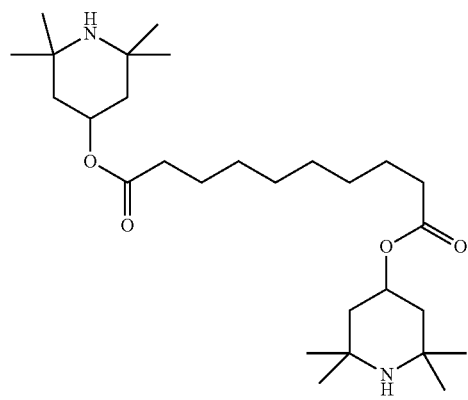
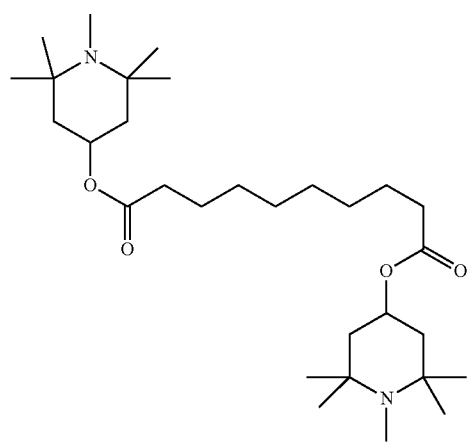
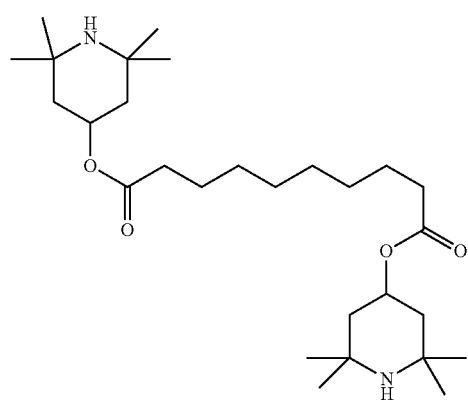

TABLE E-continued
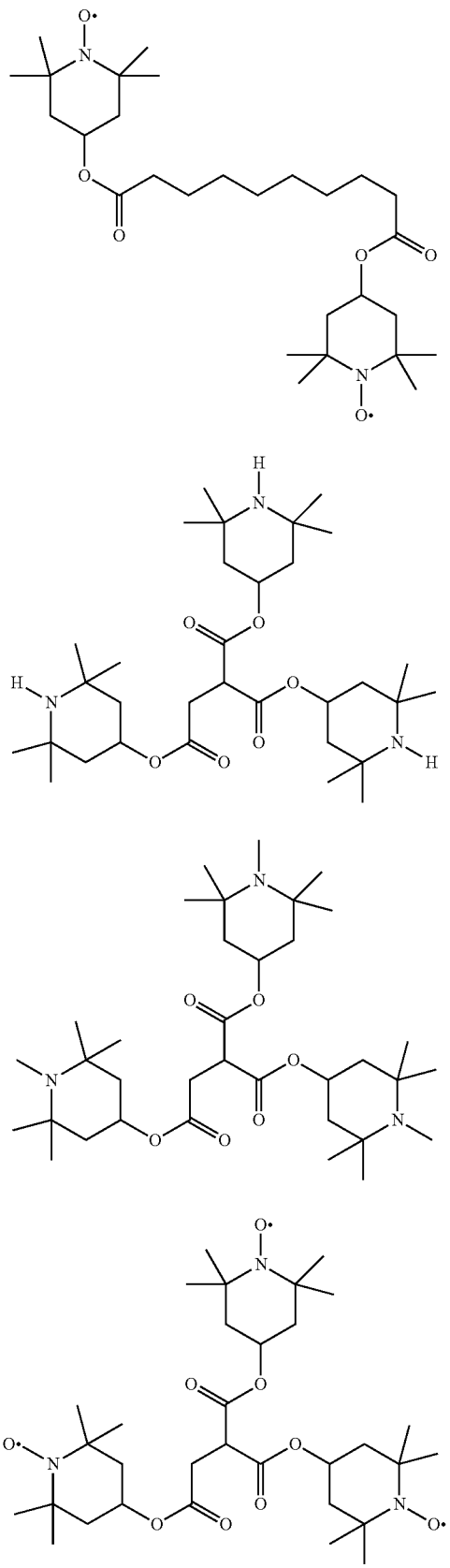

TABLE E-continued
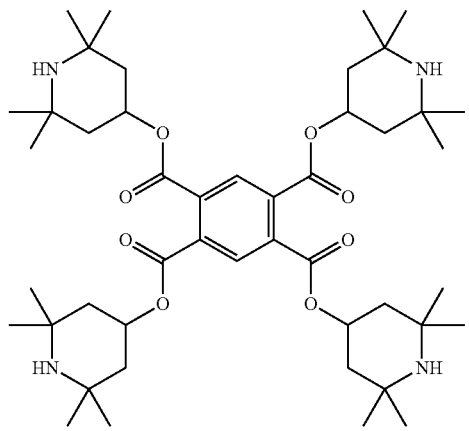
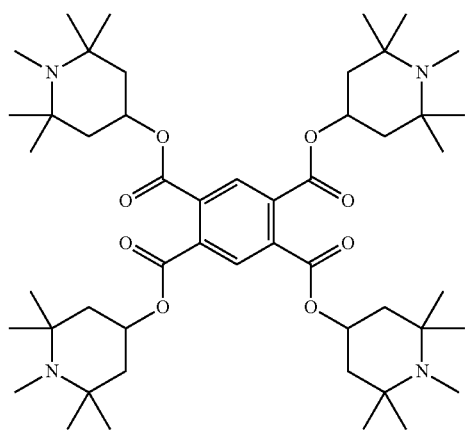
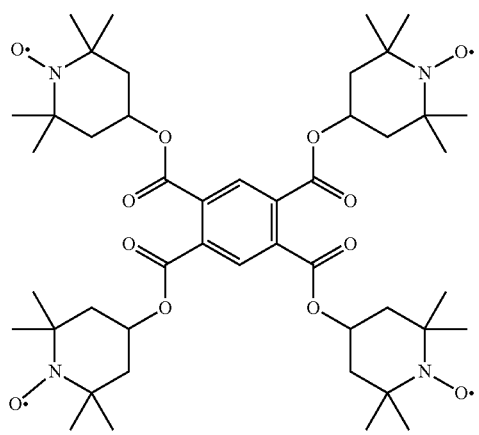

TABLE E-continued
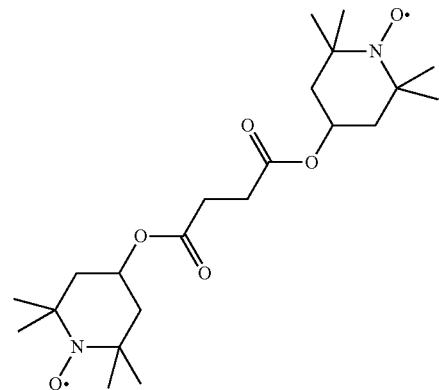
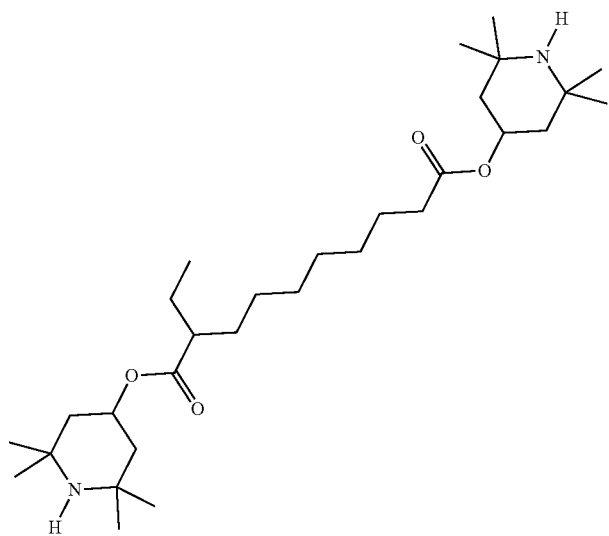
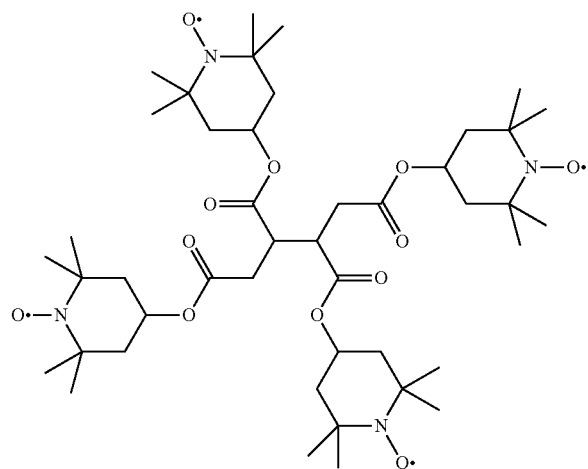
$_n$here denotes an integer from 1 to 12, preferably 1, 2, 3, 4, 5, 6, 7 or 8, terminal methyl groups are not shown.

Table E shows possible stabilisers which can be added to the LC media according to the invention.

(n here denotes an integer from 1 to 12, preferably 1, 2, 3, 4, 5, 6, 7 or 8, terminal methyl groups are not shown).

The LC media preferably comprise 0 to 10% by weight, in particular 1 ppm to 5% by weight, particularly preferably 1 ppm to 1% by weight, of stabilisers.

Table F below shows illustrative compounds which can preferably be used as chiral dopants in the mesogenic media according to the present invention.

TABLE F

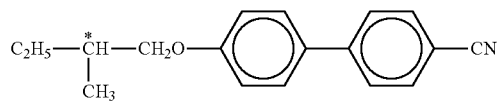

C 15

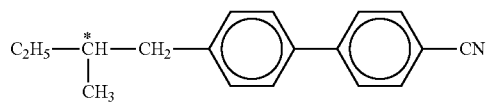

CB 15

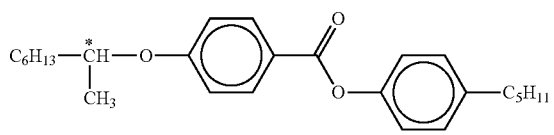

CM 21

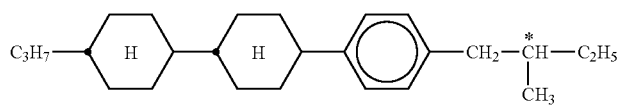

CM 44

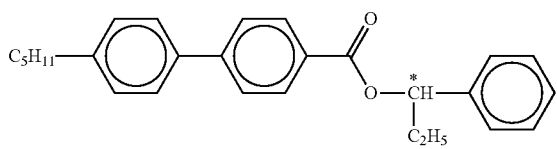

CM 45

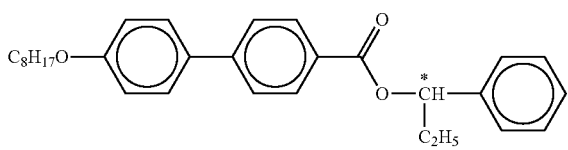

CM 47

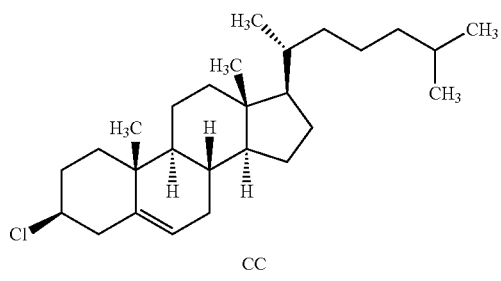

CC

TABLE F-continued
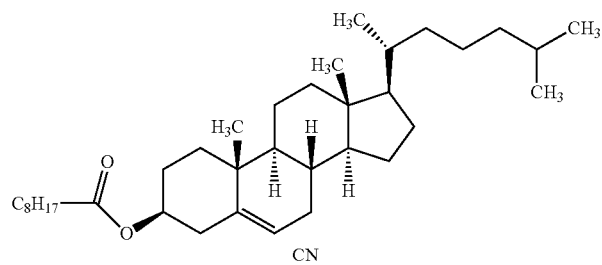
CN
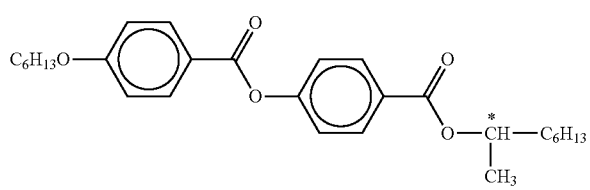
R/S-811
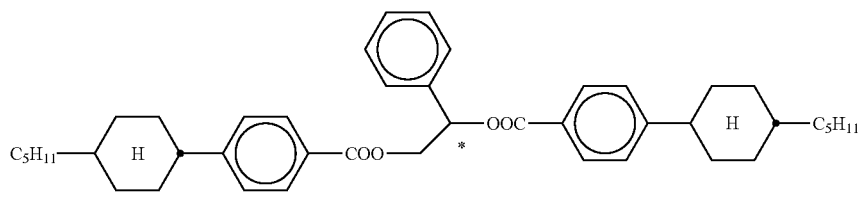
R/S-1011
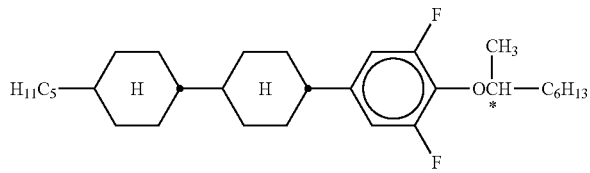
R/S-2011
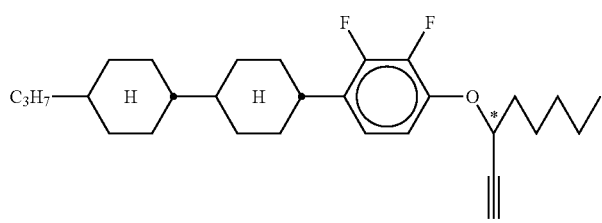
R/S-3011
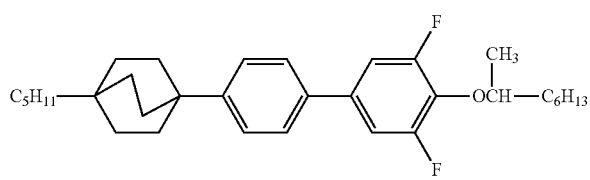
R/S-4011
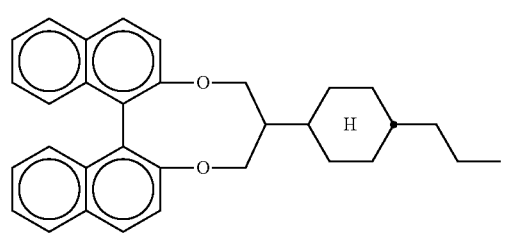
R/S-5011

In a preferred embodiment of the present invention, the mesogenic media comprise one or more compounds selected from the group of the compounds from Table F.

The mesogenic media according to the present application preferably comprise two or more, preferably four or more, compounds selected from the group consisting of the compounds from the above tables.

The liquid-crystal media according to the present invention preferably comprise seven or more, preferably eight or more, individual compounds, preferably of three or more, particularly preferably of four or more, different formulae, selected from the group of the compounds from Table D.

Hereinafter, the present invention is described in more detail and specifically with reference to the Examples, which however are not intended to limit the present invention.

EXAMPLES

Compound Examples

Synthesis Example

Synthesis of [4-[4-[4-[(E)-3-[2-methyl-4-(2-methylprop-2-enoyloxy)phenoxy]-3-oxo-prop-1-enyl]phenyl]phenoxy]-2-(2-methylprop-2-enoyloxymethyl)butyl] 2-methylprop-2-enoate (13)

1.1 Synthesis of diethyl 3-(2-benzyloxyethyl)pentanedioate (1)

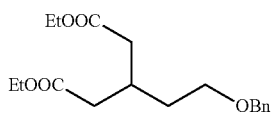

1

Under reflux 13.8 ml (90 mmol) of the diethyl malonate are added to mixture of 34.5 ml of a solution of sodium methylate in ethanol (20%, 50 mmol) and 40 ml ethanol. After 2 h 10 g (50 mmol) of 2-bromoethoxymethylbenzene are added and heating was continued overnight. Water and MTB ether are poured into the cooled reaction mixture. The aqueous layer is extracted with MTB ether. The combined organic layers are washed with brine and dried over sodium sulfate. The solvent is evaporated. The residue is purified by silica chromatography (toluene; toluene/MTB ether 9:1). The isolated material is distilled under vacuum (0.1 mbar, 116-121° C.).

1.2 Synthesis of 2-(2-benzyloxyethyl)propane-1,3-diol (2)

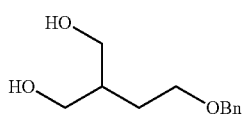

2

A solution of 5 g (20 mmol) of the malonate 1 in 60 ml toluene is added to a suspension of 930 mg (24 mmol) Lithium aluminum hydride in 8 ml Toluene. After 3 h reflux the cooled reaction mixture is quenched with ethyl acetate. The mixture is acidified with 2 mol/l hydrochloric acid (pH 3-4). The aqueous layer is extracted with MTB ether. The combined organic layers are washed with water and dried over sodium sulfate. The solvent is evaporated. The residue is purified by silica chromatography (ethyl acetate.

1.3 Synthesis of [4-benzyloxy-2-[[tert-butyl(dimethyl)silyl]oxymethyl]butoxy]-tert-butyl-dimethyl-silane (3)

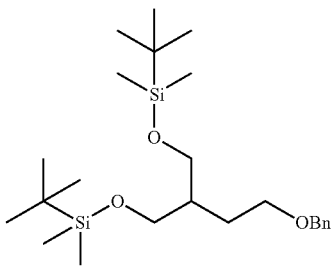

3

At room temp. 3.4 ml (25 mmol) triethyl amine are added to a mixture of 2.1 g (10 mmol) of the diol 2 and 120 mg DMAP dissolved in 30 ml dichloro methane. Afterwards a solution of 4.5 g (30 mmol) TBDMS-Cl in 15 ml dichloro methane are added to the reaction mixture at 3-4° C. After stirring 16 h at room temp. the mixture is quenched with water. The combined organic layers are washed with brine and dried over sodium sulfate. The solvent is evaporated. The residue is purified by silica chromatography (n-heptane/ethyl acetate 19:1).

1.4 Synthesis of 4-[tert-butyl(dimethyl)silyl]oxy-3-[[tert-butyl(dimethyl)silyl]oxy-methyl]-butan-1-ol (4)

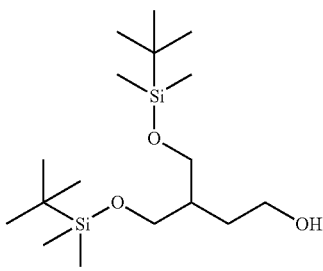

4

A solution of 500 mg (1 mmol) of 3 in 13 ml ethyl acetate is hydrogenated using Pd/C-5% at room temp. The solvent is evaporated. The residue is purified by silica chromatography (n-heptane/ethyl acetate (gradient)).

1.5 Synthesis of [4-(4-bromophenoxy)-2-[[tert-butyl(dimethyl)silyl]oxymethyl]butoxy]-tert-butyl-dimethyl-silane (5)

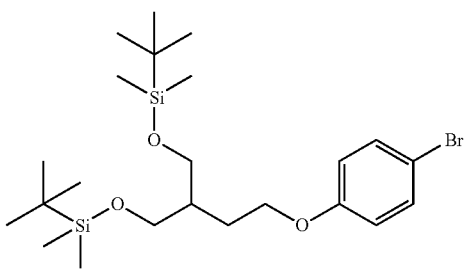

5

To a solution of 27 g (160 mmol) bromophenol, 66 g (190 mmol) 4 and 55 g (210 mmol) TPP in 250 mml THF 43 ml (218 mmol) tert-butyl (NE)-N-tert-butoxycarbonyliminocarbamate are added at room temp. After 18 h stirring the solvent is evaporated. The residue is purified by silica chromatography (Bu-Cl).

1.6 Synthesis of tert-butyl-[2-[[tert-butyl(dimethyl)silyl]oxymethyl]-4-[4-(4,4,5,5-tetramethyl-1,3,2-dioxaborolan-2-yl)phenoxy]butoxy]-dimethyl-silane (6)

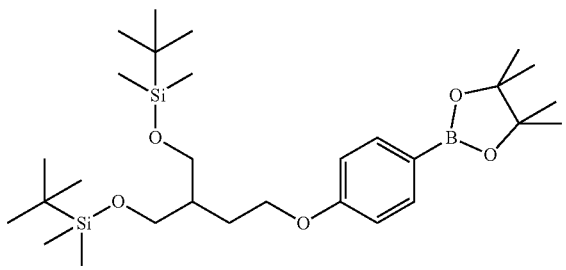

6

To a mixture of 72 g (140 mmol) of the bromide 5, 44 g (170 mmol) of 4,4,5,5-tetramethyl-2-(4,4,5,5-tetramethyl-1,3,2-dioxaborolan-2-yl)-1,3,2-dioxaborolane, 41 g potassium acetate and 3 g PdCl2-dppf 300 ml dioxane are added and stirred 3 h at 100°. The cooled reaction mixture is diluted with water and MTB ether. The organic layer is washed with brine and dried over sodium sulfate. The solvent is evaporated. The residue is purified by silica chromatography (chlorobutane/MTB ether 9:1).

1.7 Synthesis of methyl (E)-3-[4-[4-[4-[tert-butyl(dimethyl)silyl]oxy-3-[[tert-butyl(dimethyl)silyl]oxymethyl]butoxy]phenyl]phenyl]prop-2-enoate (7)

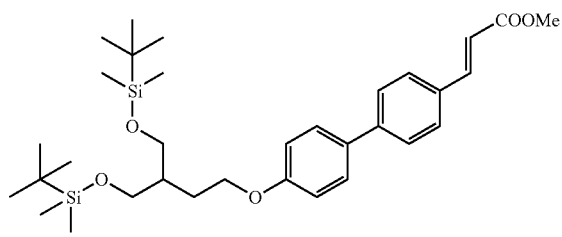

7

21 g (90 mmol) of the methyl (E)-3-(4-bromophenyl)prop-2-enoate, 50 g of the boronic ester 6, 37 g (270 mmol) sodium metaborat tetrahydrate, 1.2 g Bis(triphenyl phosphine)-palladium(II) chloride are mixed with 50 ml water und 100 ml THF. 133 mg (80% ig) hydrazinium hydroxide are added and the mixture is stirred over night at 80° C. The cooled reaction mixture is neutralized with 1M hydrochloric and diluted with water and MTB ether. The organic layer is washed with brine and dried over sodium sulfate The solvent is evaporated. The residue is purified by silica chromatography (chlorobutan).

1.8 Synthesis of (E)-3-[4-[4-[4-[tert-butyl(dimethyl)silyl]oxy-3-[[tert-butyl(dimethyl)silyl]oxymethyl]butoxy]phenyl]phenyl]prop-2-enoic acid (8)

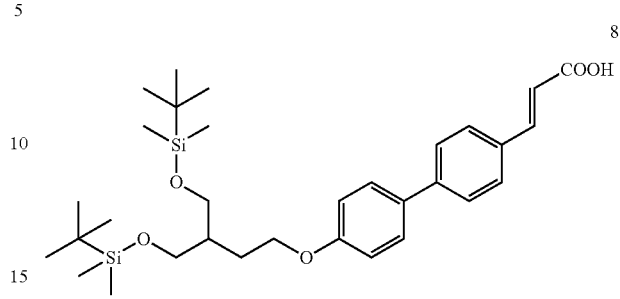

8

48.1 g (80 mmol) of the ester 7 are dissolved in 190 ml methanol and 95 ml THF. 100 ml sodium hydroxide (2 mol/l) are added and the mixture is stirred at 37° C. over night. The cooled mixture is poured onto ice, neutralized with 2 mol/l hydrochloric acid and extracted with MTB ether. The organic layer is washed with brine and dried over sodium sulfate The solvent is evaporated.

1.9 Synthesis of (4-benzyloxy-3-methyl-phenoxy)-triisopropyl-silane (9)

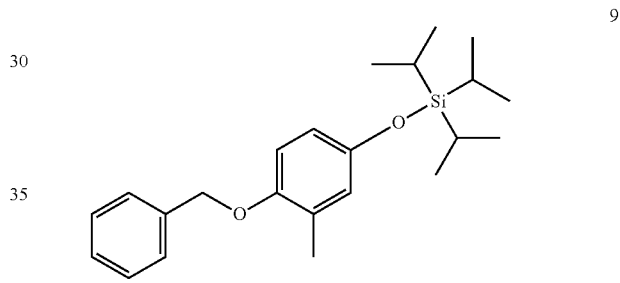

9

At room temp. 4.8 g ml (50 mmol) triethyl amine are added to a mixture of 7.0 g (34 mmol) 4-(benzyloxy)-3-methylphenol and 210 mg DMAP dissolved in 50 ml dichloro methane. Afterwards 9.4 ml (42 mmol) TBDMS-Cl are added to the reaction mixture at 3-4° C. After stirring 16 h at room temp. the mixture is quenched with water. The combined organic layers are washed with brine and dried over sodium sulfate. The solvent is evaporated. The residue is purified by silica chromatography (toluene).

1.10 Synthesis of 2-methyl-4-triisopropylsilyloxy-phenol (10)

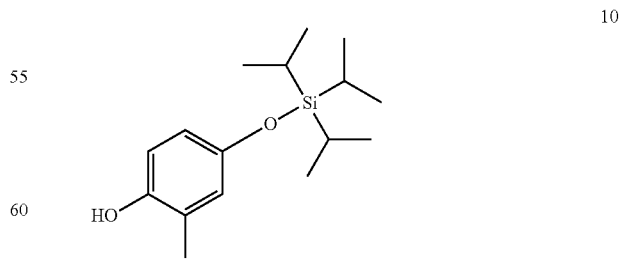

10

A solution of 12.2 g (30 mmol) 9 in 120 ml THF is hydrogenated at room temp. for 1 h (catalyst: 5% Pd/C basic). Afterwards the solvent is evaporated. The residue is purified by silica chromatography (toluene).

1.11 Synthesis of (2-methyl-4-triisopropylsilyloxy-phenyl) (E)-3-[4-[4-[4-[tert-butyl(dimethyl)silyl]oxy-3-[[tert-butyl(dimethyl)silyl]oxymethyl]butoxy]phenyl]phenyl]prop-2-enoate (11)

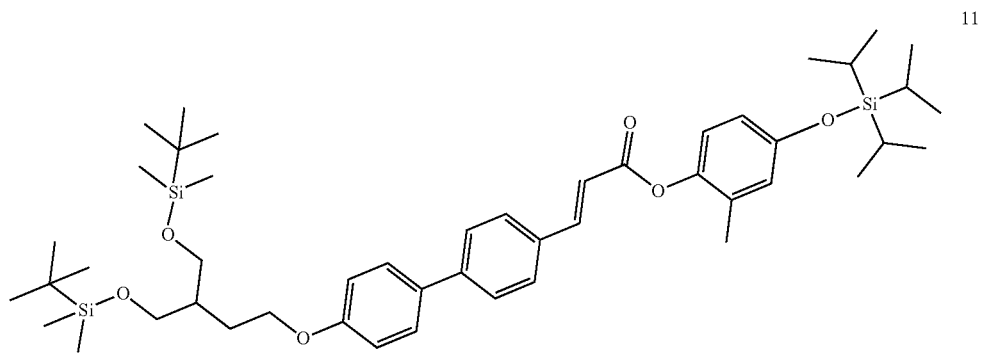 [SMILES: Cc1cc(O[Si](C(C)C)(C(C)C)C(C)C)ccc1OC(=O)/C=C/c1ccc(-c2ccc(OCCC(CO[Si](C)(C)C(C)(C)C)CO[Si](C)(C)C(C)(C)C)cc2)cc1]

To a solution of 1.7 g (2.9 mmol) of the cinnamic acid 8 and 920 mg (3.2 '' mmol) of the phenol 10 in 10 ml dichloro methane 71 mg DMAP are added. Afterwards 670 mg (3.5 mmol) of N-(3-adimrtylaminopropyl)-N'-ethyl carbodiimide hydrochloride are added to the reaction mixture portion by portion. The mixture was stirred over night at room temp. The mixture was filtered through silica gel (dichloro methane) and purified by silica chromatography (dichloro methane).

1.12 Synthesis of (4-hydroxy-2-methyl-phenyl) (E)-3-[4-[4-[4-hydroxy-3-(hydroxymethyl)butoxy]phenyl]phenyl]prop-2-enoate (12)

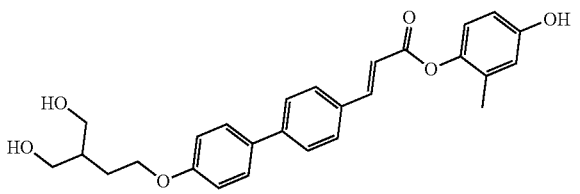

A solution of 1.6 g (98%), 1.8 mmol) of the ester 11 in 12 ml dichloro methane was treated with 3 ml triethylamine trishydrofluoride at a temperature below 10° C. The mixture is stirred over night at room temp. The reaction mixture is diluted with dichloromethane and poured into water. The aqueous layer was extracted with ethyl acetate. The organic layers are combined and diluted with toluene. The solvents are removed to dry the crude product. The crude product is suspended in acetonitrile and heated to reflux. The solid is isolated from the suspension.

1.13 Synthesis of [4-[4-[4-[(E)-3-[2-methyl-4-(2-methylprop-2-enoyloxy)phenoxy]-3-oxo-prop-1-enyl]phenyl]phenoxy]-2-(2-methylprop-2-enoyloxymethyl)butyl] 2-methylprop-2-enoate (13)

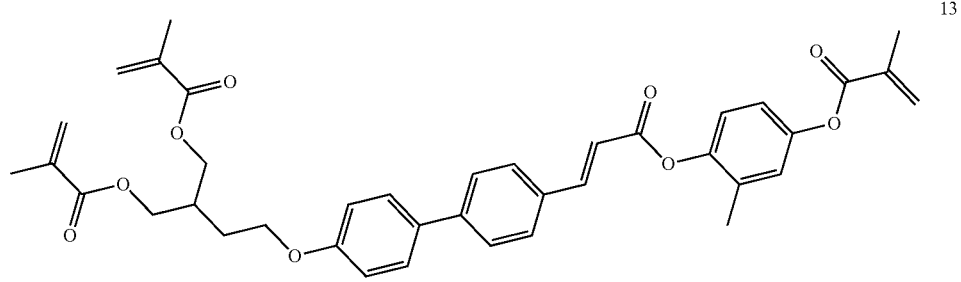 [SMILES: C=C(C)C(=O)OCC(CCOc1ccc(-c2ccc(/C=C/C(=O)Oc3ccc(OC(=O)C(=C)C)cc3C)cc2)cc1)COC(=O)C(=C)C]

A mixture of 700 mg (1.5 mmol) 12, 56 mg DMAP, 1 ml methacrylic acid and 30 ml dichloro methane was treated with a solution of 1.8 g (11 mmol) N-(3-adimrtylaminopropyl)-N'-ethyl carbodiimide in 25 ml dichloromethane at a temperature below 10° C. After stirring 30 min cooled by ice the reaction mixture is stirred at room temp. over night. The reaction mixture is filtered through silica gel (dichloro methane). The product containing fractions are combined and the solvent is evaporated. The product is purified by crystallization from acetonitrile/THF at 6° C.

Phase sequence: K 117 N (94.7) I $^1$H NMR (500 MHz, Chloroform-d) δ 7.94 (d, J=16.0 Hz, 1H), 7.66 (q, J=8.5 Hz, 4H), 7.61-7.56 (m, 2H), 7.15 (d, J=8.6 Hz, 1H), 7.09-6.98 (m, 4H), 6.70 (d, J=16.0 Hz, 1H), 6.37 (t, J=1.2 Hz, 1H), 6.14 (q, J=1.2 Hz, 2H), 5.78 (t, J=1.6 Hz, 1H), 5.60 (p, J=1.5 Hz, 2H), 4.34-4.26 (m, 4H), 4.16 (t, J=6.2 Hz, 2H), 2.50 (p, J=6.3 Hz, 1H), 2.26 (s, 3H), 2.09 (d, J=1.5 Hz, 3H), 2.05-1.94 (m, 8H).

In accordance or in analogy to the above described procedures, the following compounds are obtained:

| No. | Structure |
|---|---|
| RM-1 | Mp. 62° C. |
| RM-2 | Mp. 102° C. |
| RM-3 | Mp. 119° C. |
| RM-4 | 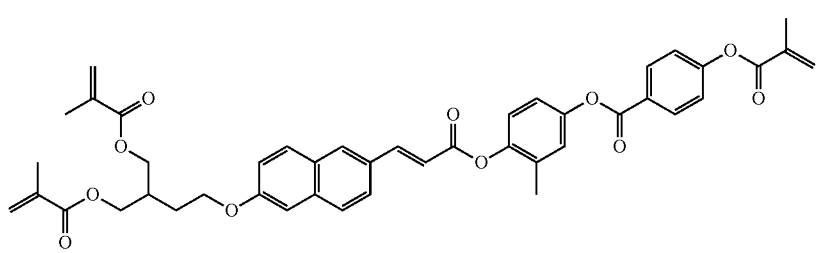 [SMILES: C=C(C)C(=O)OCC(CCOc1ccc2cc(/C=C/C(=O)Oc3ccc(OC(=O)c4ccc(OC(=O)C(=C)C)cc4)cc3C)ccc2c1)COC(=O)C(=C)C] |

-continued
| No. | Structure |
|---|---|
Mp.125° C.
RM-5
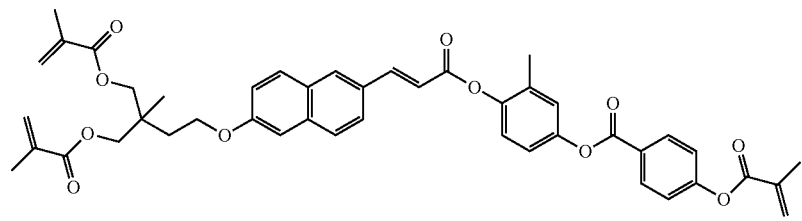 [SMILES: C=C(C)C(=O)OCC(C)(CCOc1ccc2cc(/C=C/C(=O)Oc3ccc(OC(=O)c4ccc(OC(=O)C(=C)C)cc4)cc3C)ccc2c1)COC(=O)C(=C)C]
RM-6
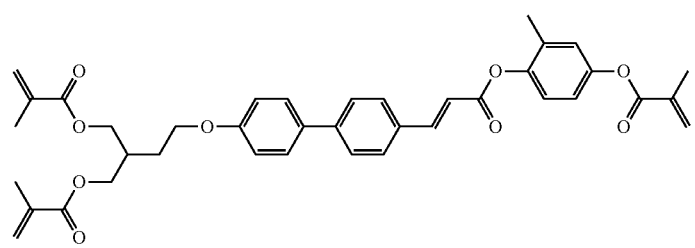 [SMILES: C=C(C)C(=O)OCC(CCOc1ccc(-c2ccc(/C=C/C(=O)Oc3ccc(OC(=O)C(=C)C)cc3C)cc2)cc1)COC(=O)C(=C)C]
UV: 237 nm, 331 nm
Mp. 117° C.
RM-7
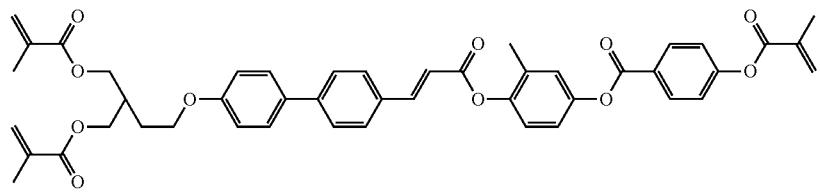 [SMILES: C=C(C)C(=O)OCC(CCOc1ccc(-c2ccc(/C=C/C(=O)Oc3ccc(OC(=O)c4ccc(OC(=O)C(=C)C)cc4)cc3C)cc2)cc1)COC(=O)C(=C)C]
Mp. 123° C.
RM-8
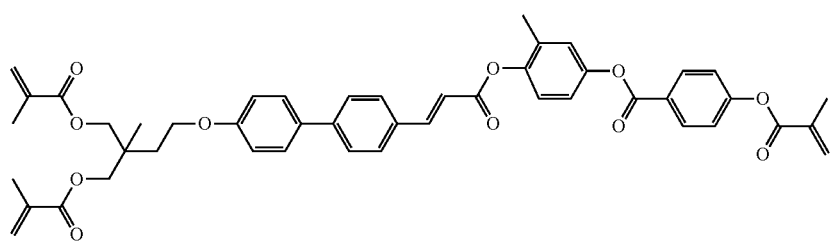 [SMILES: C=C(C)C(=O)OCC(C)(CCOc1ccc(-c2ccc(/C=C/C(=O)Oc3ccc(OC(=O)c4ccc(OC(=O)C(=C)C)cc4)cc3C)cc2)cc1)COC(=O)C(=C)C]
UV: 241 nm, 332 nm
Mp.122° C.
RM-9
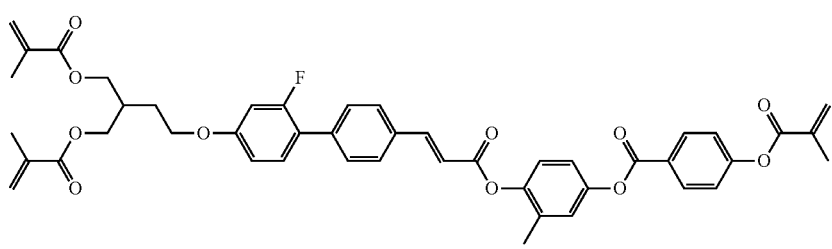 [SMILES: C=C(C)C(=O)OCC(CCOc1ccc(-c2ccc(/C=C/C(=O)Oc3ccc(OC(=O)c4ccc(OC(=O)C(=C)C)cc4)cc3C)cc2)c(F)c1)COC(=O)C(=C)C]
Mp. 129° C.

-continued
| No. | Structure |
|---|---|
| RM-10 | 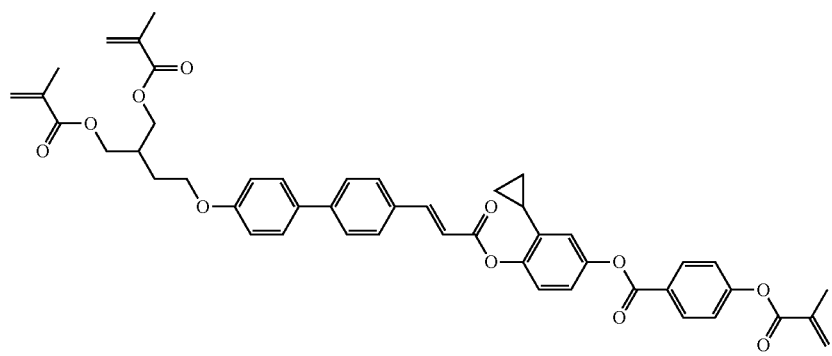 [SMILES: C=C(C)C(=O)OCC(CCOc1ccc(-c2ccc(/C=C/C(=O)Oc3ccc(OC(=O)c4ccc(OC(=O)C(=C)C)cc4)cc3C3CC3)cc2)cc1)COC(=O)C(=C)C]  Mp.135° C. |
| RM-11 | 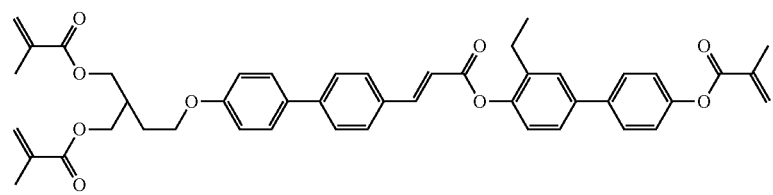 [SMILES: C=C(C)C(=O)OCC(CCOc1ccc(-c2ccc(/C=C/C(=O)Oc3ccc(-c4ccc(OC(=O)C(=C)C)cc4)cc3CC)cc2)cc1)COC(=O)C(=C)C] |
| RM-12 | 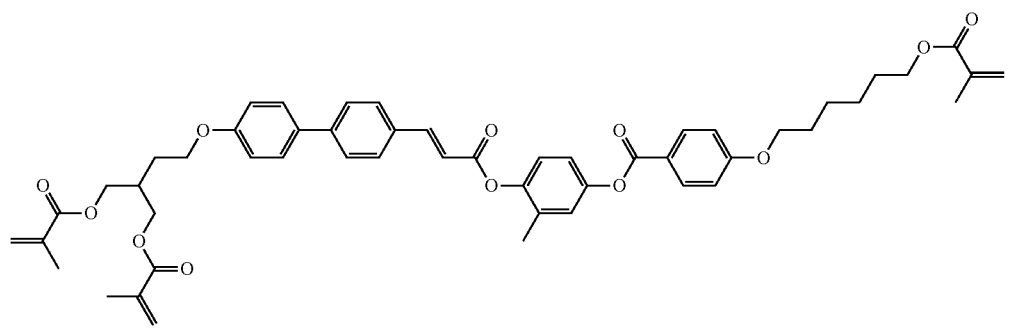 [SMILES: C=C(C)C(=O)OCCCCCCOc1ccc(C(=O)Oc2ccc(OC(=O)/C=C/c3ccc(-c4ccc(OCCC(COC(=O)C(=C)C)COC(=O)C(=C)C)cc4)cc3)c(C)c2)cc1]  Mp.86° C. |
| RM-13 | 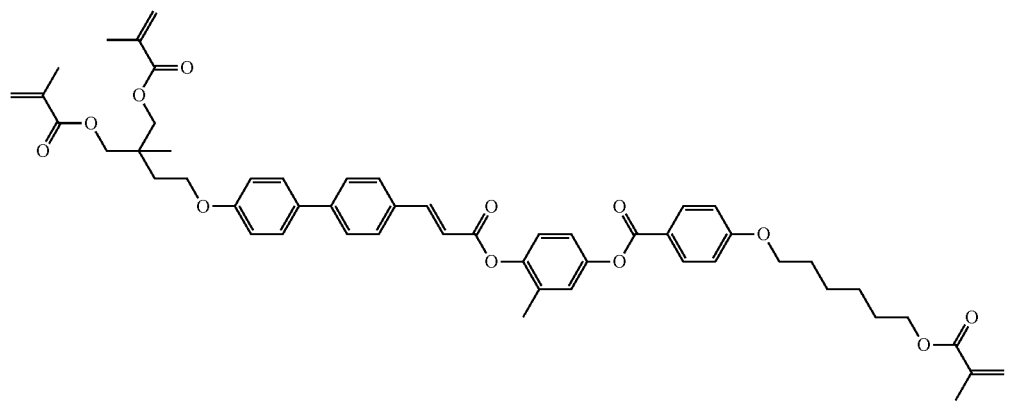 [SMILES: C=C(C)C(=O)OCCCCCCOc1ccc(C(=O)Oc2ccc(OC(=O)/C=C/c3ccc(-c4ccc(OCCC(C)(COC(=O)C(=C)C)COC(=O)C(=C)C)cc4)cc3)c(C)c2)cc1]  Mp.79° C. |

-continued
| No. | Structure |
|---|---|
| RM-14 | 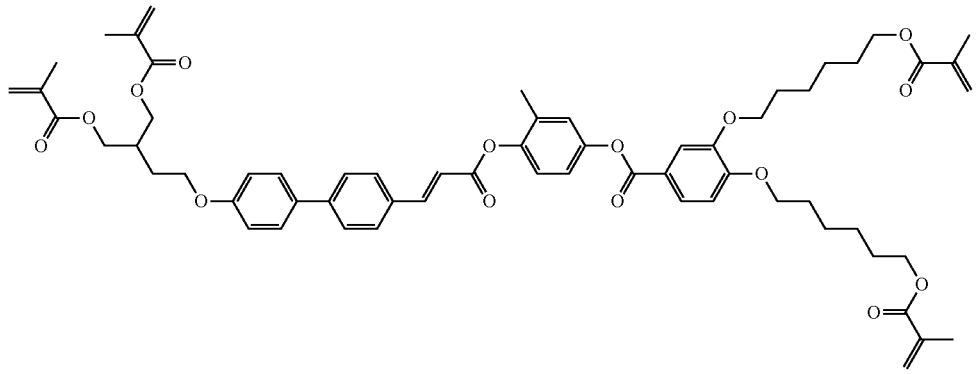 [SMILES: C=C(C)C(=O)OCCCCCCOc1ccc(C(=O)Oc2ccc(OC(=O)/C=C/c3ccc(-c4ccc(OCCC(COC(=O)C(=C)C)COC(=O)C(=C)C)cc4)cc3)c(C)c2)cc1OCCCCCCOC(=O)C(=C)C]<br>Mp.58° C. |
| RM-15 | 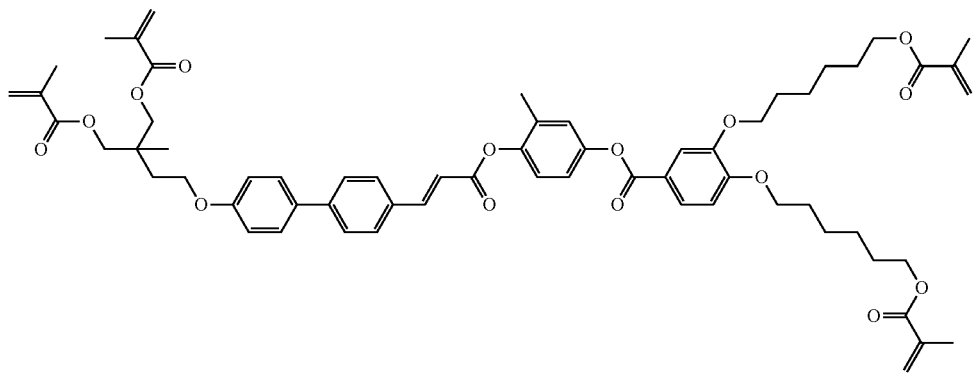 [SMILES: C=C(C)C(=O)OCCCCCCOc1ccc(C(=O)Oc2ccc(OC(=O)/C=C/c3ccc(-c4ccc(OCCC(C)(COC(=O)C(=C)C)COC(=O)C(=C)C)cc4)cc3)c(C)c2)cc1OCCCCCCOC(=O)C(=C)C]<br>UV: 233 nm, 268 nm, 330 nm<br>Mp.87° C. |
| RM-16 | 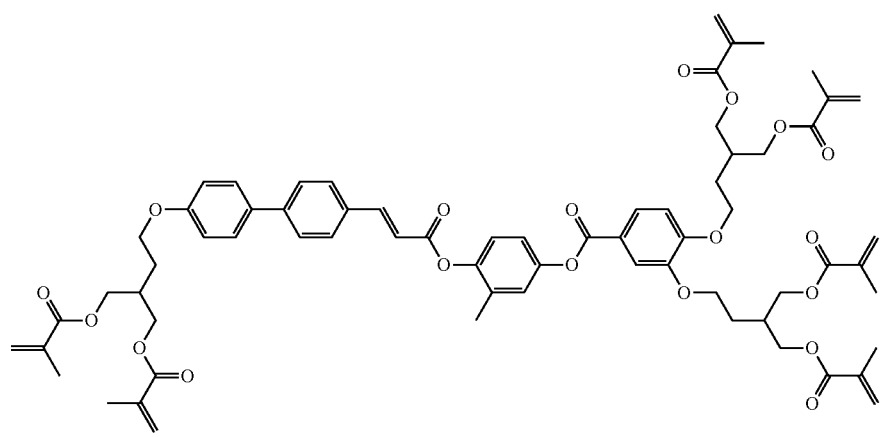 [SMILES: C=C(C)C(=O)OCC(CCOc1ccc(-c2ccc(/C=C/C(=O)Oc3ccc(OC(=O)c4ccc(OCCC(COC(=O)C(=C)C)COC(=O)C(=C)C)c(OCCC(COC(=O)C(=C)C)COC(=O)C(=C)C)c4)cc3C)cc2)cc1)COC(=O)C(=C)C] |

| No. | Structure |
|---|---|
| RM-17 | 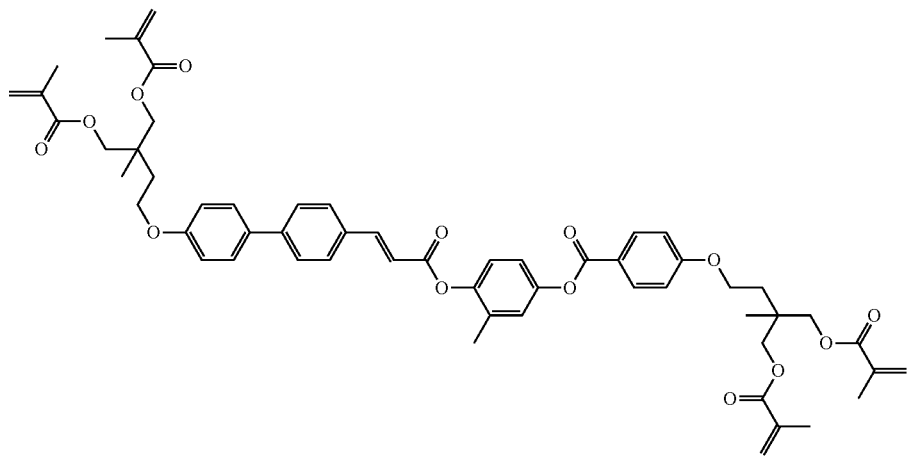 [SMILES: C=C(C)C(=O)OCC(C)(CCOc1ccc(C(=O)Oc2ccc(OC(=O)/C=C/c3ccc(-c4ccc(OCCC(C)(COC(=O)C(=C)C)COC(=O)C(=C)C)cc4)cc3)c(C)c2)cc1)COC(=O)C(=C)C] |
| RM-18 | 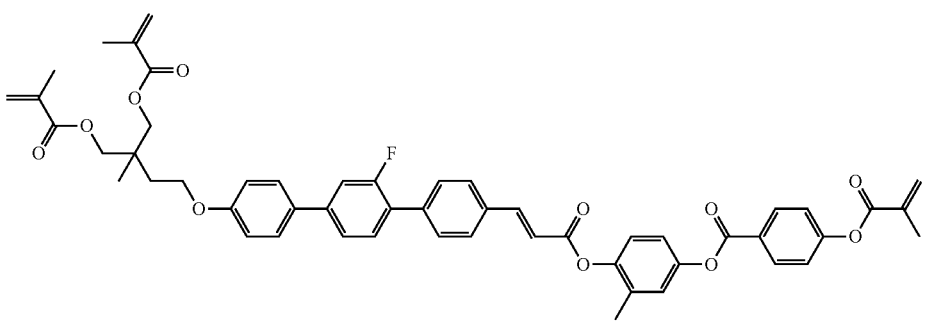 [SMILES: C=C(C)C(=O)OCC(C)(CCOc1ccc(-c2ccc(-c3ccc(/C=C/C(=O)Oc4ccc(OC(=O)c5ccc(OC(=O)C(=C)C)cc5)cc4C)cc3)c(F)c2)cc1)COC(=O)C(=C)C]
Mp.157° C. |
| RM-19 | 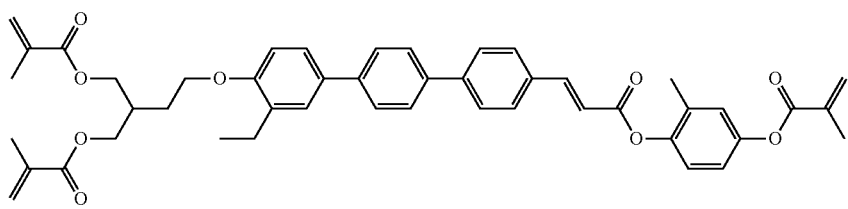 [SMILES: C=C(C)C(=O)OCC(CCOc1ccc(-c2ccc(-c3ccc(/C=C/C(=O)Oc4ccc(OC(=O)C(=C)C)cc4C)cc3)cc2)cc1CC)COC(=O)C(=C)C]
Mp.105° C. |
| RM-20 | 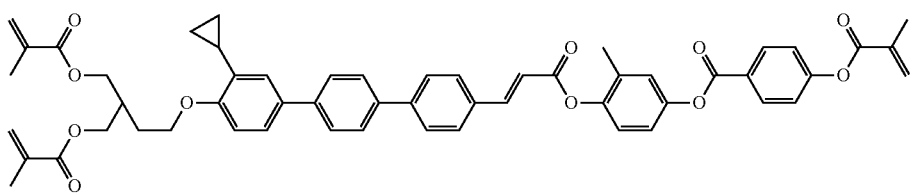 [SMILES: C=C(C)C(=O)OCC(CCOc1ccc(-c2ccc(-c3ccc(/C=C/C(=O)Oc4ccc(OC(=O)c5ccc(OC(=O)C(=C)C)cc5)cc4C)cc3)cc2)cc1C1CC1)COC(=O)C(=C)C]
Mp. 136° C. |
| RM-21 | 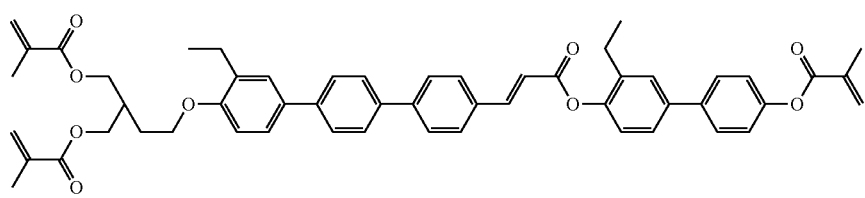 [SMILES: C=C(C)C(=O)OCC(CCOc1ccc(-c2ccc(-c3ccc(/C=C/C(=O)Oc4ccc(-c5ccc(OC(=O)C(=C)C)cc5)cc4CC)cc3)cc2)cc1CC)COC(=O)C(=C)C] |

-continued
| No. | Structure |
|---|---|
| RM-22 | 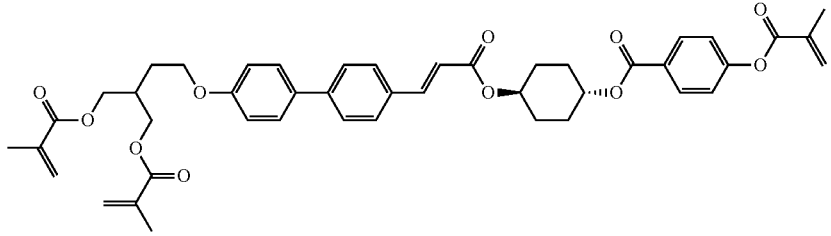 [SMILES: C=C(C)C(=O)OCC(CCOc1ccc(-c2ccc(/C=C/C(=O)O[C@H]3CC[C@H](OC(=O)c4ccc(OC(=O)C(=C)C)cc4)CC3)cc2)cc1)COC(=O)C(=C)C]<br>Mp. 97° C. |
| RM-23 | 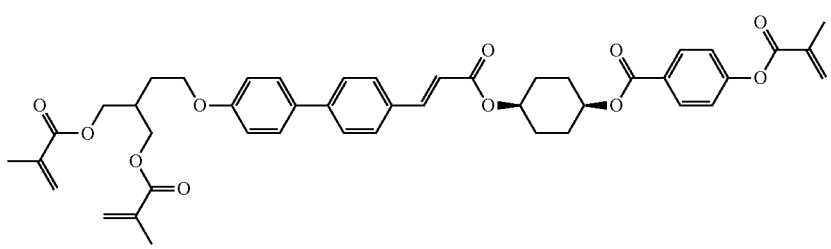 [SMILES: C=C(C)C(=O)OCC(CCOc1ccc(-c2ccc(/C=C/C(=O)O[C@H]3CC[C@@H](OC(=O)c4ccc(OC(=O)C(=C)C)cc4)CC3)cc2)cc1)COC(=O)C(=C)C]<br>Mp. 101° C. |
| RM-24 | 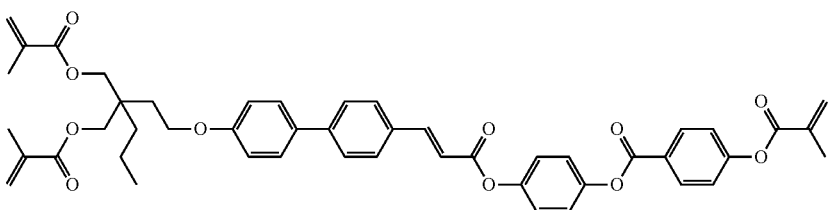<br>Mp. 132° C. |
| RM-25 | 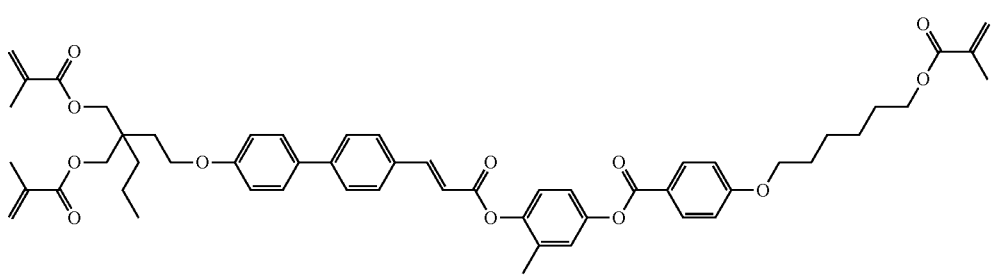 [SMILES: C=C(C)C(=O)OCCCCCCOc1ccc(C(=O)Oc2ccc(OC(=O)/C=C/c3ccc(-c4ccc(OCCC(CCC)(COC(=O)C(=C)C)COC(=O)C(=C)C)cc4)cc3)c(C)c2)cc1] |
| RM-26 | 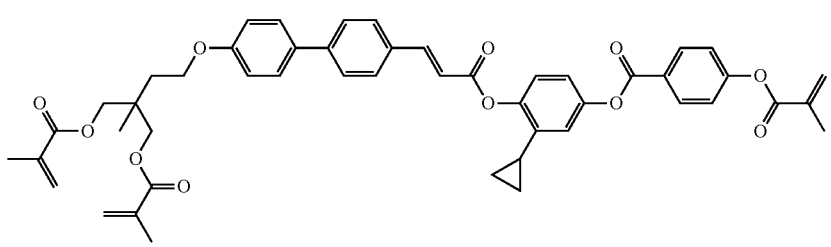 [SMILES: C=C(C)C(=O)OCC(C)(CCOc1ccc(-c2ccc(/C=C/C(=O)Oc3ccc(OC(=O)c4ccc(OC(=O)C(=C)C)cc4)cc3C3CC3)cc2)cc1)COC(=O)C(=C)C] |
| RM-27 | 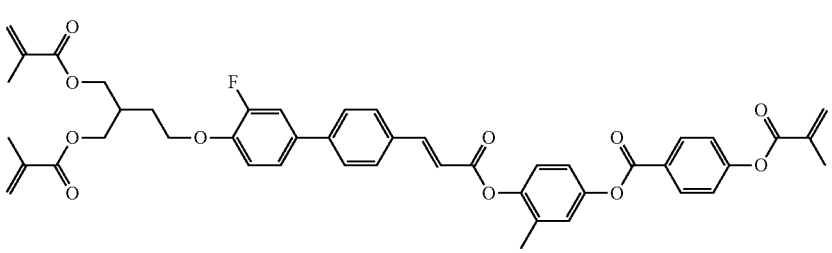 [SMILES: C=C(C)C(=O)OCC(CCOc1ccc(-c2ccc(/C=C/C(=O)Oc3ccc(OC(=O)c4ccc(OC(=O)C(=C)C)cc4)cc3C)cc2)cc1F)COC(=O)C(=C)C] |

| No. | Structure |
|---|---|
| RM-28 | 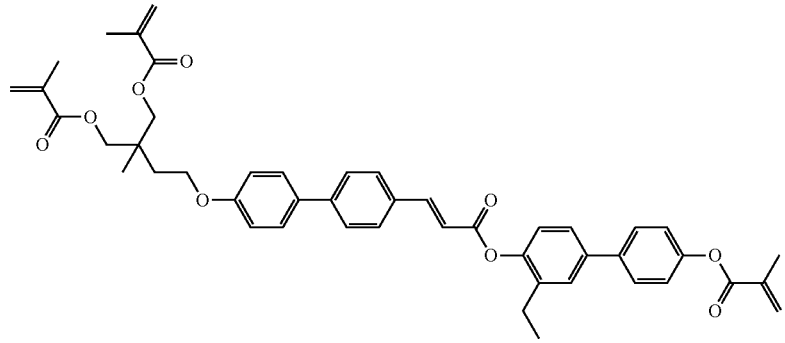 [SMILES: C=C(C)C(=O)OCC(C)(CCOc1ccc(-c2ccc(/C=C/C(=O)Oc3ccc(-c4ccc(OC(=O)C(=C)C)cc4)cc3CC)cc2)cc1)COC(=O)C(=C)C]
Mp. 140° C. |
| RM-29 | 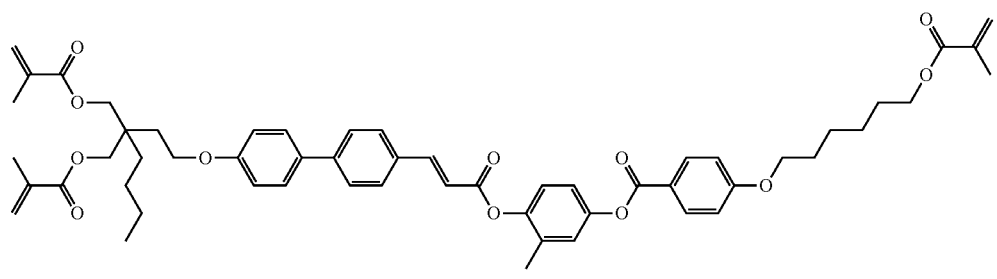 [SMILES: C=C(C)C(=O)OCCCCCCOc1ccc(C(=O)Oc2ccc(OC(=O)/C=C/c3ccc(-c4ccc(OCCC(CCCC)(COC(=O)C(=C)C)COC(=O)C(=C)C)cc4)cc3)c(C)c2)cc1]
Mp. 128° C. |
| RM-30 | 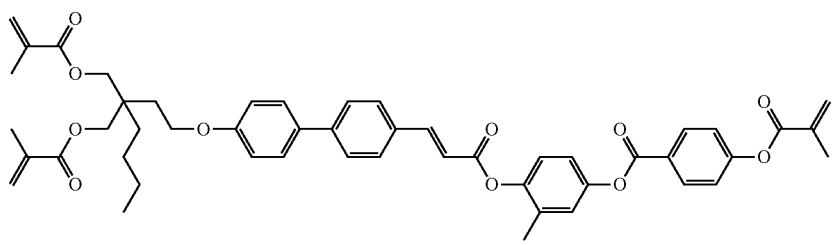 [SMILES: C=C(C)C(=O)OCC(CCCC)(CCOc1ccc(-c2ccc(/C=C/C(=O)Oc3ccc(OC(=O)c4ccc(OC(=O)C(=C)C)cc4)cc3C)cc2)cc1)COC(=O)C(=C)C]
Mp. 106° C. |
| RM-31 | 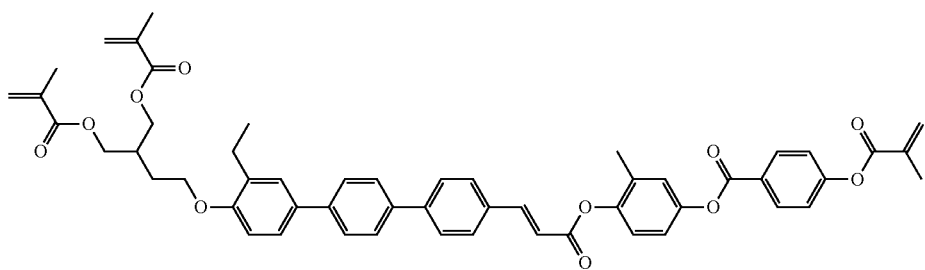 [SMILES: C=C(C)C(=O)OCC(CCOc1ccc(-c2ccc(-c3ccc(/C=C/C(=O)Oc4ccc(OC(=O)c5ccc(OC(=O)C(=C)C)cc5)cc4C)cc3)cc2)cc1CC)COC(=O)C(=C)C]
Mp. 133° C. |
| RM-32 | 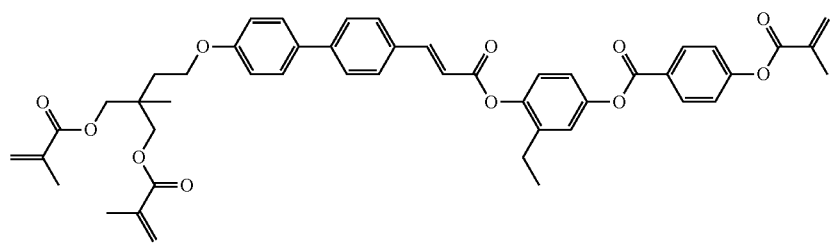 [SMILES: C=C(C)C(=O)OCC(C)(CCOc1ccc(-c2ccc(/C=C/C(=O)Oc3ccc(OC(=O)c4ccc(OC(=O)C(=C)C)cc4)cc3CC)cc2)cc1)COC(=O)C(=C)C]
Mp. 103° C. |

| No. | Structure |
|---|---|
| RM-33 | 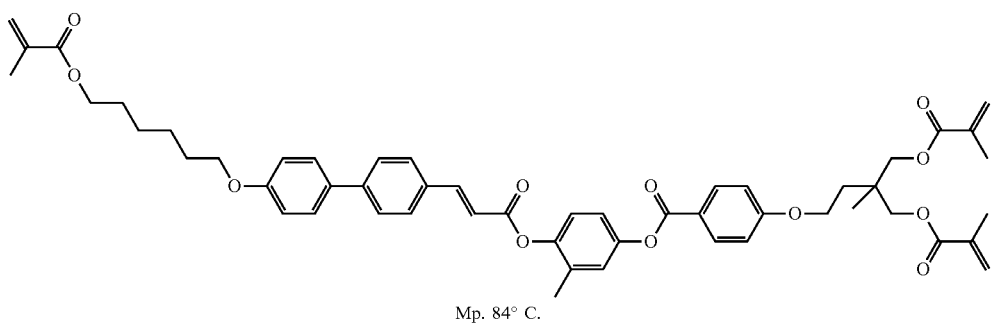<br>Mp. 84° C. |
| RM-34 | 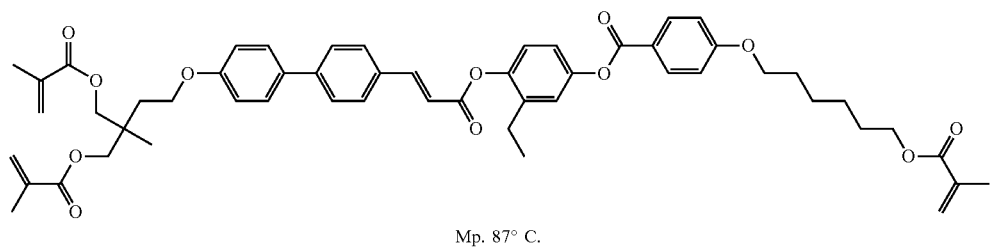<br>Mp. 87° C. |
| RM-35 | 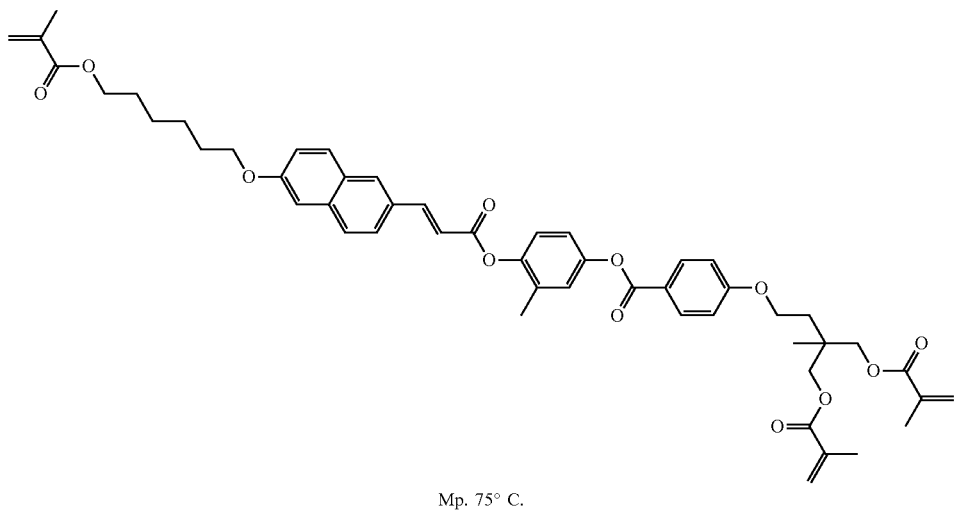<br>Mp. 75° C. |
| RM-36 | 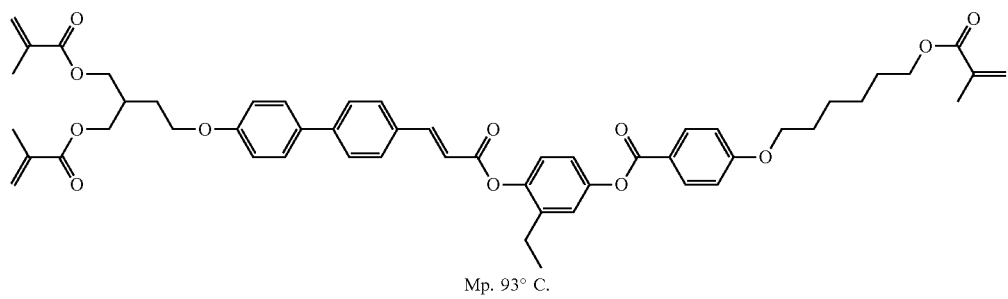<br>Mp. 93° C. |

-continued
| No. | Structure |
|---|---|
| RM-37 | 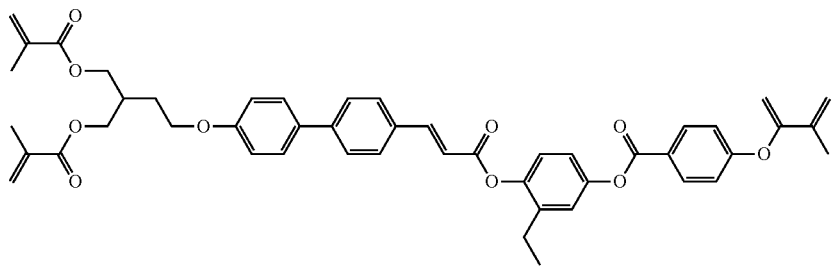<br>Mp. 135° C. |
| RM-38 | 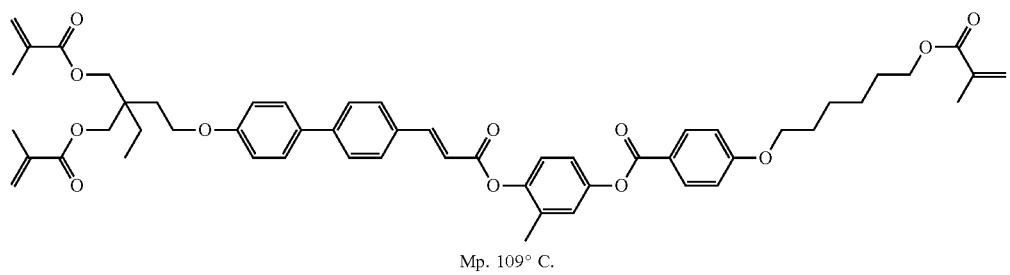 [SMILES: C=C(C)C(=O)OCCCCCCOc1ccc(C(=O)Oc2ccc(OC(=O)/C=C/c3ccc(-c4ccc(OCCC(COC(=O)C(=C)C)COC(=O)C(=C)C)cc4)cc3)c(CC)c2)cc1]<br>Mp. 109° C. |
| RM-39 | 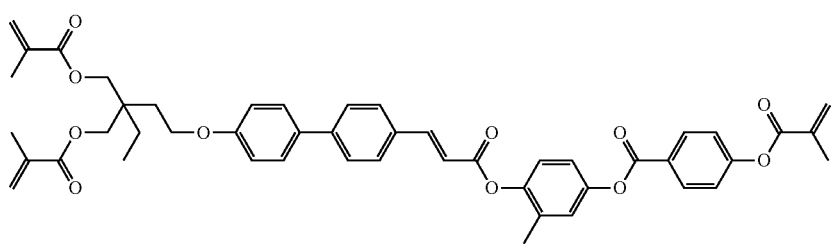 [SMILES: C=C(C)C(=O)OCC(CC)(CCOc1ccc(-c2ccc(/C=C/C(=O)Oc3ccc(OC(=O)c4ccc(OC(=O)C(=C)C)cc4)cc3C)cc2)cc1)COC(=O)C(=C)C]<br>Mp. 123° C. |
| RM-40 | 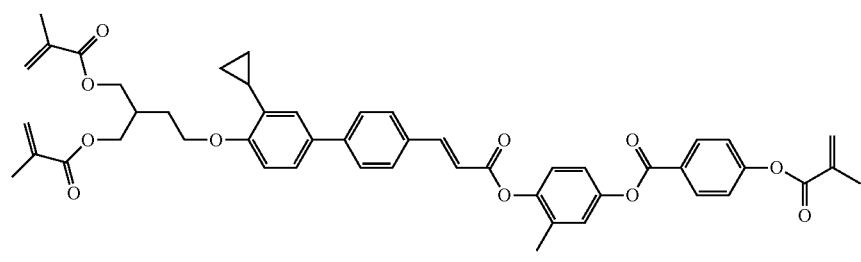 [SMILES: C=C(C)C(=O)OCC(CCOc1ccc(-c2ccc(/C=C/C(=O)Oc3ccc(OC(=O)c4ccc(OC(=O)C(=C)C)cc4)cc3C)cc2)cc1C1CC1)COC(=O)C(=C)C]<br>Mp. 106° C. |
| RM-41 | 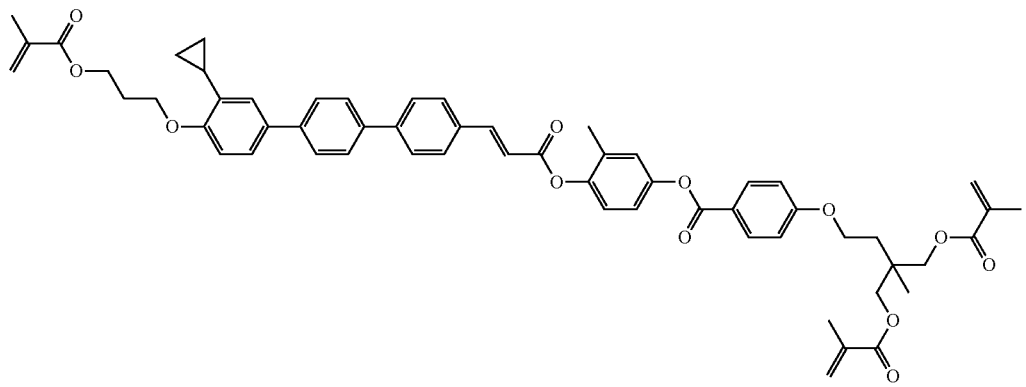 [SMILES: C=C(C)C(=O)OCCCOc1ccc(-c2ccc(-c3ccc(/C=C/C(=O)Oc4ccc(OC(=O)c5ccc(OCCC(C)(COC(=O)C(=C)C)COC(=O)C(=C)C)cc5)cc4C)cc3)cc2)cc1C1CC1]<br>Mp. 100° C. |

-continued
| No. | Structure |
|---|---|
| RM-42 | 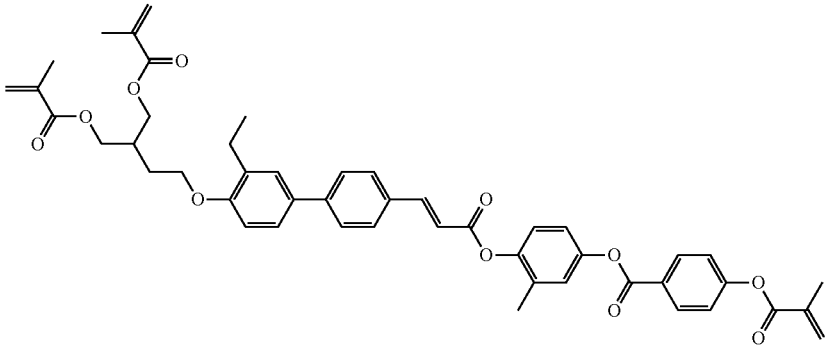 [SMILES: C=C(C)C(=O)OCC(CCOc1ccc(-c2ccc(/C=C/C(=O)Oc3ccc(OC(=O)c4ccc(OC(=O)C(=C)C)cc4)cc3C)cc2)cc1CC)COC(=O)C(=C)C]<br>Mp. 95° C. |
| RM-43 | 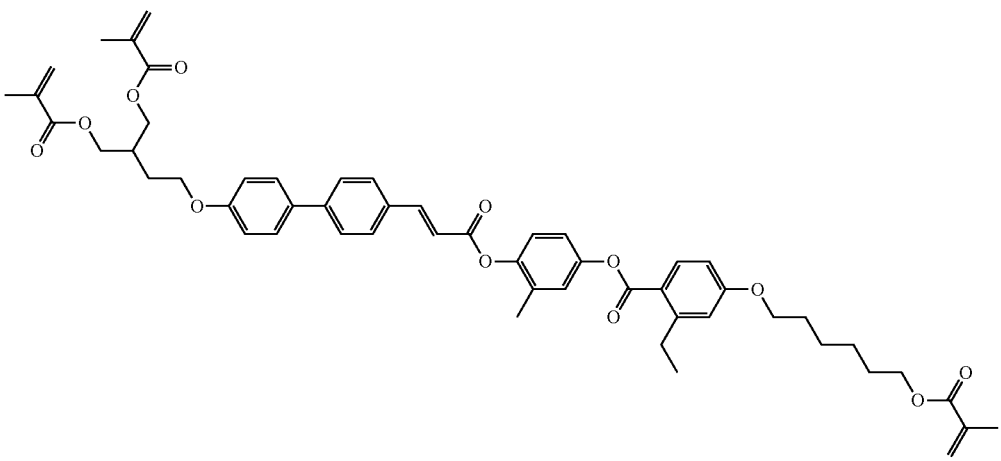 [SMILES: C=C(C)C(=O)OCCCCCCOc1ccc(C(=O)Oc2ccc(OC(=O)/C=C/c3ccc(-c4ccc(OCCC(COC(=O)C(=C)C)COC(=O)C(=C)C)cc4)cc3)c(C)c2)c(CC)c1]<br>Mp. 102° C. |
| RM-44 | 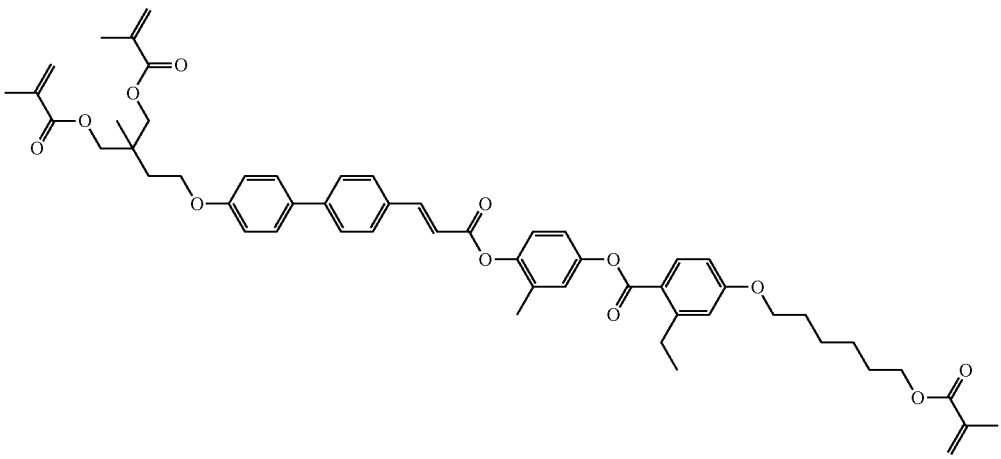 [SMILES: C=C(C)C(=O)OCCCCCCOc1ccc(C(=O)Oc2ccc(OC(=O)/C=C/c3ccc(-c4ccc(OCCC(C)(COC(=O)C(=C)C)COC(=O)C(=C)C)cc4)cc3)c(C)c2)c(CC)c1]<br>Mp. 75° C. |
| RM-45 | 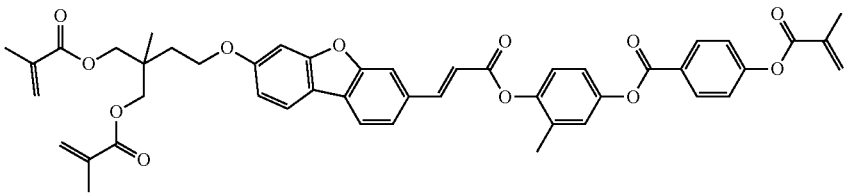 [SMILES: C=C(C)C(=O)OCC(C)(CCOc1ccc2c(c1)oc1cc(/C=C/C(=O)Oc3ccc(OC(=O)c4ccc(OC(=O)C(=C)C)cc4)cc3C)ccc12)COC(=O)C(=C)C]<br>Mp. 125° C. |

-continued
| No. | Structure |
|---|---|
| RM-46 | 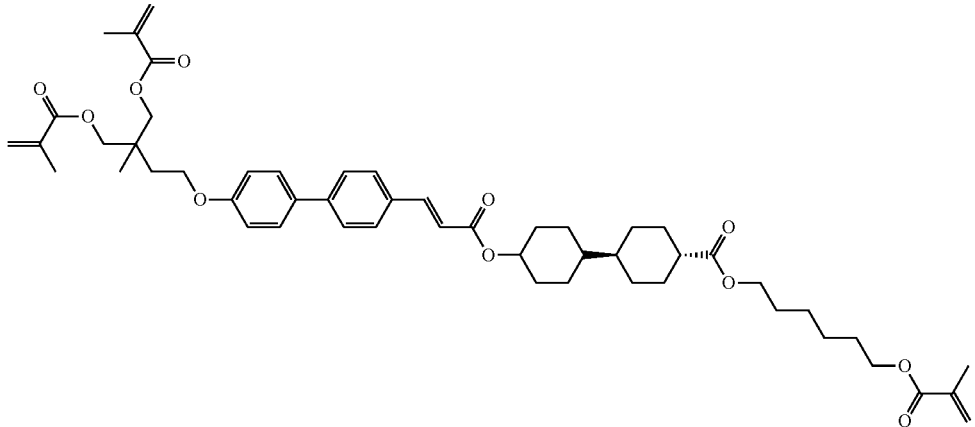 [SMILES: C=C(C)C(=O)OCCCCCCOC(=O)[C@H]1CC[C@H](C2CCC(OC(=O)/C=C/c3ccc(-c4ccc(OCCC(C)(COC(=O)C(=C)C)COC(=O)C(=C)C)cc4)cc3)CC2)CC1] Mp. 106° C. |
| RM-47 | 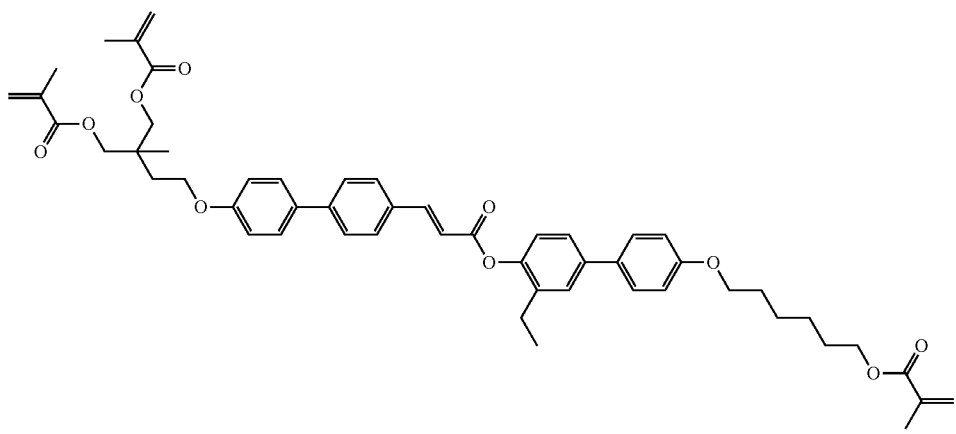 [SMILES: C=C(C)C(=O)OCCCCCCOc1ccc(-c2ccc(OC(=O)/C=C/c3ccc(-c4ccc(OCCC(C)(COC(=O)C(=C)C)COC(=O)C(=C)C)cc4)cc3)c(CC)c2)cc1] Mp. 86° C. |
| RM-48 | 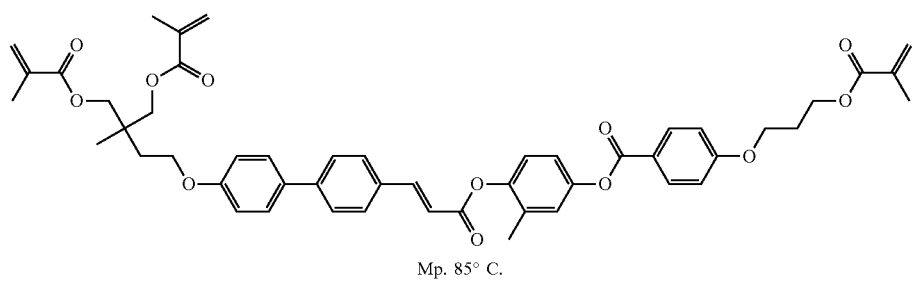 Mp. 85° C. |
| RM-49 | 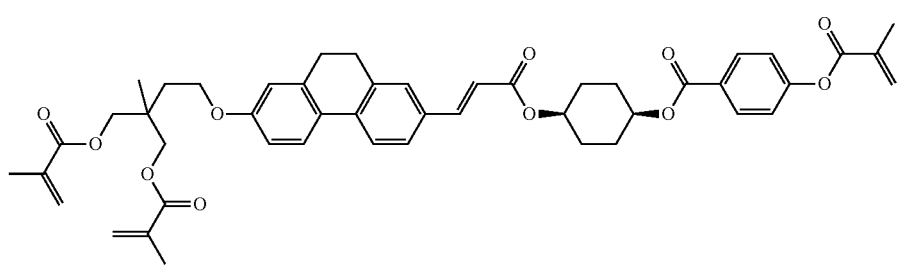 |

| No. | Structure |
| --- | --- |
| RM-50 | 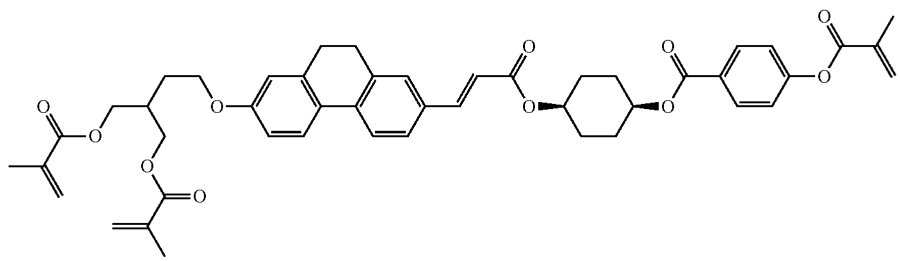 [SMILES: C=C(C)C(=O)OCC(CCOc1ccc2c(c1)CCc1cc(/C=C/C(=O)O[C@H]3CC[C@@H](OC(=O)c4ccc(OC(=O)C(=C)C)cc4)CC3)ccc1-2)COC(=O)C(=C)C] |
| RM-51 | 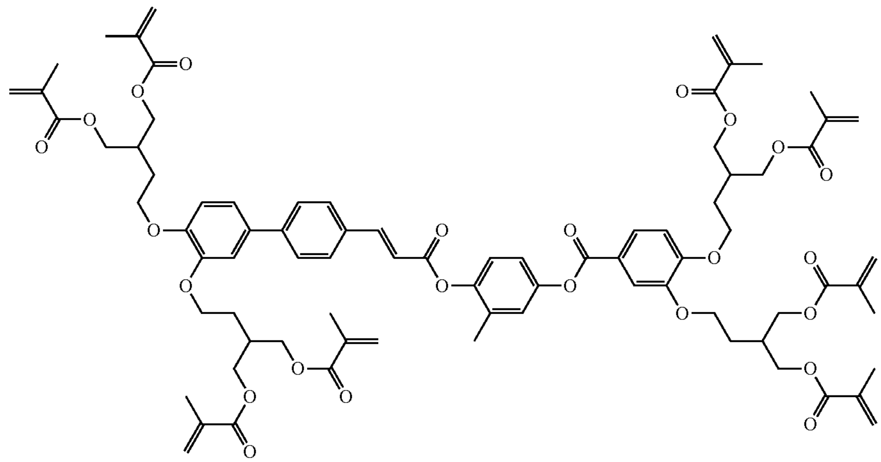 [SMILES: C=C(C)C(=O)OCC(CCOc1ccc(C(=O)Oc2ccc(OC(=O)/C=C/c3ccc(-c4ccc(OCCC(COC(=O)C(=C)C)COC(=O)C(=C)C)c(OCCC(COC(=O)C(=C)C)COC(=O)C(=C)C)c4)cc3)c(C)c2)cc1OCCC(COC(=O)C(=C)C)COC(=O)C(=C)C)COC(=O)C(=C)C] |
| RM-52 | Mp. 125° C. |
| RM-53 | Mp. 141° C. |
| RM-54 | Mp. 100° C. |

| No. | Structure |
|---|---|
| RM-55 | 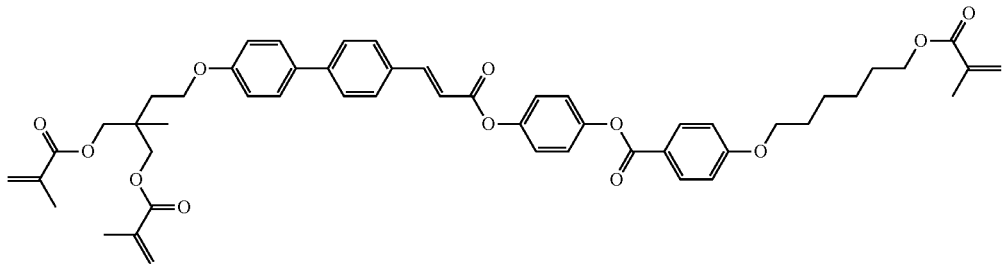 [SMILES: C=C(C)C(=O)OCCCCCCOc1ccc(C(=O)Oc2ccc(OC(=O)/C=C/c3ccc(-c4ccc(OCCC(C)(COC(=O)C(=C)C)COC(=O)C(=C)C)cc4)cc3)cc2)cc1] |

Comparative Compounds

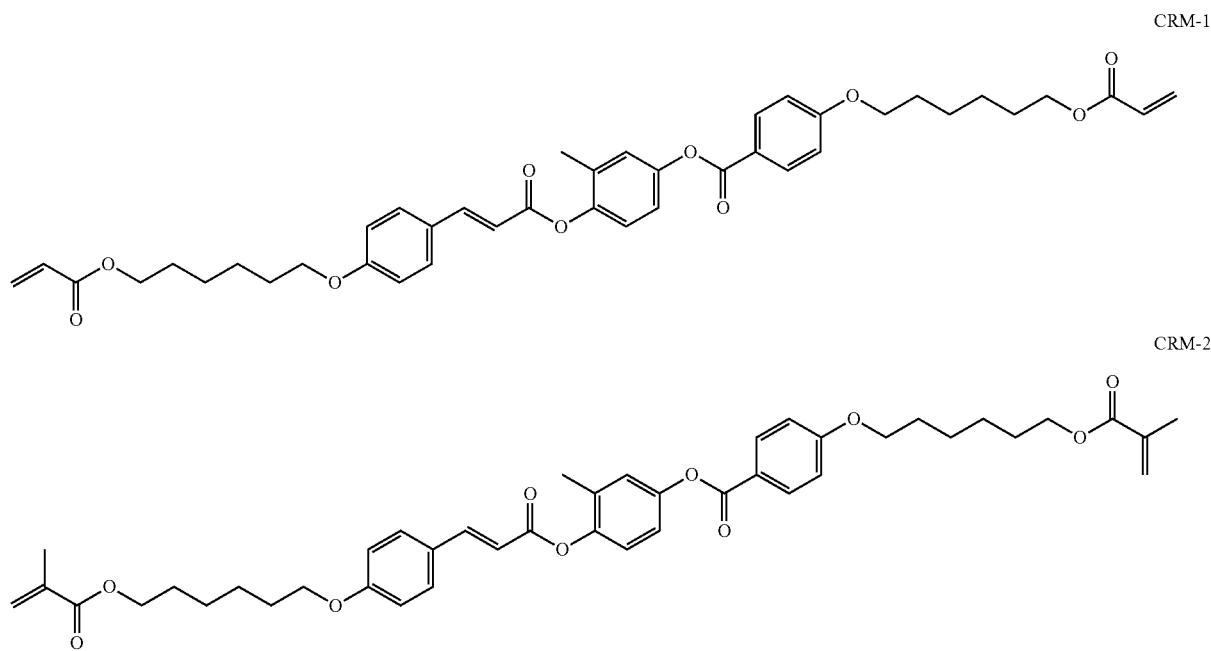

Nematic Host Mixtures

The nematic LC host mixture N-1 to N-15 are prepared as indicated in the following tables:

Mixture N-1:

| Composition [%-w/w] | | Physical properties | |
|---|---|---|---|
| CC-3-V | 36.00 | Clearing Point [° C.]: | 78 |
| CC-3-V1 | 5.00 | $n_e$ [589 nm, 20° C.]: | 1.5907 |
| CCP-V-1 | 8.00 | $\Delta n$ [589 nm, 20° C.]: | 0.1095 |
| PGP-2-2V | 3.00 | $\varepsilon_\parallel$ [1 kHz, 20° C.]: | 16.6 |
| CCQU-3-F | 9.5 | $\varepsilon_\perp$ [1 kHz, 20° C.]: | 3.7 |
| PUQU-3-F | 8.5 | $\Delta\varepsilon$ [1 kHz, 20° C.]: | 12.9 |
| APUQU-2-F | 5.00 | $K_1$ [pN, 20° C.]: | 12.1 |
| APUQU-3-F | 8.00 | $K_3$ [pN, 20° C.]: | 13.4 |
| PGUQU-3-F | 4.00 | $K_3/K_1$ [pN, 20° C.]: | 1.11 |
| PGUQU-4-F | 8.00 | $V_0$ [V, 20° C.]: | 1.01 |
| PGUQU-5-F | 5.00 | LTS bulk [h, −20° C.]: | 1000 |
| Σ | 100.0 | | |

Mixture N-2:

| Composition [%-w/w] | | Physical properties | |
|---|---|---|---|
| CC-3-V | 44.0 | Clearing Point [° C.]: | 80.5 |
| CC-3-V1 | 12.00 | $n_e$ [589 nm, 20° C.]: | 1.5865 |
| CCP-V-1 | 11.00 | $\Delta n$ [589 nm, 20° C.]: | 0.0991 |
| CCP-V2-1 | 9.00 | $\varepsilon_\parallel$ [1 kHz, 20° C.]: | 5.3 |
| PGP-2-3 | 6.00 | $\varepsilon_\perp$ [1 kHz, 20° C.]: | 2.6 |
| PGUQU-3-F | 6.00 | $\Delta\varepsilon$ [1 kHz, 20° C.]: | 2.7 |
| APUQU-3-F | 4.5 | $K_1$ [pN, 20° C.]: | 14.6 |
| PP-1-2V1 | 7.00 | $K_3$ [pN, 20° C.]: | 15.9 |
| PPGU-3-F | 0.5 | $K_3/K_1$ [pN, 20° C.]: | 1.09 |
| Σ | 100.0 | $V_0$ [V, 20° C.]: | 2.46 |
| | | LTS bulk [h, −20° C.]: | 1000 |

Mixture N-3:

| Composition [%-w/w] | | Physical properties | |
|---|---|---|---|
| CY-3-O2 | 12.00 | Clearing Point [° C.]: | 85.2 |
| CY-5-O2 | 10.5 | $n_e$ [589 nm, 20° C.]: | 1.5956 |
| CCY-3-O1 | 6.00 | $\Delta n$ [589 nm, 20° C.]: | 0.1120 |
| CCY-3-O2 | 7.00 | $\varepsilon_\parallel$ [1 kHz, 20° C.]: | 3.7 |
| CCY-5-O2 | 5.00 | $\varepsilon_\perp$ [1 kHz, 20° C.]: | 7.9 |
| CPY-2-O2 | 12.00 | $\Delta\varepsilon$ [1 kHz, 20° C.]: | −4.2 |
| CPY-3-O2 | 12.00 | | |
| PYP-2-3 | 7.5 | | |
| CC-3-V1 | 4.00 | | |
| CC-3-V | 24.00 | | |
| Σ | 100.0 | | |

Mixture N-4:

| Composition [%-w/w] | | Physical properties | |
|---|---|---|---|
| CC-3-V | 50.00 | Clearing Point [° C.]: | 79.4 |
| CC-3-V1 | 4.5 | $n_e$ [589 nm, 20° C.]: | 1.5981 |
| CCP-V-1 | 13.5 | $\Delta n$ [589 nm, 20° C.]: | 0.1094 |
| CPGU-3-OT | 6.00 | $\varepsilon_\parallel$ [1 kHz, 20° C.]: | 8.1 |
| PGP-2-2V | 6.5 | $\varepsilon_\perp$ [1 kHz, 20° C.]: | 2.9 |
| PGU-2-F | 10.00 | $\Delta\varepsilon$ [1 kHz, 20° C.]: | 5.2 |
| PGUQU-3-F | 7.00 | $K_1$ [pN, 20° C.]: | 12.6 |
| PPGU-3-F | 1.00 | $K_3$ [pN, 20° C.]: | 14.2 |
| PUQU-2-F | 1.5 | $K_3/K_1$ [pN, 20° C.]: | 1.13 |
| Σ | 100.0 | $V_0$ [V, 20° C.]: | 1.64 |
| | | LTS bulk [h, −20° C.]: | 240 |

Mixture N-5:

| Composition [%-w/w] | | Physical properties | |
|---|---|---|---|
| CCGU-3-F | 4.00 | Clearing point [° C.]: | 109.1 |
| CDUQU-3-F | 7.00 | $n_e$ [589 nm, 20° C.]: | 1.6158 |
| CPGP-5-2 | 2.00 | $\Delta n$ [589 nm, 20° C.]: | 0.1242 |
| PGUQU-3-F | 2.00 | $\varepsilon_\parallel$ [1 kHz, 20° C.]: | 9.4 |
| PGUQU-4-F | 6.00 | $\varepsilon_\perp$ [1 kHz, 20° C.]: | 3.2 |
| CCP-3OCF3 | 5.00 | $\Delta\varepsilon$ [1 kHz, 20° C.]: | 6.2 |
| CCP-4OCF3 | 4.00 | $K_1$ [pN, 20° C.]: | 17.5 |
| CCP-V-1 | 14.00 | $K_3$ [pN, 20° C.]: | 18.8 |
| CCP-V2-1 | 8.00 | $K_3/K_1$ [pN, 20° C.]: | 1.07 |
| CCQU-3-F | 3.00 | $V_0$ [V, 20° C.]: | 1.76 |
| CLP-3-T | 3.00 | | |
| PGP-2-2V | 6.5 | | |
| PGP-3-2V | 3.00 | | |
| CC-3-V1 | 8.5 | | |
| CCH-301 | 10.00 | | |
| PCH-301 | 10.00 | | |
| PP-1-2V1 | 4.00 | | |
| Σ | 100.0 | | |

Mixture N-6:

| Composition [%-w/w] | | Physical properties | |
|---|---|---|---|
| PY-3-O2 | 13.5 | Clearing point [° C.]: | 74.6 |
| CY-3-O2 | 9.00 | $n_e$ [589 nm, 20° C.]: | 1.5938 |
| CCY-3-O1 | 8.00 | $\Delta n$ [589 nm, 20° C.]: | 0.1082 |
| CCY-3-O2 | 3.00 | $\varepsilon_\parallel$ [1 kHz, 20° C.]: | 3.7 |
| CCY-4-O2 | 3.00 | $\varepsilon_\perp$ [1 kHz, 20° C.]: | 6.9 |
| CPY-2-O2 | 10.00 | $\Delta\varepsilon$ [1 kHz, 20° C.]: | −3.2 |
| CPY-3-O2 | 10.00 | $K_1$ [pN, 20° C.]: | 13.0 |
| CC-3-V | 36.5 | $K_3$ [pN, 20° C.]: | 14.6 |
| BCH-32 | 6.5 | $K_3/K_1$ [pN, 20° C.]: | 1.12 |
| PPGU-3-F | 0.5 | $V_0$ [V, 20° C.]: | 2.29 |
| Σ | 100.0 | $\gamma_1$ [mPa s, 20° C.]: | 91 |

Mixture N-7:

| Composition [%-w/w] | | Physical properties | |
|---|---|---|---|
| CY-3-O2 | 15.00 | Clearing point [° C.]: | 70.5 |
| CPY-2-O2 | 6.00 | $n_e$ [589 nm, 20° C.]: | 1.5914 |
| CPY-3-O2 | 8.00 | $\Delta n$ [589 nm, 20° C.]: | 0.1067 |
| PYP-2-3 | 16.00 | $\varepsilon_\parallel$ [1 kHz, 20° C.]: | 3.4 |
| PYP-2-4 | 3.00 | $\varepsilon_\perp$ [1 kHz, 20° C.]: | 5.9 |
| CLY-3-O2 | 8.00 | $\Delta\varepsilon$ [1 kHz, 20° C.]: | −2.5 |
| CCH-23 | 15.00 | $K_1$ [pN, 20° C.]: | 13.4 |
| CCH-34 | 7.00 | $K_3$ [pN, 20° C.]: | 12.9 |
| CCH-35 | 10.00 | $K_3/K_1$ [pN, 20° C.]: | 0.96 |
| CCH-301 | 12.00 | $V_0$ [V, 20° C.]: | 2.39 |
| Σ | 100.0 | LTS bulk [h, −20° C.]: | 1000 |

Mixture N-8:

| Composition [%-w/w] | | Physical properties | |
|---|---|---|---|
| CC-3-V1 | 9.00 | Clearing point [° C.]: | 74.7 |
| CCH-23 | 18.00 | $n_e$ [589 nm, 20° C.]: | 1.5800 |
| CCH-34 | 3.00 | $\Delta n$ [589 nm, 20° C.]: | 0.0982 |
| CCH-35 | 7.00 | $\varepsilon_\parallel$ [1 kHz, 20° C.]: | 3.5 |
| CCP-3-1 | 5.5 | $\varepsilon_\perp$ [1 kHz, 20° C.]: | 6.9 |
| CCY-3-O2 | 11.5 | $\Delta\varepsilon$ [1 kHz, 20° C.]: | −3.4 |
| CPY-2-O2 | 8.00 | $K_1$ [pN, 20° C.]: | 14.9 |
| CPY-3-O2 | 11.00 | $K_3$ [pN, 20° C.]: | 15.9 |
| CY-3-O2 | 15.5 | $K_3/K_1$ [pN, 20° C.]: | 1.07 |
| PY-3-O2 | 11.5 | $V_0$ [V, 20° C.]: | 2.28 |
| Σ | 100.0 | LTS bulk [h, −20° C.]: | 447 |

Mixture N-9:

| Composition [%-w/w] | | Physical properties | |
|---|---|---|---|
| CC-3-V | 30.00 | Clearing point [° C.]: | 87 |
| CC-3-V1 | 10.00 | $n_e$ [589 nm, 20° C.]: | 1.5829 |
| CCH-34 | 2.5 | $\Delta n$ [589 nm, 20° C.]: | 0.1019 |
| CCP-V-1 | 1.5 | $\varepsilon_\parallel$ [1 kHz, 20° C.]: | 3.5 |
| PGIY-2-O4 | 4.00 | $\varepsilon_\perp$ [1 kHz, 20° C.]: | 7.1 |
| CCY-3-O2 | 10.00 | $\Delta\varepsilon$ [1 kHz, 20° C.]: | −3.7 |
| CCY-5-O2 | 2.00 | $K_1$ [pN, 20° C.]: | 15.2 |
| CLY-3-O2 | 8.00 | $K_3$ [pN, 20° C.]: | 18.0 |
| CPY-2-O2 | 6.00 | $K_3/K_1$ [pN, 20° C.]: | 1.19 |
| CPY-3-O2 | 10.00 | $V_0$ [V, 20° C.]: | 2.35 |
| CY-3-O2 | 12.00 | LTS bulk [h, −20° C.]: | 0 |
| B-2O-O5 | 4.00 | | |
| Σ | 100.0 | | |

Mixture N-10:

| Composition [%-w/w] | | Physical properties | |
|---|---|---|---|
| CC-3-V | 36.5 | Clearing point [° C.]: | 75 |
| CC-3-V1 | 2.00 | $n_e$ [589 nm, 20° C.]: | 1.5845 |
| CCY-3-O1 | 8.00 | $\Delta n$ [589 nm, 20° C.]: | 0.1015 |
| CCY-3-O2 | 6.00 | $\varepsilon_\parallel$ [1 kHz, 20° C.]: | 3.7 |
| CCY-4-O2 | 2.5 | $\varepsilon_\perp$ [1 kHz, 20° C.]: | 7.3 |
| CLY-3-O2 | 8.00 | $\Delta\varepsilon$ [1 kHz, 20° C.]: | −3.7 |

-continued

| Composition [%-w/w] | | Physical properties | |
|---|---|---|---|
| CLY-3-O3 | 2.00 | $K_1$ [pN, 20° C.]: | 13.8 |
| CPY-2-O2 | 10.00 | $K_3$ [pN, 20° C.]: | 15.0 |
| CPY-3-O2 | 3.00 | $K_3/K_1$ [pN, 20° C.]: | 1.09 |
| CY-3-O2 | 5.5 | $V_0$ [V, 20° C.]: | 2.14 |
| PY-3-O2 | 13.00 | | |
| PY-1-O4 | 3.5 | | |
| Σ | 100.0 | | |

Mixture N-11:

| Composition [%-w/w] | | Physical properties | |
|---|---|---|---|
| CLY-3-O2 | 8.00 | Clearing point [° C.]: | 81.5 |
| CLY-5-O2 | 6.00 | $n_e$ [589 nm, 20° C.]: | 1.5834 |
| CPY-3-O2 | 10.00 | Δn [589 nm, 20° C.]: | 0.1017 |
| B(S)-2O-O4 | 6.00 | $\varepsilon_\parallel$ [1 kHz, 20° C.]: | 3.6 |
| B(S)-2O-O5 | 6.00 | $\varepsilon_\perp$ [1 kHz, 20° C.]: | 7.7 |
| CC-3-V | 36.00 | Δε [1 kHz, 20° C.]: | -4.1 |
| CC-3-V1 | 9.00 | $K_1$ [pN, 20° C.]: | 15.5 |
| CY-3-O2 | 13.00 | $K_3$ [pN, 20° C.]: | 17.0 |
| PGIY-2-O4 | 1.00 | $K_3/K_1$ [pN, 20° C.]: | 1.10 |
| CCY-3-O2 | 5.00 | $V_0$ [V, 20° C.]: | 2.15 |
| Σ | 100.0 | | |

Mixture N-12:

| Composition [%-w/w] | | Physical properties | |
|---|---|---|---|
| CC-3-V | 21.75 | cl. p. [° C.]: | 91 |
| CC-3-V1 | 10.45 | $n_e$ [589 nm, 20° C.]: | 1.5970 |
| CPP-V-3 | 9.52 | $n_o$ [589 nm, 20° C.]: | 1.4865 |
| BCH-32 | 4.74 | Δn [589 nm, 20° C.]: | 0.1105 |
| BCH-52 | 3.55 | $\varepsilon_\parallel$ [1 kHz, 20° C.]: | 3.8 |
| PYP-2-3 | 9.76 | $\varepsilon_\perp$ [1 kHz, 20° C.]: | 8.1 |
| COY-3-O1 | 3.19 | Δε [1 kHz, 20° C.]: | -4.3 |
| COY-3-O2 | 6.53 | $K_1$ [pN, 20° C.]: | 15.8 |
| COY-1V-O2 | 3.22 | $K_3$ [pN, 20° C.]: | 19.0 |
| CCOY-3-O2 | 8.74 | $K_3/K_1$ [pN, 20° C.]: | 1.20 |
| CCOY-2-O2 | 8.89 | $V_0$ [V, 20° C.]: | 2.21 |
| CCOY-V-O2 | 2.67 | | |
| CCOY-V-O3 | 2.64 | | |
| CCOY-1V-O2 | 4.35 | | |
| Σ | 100.0 | | |

Mixture N-13:

| Composition [%-w/w] | | Physical properties | |
|---|---|---|---|
| CC-3-V | 29.0 | cl. p. [° C.]: | 70 |
| CC-3-V1 | 10.0 | $n_e$ [589 nm, 20° C.]: | 1.5976 |
| CCP-V-1 | 12.0 | $n_o$ [589 nm, 20° C.]: | 1.4894 |
| CCP-V2-1 | 4.0 | Δn [589 nm, 20° C.]: | 0.1082 |
| CCY-V-O2 | 8.0 | $\varepsilon_\parallel$ [1 kHz, 20° C.]: | 3.4 |
| COY-3-O2 | 2.0 | $\varepsilon_\perp$ [1 kHz, 20° C.]: | 5.5 |
| CCOY-3-O2 | 4.0 | Δε [1 kHz, 20° C.]: | -2.2 |
| PY-3-O2 | 8.0 | $K_1$ [pN, 20° C.]: | 12.7 |
| PY-V2-O2 | 14.0 | $K_3$ [pN, 20° C.]: | 14.5 |
| PYP-2-3 | 9.0 | $K_3/K_1$ [pN, 20° C.]: | 1.14 |
| Σ | 100.0 | $V_0$ [V, 20° C.]: | 2.73 |
| | | $\gamma_1$ [mPa s, 20° C.]: | 66 |
| | | LTS bulk [h, -20° C.]: | 0 |

Mixture N-14:

| Composition [%-w/w] | | Physical properties | |
|---|---|---|---|
| CC-3-V | 29.0 | cl. p. [° C.]: | 70.5 |
| CC-3-V1 | 9.0 | $n_e$ [589 nm, 20° C.]: | 1.5976 |
| CCP-V-1 | 13.0 | $n_o$ [589 nm, 20° C.]: | 1.4889 |
| CCY-V-O2 | 10.0 | Δn [589 nm, 20° C.]: | 0.1087 |
| COY-3-O2 | 2.0 | $\varepsilon_\parallel$ [1 kHz, 20° C.]: | 3.5 |
| CCOY-3-O2 | 6.0 | $\varepsilon_\perp$ [1 kHz, 20° C.]: | 6.0 |
| PY-3-O2 | 8.0 | Δε [1 kHz, 20° C.]: | -2.5 |
| PY-V2-O2 | 14.0 | $K_1$ [pN, 20° C.]: | 12.6 |
| PYP-2-3 | 9.0 | $K_3$ [pN, 20° C.]: | 14.6 |
| Σ | 100.0 | $K_3/K_1$ [pN, 20° C.]: | 1.16 |
| | | $V_0$ [V, 20° C.]: | 2.55 |
| | | $\gamma_1$ [mPa s, 20° C.]: | 70 |
| | | LTS bulk [h, -20° C.]: | 96 |

Mixture N-15:

| Composition [%-w/w] | | Physical properties | |
|---|---|---|---|
| CC-3-V | 29.0 | cl. p. [° C.]: | 81 |
| PP-1-3 | 2.0 | $n_e$ [589 nm, 20° C.]: | 1.5909 |
| CC-3-V1 | 4.0 | $n_o$ [589 nm, 20° C.]: | 1.4840 |
| CEY-3-O2 | 4.0 | Δn [589 nm, 20° C.]: | 0.1069 |
| COY-3-O2 | 7.0 | $\varepsilon_\parallel$ [1 kHz, 20° C.]: | 3.8 |
| CAIY-3-O2 | 10.0 | $\varepsilon_\perp$ [1 kHz, 20° C.]: | 8.4 |
| PYP-2-3 | 17.0 | Δε [1 kHz, 20° C.]: | -4.6 |
| CCOY-2-O2 | 16.0 | $K_1$ [pN, 20° C.]: | 14.4 |
| CCOY-3-O2 | 11.0 | $K_3$ [pN, 20° C.]: | 16.8 |
| Σ | 100.0 | $K_3/K_1$ [pN, 20° C.]: | 1.17 |
| | | $V_0$ [V, 20° C.]: | 2.03 |
| | | $\gamma_1$ [mPa s, 20° C.]: | 134 |
| | | LTS bulk [h, -20° C.]: | 264 |

Mixture N-16:

| Composition [%-w/w] | | Physical properties | |
|---|---|---|---|
| CC-3-V | 34.0 | Clearing point [° C.]: | 100 |
| CC-3-V1 | 2.5 | $n_e$ [589 nm, 20° C.]: | 1.5782 |
| CCP-V-1 | 10.0 | Δn [589 nm, 20° C.]: | 0.1003 |
| PUQU-3-F | 7.0 | $\varepsilon_\parallel$ [1 kHz, 20° C.]: | 12.3 |
| PGUQU-3-F | 4.0 | $\varepsilon_\perp$ [1 kHz, 20° C.]: | 3.2 |
| CPGU-3-OT | 6.0 | Δε [1 kHz, 20° C.]: | 9.1 |
| CCGU-3-F | 4.0 | $K_1$ [pN, 20° C.]: | 14.2 |
| APUQU-3-F | 8.0 | $K_3$ [pN, 20° C.]: | 17.3 |
| CCU-3-F | 4.5 | $K_3/K_1$ [pN, 20° C.]: | 1.22 |
| CCP-3-OT | 4.0 | | |
| CCP-5-OT | 3.0 | | |
| CCQU-3-F | 10.0 | | |
| CPPC-3-3 | 3.0 | | |
| Σ | 100.0 | | |

Fabrication of Display Cells

Unless explicitly stated otherwise, the display cells are made with Corning AF glass of 0.7 mm thickness using 6.4 µm spacer beads and XN-1500T sealant.

For measurement of electro-optics 3 µm thick PI-free IPS cells are made of substrates commercially available from SD-tech and constructed into cells using ITO electrodes having 5 µm electrode spacing and a 3 µm electrode width.

The cells are assembled by hand and then cured using a Omnicure 2000 Mercury lamp with 35 mW/cm² the irradiation power is thereby measured by an Opsytec UV pad-e spectroradiometer.

Mixture Examples

The nematic LC mixtures M-1 to M-64 according to the invention are prepared from the nematic host mixtures N-1 to N-15 listed above and photoalignment additives of formula I, according to the compositions given in the following table.

| Mixture example | Host Mixture | c [%] of Host Mixture | Photoalignment additive Compound | c [%] |
|---|---|---|---|---|
| M-1 | N-1 | 99.70 | RM-3 | 0.30 |
| M-2 | N-1 | 99.50 | RM-3 | 0.50 |
| M-3 | N-1 | 99.00 | RM-3 | 1.00 |
| M-4 | N-1 | 99.70 | RM-2 | 0.30 |
| M-5 | N-1 | 99.50 | RM-2 | 0.50 |
| M-6 | N-1 | 99.70 | RM-9 | 0.30 |
| M-7 | N-1 | 99.50 | RM-9 | 0.50 |
| M-8 | N-1 | 99.70 | RM-15 | 0.30 |
| M-9 | N-1 | 99.50 | RM-15 | 0.50 |
| M-10 | N-1 | 99.70 | RM-8 | 0.30 |
| M-11 | N-1 | 99.50 | RM-8 | 0.50 |
| M-12 | N-1 | 99.00 | RM-8 | 1.00 |
| M-13 | N-1 | 99.70 | RM-6 | 0.30 |
| M-14 | N-1 | 99.50 | RM-6 | 0.50 |
| M-15 | N-1 | 99.00 | RM-6 | 1.00 |
| M-16 | N-1 | 99.70 | RM-14 | 0.30 |
| M-17 | N-1 | 99.50 | RM-14 | 0.50 |
| M-18 | N-1 | 99.00 | RM-14 | 1.00 |
| M-19 | N-1 | 99.70 | RM-7 | 0.30 |
| M-20 | N-1 | 99.50 | RM-7 | 0.50 |
| M-21 | N-1 | 99.00 | RM-7 | 1.00 |
| M-22 | N-2 | 99.70 | RM-2 | 0.30 |
| M-23 | N-2 | 99.50 | RM-2 | 0.50 |
| M-24 | N-3 | 99.70 | RM-2 | 0.30 |
| M-25 | N-3 | 99.50 | RM-2 | 0.50 |
| M-26 | N-3 | 99.70 | RM-15 | 0.30 |
| M-27 | N-3 | 99.50 | RM-15 | 0.50 |
| M-38 | N-4 | 99.70 | RM-2 | 0.30 |
| M-39 | N-4 | 99.50 | RM-2 | 0.50 |
| M-30 | N-4 | 99.70 | RM-15 | 0.30 |
| M-31 | N-5 | 99.70 | RM-2 | 0.30 |
| M-32 | N-8 | 99.70 | RM-15 | 0.30 |
| M-33 | N-8 | 99.50 | RM-15 | 0.50 |
| M-34 | N-9 | 99.70 | RM-3 | 0.30 |
| M-35 | N-9 | 99.50 | RM-3 | 0.50 |
| M-36 | N-9 | 99.00 | RM-3 | 1.00 |
| M-37 | N-9 | 99.70 | RM-2 | 0.30 |
| M-38 | N-9 | 99.50 | RM-2 | 0.50 |
| M-39 | N-9 | 99.70 | RM-9 | 0.30 |
| M-40 | N-9 | 99.50 | RM-9 | 0.50 |
| M-41 | N-9 | 99.70 | RM-15 | 0.30 |
| M-42 | N-9 | 99.50 | RM-15 | 0.50 |
| M-43 | N-9 | 99.70 | RM-6 | 0.30 |
| M-44 | N-9 | 99.70 | RM-7 | 0.30 |
| M-45 | N-10 | 99.70 | RM-15 | 0.30 |
| M-46 | N-10 | 99.50 | RM-15 | 0.50 |
| M-47 | N-11 | 99.70 | RM-15 | 0.30 |
| M-48 | N-11 | 99.50 | RM-15 | 0.50 |
| M-49 | N-1 | 99.70 | RM-13 | 0.30 |
| M-50 | N-1 | 99.50 | RM-13 | 0.50 |
| M-51 | N-1 | 99.30 | RM-13 | 0.70 |
| M-52 | N-1 | 99.0 | RM-13 | 1.00 |
| M-53 | N-12 | 99.70 | RM-13 | 0.30 |
| M-54 | N-12 | 99.50 | RM-13 | 0.50 |
| M-55 | N-12 | 99.30 | RM-13 | 0.70 |
| M-56 | N-13 | 99.70 | RM-13 | 0.30 |
| M-57 | N-13 | 99.50 | RM-13 | 0.50 |
| M-58 | N-13 | 99.30 | RM-13 | 0.70 |
| M-59 | N-14 | 99.70 | RM-13 | 0.30 |
| M-60 | N-14 | 99.50 | RM-13 | 0.50 |
| M-61 | N-14 | 99.30 | RM-13 | 0.70 |
| M-62 | N-15 | 99.70 | RM-13 | 0.30 |
| M-63 | N-15 | 99.50 | RM-13 | 0.50 |
| M-64 | N-15 | 99.30 | RM-13 | 0.70 |
| M-65 | N-16 | 99.70 | RM-17 | 0.30 |

Additionally, comparable nematic LC mixtures CM-1 to CM-6 to the invention are prepared from the nematic host mixtures N-1 listed above and photoalignment additives according to the prior art. The compositions are given in the following table.

| Comparative Mixture example | Host Mixture | c [%] of Host Mixture | Photoalignment additive Compound | c [%] |
|---|---|---|---|---|
| CM-1 | N-1 | 99.70 | CRM-1 | 0.30 |
| CM-2 | N-1 | 99.50 | CRM-1 | 0.50 |
| CM-3 | N-1 | 99.00 | CRM-1 | 1.00 |
| CM-4 | N-1 | 99.70 | CRM-2 | 0.30 |
| CM-5 | N-1 | 99.50 | CRM-2 | 0.50 |
| CM-6 | N-1 | 99.00 | CRM-2 | 1.00 |

Cell Filling and Curing

Unless explicitly stated otherwise, the selected LC mixtures are capillary filled using capillary action at room temp., annealed for 1 h at 100° C. and then irradiated at the same temperature with linearly polarised UV light (35 mW/cm$^2$) for the given time. The cells are then cooled to room temperature. Next, the alignment quality is studied between crossed polarisers on a light box.

| Example | Host mixture | [%] | Compound | [%] | Curing time [s] | Alignment |
|---|---|---|---|---|---|---|
| M-1 | N-1 | 99.70 | RM-3 | 0.30 | 120 | ++ |
| M-2 | N-1 | 99.50 | RM-3 | 0.50 | 60 | ++ |
| M-4 | N-1 | 99.70 | RM-2 | 0.30 | 60-120 | ++ |
| M-5 | N-1 | 99.50 | RM-2 | 0.50 | 60 | ++ |
| M-7 | N-1 | 99.50 | RM-9 | 0.50 | 120 | ++ |
| M-9 | N-1 | 99.50 | RM-15 | 0.50 | 60-120 | ++ |
| M-11 | N-1 | 99.50 | RM-8 | 0.50 | 120 | ++ |
| M-14 | N-1 | 99.50 | RM-6 | 0.50 | 120 | ++ |
| M-17 | N-1 | 99.50 | RM-14 | 0.50 | 120 | ++ |
| M-20 | N-1 | 99.50 | RM-7 | 0.50 | 120 | ++ |
| M-22 | N-2 | 99.70 | RM-2 | 0.30 | 120 | ++ |
| M-23 | N-2 | 99.50 | RM-2 | 0.50 | 60 | ++ |
| M-29 | N-3 | 99.50 | RM-15 | 0.50 | 120 | ++ |
| M-32 | N-4 | 99.70 | RM-15 | 0.30 | 120 | ++ |
| M-35 | N-8 | 99.50 | RM-15 | 0.50 | 120 | ++ |
| M-37 | N-9 | 99.50 | RM-3 | 0.50 | 60 | ++ |
| M-42 | N-9 | 99.50 | RM-9 | 0.50 | 120 | ++ |
| M-44 | N-9 | 99.50 | RM-15 | 0.50 | 120 | ++ |
| M-45 | N-9 | 99.70 | RM-6 | 0.30 | 120 | ++ |
| M-48 | N-11 | 99.50 | RM-15 | 0.50 | 120 | ++ |
| CM-2 | N-1 | 99.50 | CRM-1 | 0.50 | 120 | + |
| CM-3 | N-1 | 99.00 | CRM-1 | 1.00 | 120 | ++ |
| CM-5 | N-1 | 99.50 | CRM-2 | 0.50 | 120 | ++ |
| CM-6 | N-1 | 99.00 | CRM-2 | 1.00 | 60 | ++ |
| CM-7 | N-1 | 100.00 | — | — | — | − |

Alignment quality:
++ excellent,
+ good,
(o) acceptable,
− poor

Excellent uniform planar alignment is achieved with all mixtures despite from comparison mixture examples CM-2 and CM-7. With mixtures comprising CRM-1 is it not possible to reach the optimum dark state level at below 1% concentration.

In the comparative experiment with mixture CM-7, under all polarizer configurations an inhomogeneous transmissive state is observed.

Further, while comparing the results from examples based on mixtures M-1, M-2, M-4, M-5, M-7, M-9, M-11, M-14, M-17, M-20, M-22 in accordance with the present invention with the results from comparison examples based on CM-2, CM-3, CM-5, and CM-6, utilizing all host mixture N-1, it can be seen that either the amount of photoalignment additives can be reduced or that the curing process can be favourably accelerated.

VHR Measurements

Unless explicitly stated otherwise, the selected LC mixtures are capillary filled using capillary action at room temp., annealed for 1 h at 100° C. and then irradiated at the same temperature with linearly polarised UV light (35 mW/cm2) from an Omnicure S2000 mercury lamp with a built in 320-nm filter either utilizing an additional 360 nm long pass filter (cuts off shorter wavelengths from 320-360 nm) or without such filter. The cells are then cooled to room temperature. Next, the VHR is studied using Toyo LCM-1 LC Material Characteristics Measurement System. Unless described otherwise, the measurement of the VHR is carried out as described in T. Jacob, U. Finkenzeller in "Merck Liquid Crystals—Physical Properties of Liquid Crystals", 1997.

VHR measured at 100° C., 60 Hz and 1 V after curing without 360 nm cut off filter

| Example | Host mixture [%] | | Photoalignment compound [%] | | VHR [%] |
|---|---|---|---|---|---|
| M-2 | N-1 | 99.50 | RM-3 | 0.50 | 28.6 |
| M-5 | N-1 | 99.50 | RM-2 | 0.50 | 26.5 |
| M-16 | N-1 | 99.70 | RM-14 | 0.30 | 46.0 |
| M-19 | N-1 | 99.70 | RM-7 | 0.30 | 32.9 |

VHR measured at 100° C., 60 Hz and 1 V after curing without 360 nm cut off filter

| Example | Host mixture [%] | | Photoalignment compound [%] | | VHR [%] |
|---|---|---|---|---|---|
| M-2 | N-1 | 99.50 | RM-3 | 0.50 | 91.7 |
| M-5 | N-1 | 99.50 | RM-2 | 0.50 | 91.0 |
| M-9 | N-1 | 99.50 | RM-15 | 0.50 | 95.5 |
| M-11 | N-1 | 99.50 | RM-8 | 0.50 | 91.3 |
| M-16 | N-1 | 99.70 | RM-14 | 0.30 | 97.6 |
| M-19 | N-1 | 99.70 | RM-7 | 0.30 | 95.8 |
| M-50 | N-1 | 99.50 | RM-13 | 0.50 | 90.1 |

| Example | Host mixture [%] | | Photoalignment compound [%] | | Alignment |
|---|---|---|---|---|---|
| CM-1 | N-1 | 99.70 | CRM-1 | 0.30 | No alignment |
| CM-2 | N-1 | 99.50 | CRM-1 | 0.50 | No alignment |
| CM-3 | N-1 | 99.00 | CRM-1 | 1.00 | No alignment |
| CM-4 | N-1 | 99.70 | CRM-2 | 0.30 | No alignment |
| CM-5 | N-1 | 99.50 | CRM-2 | 0.50 | No alignment |
| CM-6 | N-1 | 99.00 | CRM-2 | 1.00 | No alignment |

As can be seen from the above-given tables the VHR of test cells in accordance with the present invention can be significantly improved by utilizing a 360 nm cut off filter while irradiating the test cells. In comparison to the test cells according to the present invention, the test cells utilizing the comparative mixtures CM-1 to CM-6 do not show any uniform alignment after curing utilizing a 360 nm cut off filter.

The invention claimed is:
1. A compound of formula I,

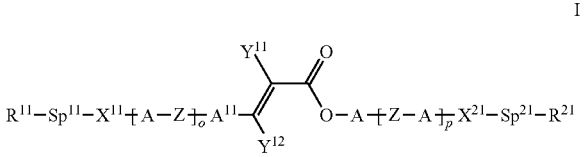

I wherein
$A^{11}$ denotes
  a) 1,4-phenylene or 1,3-phenylene, in which one or two CH groups may be replaced by N and wherein one or more H atoms may be replaced by L,
  or
  b) one of the following radicals

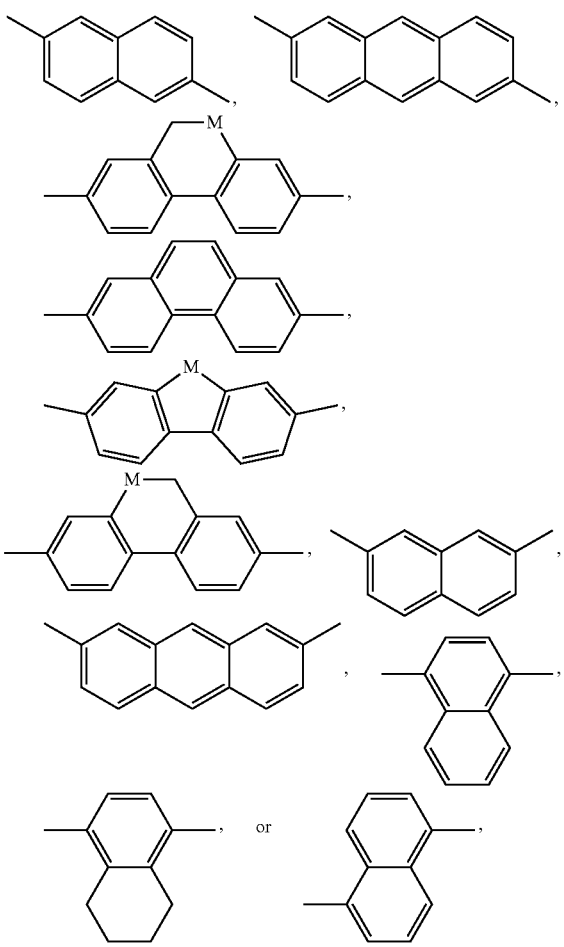

wherein one or more H atoms in these radicals may be replaced by L, and/or one or more double bonds may be replaced by single bonds, and/or one or more CH groups may be replaced by N,
A have each, independently of one another, in each occurrence one of the meanings for $A^{11}$ or
  a) trans-1,4-cyclohexylene, 1,4-cyclohexenylene, in which one or more non-adjacent $CH_2$ groups may be replaced by —O— and/or —S— and wherein one or more H atoms may be replaced by F, or b) tetrahydropyran-2,5-diyl, 1,3-dioxane-2,5-diyl, tetrahydrofuran-2,5-diyl, cyclobutane-1,3-diyl, piperidine-1,4-diyl, thiophene-2,5-diyl or selenophene-2,5-diyl, each of which may be mono- or polysubstituted by L, L denotes, independently of one another, in each occurrence, —OH, —F, —Cl, —Br, —I, —CN, —NO$_2$, SF$_5$, —NCO, —NCS, —OCN, —SCN, —C(=O)N(R$^z$)$_2$, —C(=O)R$^z$, —N(R$^z$)$_2$, optionally substituted silyl, optionally substituted aryl having 6 to 20 C atoms, or straight-chain alkyl, alkoxy, alkylcarbonyl, alkoxycarbonyl, alkylcarbonyloxy or alkoxycarbonyloxy having 1 to 25 C atoms or branched or cyclic alkyl, alkoxy, alkylcarbonyl, alkoxycarbonyl, alkylcarbonyloxy or alkoxycarbonyloxy having 3 to 25 C atoms, in which one or more H atoms may be replaced by F or Cl, or X$^{21}$—Sp$^{21}$—R$^{21}$, M denotes —O—, —S—, —CH$_2$—, —CHR$^z$— or —CRYR$^z$—, R$^y$ and R$^z$ denote each, independently of one another, in each occurrence, H, CN, F or alkyl having 1-12 C atoms, wherein one or more H atoms may be replaced by F, Y$^{11}$ and Y$^{12}$ denote each, independently of one another, in each occurrence, H, F, phenyl or optionally fluorinated alkyl having 1-12 C atoms, Z denotes in each occurrence and each independently from another a single bond, —COO—, —OCO—, —O—CO—O—, —OCH$_2$—, —CH$_2$O—, —OCF$_2$—, —CF$_2$O—, —(CH$_2$)$_n$—, —CF$_2$CF$_2$—, —CH=CH—, —CF=CF—, —CH=CH—COO—, —OCO—CH=CH—, —CO—S—, —S—CO—, —CS—S—, —S—CS—, —S—CSS— or —CC—, n denotes an integer between 2 and 8, o and p denotes independently from another 0, 1 or 2, X$^{11}$ and X$^{21}$ denote, independently from one another, in each occurrence a single bond, —CO—O—, —O—CO—, —O—COO—, —O—, —CH=CH—, —C≡C—, —CF$_2$—O—, —O—CF$_2$—, —CF$_2$— CF$_2$—, —CH$_2$—O—, —O—CH$_2$—, —CO—S—, —S—CO—, —CS—S—, —S—CS—, —S—CSS— or —S—, Sp$^{11}$ and Sp$^{21}$ denote each independently, in each occurrence a single bond or a spacer group containing 1 to 20 C atoms, in which one or more non-adjacent and non-terminal CH$_2$ groups may also be replaced by —O—, —S—, —NH—, —N(CH$_3$)—, —CO—, —O—CO—, —S—CO—, —O—COO—, —CO—S—, —CO—O—, —CF$_2$—, —CF$_2$O—, —OCF$_2$—C(OH)—, —CH(alkyl)-, —CH(alkenyl)-, —CH(alkoxyl)-, —CH(oxaalkyl)-, —CH=CH— or —C≡C—, in such a way that no two are adjacent to one another and no two groups selected from —O—CO—, —S—CO—, —O—COO—, —CO—S—, —CO—O— and —CH=CH— are adjacent to each other, R$^{11}$ denotes a group

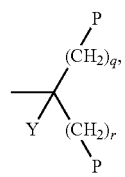

Y denotes H, F, phenyl or optionally fluorinated alkyl having 1-12 C atoms,

R$^{21}$ denotes R$^{11}$, P, halogen, CN, optionally fluorinated alkyl with 1 to 15 C atoms or optionally fluorinated alkenyl with 2 to 15 C atoms, in which one or more non adjacent CH$_2$-groups may be replaced by —O—, —S—, —CO—, —C(O)O—, —O—C(O)—, or O—C(O)—O—, P each independently from another in each occurrence a polymerizable group, q and r denotes each independently an integer from 0 to 8.

2. The compound according to claim 1, which is of one of formulae I-1 to I-9,

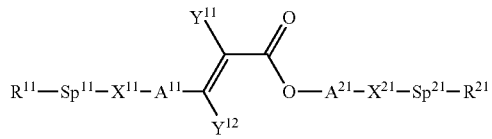

I-1

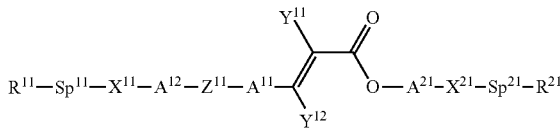

I-2

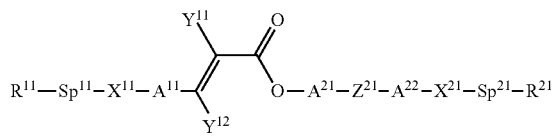

I-3

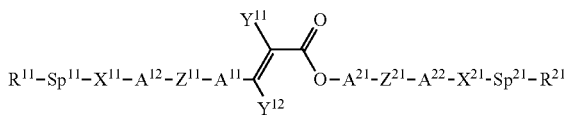

I-4

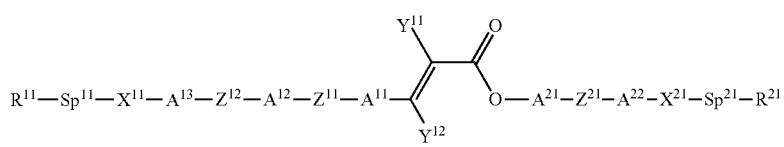

I-5

-continued

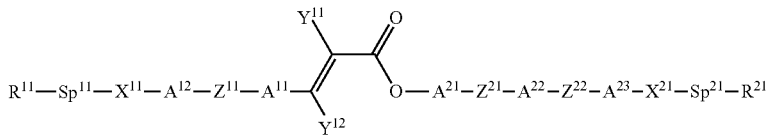

I-6

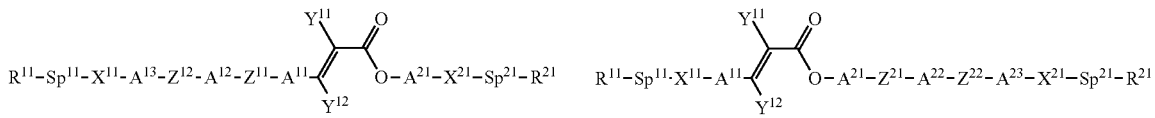

I-7

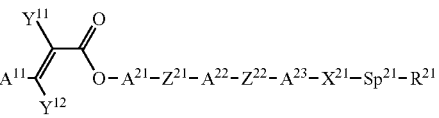

I-8

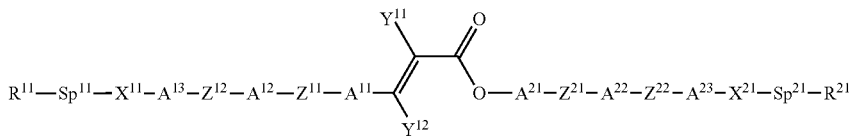

I-9 wherein
$R^{11}$, $R^{21}$, $A^{11}$, $X^{11}$, $X^{12}$, $Y^{11}$, $Y^{12}$, $Sp^{11}$, and $Sp^{12}$ have in each occurrence and each and independently from another one of the meanings as given for the compound of formula I,
$A^{12}$ to $A^{23}$ have each and independently from another one of the meanings for A as given for the compound of formula I, and
$Z^{11}$ to $Z^{22}$ have each and independently from another one of the meanings for Z as given for the compound of formula I.

3. The compound according to claim 1, which is of formula I-2-1,

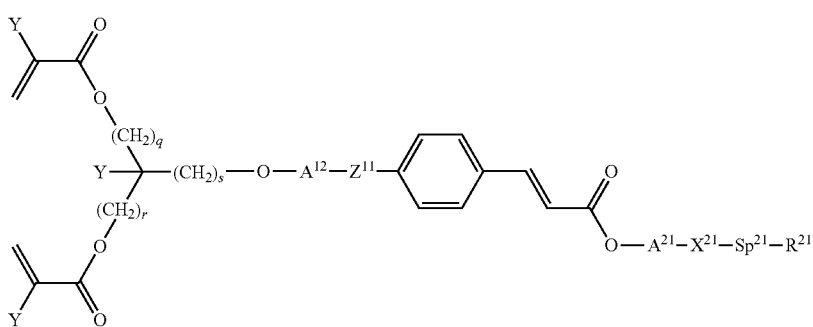

I-2-1 wherein
Y, $R^{21}$, $x^{21}$, and $Sp^{21}$ have in each occurrence and each and independently from another, one of the meanings as given for the compound of formula I,
$Z^{11}$ has one of the meanings for Z as given for the compound of formula I,
r and q denote each and independently from another 1, 2 or 3,
s denotes an integer from 1 to 6, and $A^{12}$ and $A^{21}$ denote each independently from another 1,4-phenylene or 1,3-phenylene, in which one or two CH groups may be replaced by N and wherein one or more H atoms may be replaced by L as given for formula I, or trans-1,4-cyclohexylene or 1,4-cyclohexenylene, in which one or more non-adjacent $CH_2$ groups may be replaced by —O— and/or —S— and wherein one or more H atoms may be replaced by F.

4. The compound according to claim 1, which is one of the following formulae I-3-1, I-3-2 or I-3-3,

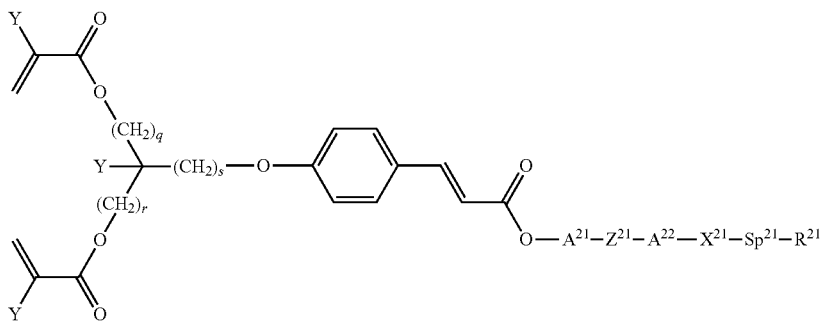

I-3-1

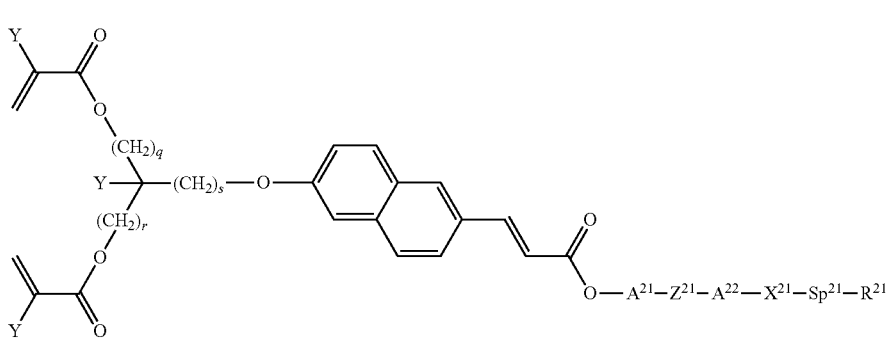

I-3-2

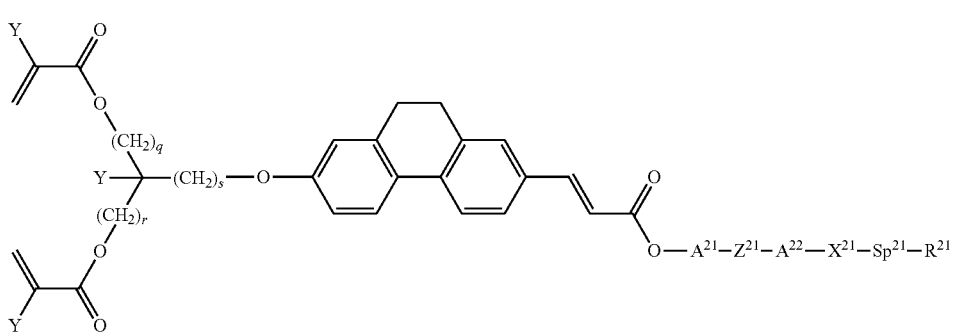

I-3-3 wherein
Y, $R^{21}$, $X^{21}$, and $Sp^{21}$ have in each occurrence and each independently from another, one of the meanings as given for the compound of formula I,
$Z^{21}$ has one of the meanings for Z as given for the compound of formula I,
r and q denote each independently from another 1, 2 or 3,
s denotes an integer from 1 to 6, and $A^{21}$ and $A^{22}$ denote each independently from another 1,4-phenylene or 1,3-phenylene, in which one or two CH groups may be replaced by N and wherein one or more H atoms may be replaced by L as given for formula I, or trans-1,4-cyclohexylene or 1,4-cyclohexenylene, in which one or more non-adjacent $CH_2$ groups may be replaced by —O— and/or —S— and wherein one or more H atoms may be replaced by F.

5. The compound according to claim 1, which is of formula I-4-1,

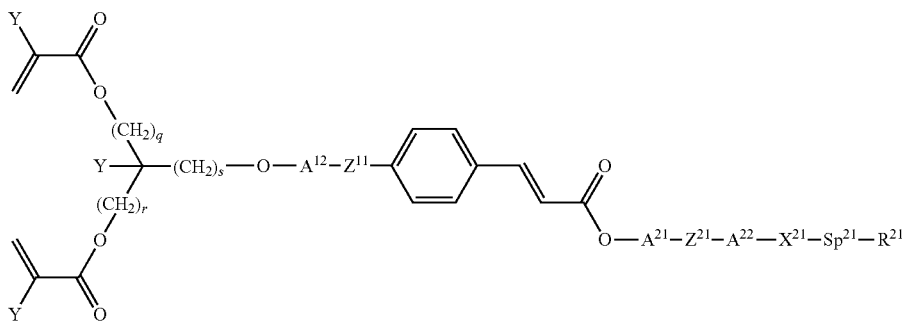

wherein
Y, $R^{21}$, $X^{21}$,
and $Sp^{21}$ have in each occurrence and each and independently from another, one of the meanings as given for the compound of formula I,
$Z^{11}$ and $Z^{21}$ have each independently from another one of the meanings for Z as given for the compound of formula I,
r and q denote each independently from another 1, 2 or 3,
s denotes an integer from 1 to 6, and
$A^{12}$, $A^{21}$
and $A^{22}$ denote each independently from another 1,4-phenylene or 1,3-phenylene, in which one or two CH groups may be replaced by N and wherein one or more H atoms may be replaced by L as given for formula I, or trans-1,4-cyclohexylene or 1,4-cyclohexenylene, in which one or more non-adjacent $CH_2$ groups may be replaced by —O— and/or —S— and wherein one or more H atoms may be replaced by F.

6. The compound according to claim 1, which is of formula I-5-1,

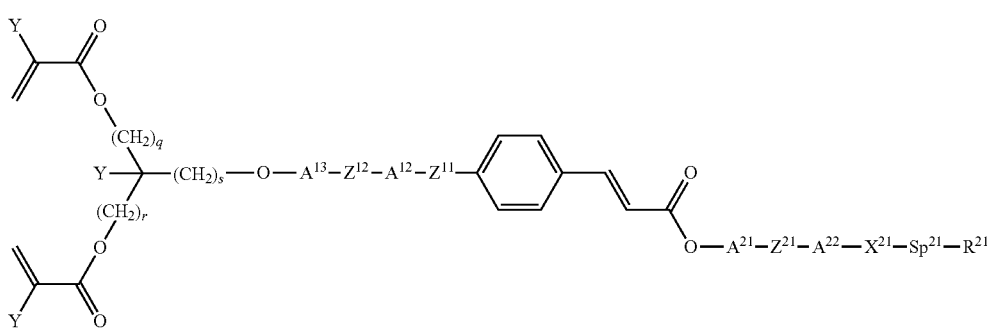

wherein
Y, $R^{21}$, $X^{21}$,
and $Sp^{21}$ have in each occurrence and each and independently from another one of the meanings as given for the compound of formula I,
$Z^{11}$, $Z^{12}$
and $Z^{21}$ have each independently from another one of the meanings for Z as given for the compound of formula I,
r and q denote each independently from another 1, 2 or 3,
s denotes an integer from 1 to 6, and
$A^{12}$, $A^{13}$, $A^{21}$
and $A^{22}$ denote each independently from another 1,4-phenylene or 1,3-phenylene, in which one or two CH groups may be replaced by N and wherein one or more H atoms may be replaced by L as given for formula I, or trans-1,4-cyclohexylene or 1,4-cyclohexenylene, in which one or more non-adjacent $CH_2$ groups may be replaced by —O— and/or —S— and wherein one or more H atoms may be replaced by F.

7. A liquid crystal mixture, comprising a component A) comprising one or more compounds of formula I according to claim 1, and a liquid-crystalline component B) as LC host mixture, comprising one or more mesogenic or liquid-crystalline compounds.

8. The liquid crystal mixture according to claim 7, wherein the total concentration of compounds of formula I in the mixture is 0.01 to 10% by weight.

9. The liquid crystal mixture according to claim 7, additionally comprising a polymerizable component C) comprising one or more polymerizable mesogenic or polymerizable isotropic compounds.

10. The liquid crystal mixture according to claim 9, wherein the concentration of polymerizable mesogenic or polymerizable isotropic compounds is 0.01 to 10% by weight.

11. The liquid crystal mixture according to claim 9, comprising one or more compounds of formula P

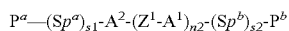

wherein $P^a$, $P^b$ each, independently of one another, denote a polymerisable group, $Sp^a$, $Sp^b$ on each occurrence, identically or differently, denote a spacer group, $s_1$, $s^2$ each, independently of one another, are 0 or 1, $A^1$, $A^2$ each, independently of one another, denote
  a) trans-1,4-cyclohexylene, 1,4-cyclohexenylene or 4,4"-bicyclohexylene, in which one or more non-adjacent CH$_2$ groups may be replaced by —O— and/or —S— and wherein one or more H atoms may be replaced by F,
  b) 1,4-phenylene or 1,3-phenylene, in which one or two CH groups may be replaced by N and wherein one or more H atoms may be replaced by L,
  c) tetrahydropyran-2,5-diyl, 1,3-dioxane-2,5-diyl, tetrahydrofuran-2,5-diyl, cyclobutane-1,3-diyl, piperidine-1,4-diyl, thiophene-2,5-diyl or selenophene-2,5-diyl, each of which may be mono- or polysubstituted by L,
  d) a saturated, partially unsaturated or fully unsaturated, and optionally substituted, polycyclic radical having 5 to 20 cyclic C atoms, one or more of which may be replaced by a heteroatom, that is selected from:

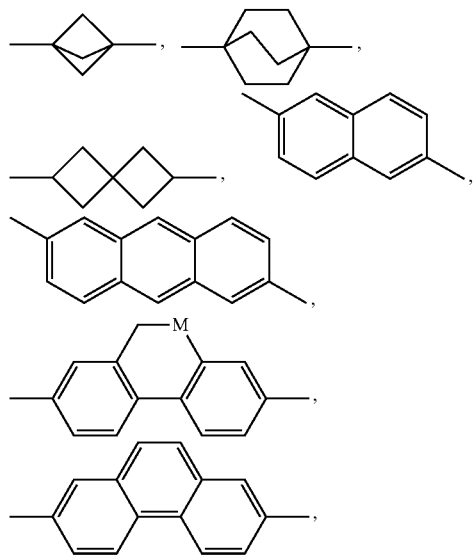

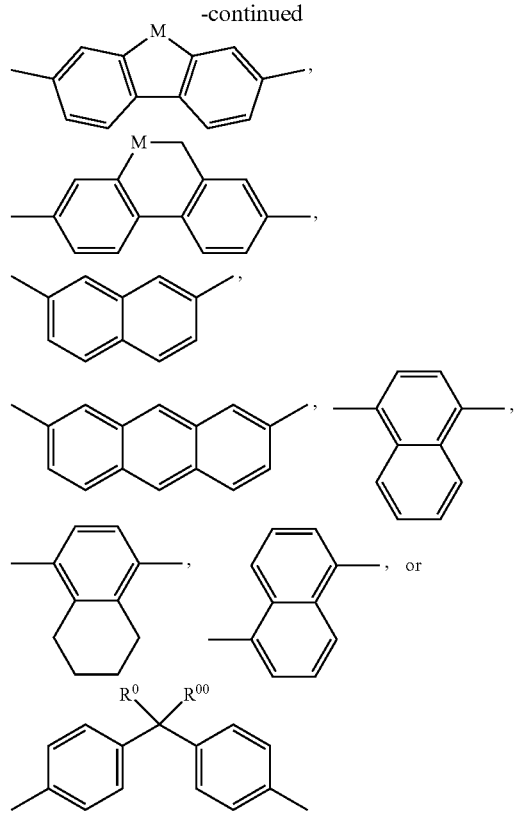

wherein one or more H atoms in these radicals may be replaced by L, and/or one or more double bonds may be replaced by single bonds, and/or one or more CH groups may be replaced by N, n2 is 0, 1, 2 or 3, $Z^1$ in each case, independently of one another, denotes —CO—O—, —O—CO—, —CH$_2$O—, —OCH$_2$—, —CF$_2$O—, —OCF$_2$—, or —(CH$_2$)$_n$—, where n is 2, 3 or 4, —O—, —CO—, —C(R$^0$R$^{00}$)—, —CH$_2$CF$_2$—, —CF$_2$CF$_2$— or a single bond, L on each occurrence, identically or differently, denotes F, Cl, CN, SCN, SF$_5$ or a straight-chain, in each case optionally fluorinated, alkyl, alkoxy, alkylcarbonyl, alkoxycarbonyl, alkylcarbonyloxy or alkoxycarbonyloxy having 1 to 12 C atoms, or a branched, in each case optionally fluorinated, alkyl, alkoxy, alkylcarbonyl, alkoxycarbonyl, alkylcarbonyloxy or alkoxycarbonyloxy having 3 to 12 C atoms, $R^0$, $R^{00}$ each, independently of one another, denote H, F or a straight-chain alkyl having 1 to 12 C atoms, or a branched alkyl having 3 to 12 C atoms, wherein one or more H atoms may be replaced by F, M denotes —O—, —S—, —CH$_2$—, —CHY$^1$— or —CY$^1$Y$^2$—, and $Y^1$ and $Y^2$ each, independently of one another, have one of the meanings indicated above for $R^0$ or denote Cl or CN.

12. The liquid crystal mixture according to claim 7, wherein the LC host mixture has negative dielectric anisotropy.

13. The liquid crystal mixture according to claim 12, wherein the LC host mixture comprises one or more compounds of the following formulae:

CY

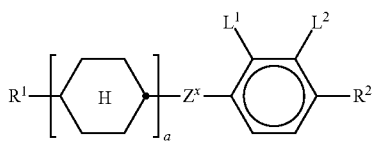

PY

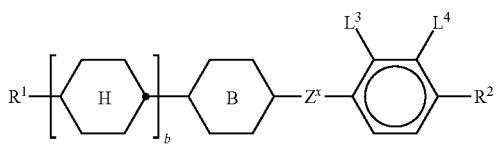

wherein
a is 1 or 2,
b is 0 or 1,

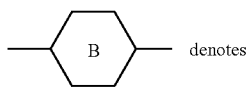 denotes

 or 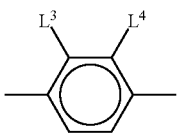

R¹ and R² each, independently of one another, denote alkyl having 1 to 12 C atoms, in which one or two non-adjacent CH₂ groups may be replaced by —O—, —CH=CH—, —CO—, —O—CO— or —CO—O— in such a way that O atoms are not linked directly to one another, $Z^x$ denotes —CH=CH—, —CH₂O—, —OCH₂—, —CF₂O—, —OCF₂—, —O—, —CH₂—, —CH₂CH₂— or a single bond, $L^{1-4}$ each, independently of one another, denote F, Cl, OCF₃, CF₃, CH₃, CH₂F or CHF₂.

14. The liquid crystal mixture according to claim 7, wherein the LC host mixture has positive dielectric anisotropy.

15. The liquid crystal mixture according to claim 14, wherein the LC host mixture comprises one or more compounds of formulae II and/or III,

II

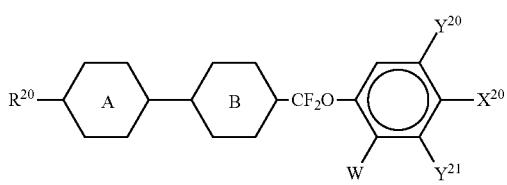

III

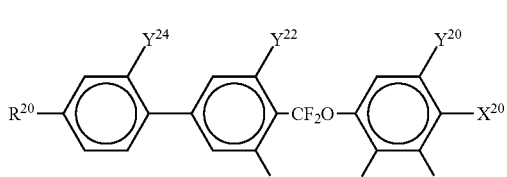

wherein $R^{20}$ each, identically or differently, denote a halogenated or unsubstituted alkyl or alkoxy radical having 1 to 15 C atoms, in which one or more CH₂ groups may each be replaced, independently of one another, by —CC—, —CF₂O—, —CH=CH—,

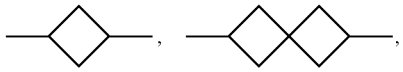

—O—, —CO—O— or —O—CO— in such a way that O atoms are not linked directly to one another, $X^{20}$ each, identically or differently, denote F, Cl, CN, SF₅, SCN, NCS, a halogenated alkyl radical, or a halogenated alkoxy radical, each having 1 to 6 C atoms, or a halogenated alkenyl radical or a halogenated alkenyloxy radical, each having 2 to 6 C atoms, $Y^{2-24}$ each, identically or differently, denote H or F, W denotes H or methyl, and

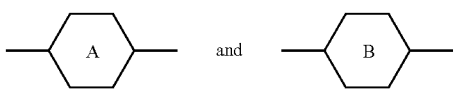

each, identically or differently, denote

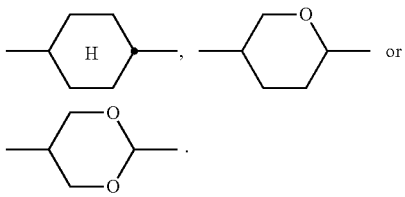

16. The liquid crystal mixture according to claim 15, comprising one or more compounds of formulae XI and/or XII

XI

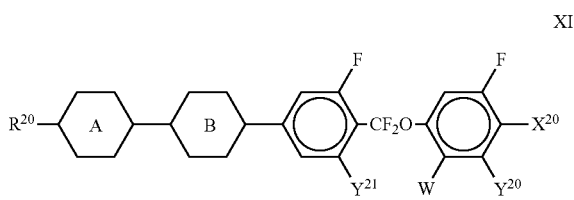

XII

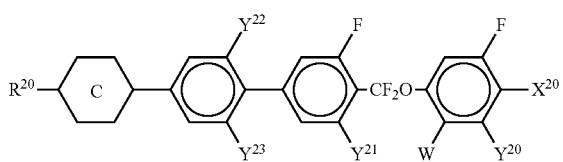

wherein $R^{20}$, $X^{20}$, W and $Y^{20-23}$ have the meanings indicated in formula III, and

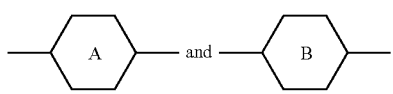

each, independently of one another, denote

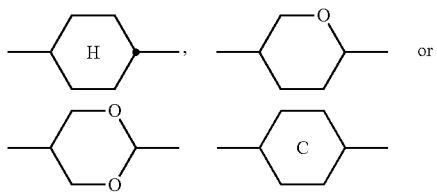

and denotes

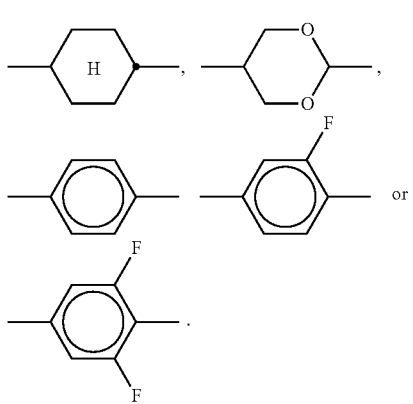

17. The liquid crystal mixture according to claim 7, wherein the LC host mixture comprises one or more compounds of formula ZK:

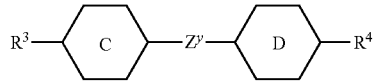

ZK in which

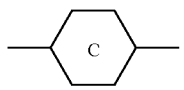

denotes

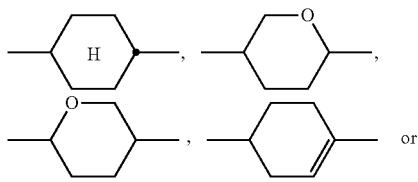

-continued

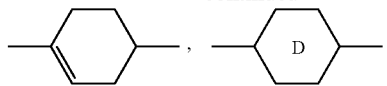

denotes

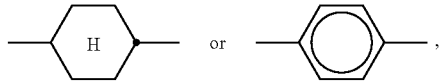

$R^3$ and $R^4$ each, independently of one another, denote alkyl having 1 to 12 C atoms, in which one or two non-adjacent $CH_2$ groups may be replaced by —O—, —CH=CH—, —CO—, —O—CO— or —CO—O— in such a way that O atoms are not linked directly to one another, $Z^y$ denotes —$CH_2CH_2$—, —CH=CH—, —$CF_2O$—, —$OCF_2$—, —$CH_2O$—, —$OCH_2$—, —CO—O—, —O—CO—, —$C_2F_4$—, —CF=CF—, —CH=CH—$CH_2O$— or a single bond.

18. The liquid crystal mixture according to claim 7, wherein the LC host mixture comprises one or more compounds of the following formulae ZK1a
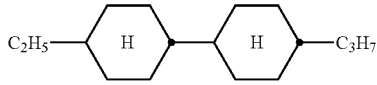

ZK1b
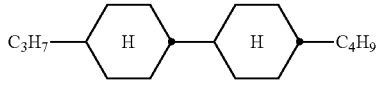

ZK1c

ZK3a

ZK3b

ZK3c
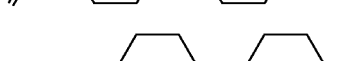

ZK3d
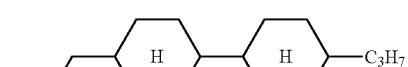

ZK3e
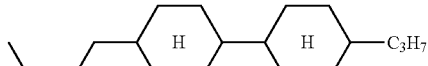

ZK3f

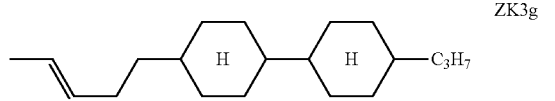
ZK3g wherein the propyl, butyl and pentyl groups are straight-chain groups.

19. The liquid crystal mixture according to claim 7, wherein the LC host mixture comprises one or more compounds of the following formulae:

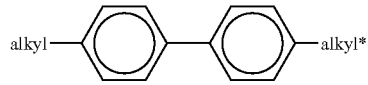
B1

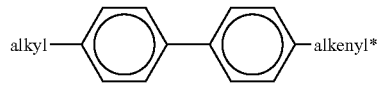
B2

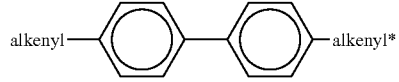
B3 in which alkyl and alkyl* each, independently of one another, denote a straight-chain alkyl radical having 1-6 C atoms, and alkenyl and alkenyl* each, independently of one another, denote a straight-chain alkenyl radical having 2-6 C atoms.

20. The liquid crystal mixture according to claim 1, wherein the LC host mixture comprises one or more compounds of the following formulae:

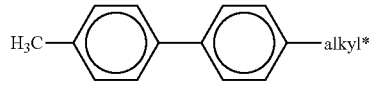
B1a

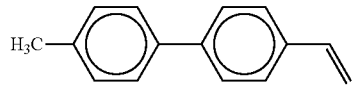
B2a

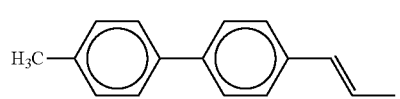
B2b

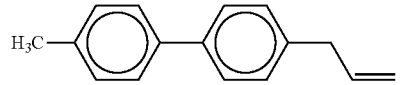
B2c

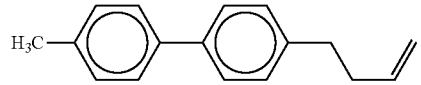
B2d

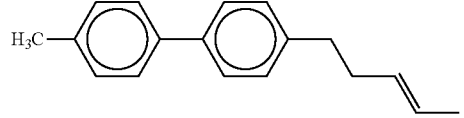
B2e in which alkyl* denotes an alkyl radical having 1-6 C atoms.

21. A process for the fabrication of a liquid crystal display, comprising
providing a first substrate which includes a pixel electrode and a common electrode for generating an electric field substantially parallel to a surface of the first substrate in the pixel region;
providing a second substrate, the second substrate being disposed opposite to the first substrate;
interposing a liquid crystal mixture according to claim 8;
irradiating the liquid crystal mixture with linearly polarised light causing photoalignment of the liquid crystal;
curing the polymerizable compounds of the liquid crystal mixture by irradiation with ultraviolet light or visible light having a wavelength of 450 nm or below.

22. The process according to claim 21, wherein the linearly polarised light is ultraviolet light or visible light having a wavelength of 450 nm or below.

23. A display, obtained by a process according to claim 21.

24. The display according to claim 23, wherein the LC host mixture is homogeneously aligned without the application of an electric field.

25. The display according to claim 23, wherein the display is an IPS or FFS display.

\* \* \* \* \*